United States Patent
Chen et al.

(10) Patent No.: US 11,702,427 B2
(45) Date of Patent: Jul. 18, 2023

(54) SUBSTITUTED 2-PYRIDONE TRICYCLIC COMPOUNDS, ANALOGUES THEREOF, AND METHODS USING SAME

(71) Applicant: Arbutus Biopharma Corporation, Burnaby (CA)

(72) Inventors: Shuai Chen, Warrington, PA (US); Bruce D. Dorsey, Ambler, PA (US); Yi Fan, Doylestown, PA (US); Dimitar B. Gotchev, Hatboro, PA (US); Jorge Quintero, Sayreville, NJ (US)

(73) Assignee: Arbutus Biopharma Corporation, Burnaby (CA)

( * ) Notice: Subject to any disclaimer, the term of this patent is extended or adjusted under 35 U.S.C. 154(b) by 0 days.

(21) Appl. No.: 16/978,117

(22) PCT Filed: Mar. 11, 2019

(86) PCT No.: PCT/US2019/021557
§ 371 (c)(1),
(2) Date: Sep. 3, 2020

(87) PCT Pub. No.: WO2019/177937
PCT Pub. Date: Sep. 13, 2019

(65) Prior Publication Data
US 2021/0017186 A1 Jan. 21, 2021

Related U.S. Application Data

(60) Provisional application No. 62/793,567, filed on Jan. 17, 2019, provisional application No. 62/720,054, filed on Aug. 20, 2018, provisional application No. 62/641,554, filed on Mar. 12, 2018.

(51) Int. Cl.
| | | |
|---|---|---|
| C07D 493/04 | (2006.01) | |
| C07D 215/02 | (2006.01) | |
| C07D 221/04 | (2006.01) | |
| C07D 471/04 | (2006.01) | |
| C07D 493/14 | (2006.01) | |

(52) U.S. Cl.
CPC ......... *C07D 493/04* (2013.01); *C07D 215/02* (2013.01); *C07D 221/04* (2013.01); *C07D 471/04* (2013.01); *C07D 493/14* (2013.01)

(58) Field of Classification Search
CPC .................................................. C07D 215/04
See application file for complete search history.

(56) References Cited

U.S. PATENT DOCUMENTS

| | | |
|---|---|---|
| 6,514,912 B1 | 2/2003 | Guarna et al. |
| 7,307,073 B2 | 12/2007 | Grove et al. |
| 8,063,037 B2 | 11/2011 | Rewinkel et al. |
| 8,629,147 B2 | 1/2014 | Anikin et al. |
| 9,458,153 B2 | 10/2016 | Han et al. |
| 2015/0210682 A1 | 7/2015 | Wang et al. |
| 2016/0020405 A1 | 1/2016 | Ito et al. |
| 2016/0122344 A1 | 5/2016 | Han et al. |
| 2016/0228432 A1 | 8/2016 | Crawford et al. |
| 2016/0296515 A1 | 10/2016 | Han et al. |
| 2017/0057952 A1 | 3/2017 | Yang et al. |
| 2017/0240548 A1 | 8/2017 | Fu et al. |
| 2018/0127416 A1 | 5/2018 | Han et al. |
| 2019/0314347 A1 | 10/2019 | Bailey et al. |
| 2019/0381014 A1 | 12/2019 | Chen et al. |
| 2020/0261432 A1 | 8/2020 | Bailey et al. |

FOREIGN PATENT DOCUMENTS

| | | |
|---|---|---|
| CA | 3126102 A1 | 7/2020 |
| CN | 108727378 A | 11/2018 |
| EP | 0093498 A2 | 11/1983 |
| JP | 60-197684 A | 10/1985 |

(Continued)

OTHER PUBLICATIONS

American Chemical Society. Chemical Abstract Service. RN 66-71-7. First made available to public/prior art date/entered into STN: Nov. 16, 1984. (Year: 1984).*
American Chemical Society. Chemical Abstract Service. RN 471852-54-7. First made available to public/Entered into STN: Nov. 8, 2002. (Year: 2002).*
Cappelli et al, Journal of Medicinal Chemistry, vol. 41, No. 5, pp. 728-741 (Year: 1998).*

(Continued)

*Primary Examiner* — Zinna Northington Davis
(74) *Attorney, Agent, or Firm* — Saul Ewing LLP; Domingos J. Silva; Kevin T. O'Brien

(57) ABSTRACT

The present invention includes in one aspect substituted 2-oxo-1,2,5,6-tetrahydrobenzo[h]quinoline-3-carboxylic acids, analogues thereof, and compositions comprising the same, which can be used to treat and/or prevent hepatitis B virus (HBV) infection and/or hepatitis D virus (HDV) in a patient. In certain embodiments, the invention provides a compound of formula (I), or a salt, solvate, geometric isomer, stereoisomer, tautomer, and any mixtures thereof:

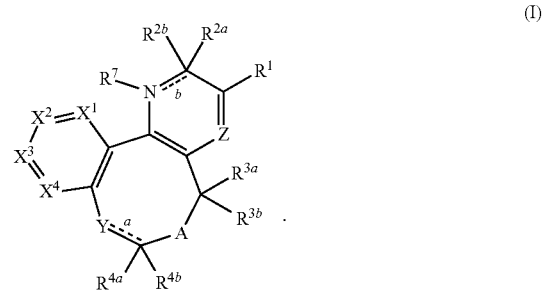

41 Claims, No Drawings

(56) References Cited

FOREIGN PATENT DOCUMENTS

| | | | |
|---|---|---|---|
| JP | H04-77 B2 | 1/1992 | |
| WO | WO-2013033228 A1 * | 3/2013 | ........... A61K 31/435 |
| WO | 2014121416 A1 | 8/2014 | |
| WO | 2015113990 A1 | 8/2015 | |
| WO | 2015173164 A1 | 11/2015 | |
| WO | 2016039938 A1 | 3/2016 | |
| WO | 2016054421 A1 | 4/2016 | |
| WO | 2016071215 A1 | 5/2016 | |
| WO | 2017013046 A1 | 1/2017 | |
| WO | 2017016960 A1 | 2/2017 | |
| WO | 2017140821 A1 | 8/2017 | |
| WO | 2017216685 A1 | 12/2017 | |
| WO | 2017216686 A1 | 12/2017 | |
| WO | 2018019297 A1 | 2/2018 | |
| WO | 2018022282 A1 | 2/2018 | |
| WO | 2018047109 A1 | 3/2018 | |
| WO | 2018073753 A1 | 4/2018 | |
| WO | 2018085619 A1 | 5/2018 | |
| WO | 2018130152 A1 | 7/2018 | |
| WO | 2018198079 A1 | 11/2018 | |
| WO | 2018219356 A1 | 12/2018 | |
| WO | 2019177937 A1 | 9/2019 | |
| WO | 2020150366 A1 | 7/2020 | |
| WO | 2022214937 A1 | 10/2022 | |

OTHER PUBLICATIONS

Janin et al, Journal of Heterocyclic Chemistry, vol. 30, No. 4, pp. 1129-1131 (Year: 1993).*

PubChem CID 132498849, Date accessed: Apr. 29, 2020, Apr. 18, 2018.

PubChem CID 13528799, date accessed Jun. 17, 2019, Feb. 8, 2007.

PubChem CID 308320, date accessed Jun. 17, 2019, Mar. 26, 2005.

Pub Chem CID 8071, Create date: Mar. 26, 2005, 2005.

PubChem CID 19035969, date accessed Jun. 17, 2019, Dec. 4, 2007.

Amii, et al., "Difluorinated Danishefsky's Diene: A Versatile C4 Building Block for the Fluorinated Six-Membered Rings", Organic Letters, vol. 3, No. 20, 2001, pp. 3103-3105.

El-Essawy, F.A., et al., "Anti-Hepatitis B Virus Activity of New 1,2,4-Triazol-2-yl- and 1,3,4-Oxadiazol-2-yl-2-pyridinone Derivatives", Zeitschrift fur Naturforschung C, vol. 63, Nos. 9-10, 2008, pp. 667-674.

Fecik, et al., "Chiral DNA Gyrase Inhibitors. 3. Probing the Chiral Preference of the Active Site of DNA Gyrase. Synthesis of 10-fluoro-6-methyl-6,7-dihydro-9-piperazinyl-2H-benzo[a]quinolizin-20-one-3-carboxylic Acid Analogues", J Med Chem, vol. 48, No. 4, Jan. 1, 2005, pp. 1229-1236.

Georgopapadakou, et al., "Monocyclic and Tricyclic Analos of Quinolones: Mechanism of Action", Antimicrobial Agents and Chemotherapy, vol. 31, No. 4, Apr. 1987, pp. 614-616.

Kaneko, M., et al., "A Novel Tricyclic Polyketide, Vanitaracin A, Specifically Inhibits the Entry of Hepatitis B and D Viruses by Targeting Sodium Taurocholate Cotransporting Polypeptide", J of Virol, vol. 89, No. 23, 2015, pp. 11945-11953.

Xu, B., et al., "A Facile Synthesis of Novel Tricyclic 4-Pyridones", Tetrahedron Letters, vol. 55, Issue 52, 2014, pp. 7194-7197.

International Search Report and Written Opinion dated Jul. 9, 2019 for corresponding PCT International Application No. PCT/US2019/021557.

"CAS Registry No. 1415332-18-1", Chemical Abstracts Services, retrieved from STN on Dec. 6, 2022, entered STN: Dec. 21, 2012, 2012.

"CAS Registry No. 2125472-46-8", Chemical Abstracts Services, retrieved from STN on Dec. 6, 2022, entered STN: Sep. 5, 2017, 2017.

Capdevila, "Silver(I)-Catalyzed C—X, C—C, C—N, and C—O Cross-Couplings Using Aminoquinoline Directing Group via Elusive Aryl-Ag(III) Species", ACS Catal, vol. 8, No. 11, 2018, pp. 10430-10436.

Case, F.H., "Substituted 1,10-Phenanthrolines IX. Cycloalkeno Derivatives", J Org Chem, vol. 21, No. 10, 1956, pp. 1069-1071.

He, et al., "A general approach to access 5,6-dihydroindolonaphthyridine ring system", Tetrahedron Letters, 58, 2017, pp. 1373-1375.

Saeki, et al., "Activation of the Human Ah Receptor by Aza-Polycyclic Aromatic Hydrocarbons and Their Halogenated Derivatives", Biol Pharm Bull, 26(4), 2003, pp. 448-452.

Singh, B., "Novel Synthesis of 1,6-Naphthyridin-2(6H)-ones, Quinolin-2(1H)-ones, and Quino[7,8-f]quinoline-2,9 (1H,10H)-dione from Common Precursors", Synthesis, vol. 1992, No. 3, 1992, pp. 279-280.

* cited by examiner

SUBSTITUTED 2-PYRIDONE TRICYCLIC COMPOUNDS, ANALOGUES THEREOF, AND METHODS USING SAME

CROSS REFERENCE TO RELATED APPLICATIONS

The present application is a 35 U.S.C. § 371 national phase application of, and claims priority to, International Application No. PCT/US2019/021557, filed Mar. 11, 2019, which claims priority under 35 U.S.C. § 119(e) to U.S. Provisional Patent Applications No. 62/641,554, filed Mar. 12, 2018, No. 62/720,054, filed Aug. 20, 2018, and No. 62/793,567, filed Jan. 17, 2019, all of which applications are hereby incorporated herein by reference in their entireties.

BACKGROUND OF THE INVENTION

Hepatitis B is one of the world's most prevalent diseases. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis, and/or other complications. Hepatitis B is caused by hepatitis B virus (HBV), a noncytopathic, liver tropic DNA virus belonging to Hepadnaviridae family.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit HBV DNA polymerase. At present, the first-line treatment choices are entecavir, tenofovir, or peg-interferon alfa-2a. However, peg-interferon alfa-2a achieves desirable serological milestones in only one third of treated patients, and is frequently associated with severe side effects. Entecavir and tenofovir require long-term or possibly lifetime administration to continuously suppress HBV replication, and may eventually fail due to emergence of drug-resistant viruses.

HBV is an enveloped virus with an unusual mode of replication, centering on the establishment of a covalently closed circular DNA (cccDNA) copy of its genome in the host cell nucleus. Pregenomic (pg) RNA is the template for reverse transcriptional replication of HBV DNA. The encapsidation of pg RNA, together with viral DNA polymerase, into a nucleocapsid is essential for the subsequent viral DNA synthesis.

Aside from being a critical structural component of the virion, the HBV envelope is a major factor in the disease process. In chronically infected individuals, serum levels of HBV surface antigen (HBsAg) can be as high as 400 µg/ml, driven by the propensity for infected cells to secrete non-infectious subviral particles at levels far in excess of infectious (Dane) particles. HBsAg comprises the principal antigenic determinant in HBV infection and is composed of the small, middle and large surface antigens (S, M and L, respectively). These proteins are produced from a single open reading frame as three separate N-glycosylated polypeptides through utilization of alternative transcriptional start sites (for L and M/S mRNAs) and initiation codons (for L, M and S).

Although the viral polymerase and HBsAg perform distinct functions, both are essential proteins for the virus to complete its life cycle and be infectious. HBV lacking HBsAg is completely defective, and cannot infect or cause infection. HBsAg protects the virus nucleocapsid, begins the infectious cycle, and mediates morphogenesis and secretion of newly forming virus from the infected cell.

People chronically infected with HBV are usually characterized by readily detectable levels of circulating antibody specific to the viral capsid (HBc), with little, if any detectable levels of antibody to HBsAg. There is evidence that chronic carriers produce antibodies to HBsAg, but these antibodies are complexed with the circulating HBsAg, which can be present in mg/mL amounts in a chronic carrier's circulation. Reducing the amount of circulating levels of HBsAg might allow any present anti-HBsA to manage the infection. Further, even if nucleocapsids free of HBsAg were to be expressed or secreted into circulation (perhaps as a result of cell death), the high levels of anti-HBc would quickly complex with them and result in their clearance.

Studies have shown that the presence of subviral particles in a culture of infected hepatocytes may have a transactivating function on viral genomic replication, and the circulating surface antigen suppresses virus-specific immune response. Furthermore, the scarcity of virus-specific cytotoxic T lymphocytes (CTLs), that is a hallmark of chronic HBV infection, may be due to repression of MHC I presentation by intracellular expression of L and M in infected hepatocytes. Existing FDA-approved therapies do not significantly affect HBsAg serum levels.

Hepatitis D virus (HDV) is a small circular enveloped RNA virus that can propagate only in the presence of the hepatitis B virus (HBV). In particular, HDV requires the HBV surface antigen protein to propagate itself. Infection with both HBV and HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B virus, hepatitis D has the highest mortality rate of all the hepatitis infections. The routes of transmission of HDV are similar to those for HBV. Infection is largely restricted to persons at high risk of HBV infection, particularly injecting drug users and persons receiving clotting factor concentrates.

Currently, there is no effective antiviral therapy available for the treatment of acute or chronic type D hepatitis. Interferon-alfa, given weekly for 12 to 18 months, is the only licensed treatment for hepatitis D. Response to this therapy is limited-in only about one-quarter of patients is serum HDV RNA undetectable 6 months post therapy.

There is thus a need in the art for novel compounds and/or compositions that can be used to treat and/or prevent HBV infection in a subject. In certain embodiments, the compounds can be used in patients that are HBV infected, patients who are at risk of becoming HBV infected, and/or patients that are infected with drug-resistant HBV. In other embodiments, the HBV-infected subject is further HDV-infected. The present invention addresses this need.

BRIEF SUMMARY OF THE INVENTION

The present invention provides certain compounds, such as but not limited to compounds of formula (I), (II), and (III), or a salt, solvate, geometric isomer, stereoisomer, tautomer, and any mixtures thereof.

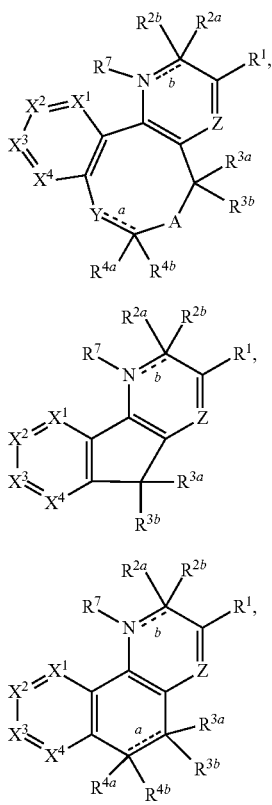

wherein the various substituents in the compounds of formula (I), (II), and (III) are defined elsewhere herein. The present invention further provides pharmaceutical compositions comprising compounds of the invention.

In one aspect, the compounds and compositions of the invention are useful for treating or preventing hepatitis virus infection in a subject. In certain embodiments, the subject is infected with hepatitis B virus (HBV). In other embodiments, the subject suffers from hepatitis B. In yet other embodiments, the subject is infected with hepatitis D virus (HDV). In yet other embodiments, the subject suffers from hepatitis D.

In another aspect, the compounds and compositions of the invention are useful for reducing or minimizing levels of at least one selected from the group consisting of hepatitis B virus surface antigen (HBsAg), hepatitis B e-antigen (HBeAg), hepatitis B core protein, and pregenomic (pg) RNA, in a HBV-infected subject.

DETAILED DESCRIPTION OF THE INVENTION

The invention relates, in certain aspects, to the discovery of certain substituted tricyclic compounds that are useful to treat and/or prevent HBV or HBV-HDV infection and related conditions in a subject. In certain embodiments, the compounds inhibit and/or reduce HBsAg secretion in a HBV-infected subject. In other embodiments, the compounds reduce or minimize levels of HBsAg in a HBV-infected subject. In yet other embodiments, the compounds reduce or minimize levels of HBeAg in a HBV-infected subject. In yet other embodiments, the compounds reduce or minimize levels of hepatitis B core protein in a HBV-infected subject. In yet other embodiments, the compounds reduce or minimize levels of pg RNA in a HBV-infected subject. In yet other embodiments, the HBV-infected subject is further HDV-infected.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Moreover, two or more steps or actions can be conducted simultaneously or not.

The following non-limiting abbreviations are used herein: cccDNA, covalently closed circular DNA; HBc, hepatitis B capsid; HBV, hepatitis B virus; HBeAg, hepatitis B e-antigen; HBsAg, hepatitis B virus surface antigen; pg RNA, pregenomic RNA.

As used herein, the articles "a" and "an" refer to one or to more than one (i.e., to at least one) of the grammatical object of the article. By way of example, "an element" means one element or more than one element.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy), and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$)alkyl, such as, but not limited to, ethyl, methyl, isopropyl, isobutyl, n-pentyl, n-hexyl, and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C—CH. The term "homopropargylic" refers to a group exemplified by —CH$_2$CH$_2$—C—CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-(C$_1$-C$_6$)alkyl" refers to a functional group wherein a one to six carbon alkanediyl chain is attached to an aryl group, e.g., —CH$_2$CH$_2$-phenyl or —CH$_2$-phenyl (or benzyl). Specific examples are aryl-CH$_2$— and aryl-CH(CH$_3$)—. The term "substituted aryl-(C$_1$-C$_6$)alkyl" refers to an aryl-(C$_1$-C$_6$)alkyl functional group in which the aryl group is substituted. A specific example is [substituted aryl]-(CH$_2$)—. Similarly, the term "heteroaryl-(C$_1$-C$_6$)alkyl" refers to a functional group wherein a one to three carbon alkanediyl chain is attached to a heteroaryl group, e.g., —CH$_2$CH$_2$-pyridyl. A specific example is heteroaryl-(CH$_2$)—. The term "substituted heteroaryl-(C$_1$-C$_6$)alkyl" refers to a heteroaryl-(C$_1$-C$_6$)alkyl functional group in which the heteroaryl group is substituted. A specific example is [substituted heteroaryl]-(CH$_2$)—.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., C$_3$-C$_6$ refers to a cyclic group comprising a ring group consisting of three to six carbon atoms) and includes straight, branched chain, or cyclic substituent groups. Examples of (C$_3$-C$_6$)cycloalkyl groups are cyclopropyl, cyclobutyl, cyclopentyl, and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include bicyclo-[2.1.1]hexanyl, bicyclo[2.2.1]heptanyl, bicyclo[3.1.1]heptanyl, 1,3-dimethyl[2.2.1] heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride (F$^-$), chloride (Cl$^-$), bromide (Br$^-$), and iodide (I$^-$).

As used herein, the term "halo" or "halogen" alone or as part of another substituent refers to, unless otherwise stated, a fluorine, chlorine, bromine, or iodine atom.

As used herein, the term "Hepatitis B virus" (or HBV) refers to a virus species of the genus Orthohepadnavirus, which is a part of the Hepadnaviridae family of viruses, and that is capable of causing liver inflammation in humans.

As used herein, the term "Hepatitis D virus" (or HDV) refers to a virus species of the genus Deltaviridae, which is capable of causing liver inflammation in humans. The HDV particle comprises an envelope, which is provided by HBV and surrounds the RNA genome and the HDV antigen. The HDV genome is a single, negative stranded, circular RNA molecule nearly 1.7 kb in length. The genome contains several sense and antisense open reading frames (ORFs), only one of which is functional and conserved. The RNA genome is replicated through an RNA intermediate, the antigenome. The genomic RNA and its complement, the antigenome, can function as ribozymes to carry out self-cleavage and self-ligation reactions. A third RNA present in the infected cell, also complementary to the genome, but 800 bp long and polyadenylated, is the mRNA for the synthesis of the delta antigen (HDAg).

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CHO—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —OCH$_2$CH$_2$CH$_3$, —CH$_2$CH$_2$CH$_2$OH, —CH$_2$CH$_2$NHCH$_3$, —CH$_2$SCH$_2$CH$_3$, and —CH$_2$CH$_2$S(=O)CH$_3$. Up to two heteroatoms may be consecutive, such as, for example, —CH$_2$NH—OCH$_3$, or —CH$_2$CH$_2$SSCH$_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates), and clathrates thereof.

As used herein, a "pharmaceutically effective amount," "therapeutically effective amount," or "effective amount" of a compound is that amount of compound that is sufficient to provide a beneficial effect to the subject to which the compound is administered.

The term "prevent," "preventing," or "prevention" as used herein means avoiding or delaying the onset of symptoms associated with a disease or condition in a subject that has not developed such symptoms at the time the administering of an agent or compound commences. Disease, condition and disorder are used interchangeably herein.

As used herein, the term "RNA Destabilizer" refers to a molecule, or a salt or solvate thereof, that reduces the total amount of HBV RNA in mammalian cell culture or in a live human subject. In a non-limiting example, an RNA Destabilizer reduces the amount of the RNA transcript(s) encoding one or more of the following HBV proteins: surface antigen, core protein, RNA polymerase, and e antigen.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably, and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl, or alkynyl, as defined elsewhere herein, substituted by one, two or three substituents independently selected from the group consisting of halogen, —OH, alkoxy, tetrahydro-2-H-pyranyl, —NH$_2$, —NH($C_1$-$C_6$ alkyl), —N($C_1$-$C_6$ alkyl)$_2$, 1-methyl-imidazol-2-yl, pyridin-2-yl, pyridin-3-yl, pyridin-4-yl, —C(=O)OH, —C(=O)$_n$O($C_1$-$C_6$)alkyl, trifluoromethyl, —C≡N, —C(=O)NH$_2$, —C(=O)NH($C_1$-$C_6$)alkyl, —C(=O)N(($C_1$-$C_6$)alkyl)$_2$, —SO$_2$NH$_2$, —SO$_2$NH($C_1$-$C_6$ alkyl), —SO$_2$N($C_1$-$C_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy, and —OH. Examples of substituted alkyls include, but are not limited to, 2,2-difluoropropyl, 2-carboxycyclopentyl and 3-chloropropyl.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido, and nitro. As used herein, where a substituent is an alkyl or alkoxy group, the carbon chain may be branched, straight or cyclic.

Unless otherwise noted, when two substituents are taken together to form a ring having a specified number of ring atoms (e.g., two groups taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Compounds

The invention includes certain compound recited herein, as well as any salt, solvate, geometric isomer (such as, in a non-limiting example, any geometric isomer and any mixtures thereof, such as, in a non-limiting example, mixtures in any proportions of any geometric isomers thereof), stereoisomer (such as, in a non-limiting example, any enantiomer or diastereoisomer, and any mixtures thereof, such as, in a non-limiting example, mixtures in any proportions of any enantiomers and/or diastereoisomers thereof), tautomer (such as, in a non-limiting example, any tautomer and any mixtures thereof, such as, in a non-limiting example, mixtures in any proportions of any tautomers thereof), and any mixtures thereof.

The invention includes a compound of formula (I), or a salt, solvate, geometric isomer, stereoisomer, tautomer, and any mixtures thereof:

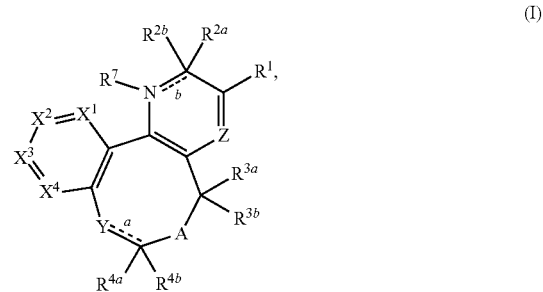

(I)

wherein:

A is selected from the group consisting of null (i.e., the two carbon atoms bonded to A are directly bonded through a chemical bond) and CR$^9$R$^9$;

Z is selected from the group consisting of N and CR$^{12}$;

R$^1$ is selected from the group consisting of H; halo; —OR$^8$; —C(R$^9$)(R$^9$)OR$^8$ (such as, for example, —CH$_2$OR$^8$, such as, for example, —CH$_2$OH); —C(=O)R$^8$; —C(=O)OR$^8$ (such as, for example, —C(=O)OH or —C(=O)O—$C_1$-$C_6$ alkyl); —C(=O)NHR$^8$; —C(=O)NH—OR$^8$ (such as, for example, —C(=O)NH—OH); —C(=O)NHNHR$^8$; —C(=O)NHNHC(=O)R$^8$; —C(=O)NHS(=O)$_2$R$^8$;

—$CH_2C(=O)OR^8$; —CN; —$NH_2$; —$N(R^8)C(=O)H$; —$N(R^8)C(=O)R^{10}$; —$N(R^8)C(=O)OR^{10}$; —$N(R^8)C(=O)NHR^8$; —$NR^9S(=O)_2R^{10}$; —$P(=O)(OR^8)_2$; —$B(OR^8)_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with one or more independently selected $C_1$-$C_6$ alkyl; pyrimidin-2-yl optionally substituted with one or more independently selected $C_1$-$C_6$ alkyl; (pyridin-2-yl)methyl; (pyrimidin-2-yl)methyl; (pyrimidin-2-yl)amino; bis-(pyrimidin-2-yl)-amino; 5-$R^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl; and 3-$R^{10}$-1,2,4-oxadiazol-5-yl;

$R^{2a}$, $R^{2b}$, and $R^7$ are selected such that:

(i) $R^{2a}$ and $R^{2b}$ combine to form =O; bond b is a single bond; and $R^7$ is selected from the group consisting of H, optionally substituted $C_1$-$C_6$ alkyl (e.g., optionally substituted benzyl, or $C_1$-$C_6$ alkyl optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth), and optionally substituted $C_3$-$C_8$ cycloalkyl (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth); or (ii) $R^{2a}$ is selected from the group consisting of H, halogen, and optionally substituted $C_1$-$C_6$ alkoxy (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth); $R^{2b}$ is null; bond b is a double bond; and $R^7$ is null;

bond a is a single or double bond, wherein:

(i) if bond a is a single bond, then:
Y is selected from the group consisting of C(=O), $CHR^5$, O, S, S(=O), $S(=O)_2$, and $NR^5$, wherein:
if Y is selected from the group consisting of $CHR^5$, O, and $NR^5$, then $R^{4a}$ and $R^{4b}$ optionally combine with each other to form =O; or
if Y is CH and $R^5$ is null, then $R^{4b}$ is $CH_2$, and Y and $R^{4b}$ form a single bond to generate cyclopropyl;

(ii) if bond a is a double bond, then Y is $CR^5$ and $R^{4b}$ is null;

$R^{3a}$, $R^{3b}$, $R^{4a}$, and $R^{4b}$ are each independently selected from the group consisting of H, alkyl-substituted oxetanyl, optionally substituted $C_1$-$C_6$ alkyl (e.g., optionally substituted with 1-3 groups independently selected from the group consisting of F, Cl, Br, I, OH, and OMe), and optionally substituted $C_3$-$C_8$ cycloalkyl (e.g., optionally substituted with 1-3 groups independently selected from the group consisting of F, Cl, Br, I, OH, and OMe);

or one pair selected from the group consisting of $R^{3a}/R^{3b}$, $R^{4a}/R^{4b}$, and $R^{3a}/R^{4a}$ combine to form a divalent group selected from the group consisting of $C_1$-$C_6$ alkanediyl, —$(CH_2)_nO(CH_2)_n$—, —$(CH_2)_nNR^9(CH_2)_n$—, —$(CH_2)_nS(CH_2)_n$—, —$(CH_2)_nS(=O)(CH_2)_n$—, and —$(CH_2)_nS(=O)_2(CH_2)_n$—, wherein each occurrence of n is independently selected from the group consisting of 1 and 2 and wherein each divalent group is optionally substituted with at least one $C_1$-$C_6$ alkyl or halo;

each occurrence of $R^5$ is independently selected from the group consisting of H, optionally substituted $C_1$-$C_6$ alkyl, and optionally substituted $C_3$-$C_8$ cycloalkyl;

$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;

or either $X^3$ and $X^4$, or $X^1$ and $X^2$, combine to form —S—;

wherein 0-2 substituents selected from the group consisting of $X^1$, $X^2$, $X^3$ and $X^4$ are N, each of which, if present, is optionally substituted with $C_1$-$C_6$ alkyl if the adjacent carbon atom in the ring is substituted with —OH;

$R^{6I}$, $R^{6II}$, $R^{6III}$, and $R^{6IV}$ are independently selected from the group consisting of H, halo, —CN, pyrrolidinyl, optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl), optionally substituted $C_1$-$C_6$ alkenyl, optionally substituted $C_3$-$C_8$ cycloalkyl, optionally substituted heterocyclyl (e.g., morpholinyl or tetrahydropyranyl), —OR, $C_1$-$C_6$ haloalkoxy (such as but not limited to $OCF_2H$ and $OCH_2CF_2H$), —N(R)(R), —$NO_2$, —$S(=O)_2N(R)(R)$, acyl, and $C_1$-$C_6$ alkoxycarbonyl, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl, wherein each occurrence of R' is independently selected from the group consisting of —$NH_2$, —$NH(C_1$-$C_6$ alkyl), —$N(C_1$-$C_6$ alkyl)($C_1$-$C_6$ alkyl), —NHC(=O)O'Bu, —$N(C_1$-$C_6$ alkyl)C(=O)O'Bu, or a 5- or 6-membered heterocyclic group (such as, but not limited to, pyrrolidinyl, morpholinyl, piperidinyl, piperazinyl, and so forth), which is optionally N-linked;

or $X^2$ is $CR^{6II}$, $X^3$ is $CR^{6III}$, and $R^{6II}$ and $R^{6III}$ combine to form a divalent group selected from the group consisting of —$O(CR^9R^{11})O$—, —$O(CR^9R^{11})(CR^9R^{11})O$—, —$O(CR^9R^{11})(CR^9R^{11})$—, and $O(CR^9R^{11})(CR^9R^{11})(CR^9R^{11})$—;

or $X^3$ is $CR^{6III}$, $X^4$ is $CR^{6IV}$, and $R^{6III}$ and $R^{6IV}$ combine to form a divalent group selected from the group consisting of —$O(CR^9R^{11})O$—, —$O(CR^9R^{11})(CR^9R^{11})O$—, —$O(CR^9R^{11})(CR^9R^{11})$—, and —$O(CR^9R^{11})(CR^9R^{11})(CR^9R^{11})$—;

each occurrence of $R^8$ is independently selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl (e.g., methyl or ethyl);

each occurrence of $R^{10}$ is independently selected from the group consisting of optionally substituted $C_1$-$C_6$ alkyl and optionally substituted phenyl; and, each occurrence of $R^{11}$ is independently selected from the group consisting of H, OH, $C_1$-$C_6$ alkyl, $C_1$-$C_6$ alkoxy, alkoxy-$C_1$-$C_6$ alkyl, and alkoxy-$C_1$-$C_6$ alkoxy, wherein two $R^{11}$ groups bound to the same carbon atom are not simultaneously OH, and wherein $R^{11}$ is not OH if $R^{11}$ is bound to a carbon that is further bound to an oxygen atom;

or wherein two $R^{11}$ groups combine with the carbon atom to which they are bound to form a moiety selected from the group consisting of C=O, C=$CH_2$, and oxetane-3,3-diyl;

and $R^{12}$ is selected from the group consisting of H, OH, halo, optionally substituted $C_1$-$C_6$ alkoxy (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth), optionally substituted $C_1$-$C_6$ alkyl (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth), and optionally substituted $C_3$-$C_8$ cycloalkyl (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth).

In certain embodiments, the compound of formula (I) is a compound of formula (Ia), or a salt, solvate, geometric isomer, stereoisomer, tautomer, and any mixtures thereof:

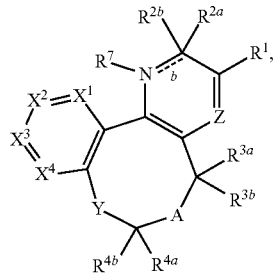

(Ia)

wherein Y is selected from the group consisting of $CHR^5$ and O.

In certain embodiments, the compound of formula (I) is a compound of formula (Ib), or a salt, solvate, geometric isomer, stereo isomer, tautomer, and any mixtures thereof:

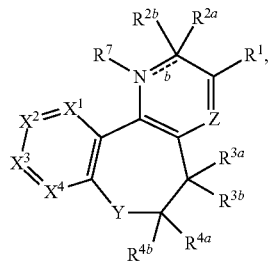

(Ib)

wherein Y is selected from the group consisting of $CHR^5$ and O.

In certain embodiments, at least one of $X^1$, $X^2$, $X^3$, and $X^4$ is N. In certain embodiments, one of $X^1$, $X^2$, $X^3$, and $X^4$ is N. In certain embodiments, two of $X^1$, $X^2$, $X^3$, and $X^4$ are N.

In certain embodiments, in (I) and/or (Ia)-(Ib), at least one of $R^{3a}$ or $R^{3b}$ is independently selected from the group consisting of optionally substituted $C_1$-$C_6$ alkyl and optionally substituted $C_3$-$C_8$ cycloalkyl. In certain embodiments, in (I) and/or (Ia)-(Ib), at least one of $R^{3a}$ or $R^{3b}$ is independently selected from the group consisting of n-propyl, isopropyl, n-butyl, isobutyl, sec-butyl, and tert-butyl.

In certain embodiments, in (I) and/or (Ia)-(Ib), none of $R^{6I}$, $R^{6II}$, $R^{6III}$, and $R^{6IV}$, if present, are N-linked (i.e., linked to the ring through a N atom). In certain embodiments, in (I) and/or (Ia)-(Ib), none of $R^{6I}$, $R^{6II}$, $R^{6III}$, and $R^{6IV}$, if present, comprise a basic nitrogen group. In certain embodiments, in (I) and/or (Ia)-(Ib), at least one of $R^{6I}$, $R^{6II}$, $R^{6III}$, and $R^{6IV}$, if present, is N-linked (i.e., linked to the ring through a N atom). In certain embodiments, in (I) and/or (Ia)-(Ib), at least one of $R^{6I}$, $R^{6II}$, $R^{6III}$ and $R^{6IV}$, if present, comprises a basic nitrogen group. In certain embodiments, in (I) and/or (Ia)-(Ib), at least one of $R^{6II}$ and $R^{6III}$, if present, is independently O-linked (i.e., linked to the ring through a O atom). In certain embodiments, in (I) and/or (Ia)-(Ib), both of $R^{6II}$ and $R^{6III}$, if present, are independently O-linked.

In certain embodiments, the compound of formula (I) is

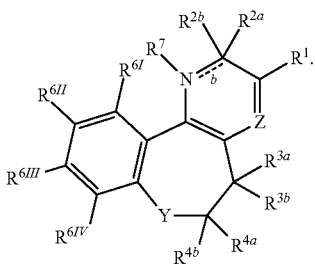

(Ic)

In certain embodiments, the compound of formula (I) is

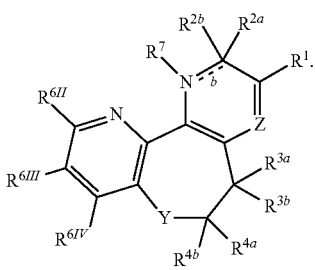

(Id)

In certain embodiments, the compound of formula (I) is

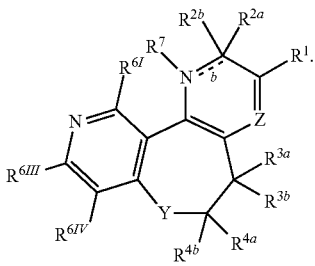

(Ie)

In certain embodiments, the compound of formula (I) is

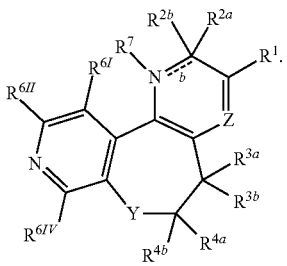

(If)

In certain embodiments, the compound of formula (I) is

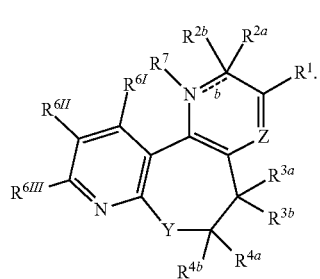

(Ig)

In certain embodiments, the compound of formula (I) is

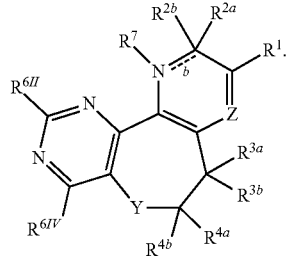

(Ih)

In certain embodiments, the compound of formula (I) is

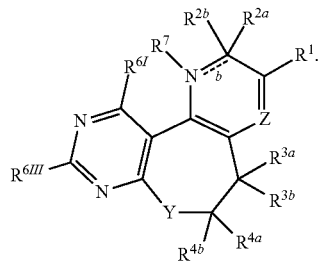

(Ii)

In certain embodiments, the compound of formula (I) is

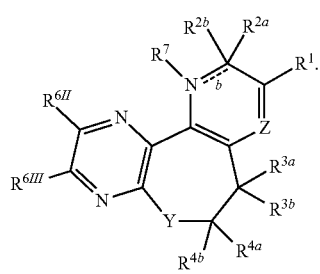

(Ij)

In certain embodiments, the compound of formula (I) is

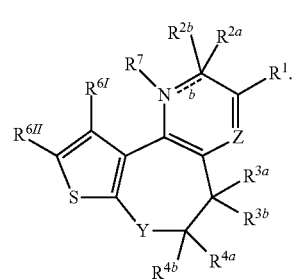

(Ik)

In certain embodiments, the compound of formula (I) is

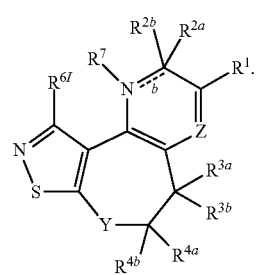

(Il)

In certain embodiments, the compound of formula (I) is

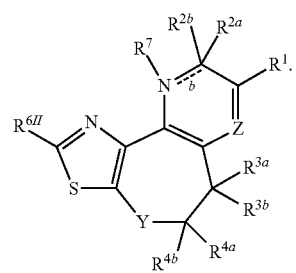

(Im)

In certain embodiments, the compound of formula (I) is

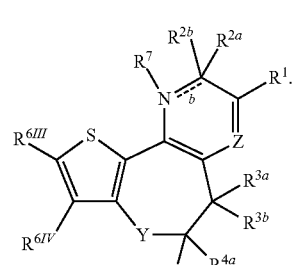

(In)

In certain embodiments, the compound of formula (I) is

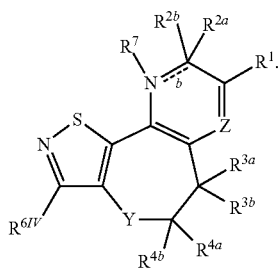

(Io)

In certain embodiments, the compound of formula (I) is

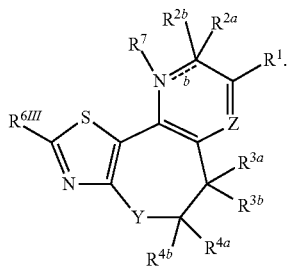

(Ip)

The invention further includes a compound of formula (II), or a salt, solvate, geometric isomer, stereoisomer, tautomer and any mixtures thereof:

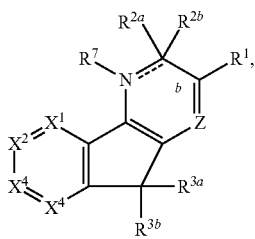

(II)

wherein:

Z is selected from the group consisting of N and $CR^{12}$;
$R^1$ is selected from the group consisting of H; halo; —$OR^8$; —$C(R^9)(R^9)OR^8$ (such as, for example, —$CH_2OR^8$, such as, for example, —$CH_2OH$); —$C(=O)R^8$; —$C(=O)OR^8$ (such as, for example, —$C(=O)OH$ or —$C(=O)O$—$C_1$-$C_6$ alkyl); —$C(=O)NHR^8$; —$C(=O)NH$—$OR^8$ (such as, for example, —$C(=O)NH$—$OH$); —$C(=O)NHNHR^8$; —$C(=O)NHNHC(=O)R^8$; —$C(=O)NHS(=O)_2R^8$; —$CH_2C(=O)OR^8$; —CN; —$NH_2$; —$N(R^8)C(=O)H$; —$N(R^8)C(=O)R^{10}$; —$N(R^8)C(=O)OR^{10}$; —$N(R^8)C(=O)NHR^8$; —$NR^9S(=O)_2R^{10}$; —$P(=O)(OR^8)_2$; —$B(OR^8)_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with one or more independently selected $C_1$-$C_6$ alkyl; pyrimidin-2-yl optionally substituted with one or more independently selected $C_1$-$C_6$ alkyl; (pyridin-2-yl)methyl; (pyrimidin-2-yl)methyl; (pyrimidin-2-yl)amino; bis-(pyrimidin-2-yl)-amino; 5-$R^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl; and 3-$R^{10}$-1,2,4-oxadiazol-5-yl;

$R^{2a}$, $R^{2b}$, and $R^7$ are selected such that:
 (i) $R^{2a}$ and $R^{2b}$ combine to form =O; bond b is a single bond; and $R^7$ is selected from the group consisting of H, optionally substituted $C_1$-$C_6$ alkyl (e.g., optionally substituted benzyl, or $C_1$-$C_6$ alkyl optionally substituted with at least one selected from OH, $C_1$-$C_6$ alkoxy, F, Cl, Br, I, —$NH_2$, —NH($C_1$-$C_6$ alkyl), —N($C_1$-$C_6$ alkyl)($C_1$-$C_6$ alkyl), and so forth)), and optionally substituted $C_3$-$C_8$ cycloalkyl (e.g., optionally substituted with at least one selected from OH, $C_1$-$C_6$ alkoxy, F, Cl, Br, I, —$NH_2$, —NH($C_1$-$C_6$ alkyl), —N($C_1$-$C_6$ alkyl)($C_1$-$C_6$ alkyl), and so forth); or
 (ii) $R^{2a}$ is selected from the group consisting of H, halogen, and optionally substituted $C_1$-$C_6$ alkoxy (e.g., optionally substituted benzyl, or $C_1$-$C_6$ alkyl optionally substituted with at least one selected from OH, $C_1$-$C_6$ alkoxy, F, Cl, Br, I, —$NH_2$, —NH($C_1$-$C_6$ alkyl), —N($C_1$-$C_6$ alkyl)($C_1$-$C_6$ alkyl), and so forth); $R^{2b}$ is null; bond b is a double bond; and $R^7$ is null;

$R^{3a}$ and $R^{3b}$ are each independently selected from the group consisting of H, alkyl-substituted oxetanyl, optionally substituted $C_1$-$C_6$ alkyl (e.g., optionally substituted with 1-3 groups independently selected from the group consisting of F, Cl, Br, I, OH, and OMe), and optionally substituted $C_3$-$C_8$ cycloalkyl (e.g., optionally substituted with 1-3 groups independently selected from the group consisting of F, Cl, Br, I, OH, and OMe);
or $R^{3a}$ and $R^{3b}$ combine to form a divalent group selected from the group consisting of $C_1$-$C_6$ alkanediyl, —$(CH_2)_nO(CH_2)_n$—, —$(CH_2)_nNR^9(CH_2)_n$—, —$(CH_2)_nS(CH_2)_n$—, —$(CH_2)_nS(=O)(CH_2)_n$—, and —$(CH_2)_nS(=O)_2(CH_2)_n$—, wherein each occurrence of n is independently selected from the group consisting of 1 and 2 and wherein each divalent group is optionally substituted with at least one $C_1$-$C_6$ alkyl or halo;

$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;
or either $X^3$ and $X^4$, or $X^1$ and $X^2$, combine to form —S—;
 wherein 0-2 substituents selected from the group consisting of $X^1$, $X^2$, $X^3$ and $X^4$ are N, each of which, if present, is optionally substituted with $C_1$-$C_6$ alkyl if the adjacent carbon atom in the ring is substituted with —OH;

$R^{6I}$, $R^{6II}$, $R^{6III}$ and $R^{6IV}$ are independently selected from the group consisting of H, halo, —CN, pyrrolidinyl, optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl), optionally substituted $C_1$-$C_6$ alkenyl, optionally substituted $C_3$-$C_8$ cycloalkyl, optionally substituted heterocyclyl (e.g., morpholinyl or tetrapyranyl), —OR, —N(R)(R), $C_1$-$C_6$ haloalkoxy (such as but not limited to $OCF_2H$ and $OCH_2CF_2H$), —N(R)(R), —$NO_2$, —$S(=O)_2N(R)(R)$, acyl, and $C_1$-$C_6$ alkoxycarbonyl,
 wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl,
 wherein each occurrence of R' is independently selected from the group consisting of —$NH_2$, —NH($C_1$-$C_6$ alkyl), —N($C_1$-$C_6$ alkyl)($C_1$-$C_6$ alkyl), —NHC(=O)O'Bu, —N($C_1$-$C_6$ alkyl)C(=O)O'Bu, and a 5- or 6-membered heterocyclic group (such as, but not limited to, pyrrolidinyl, morpholinyl, piperidinyl, piperazinyl, and so forth), which is optionally N-linked;

or $X^2$ is $CR^{6II}$, $X^3$ is $CR^{6III}$ and $R^{6II}$ and $R^{6III}$ combine to form a divalent group selected from the group consisting of $-O(CR^9R^{11})O-$, $-O(CR^9R^{11})(CR^9R^{11})O-$, $-O(CR^9R^{11})(CR^9R^{11})-$, and $-O(CR^9R^{11})(CR^9R^{11})(CR^9R^{11})-$;

or $X^3$ is $CR^{6III}$, $X^4$ is $CR^{6IV}$, and $R^{6III}$ and $R^{6IV}$ combine to form a divalent group selected from the group consisting of $-O(CR^9R^{11})O-$, $-O(CR^9R^{11})(CR^9R^{11})O-$, $-O(CR^9R^{11})(CR^9R^{11})-$, and $-O(CR^9R^{11})(CR^9R^{11})(CR^9R^{11})-$;

each occurrence of $R^8$ is independently selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl (e.g., methyl or ethyl);

each occurrence of $R^{10}$ is independently selected from the group consisting of optionally substituted $C_1$-$C_6$ alkyl, and optionally substituted phenyl; and, each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; and wherein $R^{11}$ is not OH if it is bound to a carbon that is further bound to an oxygen atom;

or wherein two $R^{11}$ groups combine with the carbon atom to which they are bound to form a moiety selected from the group consisting of C=O, C=CH$_2$ and oxetane-3,3-diyl; and $R^{12}$ is selected from the group consisting of H, OH, halo, optionally substituted $C_1$-$C_6$ alkoxy (e.g., optionally substituted with at least one selected from OH, $C_1$-$C_6$ alkoxy, F, Cl, Br, I, $-NH_2$, $-NH(C_1$-$C_6$ alkyl), $-N(C_1$-$C_6$ alkyl)($C_1$-$C_6$ alkyl), and so forth), optionally substituted $C_1$-$C_6$ alkyl (e.g., optionally substituted with at least one selected from OH, $C_1$-$C_6$ alkoxy, F, Cl, Br, I, $-NH_2$, $-NH(C_1$-$C_6$ alkyl), $-N(C_1$-$C_6$ alkyl)($C_1$-$C_6$ alkyl), and so forth), and optionally substituted $C_3$-$C_8$ cycloalkyl (e.g., optionally substituted with at least one selected from OH, $C_1$-$C_6$ alkoxy, F, Cl, Br, I, $-NH_2$, $-NH(C_1$-$C_6$ alkyl), $-N(C_1$-$C_6$ alkyl)($C_1$-$C_6$ alkyl), and so forth).

In certain embodiments, at least one of $X^1$, $X^2$, $X^3$, and $X^4$ is N. In certain embodiments, one of $X^1$, $X^2$, $X^3$, and $X^4$ is N. In certain embodiments, two of $X^1$, $X^2$, $X^3$, and $X^4$ are N.

In certain embodiments, in (II), at least one of $R^{3a}$ or $R^{3b}$ is independently selected from the group consisting of optionally substituted $C_1$-$C_6$ alkyl and optionally substituted $C_3$-$C_8$ cycloalkyl. In certain embodiments, in (II), at least one of $R^{3a}$ or $R^{3b}$ is independently selected from the group consisting of n-propyl, isopropyl, n-butyl, isobutyl, sec-butyl, and tert-butyl.

In certain embodiments, in (II), none of $R^{6I}$, $R^{6II}$, $R^{6III}$ and $R^{6IV}$, if present, are N-linked (i.e., linked to the ring through a N atom). In certain embodiments, in (II), none of $R^{6I}$, $R^{6II}$, $R^{6III}$ and $R^{6IV}$, if present, comprise a basic nitrogen group. In certain embodiments, in (II), at least one of $R^{6I}$, $R^{6II}$, $R^{6III}$ and $R^{6IV}$, if present, is N-linked (i.e., linked to the ring through a N atom). In certain embodiments, in (II), at least one of $R^{6I}$, $R^{6II}$, $R^{6III}$ and $R^{6IV}$, present, comprises a basic nitrogen group. In certain embodiments, in (II), at least one of $R^{6II}$ and $R^{6III}$, if present, is independently O-linked (i.e., linked to the ring through a O atom). In certain embodiments, in (II), both of $R^{6II}$ and $R^{6III}$, if present, are independently O-linked.

In certain embodiments, the compound of formula (II) is

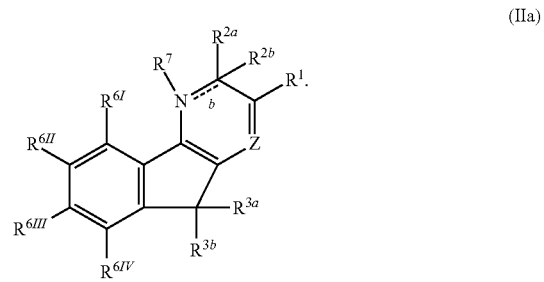

(IIa)

In certain embodiments, the compound of formula (II) is

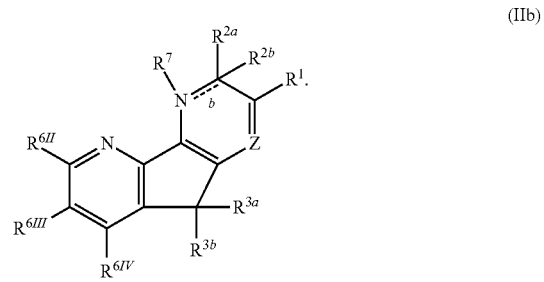

(IIb)

In certain embodiments, the compound of formula (II) is

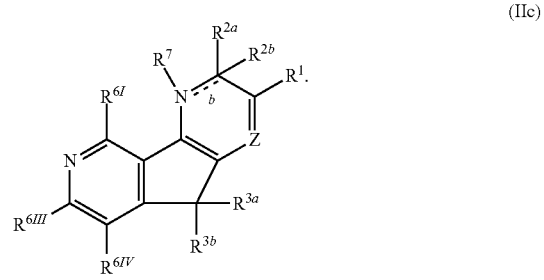

(IIc)

In certain embodiments, the compound of formula (II) is

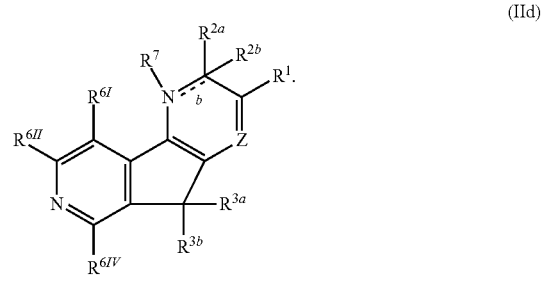

(IId)

In certain embodiments, the compound of formula (II) is

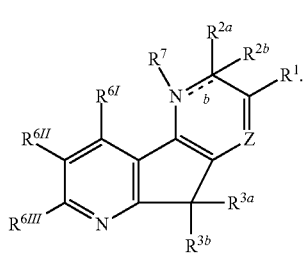
(IIe)

In certain embodiments, the compound of formula (II) is

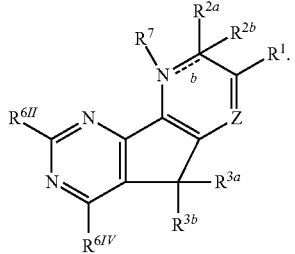
(IIf)

In certain embodiments, the compound of formula (II) is

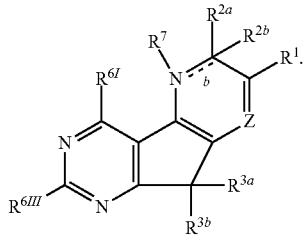
(IIg)

In certain embodiments, the compound of formula (II) is

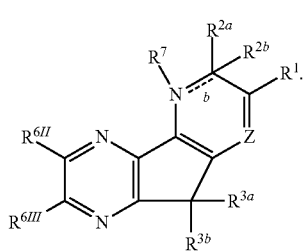
(IIh)

In certain embodiments, the compound of formula (II) is (IIi)

In certain embodiments, the compound of formula (II) is

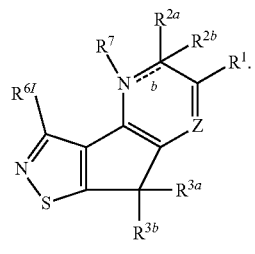
(IIj)

In certain embodiments, the compound of formula (II) is

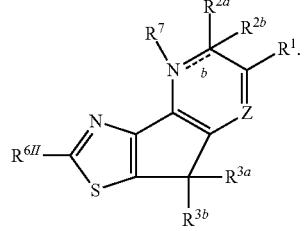
(IIk)

In certain embodiments, the compound of formula (II) is

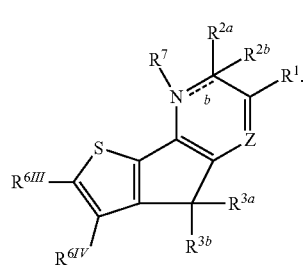
(IIl)

In certain embodiments, the compound of formula (II) is

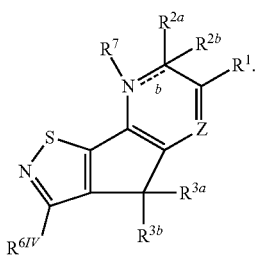
(IIm)

In certain embodiments, the compound of formula (II) is

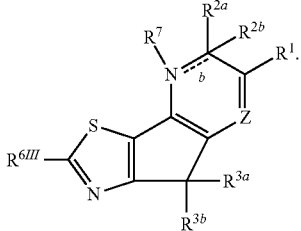
(IIn)

The invention includes a compound of formula (III), or a salt, solvate, geometric isomer, stereoisomer, tautomer and any mixtures thereof:

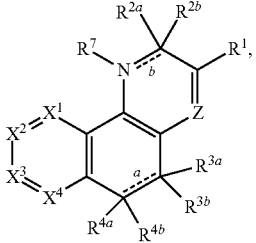
(III)

wherein:
Z is selected from the group consisting of N and $CR^{12}$;
$R^1$ is selected from the group consisting of H; halo; —$OR^8$; —$C(R^9)(R^9)OR^8$ (such as, for example, —$CH_2OR^8$, such as, for example, —$CH_2OH$); —$C(=O)R^8$; —$C(=O)OR^8$ (such as, for example, —$C(=O)OH$ or —$C(=O)O$—$C_1$-$C_6$ alkyl); —$C(=O)NHR^8$, —$C(=O)NH$—$OR^8$ (such as, for example, —$C(=O)NH$—$OH$); —$C(=O)NHNHR^8$; —$C(=O)NHNHC(=O)R^8$; —$C(=O)NHS(=O)_2R^8$; —$CH_2C(=O)OR^8$; —CN; —$NH_2$; —$N(R^8)C(=O)H$; —$N(R^8)C(=O)R^{10}$; —$N(R^8)C(=O)OR^{10}$; —$N(R^8)C(=O)NHR^8$; —$NR^9S(=O)_2R^{10}$; —$P(=O)(OR^8)_2$; —$B(OR^8)_2$; 2,5-dioxo-pyrrolidin-1-yl; 2H-tetrazol-5-yl; 3-hydroxy-isoxazol-5-yl; 1,4-dihydro-5-oxo-5H-tetrazol-1-yl; pyridin-2-yl optionally substituted with one or more independently selected $C_1$-$C_6$ alkyl; pyrimidin-2-yl optionally substituted with one or more independently selected $C_1$-$C_6$ alkyl; (pyridin-2-yl)methyl; (pyrimidin-2-yl)methyl; (pyrimidin-2-yl)amino; bis-(pyrimidin-2-yl)-amino; 5-$R^8$-1,3,4,-thiadiazol-2-yl; 5-thioxo-4,5-dihydro-1H-1,2,4-triazol-3-yl; 1H-1,2,4-triazol-5-yl; 1,3,4-oxadiazol-2-yl; 1,2,4-oxadiazol-5-yl; and 3-$R^{10}$-1,2,4-oxadiazol-5-yl;

$R^{2a}$, $R^{2b}$, and $R^7$ are selected such that:
(i) $R^{2a}$ and $R^{2b}$ combine to form =O; bond b is a single bond; and $R^7$ is selected from the group consisting of H, optionally substituted $C_1$-$C_6$ alkyl (e.g., optionally substituted benzyl, or $C_1$-$C_6$ alkyl optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth)), and optionally substituted $C_3$-$C_8$ cycloalkyl (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth); or
(ii) $R^{2a}$ is selected from the group consisting of H, halogen, and optionally substituted $C_1$-$C_6$ alkoxy (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth); $R^{2b}$ is null; bond b is a double bond; and $R^7$ is null;
$R^{3a}$, $R^{3b}$, $R^{4a}$, and $R^{4b}$ are each independently selected from the group consisting of H, alkyl-substituted oxetanyl, optionally substituted $C_1$-$C_6$ alkyl (e.g., optionally substituted with 1-3 groups independently selected from the group consisting of F, Cl, Br, I, OH and OMe), and optionally substituted $C_3$-$C_8$ cycloalkyl (e.g., optionally substituted with 1-3 groups independently selected from the group consisting of F, Cl, Br, I, OH and OMe);
or one pair selected from the group consisting of $R^{3a}/R^{3b}$, $R^{4a}/R^{4b}$, and $R^{3a}/R^{4a}$ combine to form a divalent group selected from the group consisting of $C_1$-$C_6$ alkanediyl, —$(CH_2)_nO(CH_2)_n$—, —$(CH_2)_nNR^9(CH_2)_n$—, —$(CH_2)_nS(CH_2)_n$—, —$(CH_2)_nS(=O)(CH_2)_n$—, and —$(CH_2)_nS(=O)_2(CH_2)_n$—, wherein each occurrence of n is independently selected from the group consisting of 1 and 2 and wherein each divalent group is optionally substituted with at least one $C_1$-$C_6$ alkyl or halo;
bond a is single; or bond a is double and $R^{3b}$ and $R^{4b}$ are both null;
$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;
or either $X^3$ and $X^4$, or $X^1$ and $X^2$, combine to form —S—;
wherein 0-2 substituents selected from the group consisting of $X^1$, $X^2$, $X^3$ and $X^4$ are N, each of which, if present, is optionally substituted with $C_1$-$C_6$ alkyl if the adjacent carbon atom in the ring is substituted with —OH;
$R^{6I}$, $R^{6II}$, $R^{6III}$ and $R^{6IV}$ are independently selected from the group consisting of H, halo, —CN, pyrrolidinyl, optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl), optionally substituted $C_1$-$C_6$ alkenyl, optionally substituted $C_3$-$C_8$ cycloalkyl, optionally substituted heterocyclyl (e.g., morpholinyl or tetrahydropyranyl), —OR, $C_1$-$C_6$ haloalkoxy (such as but not limited to $OCF_2H$ and $OCH_2CF_2H$), —N(R)(R), —$NO_2$, —$S(=O)_2N(R)(R)$, acyl, and $C_1$-$C_6$ alkoxycarbonyl,
wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl,
wherein each occurrence of R' is selected from the group consisting of —$NH_2$, —$NH(C_1$-$C_6$ alkyl), —$N(C_1$-$C_6$ alkyl)($C_1$-$C_6$ alkyl), —$NHC(=O)O^tBu$, —$N(C_1$-$C_6$ alkyl)$C(=O)O^tBu$, and a 5- or 6-membered heterocyclic group (such as, but not limited to, pyrrolidinyl, morpholinyl, piperidinyl, piperazinyl, and so forth), which is optionally N-linked;

or $X^2$ is $CR^{6II}$, $X^3$ is $CR^{6III}$ and $R^{6II}$ and $R^{6III}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;

or $X^3$ is $CR^{6III}$, $X^4$ is $CR^{6IV}$, and $R^{6III}$ and $R^{6IV}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;

each occurrence of $R^8$ is independently selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl (e.g., methyl or ethyl);

each occurrence of $R^{10}$ is independently selected from the group consisting of optionally substituted $C_1$-$C_6$ alkyl and optionally substituted phenyl; and, each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; wherein $R^{11}$ is not OH if it is bound to a carbon that is further bound to an oxygen atom;

or two $R^{11}$ groups combine with the carbon atom to which they are bound to form a moiety selected from the group consisting of C=O, C=CH$_2$ and oxetane-3,3-diyl;

and $R^{12}$ is selected from the group consisting of H, OH, halo, optionally substituted $C_1$-$C_6$ alkoxy (e.g., optionally substituted with at least one selected from OH, $C_1$-$C_6$ alkoxy, F, Cl, Br, I, —NH$_2$, —NH($C_1$-$C_6$ alkyl), —N($C_1$-$C_6$ alkyl)($C_1$-$C_6$ alkyl), and so forth), optionally substituted $C_1$-$C_6$ alkyl (e.g., optionally substituted with at least one selected from OH, $C_1$-$C_6$ alkoxy, F, Cl, Br, I, —NH$_2$, —NH($C_1$-$C_6$ alkyl), —N($C_1$-$C_6$ alkyl)($C_1$-$C_6$ alkyl), and so forth), and optionally substituted $C_3$-$C_8$ cycloalkyl (e.g., optionally substituted with at least one selected from OH, $C_1$-$C_6$ alkoxy, F, Cl, Br, I, —NH$_2$, —NH($C_1$-$C_6$ alkyl), —N($C_1$-$C_6$ alkyl)($C_1$-$C_6$ alkyl), and so forth).

In certain embodiments, the compound of formula (III) is

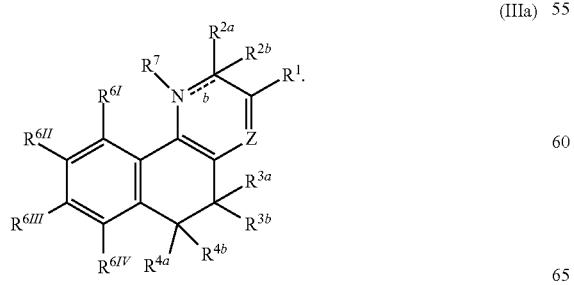
(IIIa)

In other embodiments, the compound of formula (III) is

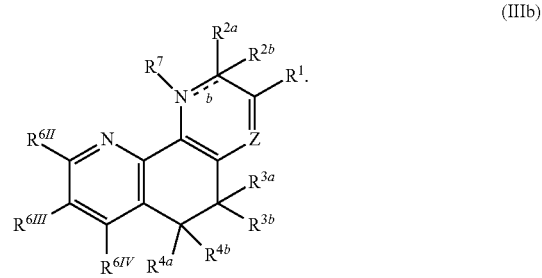
(IIIb)

In yet other embodiments, the compound of formula (III) is

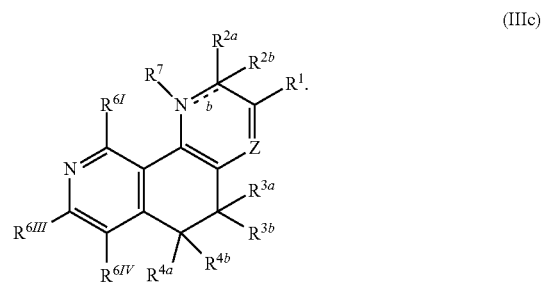
(IIIc)

In yet other embodiments, the compound of formula (III) is

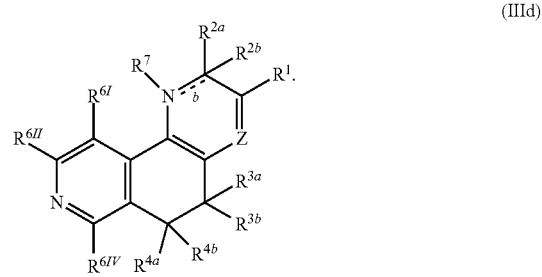
(IIId)

In yet other embodiments, the compound of formula (III) is

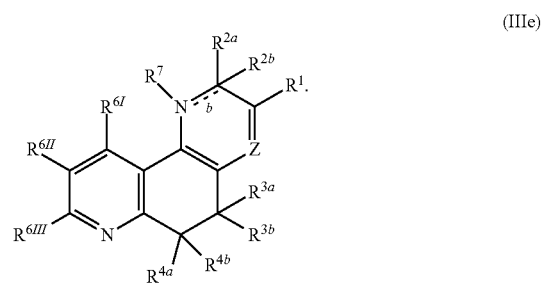
(IIIe)

In yet other embodiments, the compound of formula (III) is

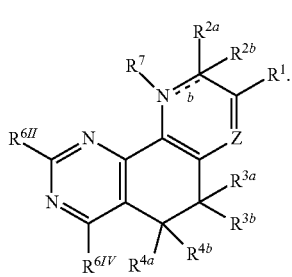

(IIIf)

In yet other embodiments, the compound of formula (III) is

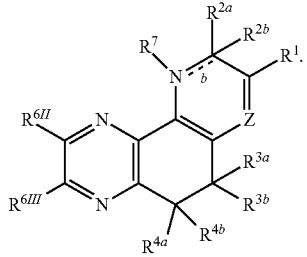

(IIIg)

In yet other embodiments, the compound of formula (III) is

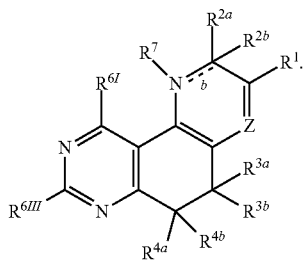

(IIIh)

In yet other embodiments, the compound of formula (III) is

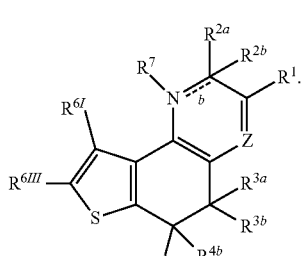

(IIIi)

In yet other embodiments, the compound of formula (III) is

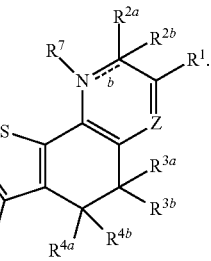

(IIIj)

In yet other embodiments, the compound of formula (III) is

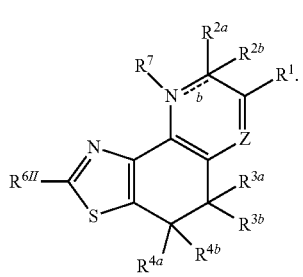

(IIIk)

In yet other embodiments, the compound of formula (III) is

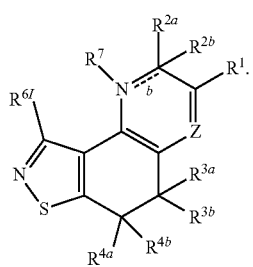

(IIIl)

In yet other embodiments, the compound of formula (III) is

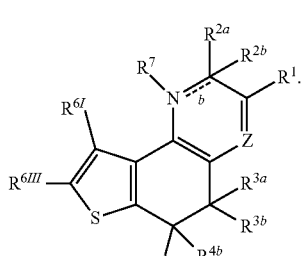

(IIIm)

In yet other embodiments, the compound of formula (III) is

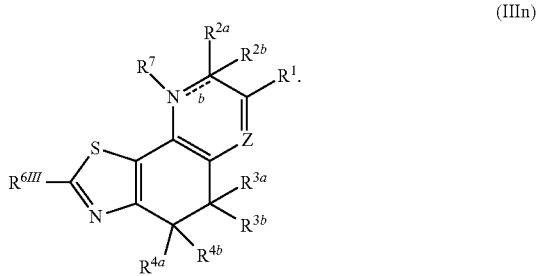

(IIIn)

In certain embodiments, in any of (III) and (IIIa)-(IIIn), at least one of $R^{3a}$ or $R^{3b}$ is independently optionally substituted $C_1$-$C_6$ alkyl or optionally substituted $C_3$-$C_8$ cycloalkyl. In certain embodiments, in any of (III) and (IIIa)-(IIIn), at least one of $R^{3a}$ or $R^{3b}$ is independently selected from the group consisting of n-propyl, isopropyl, n-butyl, isobutyl, sec-butyl, and tert-butyl.

In certain embodiments, in any of (III) and (IIIa)-(IIIn), none of $R^{6I}$, $R^{6II}$, $R^{6III}$ and $R^{6IV}$, if present, are N-linked (i.e., linked to the ring through a N atom). In certain embodiments, in any of (III) and (IIIa)-(IIIn), none of $R^{6I}$, $R^{6II}$, $R^{6III}$ and $R^{6IV}$, if present, comprise a basic nitrogen group. In certain embodiments, in any of (III) and (IIIa)-(IIIn), at least one of $R^{6I}$, $R^{6II}$, $R^{6III}$ and $R^{6IV}$, if present, is N-linked (i.e., linked to the ring through a N atom). In certain embodiments, in any of (III) and (IIIa)-(IIIn), at least one of $R^{6I}$, $R^{6II}$, $R^{6III}$ and $R^{6IV}$, if present, comprises a basic nitrogen group. In certain embodiments, in any of (III) and (IIIa)-(IIIn), at least one of $R^{6II}$ and $R^{6III}$, if present, is independently O-linked (i.e., linked to the ring through a O atom). In certain embodiments, in any of (III) and (IIIa)-(IIIn), both of $R^{6II}$ and $R^{6III}$, if present, are independently O-linked.

In certain embodiments, each occurrence of alkyl, alkenyl, or cycloalkyl is independently optionally substituted with at least one substituent selected from the group consisting of $C_1$-$C_6$ alkyl, halo, —OR", phenyl (thus yielding, in non-limiting examples, optionally substituted phenyl-($C_1$-$C_3$ alkyl), such as, but not limited to, benzyl or substituted benzyl), and —N(R")(R"), wherein each occurrence of R" is independently H, $C_1$-$C_6$ alkyl, or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), —NO$_2$, —S(=O)$_2$N(R")(R"), acyl, and $C_1$-$C_6$ alkoxycarbonyl, wherein each occurrence of R" is independently H, $C_1$-$C_6$ alkyl, or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), and $C_1$-$C_6$ alkoxycarbonyl, wherein each occurrence of R" is independently H, $C_1$-$C_6$ alkyl, or $C_3$-$C_8$ cycloalkyl.

In certain embodiments, $X^1$=$CR^{6I}$; $X^2$=$CR^{6II}$; $X^3$=$CR^{6III}$; and $X^4$=$CR^{6IV}$.

In certain embodiments, $X^1$=N; $X^2$=$CR^{6II}$; $X^3$=$CR^{6III}$; and $X^4$=$CR^{6IV}$.

In certain embodiments, $X^1$=$CR^{6I}$; $X^2$=N; $X^3$=$CR^{6III}$; and $X^4$=$CR^{6IV}$.

In certain embodiments, $X^1$=$CR^{6I}$; $X^2$=$CR^{6II}$; $X^3$=N; and $X^4$=$CR^{6IV}$.

In certain embodiments, $X^1$=$CR^{6I}$; $X^2$=$CR^{6II}$; $X^3$=$CR^{6III}$; and $X^4$=N.

In certain embodiments, $X^1$=N; $X^2$=$CR^{6I}$; $X^3$=N; and $X^4$=$CR^{6IV}$.

In certain embodiments, $X^1$=$CR^{6I}$; $X^2$=N; $X^3$=$CR^{6III}$; and $X^4$=N.

In certain embodiments, $X^1$=N; $X^2$=$CR^{II}$; $X^3$=$CR^{6III}$; and $X^4$=N.

In certain embodiments, $X^1$ is selected from the group consisting of $CR^{6I}$ and N, $X^2$ is selected from the group consisting of $CR^{6II}$ and N, and $X^3$ and $X^4$ combine to form —S—.

In certain embodiments, $X^3$ is selected from the group consisting of $CR^{6III}$ and N, $X^4$ is selected from the group consisting of $CR^{6IV}$ and N, and $X^1$ and $X^2$ combine to form —S—.

In certain embodiments, A is null. In certain embodiments, A is $CR^9R^9$.

In certain embodiments, $R^1$ is selected from the group consisting of H; halo; —C(=O)OR$^8$; —C(=O)NHR$^8$; —C(=O)NH—OR$^8$; —C(=O)NHNHR$^8$; —C(=O)NHNHC(=O)R$^8$. —C(=O)NHS(=O)$_2$RB; —CN; and 1H-1,2,4-triazol-5-yl. In certain embodiments, $R^1$ is H. In certain embodiments, $R^1$ is F. In certain embodiments, $R^1$ is Cl. In certain embodiments, $R^1$ is Br. In certain embodiments, $R^1$ is I. In certain embodiments, $R^1$ is —C(=O)OR$^8$ (such as, for example, —C(=O)OH or —C(=O)O—$C_1$-$C_6$ alkyl). In certain embodiments, $R^1$ is —C(=O)NHR$^8$ (such as, for example, —C(=O)NH$_2$, —C(=O)NHMe, —C(=O)N(Me)$_2$, or —C(=O)NH(CH$_2$CH$_2$OCH$_3$)). In certain embodiments, $R^1$ is —C(=O)NH—OR$^8$ (such as, for example, —C(=O)NH—OH). In certain embodiments, $R^1$ is —C(=O)NHNHR$^8$. In certain embodiments, $R^1$ is —C(=O)NHNHC(=O)R$^8$. In certain embodiments, $R^1$ is —C(=O)NHS(=O)$_2$R$^8$. In certain embodiments, $R^1$ is 1H-1,2,4-triazol-5-yl. In certain embodiments, $R^1$ is selected from the group consisting of —C(=O)OH, —C(=O)OMe, —C(=O)OEt, —C(=O)O-nPr, —C(=O)O-iPr, —C(=O)O-cyclopentyl, and —C(=O)O-cyclohexyl. In certain embodiments, $R^1$ is —C(=O)OH. In certain embodiments, $R^1$ is —C(=O)OMe. In certain embodiments, $R^1$ is —C(=O)OEt. In certain embodiments, $R^1$ is —C(=O)O-nPr. In certain embodiments, $R^1$ is —C(=O)O-iPr. In certain embodiments, $R^1$ is —C(=O)O-cyclopentyl. In certain embodiments, $R^1$ is —C(=O)O-cyclohexyl. In certain embodiments, $R^1$ is —C(=O)NH$_2$. In certain embodiments, $R^1$ is —C(=O)NHMe. In certain embodiments, $R^1$ is —C(=O)N(Me)$_2$. In certain embodiments, $R^1$ is —C(=O)NH(CH$_2$CH$_2$OCH$_3$)). In certain embodiments, $R^1$ is C(=O)NH—OH.

In certain embodiments, $R^{2a}$ and $R^{2b}$ combine to form =O. In certain embodiments, $R^{2a}$ is F and $R^{2b}$ is null. In certain embodiments, $R^{2a}$ is Cl and $R^{2b}$ is null. In certain embodiments, $R^{2a}$ is Br and $R^{2b}$ is null. In certain embodiments, $R^{2a}$ is I and $R^{2b}$ is null. In certain embodiments, $R^{2a}$ is methoxy and $R^{2b}$ is null.

In certain embodiments, bond a is a single bond. In other embodiments, bond a is a double bond.

In certain embodiments, bond b is a single bond. In other embodiments, bond b is a double bond.

In certain embodiments, bond a is a single bond, and Y is selected from the group consisting of CHR$^5$ and O.

In certain embodiments, $R^{3a}$ is H. In certain embodiments, $R^{3a}$ is not H. In certain embodiments, $R^{3a}$ is alkyl-substituted oxetanyl. In certain embodiments, $R^{3a}$ is optionally substituted $C_1$-$C_6$ alkyl. In certain embodiments, $R^{3a}$ is optionally substituted $C_3$-$C_8$ cycloalkyl. In certain embodiments, $R^{3b}$ is H. In certain embodiments, $R^{3b}$ is not H. In certain embodiments, $R^{3b}$ is alkyl-substituted oxetanyl. In certain embodiments, $R^{3b}$ is optionally substituted $C_1$-$C_6$ alkyl. In certain embodiments, $R^{3b}$ is optionally substituted $C_3$-$C_8$ cycloalkyl. In certain embodiments, $R^{4a}$ is H. In certain embodiments, $R^{4a}$ is not H. In certain embodiments, $R^{4a}$ is alkyl-substituted oxetanyl. In certain embodiments, $R^{4a}$ is optionally substituted $C_1$-$C_6$ alkyl. In certain embodiments, $R^{4a}$ is optionally substituted $C_3$-$C_8$ cycloalkyl. In certain embodiments, $R^{4b}$ is H. In certain embodiments, $R^{4b}$ is not H. In certain embodiments, $R^{4b}$ is alkyl-substituted oxetanyl. In certain embodiments, $R^{4b}$ is optionally substituted $C_1$-$C_6$ alkyl. In certain embodiments, $R^{4b}$ is optionally substituted $C_3$-$C_8$ cycloalkyl.

In certain embodiments, the $C_1$-$C_6$ alkyl group is optionally substituted with 1-3 groups independently selected from the group consisting of F, Cl, Br, I, OH, and OMe. In certain embodiments, the $C_3$-$C_8$ cycloalkyl group is optionally substituted with 1-3 groups independently selected from the group consisting of F, Cl, Br, I, OH, and OMe.

In certain embodiments, $R^{3a}$ is H and $R^{3b}$ is isopropyl. In certain embodiments, $R^{3a}$ is H and $R^{3b}$ is tert-butyl. In certain embodiments, $R^{3a}$ is methyl and $R^{3b}$ is isopropyl. In certain embodiments, $R^{3a}$ is methyl and $R^{3b}$ is tert-butyl. In certain embodiments, $R^{3a}$ is methyl and $R^{3b}$ is methyl. In certain embodiments, $R^{3a}$ is methyl and $R^{3b}$ is ethyl. In certain embodiments, $R^{3a}$ is ethyl and $R^{3b}$ is ethyl.

In certain embodiments, one pair selected from the group consisting of $R^{3a}/R^{3b}$, $R^{4a}/R^{4b}$ and $R^{3a}/R^{4a}$ combine to form $C_1$-$C_6$ alkanediyl. In certain embodiments, one pair selected from the group consisting of $R^{3a}/R^{3b}$, $R^{4a}/R^{4b}$, and $R^{3a}/R^{4a}$ combine to form $-(CH_2)_nO(CH_2)_n-$, which is optionally substituted with at least one $C_1$-$C_6$ alkyl or halo, wherein each occurrence of n is independently selected from the group consisting of 1 and 2. In certain embodiments, one pair selected from the group consisting of $R^{3a}/R^{3b}$, $R^{4a}/R^{4b}$ and $R^{3a}/R^{4a}$ combine to form $-(CH_2)_nNR^9(CH_2)_n-$, which is optionally substituted with at least one $C_1$-$C_6$ alkyl or halo, wherein each occurrence of n is independently selected from the group consisting of 1 and 2.

In certain embodiments, $R^{3a}$ and $R^{3b}$ are independently selected from the group consisting of H, methyl, ethyl, n-propyl, isopropyl, n-butyl, isobutyl, sec-butyl, tert-butyl, hydroxymethyl, 2-hydroxy-ethyl, 2-methoxy-ethyl, methoxymethyl, 2-methyl-1-methoxy-prop-2-yl, 2-methyl-1-hydroxy-prop-2-yl, and trifluoroethyl. In certain embodiments, $R^{4a}$ and $R^{4b}$ are independently selected from the group consisting of H, methyl, ethyl, n-propyl, isopropyl, n-butyl, isobutyl, sec-butyl, tert-butyl, hydroxymethyl, 2-hydroxy-ethyl, 2-methoxy-ethyl, methoxymethyl, and 2-methyl-1-methoxy-prop-2-yl. In certain embodiments, $R^{4a}$ is selected from the group consisting of H, methyl, ethyl, 2-hydroxy-ethyl, and 2-methoxy-ethyl. In certain embodiments, $R^{3a}$ and $R^{3b}$ combine to form 1,1-methanediyl (i.e., an exocyclic double bond). In certain embodiments, $R^{3a}$ and $R^{3b}$ combine to form 1,2-ethanediyl. In certain embodiments, $R^{3a}$ and $R^{3b}$ combine to form 1,3-propanediyl. In certain embodiments, $R^{3a}$ and $R^{3b}$ combine to form 1,4-butanediyl. In certain embodiments, $R^{3a}$ and $R^{3b}$ combine to form 1,5-pentanediyl. In certain embodiments, $R^{3a}$ and $R^{3b}$ combine to form 1,6-hexanediyl. In certain embodiments, $R^{3a}$ and $R^{4a}$ combine to form 1,2-ethanediyl. In certain embodiments, $R^{3a}$ and $R^{4a}$ combine to form 1,2-propanediyl. In certain embodiments, $R^{3a}$ and $R^{4a}$ combine to form 1,3-propanediyl. In certain embodiments, $R^{3a}$ and $R^{4a}$ combine to form (1- or 2-methyl)-1,4-butanediyl. In certain embodiments, $R^{3a}$ and $R^{4a}$ combine to form (1,1-, 1,2-, 1,3-, or 2,2-dimethyl)-1,3-propanediyl. In certain embodiments, $R^{3a}$ and $R^{4a}$ combine to form 1,5-pentanediyl. In certain embodiments, $R^{3a}$ and $R^{4a}$ combine to form 1,6-hexanediyl.

In certain embodiments, $R^5$ is H. In certain embodiments, $R^5$ is optionally substituted $C_1$-$C_6$ alkyl. In certain embodiments, $R^5$ is optionally substituted $C_3$—C cycloalkyl.

In certain embodiments, $X^1$ is $CR^{6I}$. In certain embodiments, $X^1$ is N. In certain embodiments, $X^2$ is $CR^{6II}$. In certain embodiments, $X^2$ is N. In certain embodiments, $X^3$ is $CR^{6III}$. In certain embodiments, $X^3$ is N. In certain embodiments, $X^4$ is $CR^{6IV}$. In certain embodiments, $X^4$ is N. In certain embodiments, $X^3$ and $X^4$ combine to form —S—. In certain embodiments, $X^1$ and $X^2$ combine to form —S—.

In certain embodiments, none of $X^1$, $X^2$, $X^3$ and $X^4$ is N. In certain embodiments, only one from the group consisting of $X^1$, $X^2$, $X^3$ and $X^4$ is N. In certain embodiments, only two from the group consisting of $X^1$, $X^2$, $X^3$ and $X^4$ are N. In certain embodiments, if at least one N is present in the ring comprising $X^1$-$X^4$, the at least one N is optionally substituted with $C_1$-$C_6$ alkyl if the adjacent carbon atom in the ring is substituted with —OH. In certain embodiments, $X^1$ is CH. In certain embodiments, $X^4$ is CH. In certain embodiments, $X^1$ is N. In certain embodiments, $X^4$ is N. In certain embodiments, $X^2$ is $CR^{6II}$, wherein $R^{6II}$ is not H. In certain embodiments, $X^3$ is $CR^{6III}$, wherein $R^{6III}$ is not H.

In certain embodiments, $R^{6I}$ is H. In certain embodiments, $R^{6I}$ is halo. In certain embodiments, $R^{6I}$ is —CN. In certain embodiments, $R^{6I}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6I}$ is optionally substituted $C_3$-$C_8$ cycloalkyl. In certain embodiments, $R^{6I}$ is —OR. In certain embodiments, $R^{6I}$ is —N(R)(R). In certain embodiments, $R^{6I}$ is $C_1$-$C_6$ haloalkoxy (such as but not limited to $OCF_2H$ and $OCH_2CF_2H$).

In certain embodiments, $R^{6II}$ is H. In certain embodiments, $R^{6II}$ is halo. In certain embodiments, $R^{6II}$ is —CN. In certain embodiments, $R^{6II}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6II}$ is optionally substituted $C_3$-$C_8$ cycloalkyl. In certain embodiments, $R^{6II}$ is —OR. In certain embodiments, $R^{6I}$ is —N(R)(R). In certain embodiments, $R^{6II}$ is $C_1$-$C_6$ haloalkoxy (such as but not limited to $OCF_2H$ and $OCH_2CF_2H$).

In certain embodiments, $R^{6III}$ is H. In certain embodiments, $R^{6III}$ is halo. In certain embodiments, $R^{6III}$ is —CN. In certain embodiments, $R^{6III}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6III}$ is optionally substituted $C_3$-$C_8$ cycloalkyl. In certain embodiments, $R^{6III}$ is —OR. In certain embodiments, $R^{6I}$ is —N(R)(R). In certain embodiments, $R^{6III}$ is $C_1$-$C_6$ haloalkoxy (such as but not limited to $OCF_2H$ and $OCH_2CF_2H$).

In certain embodiments, $R^{6IV}$ is H. In certain embodiments, $R^{6IV}$ is halo. In certain embodiments, $R^{6IV}$ is —CN. In certain embodiments, $R^{6IV}$ is optionally substituted $C_1$-$C_6$ alkyl (e.g., $C_1$-$C_6$ hydroxyalkyl, alkoxy-$C_1$-$C_6$ alkyl, and/or $C_1$-$C_6$ haloalkyl). In certain embodiments, $R^{6IV}$ is optionally substituted $C_3$-$C_8$ cycloalkyl. In certain embodiments, $R^{6IV}$ is —OR. In certain embodiments, $R^{6I}$ is —N(R)(R). In certain embodiments, $R^{6IV}$ is $C_1$-$C_6$ haloalkoxy (such as but not limited to $OCF_2H$ and $OCH_2CF_2H$).

In certain embodiments, $R^{6I}$ is selected from the group consisting of H, F, Cl, Br, I, ethyl, n-propyl, isopropyl, cyclopropyl, CN, methoxy, ethoxy, n-propoxy, isopropoxyl, n-butoxy, sec-butoxy, isobutoxy, tert-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxybut-1-oxy, 4-hydroxy-but-1-oxy, 2-hydroxy-ethoxy, 3-hydroxy-prop-1-yl, 4-hydroxy-but-1-yl, N-methylamino, N,N-dimethylamino, N-(2-methoxyethyl)amino, methoxymethyl, 2-methoxyethyl, tetrahydropyran-4-yl, 3-hydroxy-2,2-dimethyl-prop-1-oxy, cyclopropylmethoxy, 2,2-difluoroethoxy, 2,2,2-trifluoroethoxy, and 2-(2-haloethoxy)-ethoxy.

In certain embodiments, $R^{6II}$ is selected from the group consisting of H, F, Cl, Br, I, ethyl, n-propyl, isopropyl, cyclopropyl, CN, amino, methylamino, dimethylamino, N-(2-methoxyethyl)amino, methoxyethylamino, methoxymethyl, 2-methoxyethyl, tetrahydropyran-4-yl, pyrrolidinyl, methoxy, ethoxy, n-propoxy, isopropoxyl, n-butoxy, sec-butoxy, isobutoxy, tert-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropylmethoxy, 2,2-difluoroethoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-but1-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy.

In certain embodiments, $R^{6III}$ is selected from the group consisting of H, F, Cl, Br, I, ethyl, n-propyl, isopropyl, cyclopropyl, CN, amino, methylamino, dimethylamino, N-(2-methoxyethyl)amino, methoxyethylamino, methoxymethyl, 2-methoxyethyl, tetrahydropyran-4-yl, pyrrolidinyl, methoxy, ethoxy, n-propoxy, isopropoxyl, n-butoxy, sec-butoxy, isobutoxy, tert-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, 3-hydroxy-2,2-dimethyl-prop-1-oxy, cyclopropylmethoxy, 2,2-difluoroethoxy, 2,2,2-trifluoroethoxy, 2-(2-haloethoxy)-ethoxy, 2-(N-morpholino)-ethyl, 2-(N-morpholino)-ethoxy, 3-(N-morpholino)-prop-1-yl, 3-(N-morpholino)-prop-1-oxy, 4-(N-morpholino)-but-1-yl, 4-(N-morpholino)-but1-oxy, 2-amino-ethyl, 2-(NHC(=O)O$^t$Bu)-ethyl, 2-amino-ethoxy, 2-(NHC(=O)O$^t$Bu)-ethoxy, 3-amino-prop-1-yl, 3-(NHC(=O)O$^t$Bu)-prop-1-yl, 3-amino-prop-1-oxy, 3-(NHC(=O)O$^t$Bu)-prop-1-oxy, 4-amino-but-1-yl, 4-(NHC(=O)O$^t$Bu)-but-1-yl, 4-amino-but-1-oxy, and 4-(NHC(=O)O$^t$Bu)-but-1-oxy.

In certain embodiments, $R^{6IV}$ is selected from the group consisting of H, F, Cl, Br, I, ethyl, n-propyl, isopropyl, cyclopropyl, CN, methoxy, ethoxy, n-propoxy, isopropoxyl, n-butoxy, sec-butoxy, isobutoxy, tert-butoxy, 2-methoxy-ethoxy, 2-hydroxy-ethoxy, 3-methoxy-prop-1-yl, 3-hydroxy-prop-1-yl, 3-methoxy-prop-1-oxy, 3-hydroxy-prop-1-oxy, 4-methoxy-but-1-yl, 4-hydroxy-but-1-yl, 4-methoxy-but-1-oxy, 4-hydroxy-but-1-oxy, 2-hydroxy-ethoxy, 3-hydroxy-prop-1-yl, 4-hydroxy-but-1-yl, N-methylamino, N,N-dimethylamino, N-(2-methoxyethyl)amino, methoxymethyl, 2-methoxyethyl, tetrahydropyran-4-yl, 3-hydroxy-2,2-dimethyl-prop-1-oxy, cyclopropylmethoxy, 2,2-difluoroethoxy, 2,2,2-trifluoroethoxy, and 2-(2-haloethoxy)-ethoxy.

In certain embodiments, $X^1$ is $CR^{6I}$, $X^2$ is $CR^{6II}$, $X^3$ is $CR^{6III}$, and $X^4$ is $CR^{6IV}$.

In certain embodiments, $R^{6I}$ is H, $R^{6II}$ is H, $R^{6III}$ is 3-methoxy-propoxy, and $R^{6IV}$ is H. In certain embodiments, $R^{6I}$ is H, $R^{6II}$ is H, $R^{6III}$ is 4-methoxy-butoxy, and $R^{6IV}$ is H. In certain embodiments, $R^{6I}$ is H, $R^{6II}$ is methoxymethyl, $R^{6III}$ is 3-methoxy-propoxy, and $R^{6IV}$ is H. In certain embodiments, $R^{6I}$ is H, $R^{6II}$ is methoxymethyl, $R^{6III}$ is 4-methoxy-butoxy, and $R^{6IV}$ is H. In certain embodiments, $R^{6I}$ is H, $R^{6II}$ is 2-methoxyethyl, $R^{6III}$ is 3-methoxy-propoxy, and $R^{6IV}$ is H. In certain embodiments, $R^{6I}$ is H, $R^{6II}$ is 2-methoxyethyl, $R^{6III}$ is 4-methoxy-butoxy, and $R^{6IV}$ is H. In certain embodiments, $R^{6I}$ is H, $R^{6II}$ is methoxy, $R^{6III}$ is 3-methoxy-propoxy, and $R^{6IV}$ is H. In certain embodiments, $R^{6I}$ is H, $R^{6II}$ is methoxy, $R^{6III}$ is 4-methoxy-butoxy, and $R^{6IV}$ is H. In certain embodiments, $R^{6I}$ is H, $R^{6II}$ is ethoxy, $R^{6III}$ is 3-methoxy-propoxy, and $R^{6IV}$ is H. In certain embodiments, $R^{6I}$ is H, $R^{6II}$ is ethoxy, $R^{6III}$ is 4-methoxy-butoxy, and $R^{6IV}$ is H. In certain embodiments, $R^{6I}$ is H, $R^{6II}$ is 2,2-difluoroethoxy, $R^{6III}$ is 3-methoxy-propoxy, and $R^{6IV}$ is H. In certain embodiments, $R^{6I}$ is H, $R^{II}$ is 2,2-difluoroethoxy, $R^{6III}$ is 4-butoxy-propoxy, and $R^{6IV}$ is H. In certain embodiments, $R^{6I}$ is H, $R^{6II}$ is methylamino, $R^{6III}$ is 3-methoxy-propoxy, and $R^{6IV}$ is H. In certain embodiments, $R^{6I}$ is H, $R^{6II}$ is methylamino, $R^{6III}$ is 4-methoxy-butoxy, and $R^{6IV}$ is H. In certain embodiments, $R^{6I}$ is H, $R^{6II}$ is dimethylamino, $R^{6III}$ is 3-methoxy-propoxy, and $R^{6IV}$ is H. In certain embodiments, $R^{6I}$ is H, $R^{6II}$ is dimethylamino, $R^{6III}$ is 4-methoxy-butoxy, and $R^{6IV}$ is H. In certain embodiments, $R^{6I}$ is H, $R^{6II}$ is (2-methoxyethyl)amino, $R^{6III}$ is 3-methoxy-propoxy, and $R^{6IV}$ is H. In certain embodiments, $R^{6I}$ is H, $R^{6II}$ is (2-methoxyethyl)amino, $R^{6III}$ is 4-methoxy-butoxy, and $R^{6IV}$ is H. In certain embodiments, $R^{6I}$ is H, $R^{6II}$ is chloro, $R^{6III}$ is 3-methoxy-propoxy, and $R^{6IV}$ is H. In certain embodiments, $R^{6I}$ is H, $R^{6II}$ is chloro, $R^{6III}$ is 4-methoxy-butoxy, and $R^{6IV}$ is H. In certain embodiments, $R^{6I}$ is H, $R^{6II}$ is ethyl, $R^{6III}$ is 3-methoxy-propoxy, and $R^{6IV}$ is H. In certain embodiments, $R^{6I}$ is H, $R^{6II}$ is ethyl, $R^{6III}$ is 4-methoxy-butoxy, and $R^{6IV}$ is H. In certain embodiments, $R^{6I}$ is H, $R^{6II}$ is cyclopropyl, $R^{6III}$ is 3-methoxy-propoxy, and $R^{6IV}$ is H. In certain embodiments, $R^{6I}$ is H, $R^{6II}$ is cyclopropyl, $R^{6III}$ is 4-methoxy-butoxy, and $R^{6IV}$ is H. In certain embodiments, $R^{6I}$ is H, $R^{6II}$ is n-propyl, $R^{6III}$ is 3-methoxy-propoxy, and $R^{6IV}$ is H. In certain embodiments, $R^{6I}$ is H, $R^{6II}$ is n-propyl, $R^{6III}$ is 4-methoxy-butoxy, and $R^{6IV}$ is H. In certain embodiments, $R^{6I}$ is H, $R^{6II}$ is 4-tetrahydropyran, $R^{6III}$ is 3-methoxy-propoxy, and $R^{6IV}$ is H. In certain embodiments, $R^{6I}$ is H, $R^{6II}$ is 4-tetrahydropyran, $R^{6III}$ is 4-methoxy-butoxy, and $R^{6IV}$ is H. In certain embodiments, $R^{6I}$ is H, $R^{6II}$ is isopropyl, $R^{6III}$ is 3-methoxy-propoxy, and $R^{IV}$ is H. In certain embodiments $R^{6I}$ is H $R^{6II}$ is isopropyl, $R^{6III}$ is 4-methoxy-butoxy, and $R^{6IV}$ is H. In certain embodiments, $R^{6I}$ is H, $R^{6II}$ is methoxy, $R^{6III}$ is methoxy, and $R^{6IV}$ is H. In certain embodiments, $R^{6I}$ is H, $R^{6II}$ is chloro, $R^{6III}$ is methoxy, and $R^{6IV}$ p is H. In certain embodiments, $R^{6I}$ is H, $R^{6II}$ is cyclopropyl, $R^{6III}$ is methoxy, and $R^{6IV}$ is H.

In certain embodiments, $X^1$ is N, $X^2$ is $CR^{6II}$, $X^3$ is $CR^{6III}$, and $X^4$ is $CR^{6IV}$.

In certain embodiments, $X^1$ is N, $R^{6II}$ is H, $R^{III}$ is 3-methoxy-propoxy, and $R^{6IV}$ is H. In certain embodiments, $X^1$ is N, $R^{6II}$ is H, $R^{6III}$ is 4-methoxy-butoxy, and $R^{6IV}$ is H. In certain embodiments, $X^1$ is N, $R^{6II}$ is methoxymethyl, $R^{6III}$ is 3-methoxy-propoxy, and $R^{6IV}$ is H. In certain embodiments, $X^1$ is N, $R^{6II}$ is methoxymethyl, $R^{6III}$ is 4-methoxy-butoxy, and $R^{6IV}$ is H. In certain embodiments, $X^1$ is N, $R^{6II}$ is 2-methoxyethyl, $R^{III}$ is 3-methoxy-propoxy, and $R^{6IV}$ is H. In certain embodiments, $X^1$ is N, $R^{6II}$ is 2-methoxyethyl, $R^{6III}$ is 4-methoxy-butoxy, and $R^{6IV}$ is H. In certain embodiments, $X^1$ is N, $R^{6II}$ is methoxy, $R^{6III}$ is 3-methoxy-propoxy, and $R^{6IV}$ is H. In certain embodiments, $X^1$ is N, $R^{6II}$ is methoxy, $R^{6III}$ is 4-methoxy-butoxy, and $R^{6IV}$ is H. In certain embodiments, $X^1$ is N, $R^{6II}$ is ethoxy, $R^{6III}$ is 3-methoxy-propoxy, and $R^{6IV}$ is H. In certain embodiments, $X^1$ is N, $R^{6II}$ is ethoxy, $R^{6III}$ is 4-methoxy-butoxy, and $R^{6IV}$ is H. In certain embodiments, $X^1$ is N, $R^{6II}$ is 2,2-difluoroethoxy, $R^{6III}$ is 3-methoxy-propoxy, and $R^{6IV}$ is H. In certain embodiments, $X^1$ is N, $R^{6II}$ is 2,2-difluoroethoxy, $R^{6III}$ is 4-butoxy-propoxy, and $R^{6IV}$ is H. In certain embodiments, $X^1$ is N, $R^{6II}$ is methylamino, $R^{6III}$ is 3-methoxy-propoxy, and $R^{6IV}$ is H. In certain embodiments, $X^1$ is N, $R^{6II}$ is methylamino, $R^{6III}$ is 4-methoxy-butoxy, and $R^{6IV}$ is H. In certain embodiments, $X^1$ is N, $R^{6II}$ is dimethylamino, $R^{6III}$ is 3-methoxy-propoxy, and $R^{6IV}$ is H. In certain embodiments, $X^1$ is N, $R^{6II}$ is dimethylamino, $R^{6III}$ is 4-methoxy-butoxy, and $R^{6IV}$ is H. In certain embodiments, $X^1$ is N, $R^{6II}$ is (2-methoxyethyl)amino, $R^{6III}$ is 3-methoxy-propoxy, and $R^{6IV}$ is H. In certain embodiments, $X^1$ is N, $R^{6II}$ is (2-methoxyethyl)amino, $R^{6III}$ is 4-methoxy-butoxy, and $R^{6IV}$ is H. In certain embodiments, $X^1$ is N, $R^{6II}$ is chloro, $R^{6III}$ is 3-methoxy-propoxy, and $R^{6IV}$ is H. In certain embodiments, $X^1$ is N, $R^{6II}$ is chloro, $R^{6III}$ is 4-methoxy-butoxy, and $R^{IV}$ is H. In certain embodiments, $X^1$ is N, $R^{6II}$ is ethyl, $R^{6III}$ is 3-methoxy-propoxy, and $R^{6IV}$ is H. In certain embodiments, $X^1$ is N, $R^{6II}$ is ethyl, $R^{6III}$ is 4-methoxy-butoxy, and $R^{6IV}$ is H. In certain embodiments, $X^1$ is N, $R^{6II}$ is cyclopropyl, $R^{6III}$ is 3-methoxy-propoxy, and $R^{6IV}$ is H. In certain embodiments, $X^1$ is N, $R^{6II}$ is cyclopropyl, $R^{6III}$ is 4-methoxy-butoxy, and $R^{6IV}$ is H. In certain embodiments, $X^1$ is N, $R^{6II}$ is n-propyl, $R^{6III}$ is 3-methoxy-propoxy, and $R^{6IV}$ is H. In certain embodiments, $X^1$ is N, $R^{6II}$ is n-propyl, $R^{6III}$ is 4-methoxy-butoxy, and $R^{6IV}$ is H. In certain embodiments, $X^1$ is N, $R^{6II}$ is 4-tetrahydropyran, $R^{6III}$ is 3-methoxy-propoxy, and $R^{6IV}$ is H. In certain embodiments, $X^1$ is N, $R^{6II}$ is 4-tetrahydropyran, $R^{6III}$ is 4-methoxy-butoxy, and $R^{6IV}$ is H. In certain embodiments, $X^1$ is N, $R^{6II}$ is isopropyl, $R^{6III}$ is 3-methoxy-propoxy, and $R^{6IV}$ is H. In certain embodiments, $X^1$ is N, $R^{6II}$ is isopropyl, $R^{6III}$ is 4-methoxy-butoxy, and $R^{6IV}$ is H. In certain embodiments, $X^1$ is N, $R^{6II}$ is methoxy, $R^{6III}$ is methoxy, and $R^{6IV}$ is H. In certain embodiments, $X^1$ is N, $R^{6II}$ is chloro, $R^{6III}$ is methoxy, and $R^{6IV}$ is H. In certain embodiments, $X^1$ is N, $R^{6II}$ is cyclopropyl, $R^{6III}$ is methoxy, and $R^{6IV}$ is H.

In certain embodiments, each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl. In certain embodiments, each occurrence of R' is independently selected from the group consisting of —$NH_2$, —$NH(C_1$-$C_6$ alkyl), —$N(C_1$-$C_6$ alkyl)($C_1$-$C_6$ alkyl), —NHC(=O)O$^t$Bu, —N($C_1$-$C_6$ alkyl)C(=O)O$^t$Bu, or a 5- or 6-membered heterocyclic group (such as, but not limited to, pyrrolidinyl, morpholinyl, piperidinyl, piperazinyl, and so forth), which is optionally N-linked.

In certain embodiments, $X^2$ is $CR^{6II}$, $X^3$ is $CR^{6III}$, and $R^{6II}$ and $R^{6III}$ combine to form a divalent group selected from the group consisting of —O($CR^9R^{11}$)O—, —O($CR^9R^{11}$)($CR^9R^{11}$)O—, —O($CR^9R^{11}$)($CR^9R^{11}$)—, and —O($CR^9R^{11}$)($CR^9R^{11}$)($CR^9R^{11}$)—.

In certain embodiments, $X^3$ is $CR^{6III}$, $X^4$ is $CR^{6IV}$ and $R^{6III}$ and $R^{6IV}$ combine to form a divalent group selected from the group consisting of —O($CR^9R^{11}$)O—, —O($CR^9R^{11}$)($CR^9R^{11}$)O—, —O($CR^9R^{11}$)($CR^9R^{11}$)—, and —O($CR^9R^{11}$)($CR^9R^{11}$)($CR^9R^{11}$)—.

In certain embodiments, $R^7$ is H. In certain embodiments, $R^7$ is optionally substituted $C_1$-$C_6$ alkyl (e.g., optionally substituted with 1-3 independently selected halo groups). In certain embodiments, $R^7$ is optionally substituted $C_3$-$C_8$ cycloalkyl. In certain embodiments, $R^7$ is benzyl. In certain embodiments, $R^7$ is optionally substituted benzyl. In certain embodiments, $R^7$ is methyl. In certain embodiments, $R^7$ is ethyl. In certain embodiments, $R^7$ is n-propyl. In certain embodiments, $R^7$ is isopropyl.

In certain embodiments, each occurrence of $R^8$ is independently selected from the group consisting of H, optionally substituted $C_1$-$C_6$ alkyl, and optionally substituted $C_3$-$C_8$ cycloalkyl. In certain embodiments, $R^8$ is methyl. In certain embodiments, $R^8$ is ethyl.

In certain embodiments, each occurrence of $R^9$ is independently selected from the group consisting of H and $C_1$-$C_6$ alkyl (e.g., methyl or ethyl).

In certain embodiments, each occurrence of $R^{10}$ is independently selected from the group consisting of optionally substituted $C_1$-$C_6$ alkyl and optionally substituted phenyl.

In certain embodiments, each occurrence of $R^{11}$ is independently selected from the group consisting of H, OH, $C_1$-$C_6$ alkyl, $C_1$-$C_6$ alkoxy, alkoxy-$C_1$-$C_6$ alkyl, and alkoxy-$C_1$-$C_6$ alkoxy, wherein two $R^{11}$ groups bound to the same carbon atom are not simultaneously OH; and wherein $R^{11}$ is not OH if it is bound to a carbon that is further bound to an oxygen atom. In certain embodiments, two $R^{11}$ groups combine with the carbon atom to which they are bound to form a moiety selected from the group consisting of C=O, C=$CH_2$ and oxetane-3,3-diyl.

In certain embodiments, Z is N. In certain embodiments, Z is $CR^{12}$.

In certain embodiments, $R^{12}$ is H. In certain embodiments, $R^{12}$ is OH. In certain embodiments, $R^{12}$ is halo. In certain embodiments, $R^{12}$ is $C_1$-$C_6$ alkoxy. In certain embodiments, $R^{12}$ is optionally substituted $C_1$-$C_6$ alkyl (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth). In certain embodiments, $R^{12}$ is optionally substituted $C_3$-$C_8$ cycloalkyl (e.g., optionally substituted with at least one selected from OH, $C_1$-$C_6$ alkoxy, F, Cl, Br, I, —$NH_2$, —$NH(C_1$-$C_6$ alkyl), —$N(C_1$-$C_6$ alkyl)($C_1$-$C_6$ alkyl), and so forth). In certain embodiments, $R^{12}$ is F. In certain embodiments, $R^{12}$ is methoxy. In certain embodiments, $R^{12}$ is ethoxy. In certain embodiments, $R^{12}$ is methyl. In certain embodiments, $R^{12}$ is ethyl. In certain embodiments, $R^{12}$ is n-propyl. In certain embodiments, $R^{12}$ is isopropyl.

In certain embodiments, the compounds of the invention, or a salt, solvate, stereoisomer (such as, in a non-limiting example, an enantiomer or diastereoisomer thereof), any mixture of one or more stereoisomers (such as, in a non-limiting example, mixtures in any proportion of enantiomers thereof, and/or mixtures in any proportion of diastereoisomers thereof), tautomer, and/or any mixture of tautomers thereof, are recited in Table 1.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating HBV and/or HDV infections. These additional agents may comprise compounds or compositions identified herein, or compounds (e.g., commercially available compounds) known to treat, prevent, or reduce the symptoms of HBV and/or HDV infections.

Non-limiting examples of one or more additional agents useful for treating HBV infections include: (a) reverse transcriptase inhibitors; (b) capsid inhibitors; (c) cccDNA formation inhibitors; (d) sAg secretion inhibitors; (e) oligomeric nucleotides targeted to the Hepatitis B genome; (f) immunostimulators; and (g) RNA destabilizer.

(a) Reverse Transcriptase Inhibitors

In certain embodiments, the reverse transcriptase inhibitor is a reverse-transcriptase inhibitor (NARTI or NRTI). In other embodiments, the reverse transcriptase inhibitor is a nucleotide analog reverse-transcriptase inhibitor (NtARTI or NtRTI).

Reported reverse transcriptase inhibitors include, but are not limited to, entecavir, clevudine, telbivudine, lamivudine, adefovir, and tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074, incorporated herein in its entirety by reference), emtricitabine, abacavir, elvucitabine, ganciclovir, lobucavir, famciclovir, penciclovir, and amdoxovir.

Reported reverse transcriptase inhibitors further include, but are not limited to, entecavir, lamivudine, and (1R,2R,3R,5R)-3-(6-amino-9H-9-purinyl)-2-fluoro-5-(hydroxymethyl)-4-methylenecyclopentan-1-ol.

Reported reverse transcriptase inhibitors further include, but are not limited to, a covalently bound phosphoramidate or phosphonamidate moiety of the above-mentioned reverse transcriptase inhibitors, or as described in for example U.S. Pat. No. 8,816,074, US Patent Application Publications No. US 2011/0245484 A1, and US 2008/0286230A1, all of which incorporated herein in their entireties by reference.

Reported reverse transcriptase inhibitors further include, but are not limited to, nucleotide analogs that comprise a phosphoramidate moiety, such as, for example, methyl ((((1R,3R,4R,5R)-3-(6-amino-9H-purin-9-yl)-4-fluoro-5-hydroxy-2-methylenecyclopentyl) methoxy)(phenoxy) phosphoryl)-(D or L)-alaninate and methyl ((((1R,2R,3R,4R)-3-fluoro-2-hydroxy-5-methylene-4-(6-oxo-1,6-dihydro-9H-purin-9-yl)cyclopentyl)methoxy)(phenoxy) phosphoryl)-(D or L)-alaninate. Also included are the individual diastereomers thereof, which include, for example, methyl ((R)-(((1R,3R,4R,5R)-3-(6-amino-9H-purin-9-yl)-4-fluoro-5-hydroxy-2-methylenecyclopentyl)methoxy)(phenoxy)

phosphoryl)-(D or L)-alaninate and methyl ((S)-(((1R,3R,4R,5R)-3-(6-amino-9H-purin-9-yl)-4-fluoro-5-hydroxy-2-methylenecyclopentyl) methoxy)(phenoxy)phosphoryl)-(D or L)-alaninate.

Reported reverse transcriptase inhibitors further include, but are not limited to, compounds comprising a phosphonamidate moiety, such as, for example, tenofovir alafenamide, as well as those described in U.S. Patent Application Publication No. US 2008/0286230 A1, incorporated herein in its entirety by reference. Methods for preparing stereoselective phosphoramidate or phosphonamidate containing actives are described in, for example, U.S. Pat. No. 8,816,074, as well as U.S. Patent Application Publications No. US 2011/0245484 A1 and US 2008/0286230 A1, all of which incorporated herein in their entireties by reference.

(b) Capsid Inhibitors

As described herein, the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA (pgRNA). Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

Reported capsid inhibitors include, but are not limited to, compounds described in International Patent Applications Publication Nos WO 2013006394, WO 2014106019, and WO2014089296, all of which incorporated herein in their entireties by reference.

Reported capsid inhibitors also include, but are not limited to, the following compounds and pharmaceutically acceptable salts and/or solvates thereof: Bay-41-4109 (see Int'l Patent Application Publication No. WO 2013144129), AT-61 (see Int'l Patent Application Publication No. WO 1998033501; and King, et al., 1998, Antimicrob. Agents Chemother. 42(12):3179-3186), DVR-01 and DVR-23 (see Int'l Patent Application Publication No. WO 2013006394; and Campagna, et al., 2013, J. Virol. 87(12):6931, all of which incorporated herein in their entireties by reference.

In addition, reported capsid inhibitors include, but are not limited to, those generally and specifically described in U.S. Patent Application Publication Nos. US 2015/0225355, US 2015/0132258, US 2016/0083383, US 2016/0052921 and Int'l Patent Application Publication Nos. WO 2013096744, WO 2014165128, WO 2014033170, WO 2014033167, WO 2014033176, WO 2014131847, WO 2014161888, WO 2014184350, WO 2014184365, WO 2015059212, WO 2015011281, WO 2015118057, WO 2015109130, WO 2015073774, WO 2015180631, WO 2015138895, WO 2016089990, WO 2017015451, WO 2016183266, WO 2017011552, WO 2017048950, WO2017048954, WO 2017048962, WO 2017064156 and are incorporated herein in their entirety by reference.

(c) cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

Reported cccDNA formation inhibitors include, but are not limited to, compounds described in Int'l Patent Application Publication No. WO 2013130703, and are incorporated herein in their entirety by reference.

In addition, reported cccDNA formation inhibitors include, but are not limited to, those generally and specifically described in U.S. Patent Application Publication No. US 2015/0038515 A1, and are incorporated herein in their entirety by reference.

(d) sAg Secretion Inhibitors

As described herein, the term "sAg secretion inhibitor" includes compounds that are capable of inhibiting, either directly or indirectly, the secretion of sAg (S, M and/or L surface antigens) bearing subviral particles and/or DNA containing viral particles from HBV-infected cells. For example, in certain embodiments, the inhibitor detectably inhibits the secretion of sAg as measured, e.g., using assays known in the art or described herein, e.g., ELISA assay or by Western Blot. In certain embodiments, the inhibitor inhibits the secretion of sAg by at least 5%, at least 10%, at least 20%, at least 50%, at least 75%, or at least 90%. In certain embodiments, the inhibitor reduces serum levels of sAg in a patient by at least 5%, at least 10%, at least 20%, at least 50%, at least 75%, or at least 90%.

Reported sAg secretion inhibitors include compounds described in U.S. Pat. No. 8,921,381, as well as compounds described in U.S. Patent Application Publication Nos. US 2015/0087659 and US 2013/0303552, all of which are incorporated herein in their entireties by reference.

In addition, reported sAg secretion inhibitors include, but are not limited to, those generally and specifically described in Int'l Patent Application Publication Nos. WO 2015113990, WO 2015173164, US 2016/0122344, WO 2016107832, WO 2016023877, WO 2016128335, WO 2016177655, WO 2016071215, WO 2017013046, WO 2017016921, WO 2017016960, WO 2017017042, WO 2017017043, WO 2017102648, WO 2017108630, WO 2017114812, WO 2017140821, WO 2018085619, and are incorporated herein in their entirety by reference.

(e) Immunostimulators

The term "immunostimulator" includes compounds that are capable of modulating an immune response (e.g., stimulate an immune response (e.g., an adjuvant)). Immunostimulators include, but are not limited to, polyinosinic:polycytidylic acid (poly I:C) and interferons.

Reported immunostimulators include, but are not limited to, agonists of stimulator of IFN genes (STING) and interleukins. Reported immunostimulators further include, but are not limited to, HBsAg release inhibitors, TLR-7 agonists (such as, but not limited to, GS-9620, RG-7795), T-cell stimulators (such as, but not limited to, GS-4774), RIG-1 inhibitors (such as, but not limited to, SB-9200), and SMAC-mimetics (such as, but not limited to, Birinapant).

(f) Oligomeric Nucleotides

Reported oligomeric nucleotides targeted to the Hepatitis B genome include, but are not limited to, Arrowhead-ARC-520 (see U.S. Pat. No. 8,809,293; and Wooddell et al., 2013, Molecular Therapy 21(5):973-985, all of which incorporated herein in their entireties by reference).

In certain embodiments, the oligomeric nucleotides can be designed to target one or more genes and/or transcripts of the HBV genome. Oligomeric nucleotide targeted to the Hepatitis B genome also include, but are not limited to, isolated, double stranded, siRNA molecules, that each include a sense strand and an antisense strand that is hybridized to the sense strand. In certain embodiments, the siRNA target one or more genes and/or transcripts of the HBV genome.

A synergistic effect may be calculated, for example, using suitable methods such as, for example, the Sigmoid-$E_{max}$ equation (Holford & Schemer, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It should be contemplated that the invention includes each and every one of the synthetic schemes described and/or depicted herein.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

In certain embodiments, a compound of the invention can be prepared, for example, according to the illustrative synthetic methods outlined in Scheme I. Bromide 1-1 can be converted to an activated electrophile, such as but not limited to a Grignard reagent through treatment with magnesium in anhydrous solvent, and then reacted with a substituted (E)-4-oxobut-2-enoate to yield 1-2. Reduction of 1-2 affords 1-3, which phenol group can be alkylated under basic conditions to afford 1-4. Hydrolysis of the ester group affords 1-5, which cyclizes under acidic conditions (using for example polyphoshoric acid or PPA) to afford 1-6. The ketone in 1-6 can be converted to the corresponding imine 1-7, which is then coupled with a dialkyl 2-(alkoxymethylene)malonate to afford the tricylic compound 1-8, or an equivalent ester depending on the malonate ester used. Hydrolysis of the ester in 1-8 under acidic, neutral, or basic conditions affords the acid 1-9, which can be separated into its enantiomers.

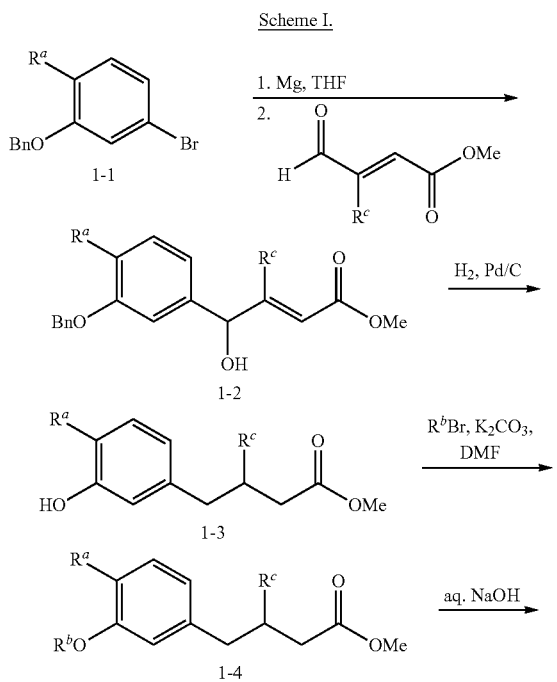

Scheme I.

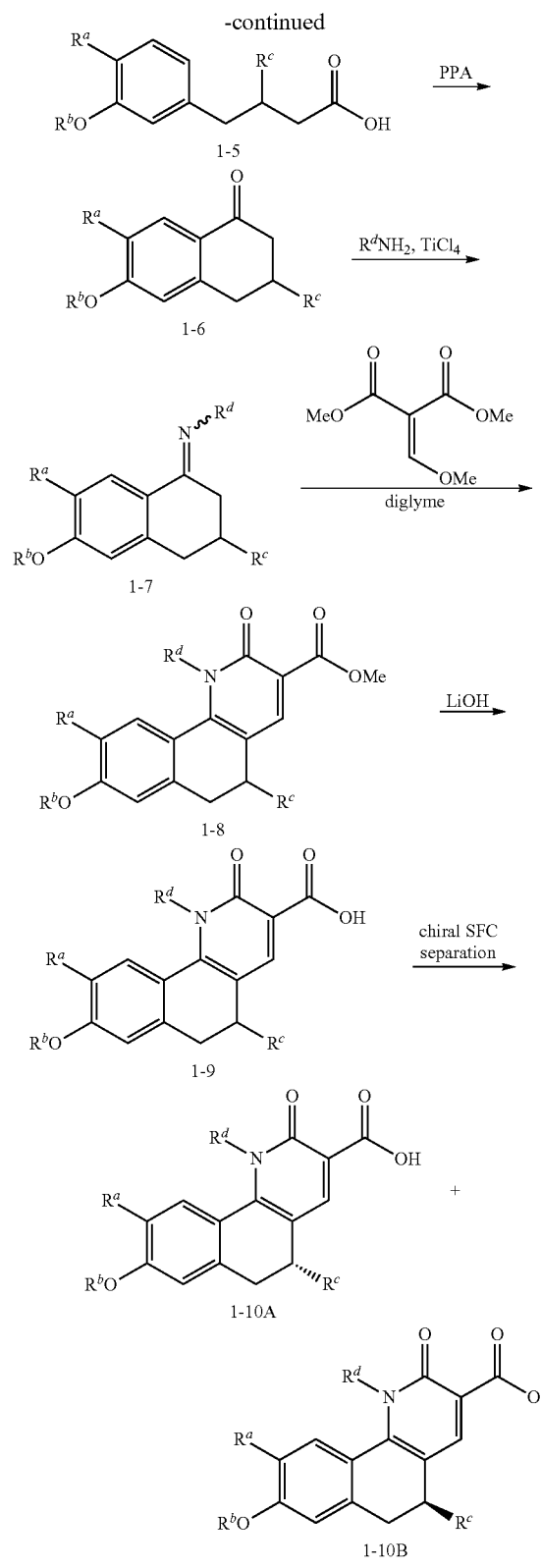

affords 2-3 (or an equivalent ester depending on the acetate ester used), which can be reduced to alcohol 2-4, and then converted to 2-5. Reduction of 2-5 affords 2-6, which can be hydrolyzed to acid 2-7 and then cyclized to 2-8. The ketone in 2-8 can be converted to the corresponding imine 2-9, which is then coupled with a dialkyl 2-(alkoxymethylene) malonate to afford the tricylic compound 2-10 (or an equivalent ester based on the malonate ester used). Removal of the protective benzyl group affords the ester 2-11, which can be converted to acid 2-12, which can be separated into its enantiomers.

Scheme II.

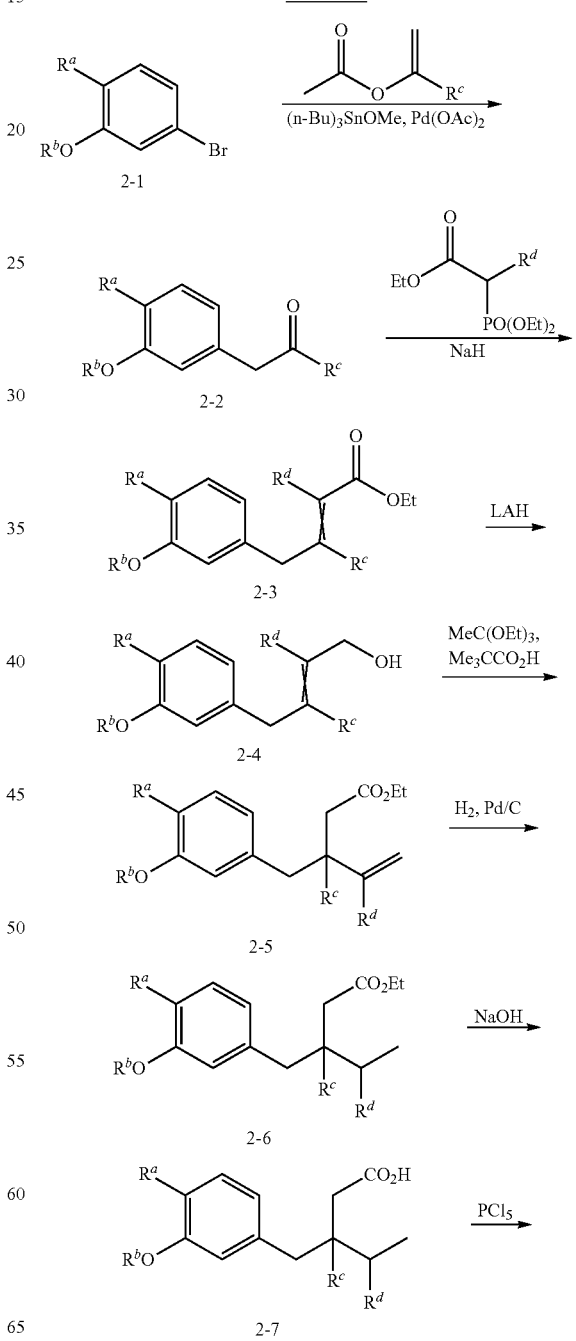

In certain embodiments, a compound of the invention can be prepared, for example, according to the illustrative synthetic methods outlined in Scheme II. Bromide 2-1 can be converted to ketone 2-2 using for example palladium-catalyzed Stille coupling. Reaction of 2-2 with a substituted 2-(dialkoxyphosphoryl)acetate under basic conditions

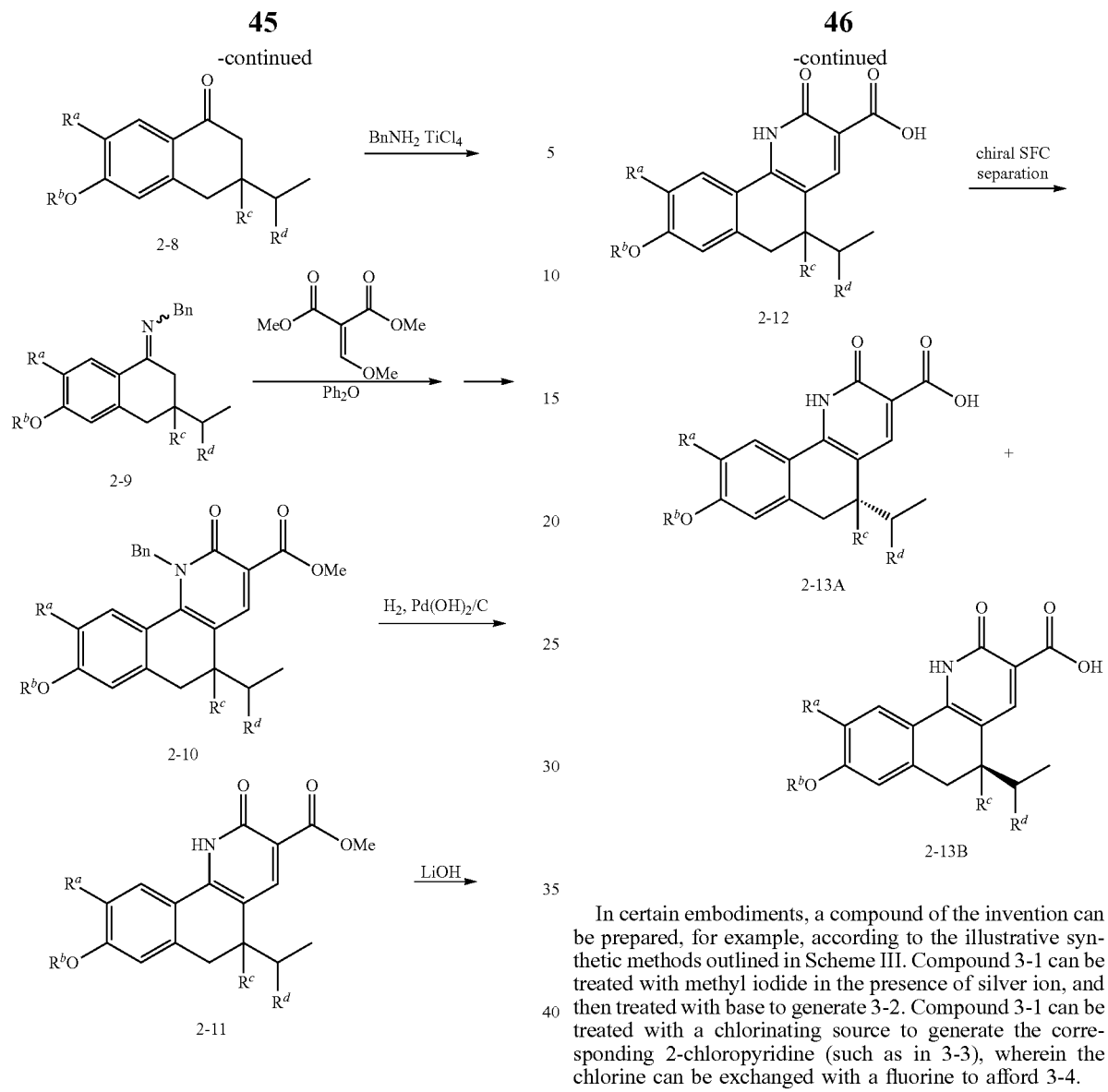

In certain embodiments, a compound of the invention can be prepared, for example, according to the illustrative synthetic methods outlined in Scheme III. Compound 3-1 can be treated with methyl iodide in the presence of silver ion, and then treated with base to generate 3-2. Compound 3-1 can be treated with a chlorinating source to generate the corresponding 2-chloropyridine (such as in 3-3), wherein the chlorine can be exchanged with a fluorine to afford 3-4.

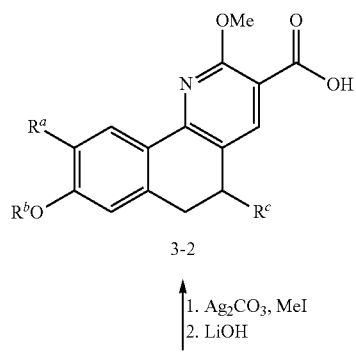

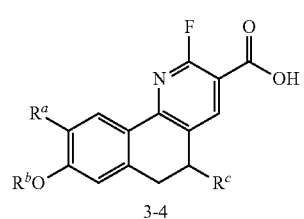 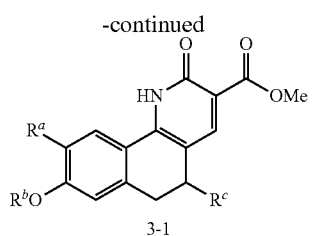 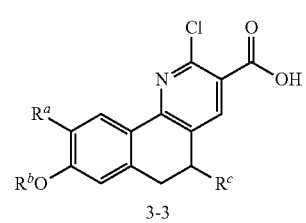

In certain embodiments, a compound of the invention can be prepared, for example, according to the illustrative synthetic methods outlined in Scheme IV. Imine 4-1 can be coupled with a dialkyl 2-(alkoxymethylene)malonate to afford the tricylic compound 4-2, or an equivalent ester based on the malonate ester used. Removal of the protective benzyl group affords the ester 4-3, which can be converted to acid 4-4, which can be separated into its enantiomers.

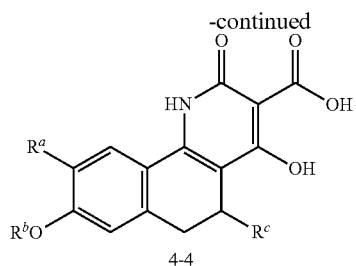

Scheme IV.

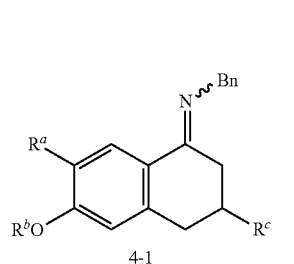

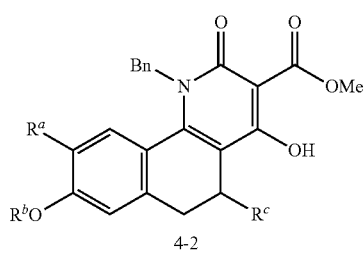

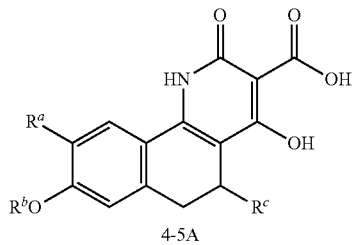

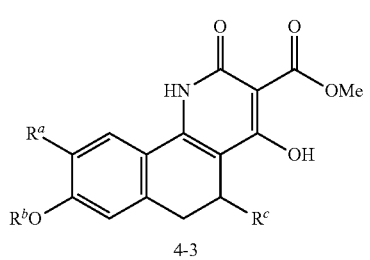

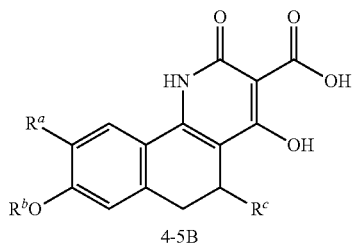

In certain embodiments, a compound of the invention can be prepared, for example, according to the illustrative synthetic methods outlined in Scheme V:

Scheme V.
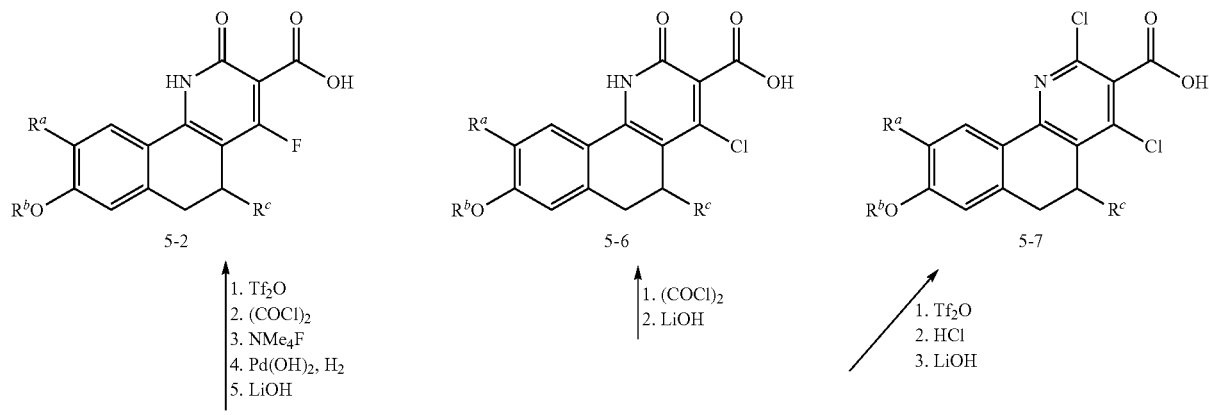
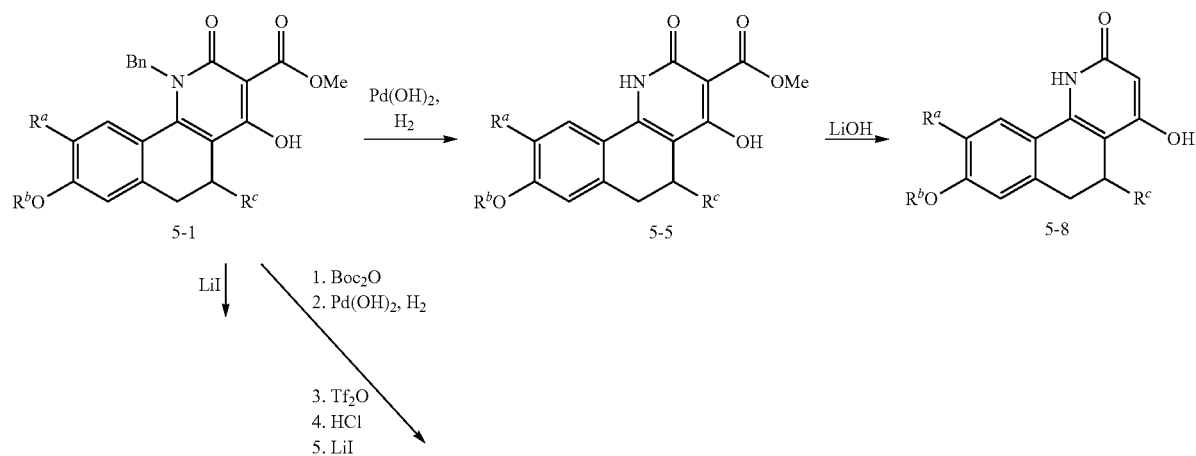
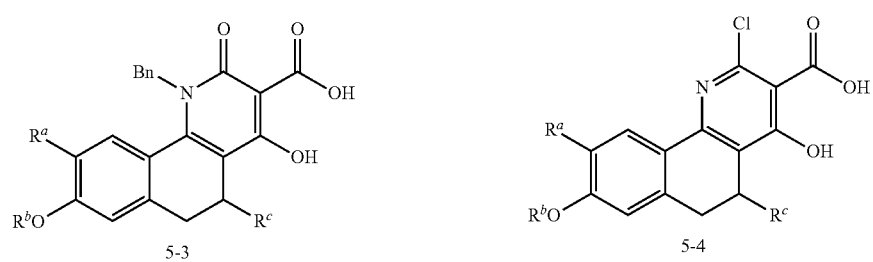

In certain embodiments, a compound of the invention can be prepared, for example, according to the illustrative synthetic methods outlined in Scheme VI. 6-1 can be activated as the corresponding triflate 6-2, and then converted to the corresponding 2-chloropyridine analogue 6-3, which can be hydrolyzed to 6-4 under acidic, neutral, or basic conditions.

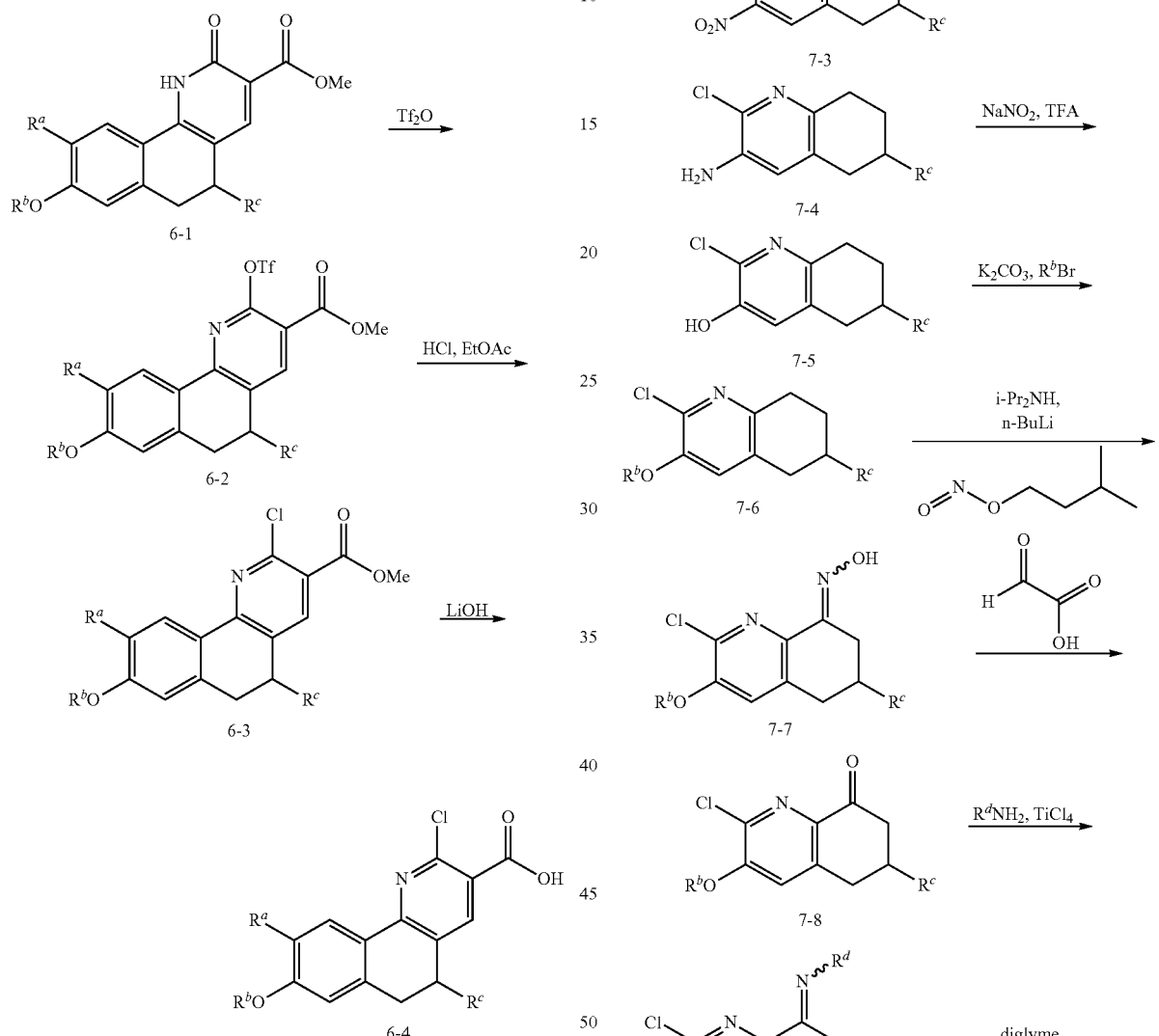

In certain embodiments, a compound of the invention can be prepared, for example, according to the illustrative synthetic methods outlined in Scheme VII.

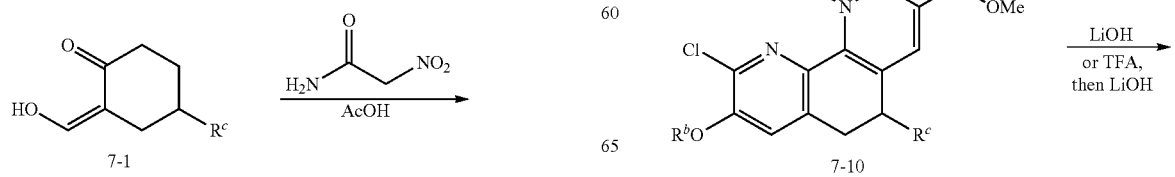

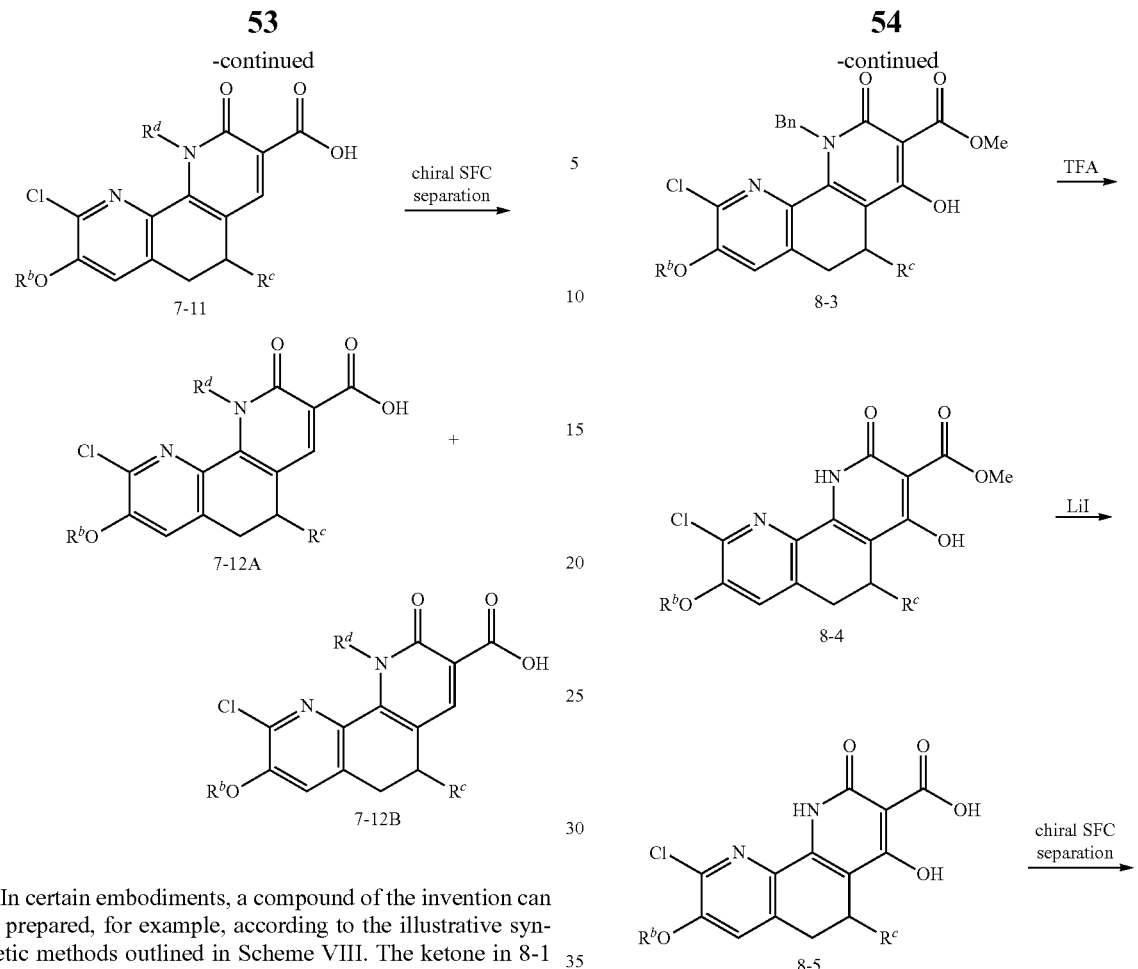

In certain embodiments, a compound of the invention can be prepared, for example, according to the illustrative synthetic methods outlined in Scheme VIII. The ketone in 8-1 can be converted to the corresponding imine 8-2, which is then coupled with a dialkyl 2-(alkoxymethylene)malonate to afford the tricylic compound 8-3, or an equivalent ester based on the malonate ester used. Removal of the protective benzyl group affords the ester 8-4, which can be hydrolyzed to acid 8-5, which can be separated into its enantiomers.

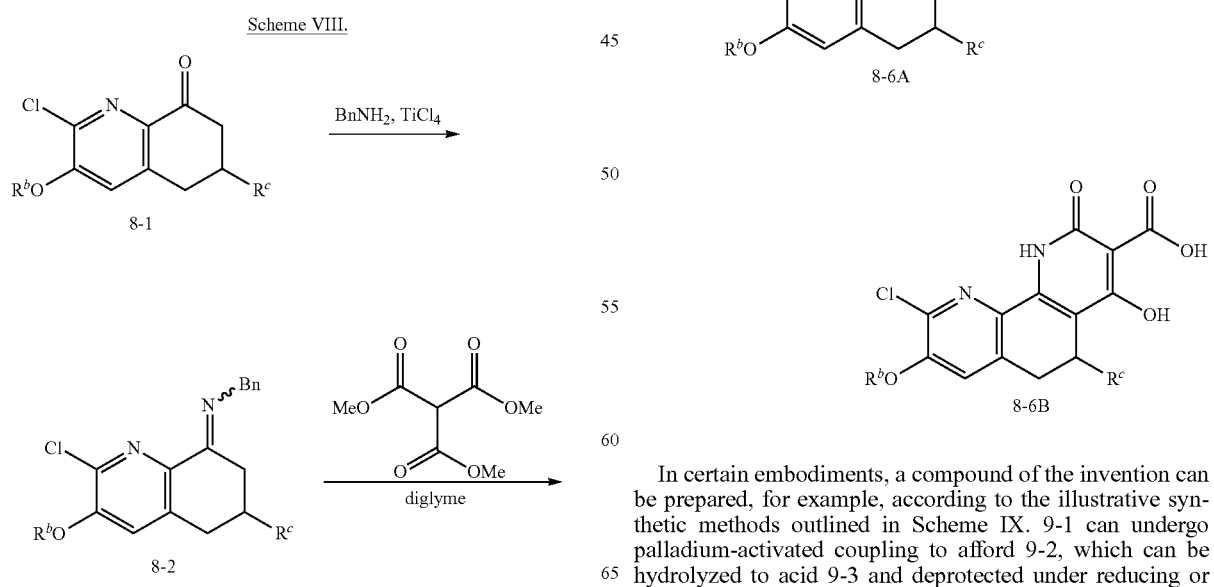

In certain embodiments, a compound of the invention can be prepared, for example, according to the illustrative synthetic methods outlined in Scheme IX. 9-1 can undergo palladium-activated coupling to afford 9-2, which can be hydrolyzed to acid 9-3 and deprotected under reducing or acidic conditions to afford 9-4, which can be separated into its enantiomers.

Scheme IX.

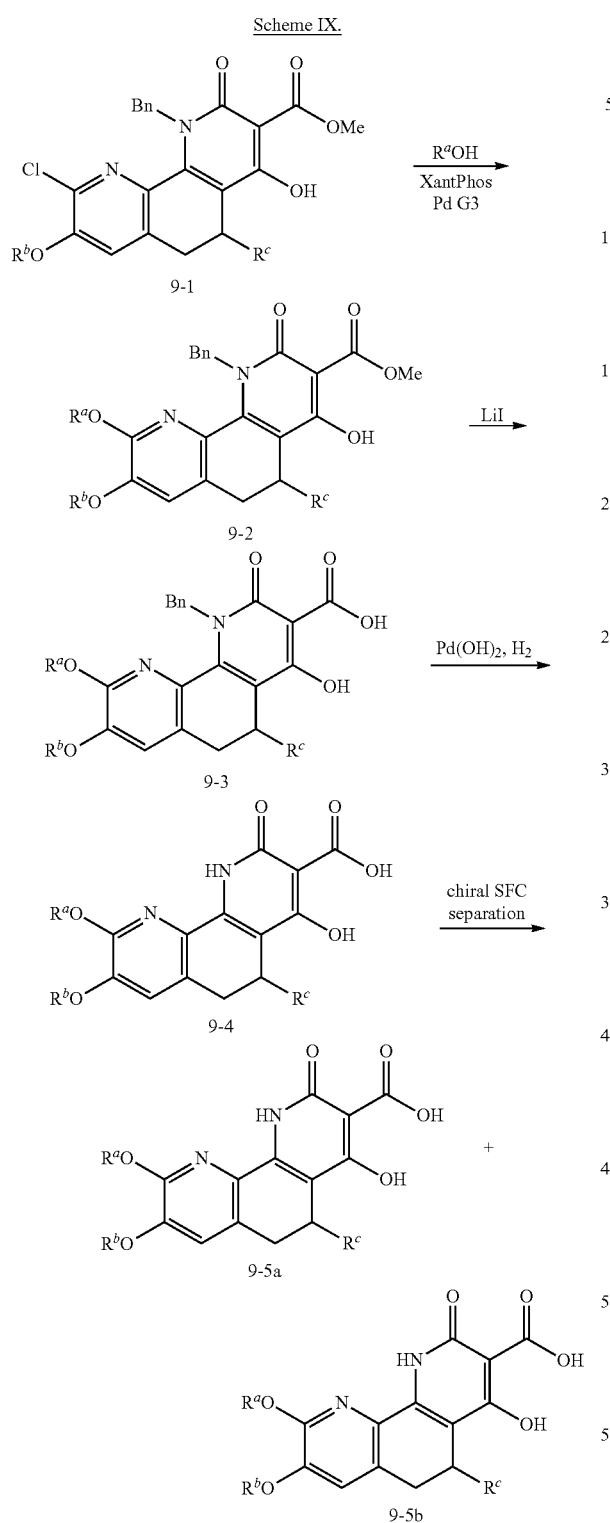

Scheme X.

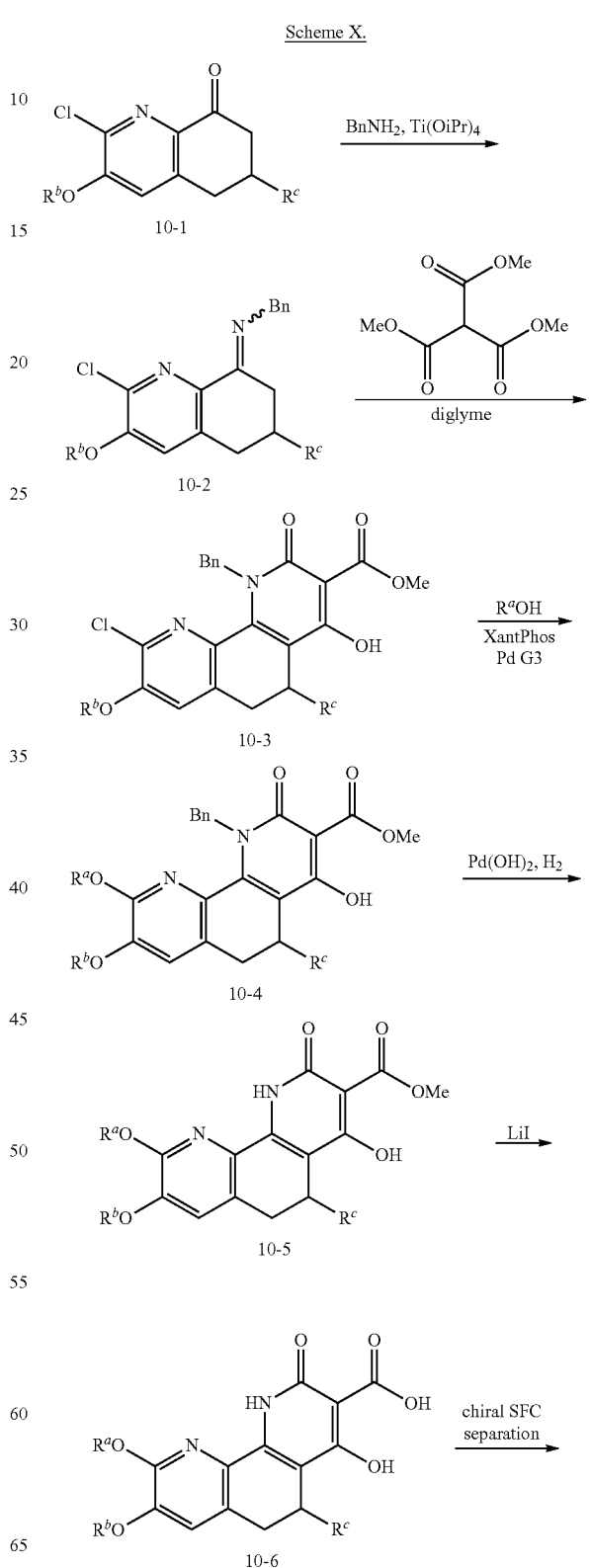

can be deprotected under reducing or acidic conditions to afford 10-5. The ester can be hydrolyzed to the corresponding acid 10-6, which can then be separated in its enantiomers.

In certain embodiments, a compound of the invention can be prepared, for example, according to the illustrative synthetic methods outlined in Scheme X. 10-1 can be converted to imine 10-2, which is then coupled with a dialkyl 2-(alkoxymethylene)malonate to afford 10-3, or any other ester depending of malonate ester used. 10-3 can be subjected to palladium-catalyzed coupling to afford 10-4, which

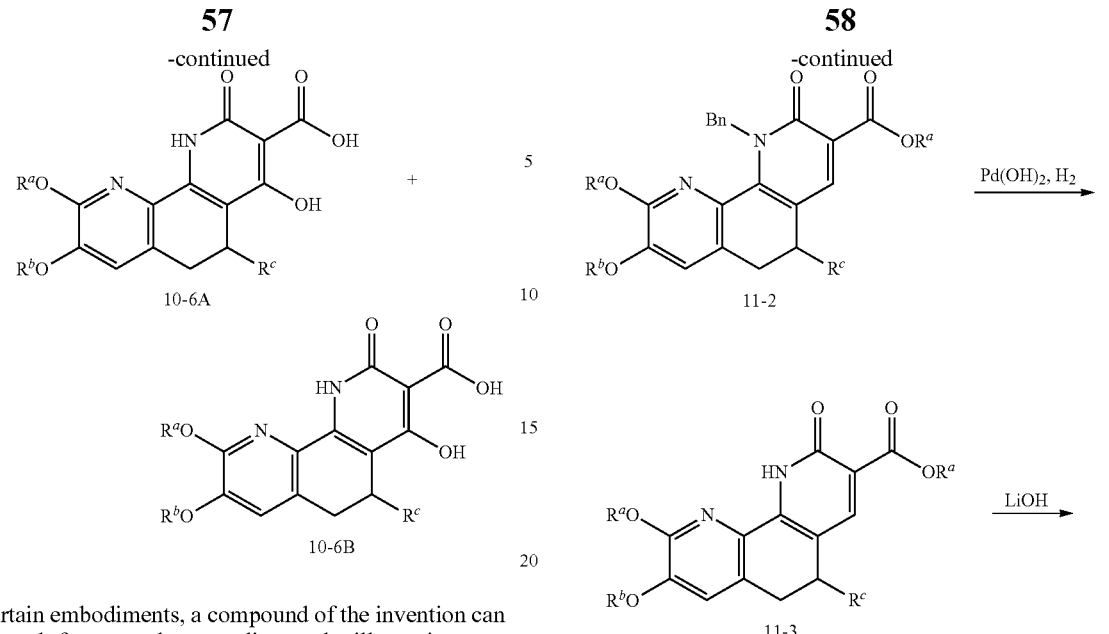

In certain embodiments, a compound of the invention can be prepared, for example, according to the illustrative synthetic methods outlined in Scheme XI. 11-1 can be subjected to palladium-catalyzed coupling to afford 11-2, which can be deprotected under reducing or acidic conditions to afford 11-3. The ester can be hydrolyzed to the corresponding acid 11-4, which can then be separated in its enantiomers.

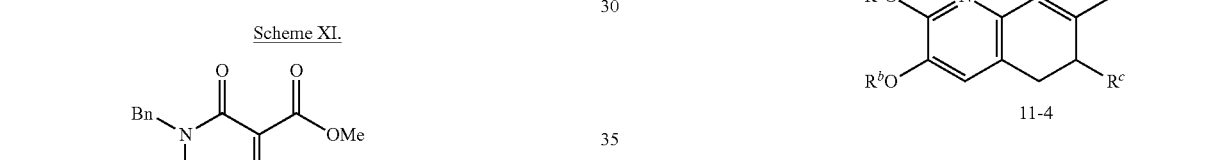

In certain embodiments, a compound of the invention can be prepared, for example, according to the illustrative synthetic methods outlined in Scheme XII. 12-1 can undergo palladium-activated coupling to afford 12-2 or 12-4, which can then be deprotected under reducing or acidic conditions to afford 12-3 or 12-5, respectively.

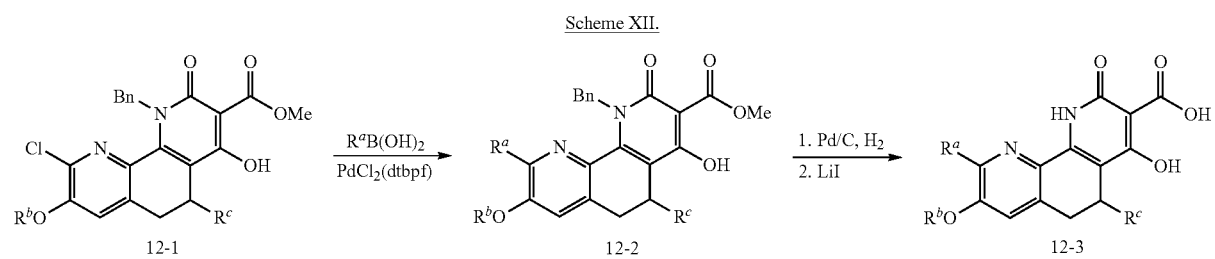

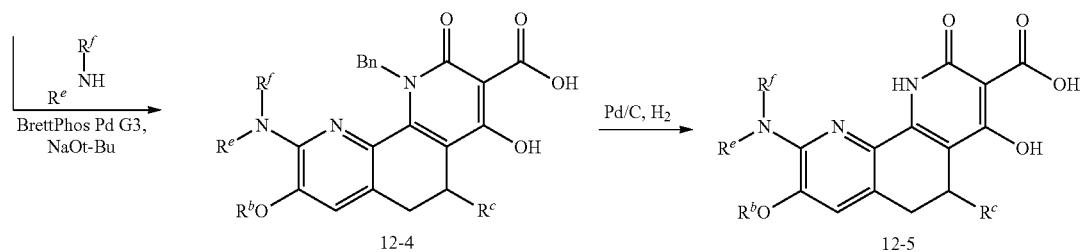

In certain embodiments, a compound of the invention can be prepared, for example, according to the illustrative synthetic methods outlined in Scheme XIII. 13-1 can be converted to the acyl chloride 13-2, which then can be subjected to a cyclization reaction to afford tetrazole 13-3 and can be deprotected to afford 13-4.

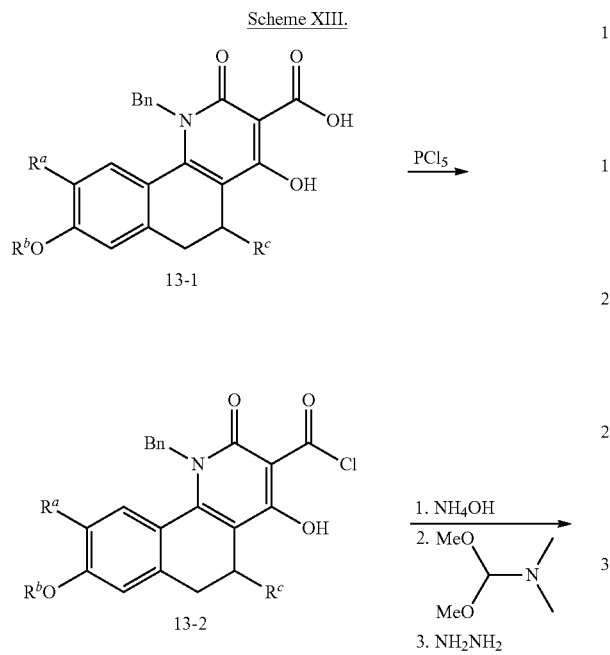

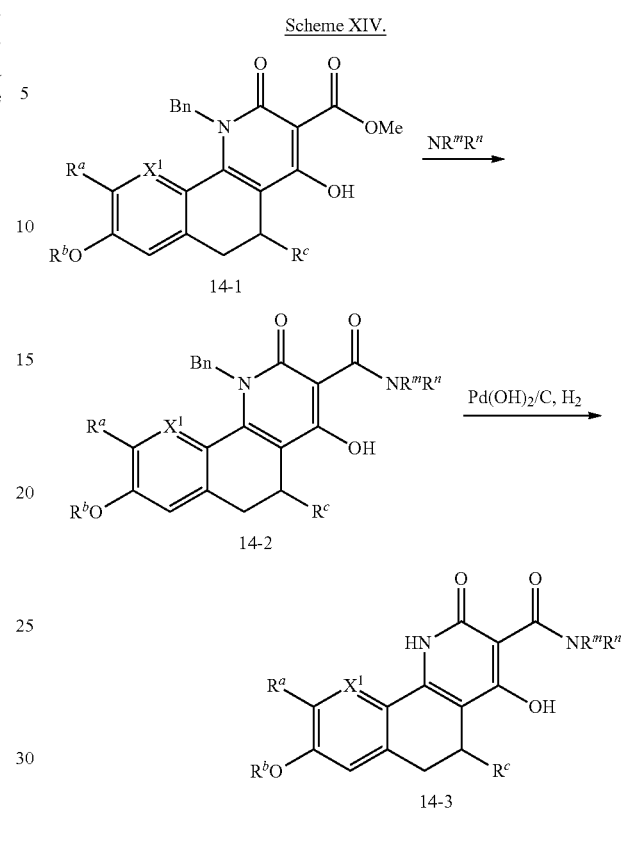

In certain embodiments, a compound of the invention can be prepared, for example, according to the illustrative synthetic methods outlined in Scheme XIV. 14-1 can be treated with an amine to afford 14-2, which can then be deprotected to 14-3.

In certain embodiments, a compound of the invention can be prepared, for example, according to the illustrative synthetic methods outlined in Scheme XV. 15-1 can be treated with a hydroxylamine to afford 15-2, which can then be deprotected to 15-3.

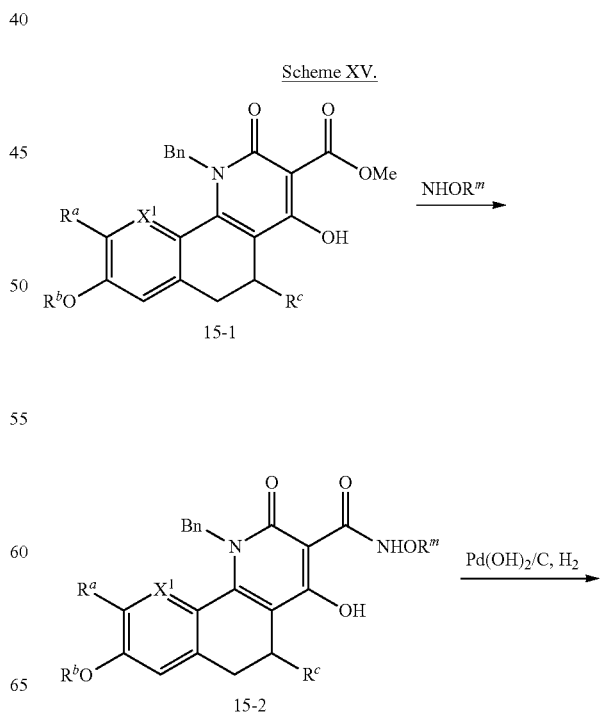

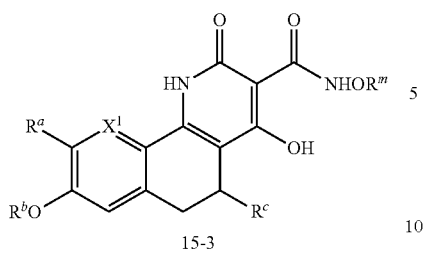

15-3

In certain embodiments, a compound of the invention can be prepared, for example, according to the illustrative synthetic methods outlined in Scheme XVI. 16-1 can be converted to the corresponding triflate derivative 16-2, which then can be converted to the chloride derivative 16-3.

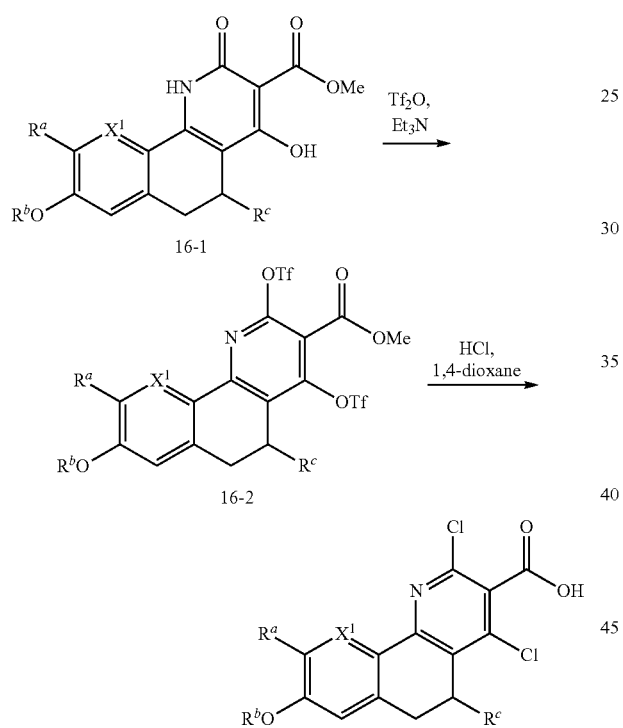

In certain embodiments, a compound of the invention can be prepared, for example, according to the illustrative synthetic methods outlined in Scheme XVII.

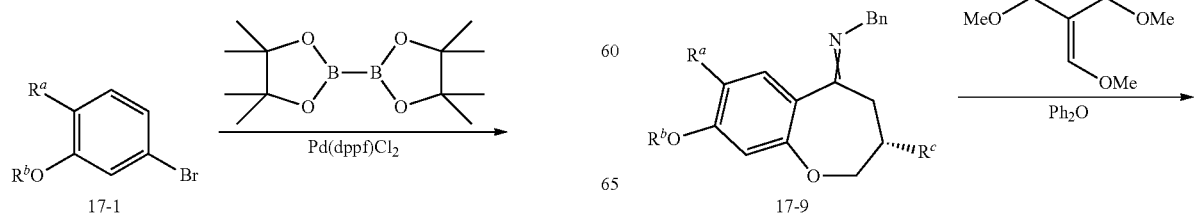

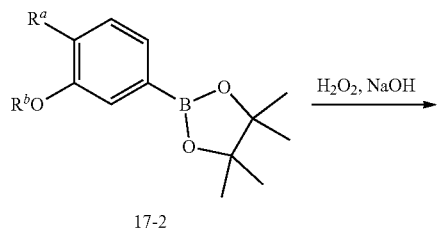

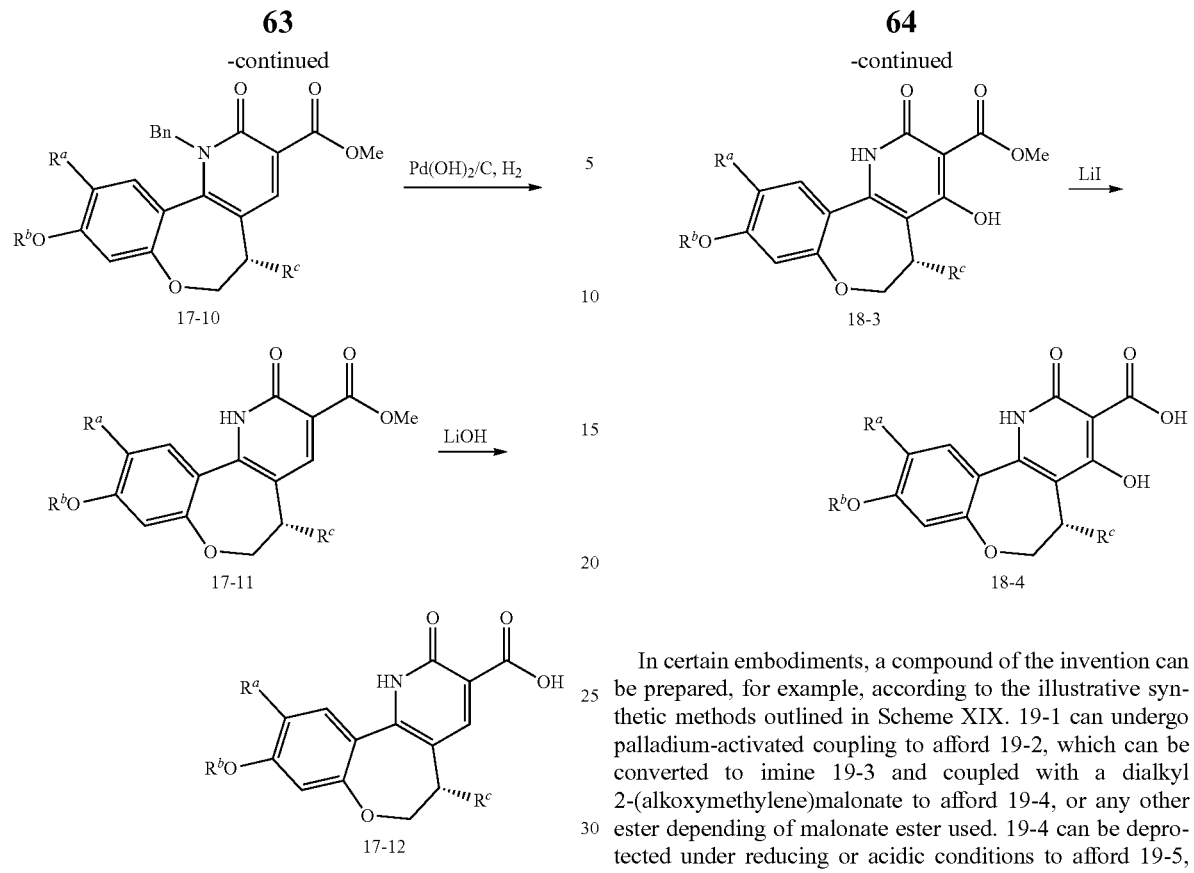

In certain embodiments, a compound of the invention can be prepared, for example, according to the illustrative synthetic methods outlined in Scheme XVIII. 18-1 can be coupled with a dialkyl 2-(alkoxymethylene)malonate to afford 18-2, or any other ester depending of malonate ester used. 18-2 can be deprotected under reducing or acidic conditions to afford 18-3, which can be hydrolyzed to the corresponding acid 18-4.

In certain embodiments, a compound of the invention can be prepared, for example, according to the illustrative synthetic methods outlined in Scheme XIX. 19-1 can undergo palladium-activated coupling to afford 19-2, which can be converted to imine 19-3 and coupled with a dialkyl 2-(alkoxymethylene)malonate to afford 19-4, or any other ester depending of malonate ester used. 19-4 can be deprotected under reducing or acidic conditions to afford 19-5, which can be hydrolyzed to the corresponding acid 19-6.

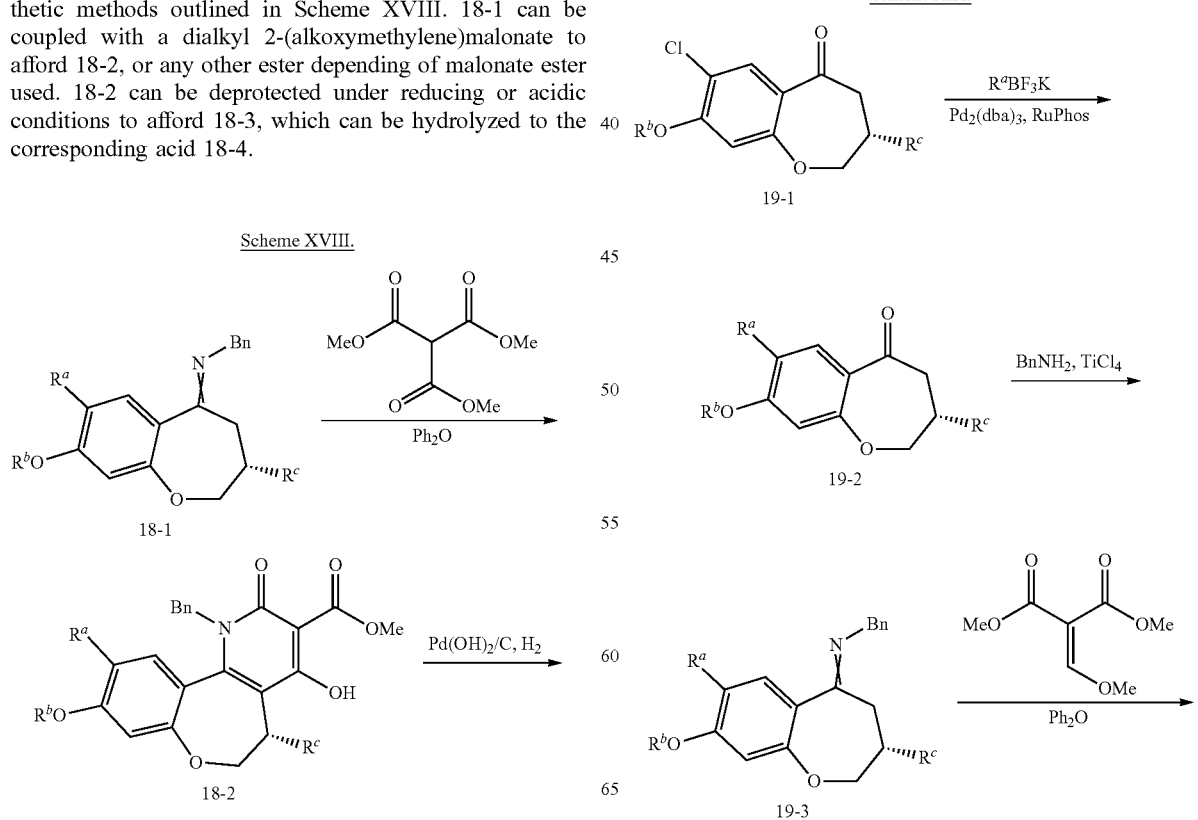

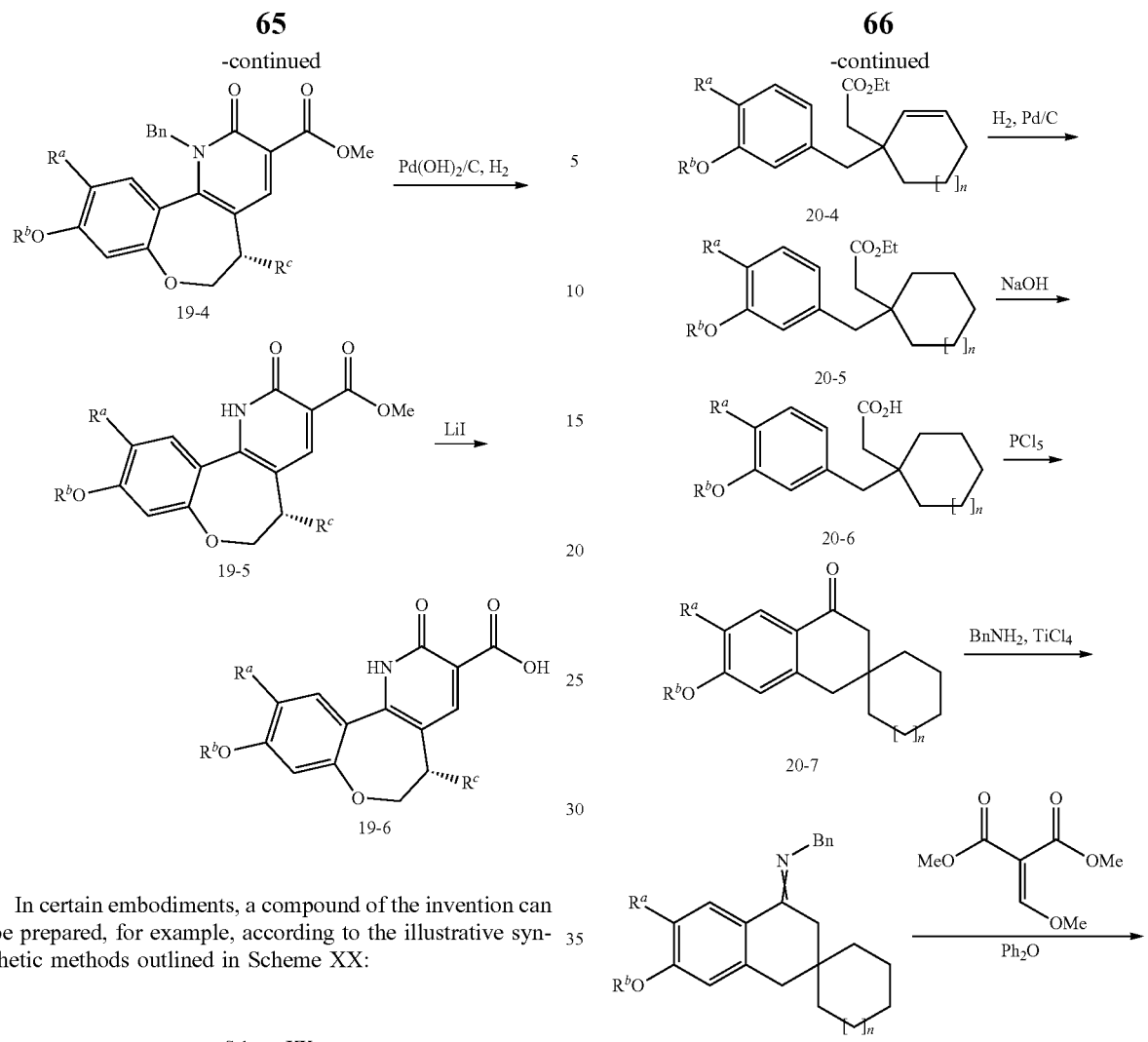
In certain embodiments, a compound of the invention can be prepared, for example, according to the illustrative synthetic methods outlined in Scheme XX:
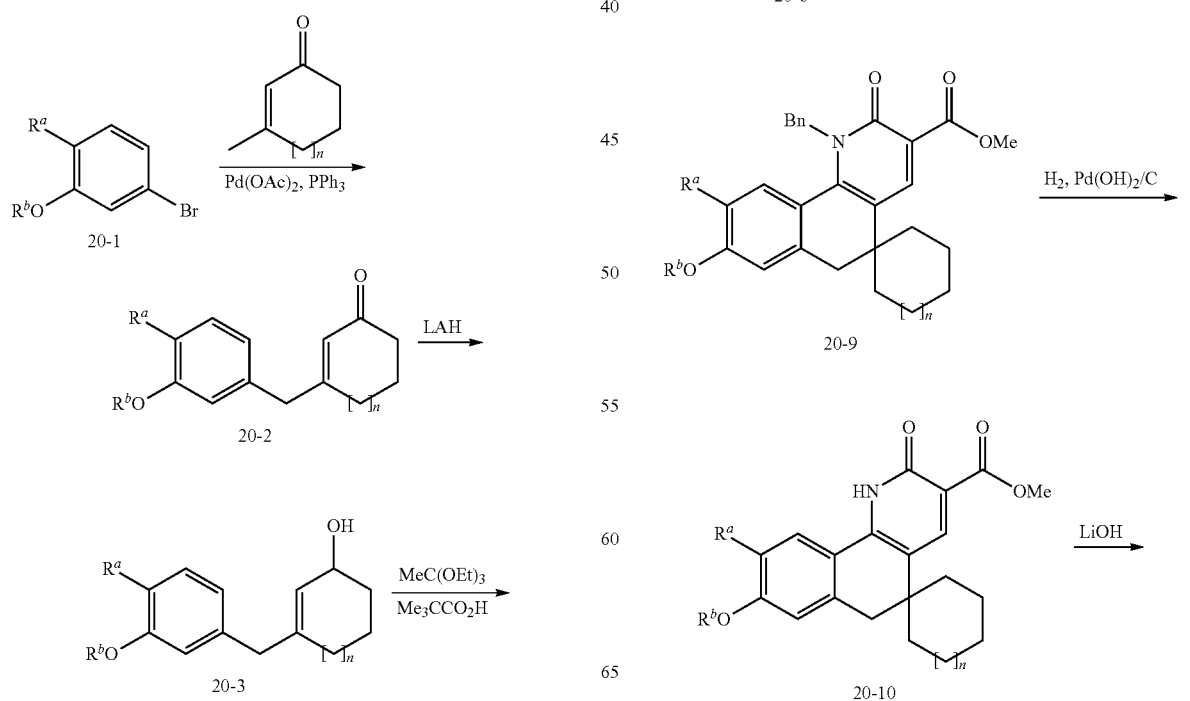

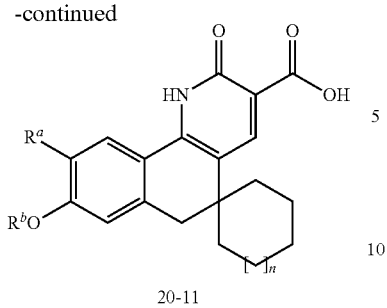
20-11
In certain embodiments, a compound of the invention can be prepared, for example, according to the illustrative synthetic methods outlined in Scheme XXI:
Scheme XXI.
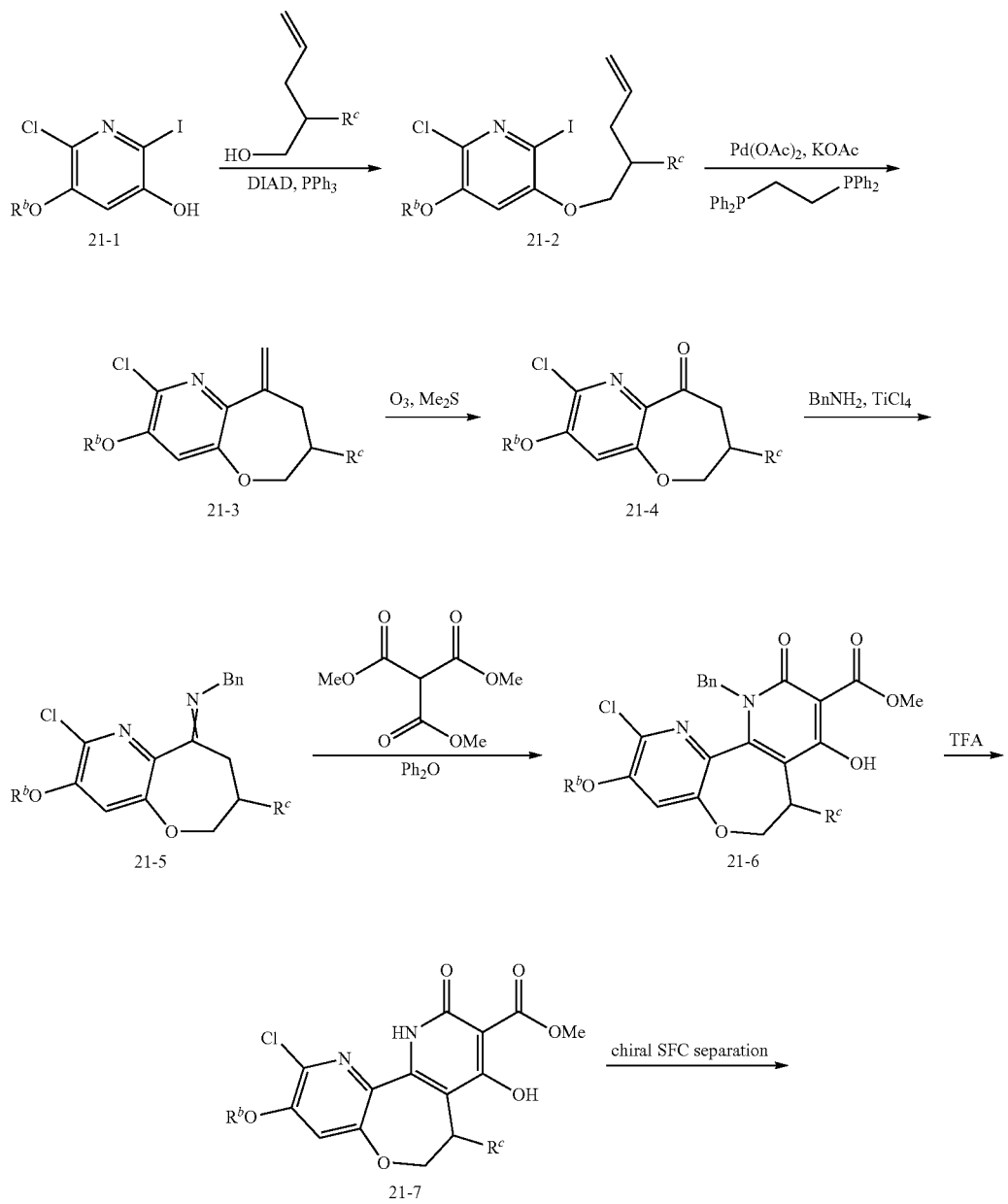

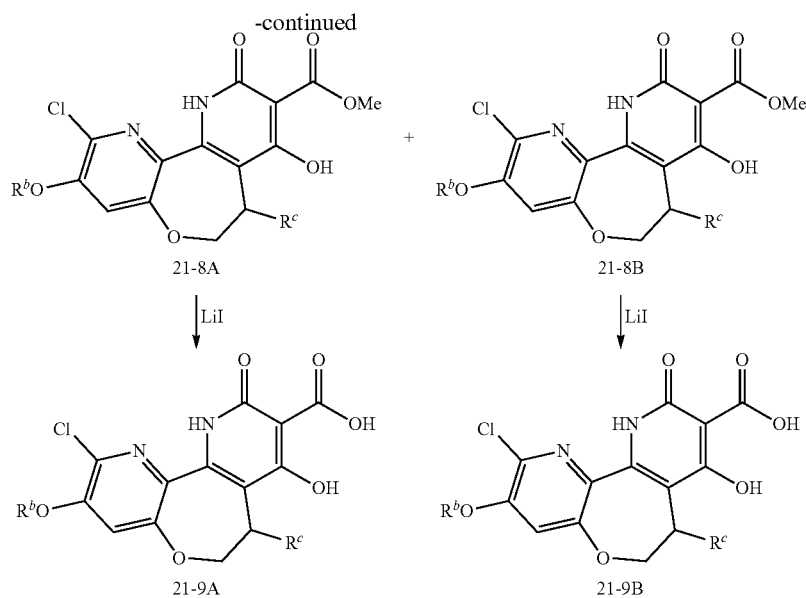

21-8A + 21-8B

↓ LiI    ↓ LiI 21-9A    21-9B

In certain embodiments, a compound of the invention can be prepared, for example, according to the illustrative synthetic methods outlined in Scheme XXII. 22-1 can undergo palladium-activated coupling to afford 22-2, which can be converted to imine 22-3 and coupled with a dialkyl 2-(alkoxymethylene)malonate to afford 22-4, or any other ester depending of malonate ester used. 22-4 can be deprotected under reducing or acidic conditions to afford 22-5, which can be hydrolyzed to the corresponding acid 22-6.

Scheme XXII.

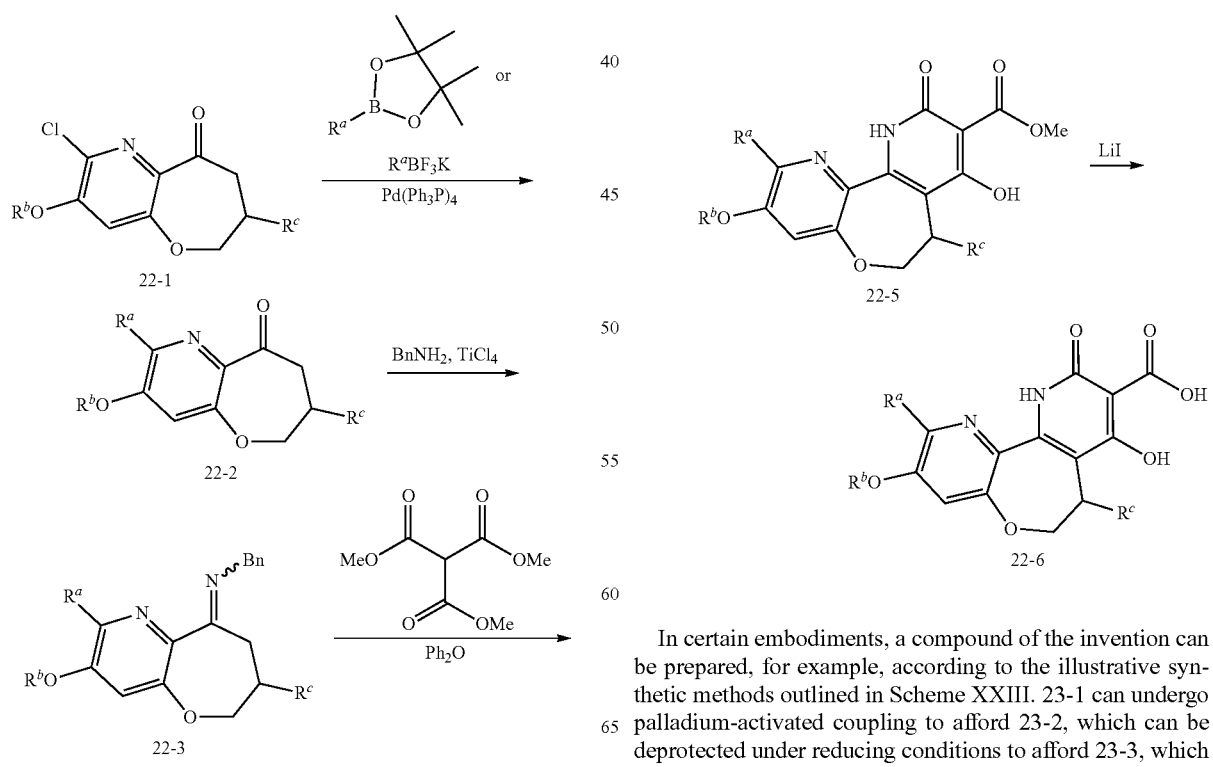

In certain embodiments, a compound of the invention can be prepared, for example, according to the illustrative synthetic methods outlined in Scheme XXIII. 23-1 can undergo palladium-activated coupling to afford 23-2, which can be deprotected under reducing conditions to afford 23-3, which can be hydrolyzed to the corresponding acid 23-4.

Scheme XXIII.
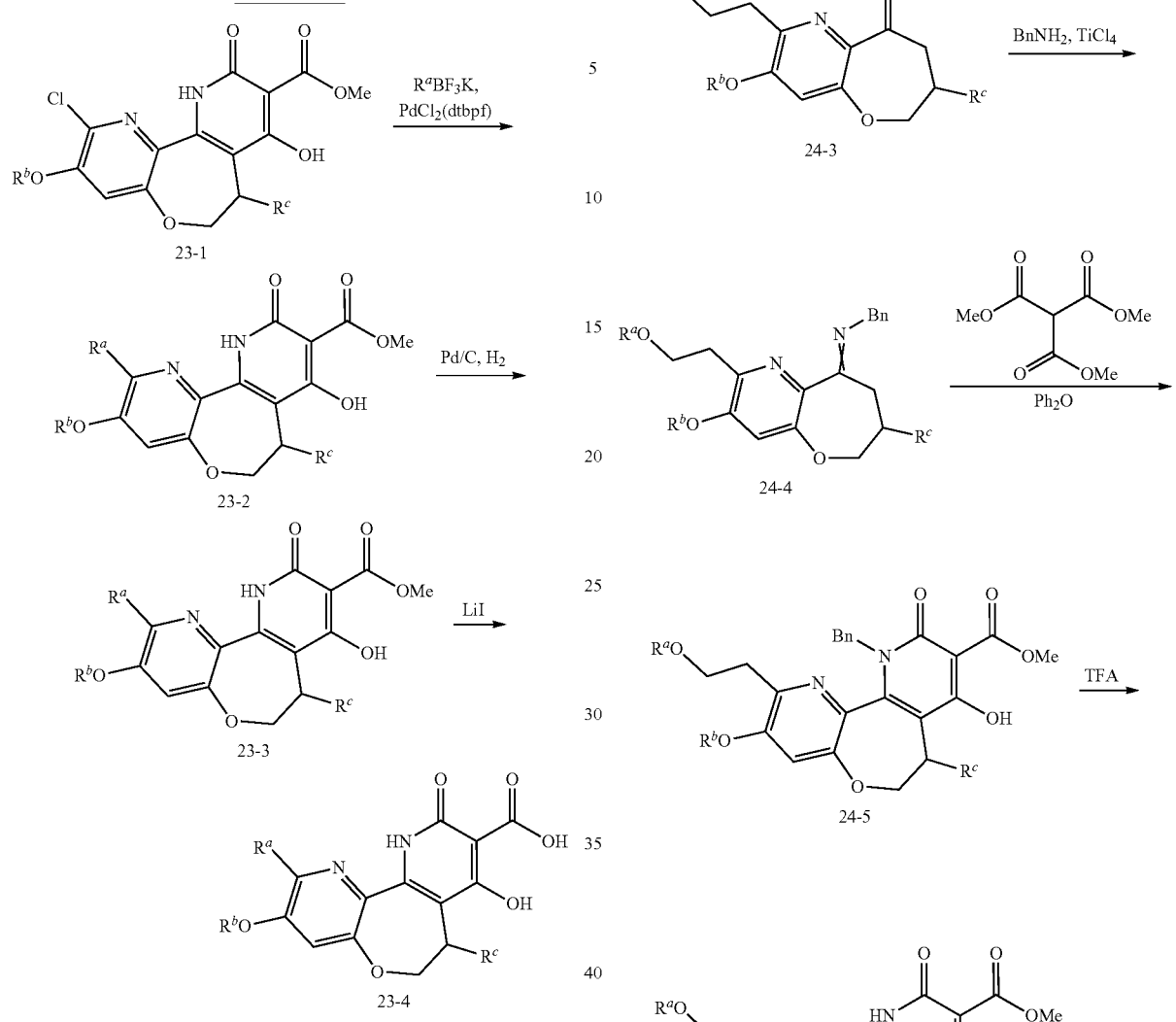
In certain embodiments, a compound of the invention can be prepared, for example, according to the illustrative synthetic methods outlined in Scheme XXIV:
Scheme XXIV.
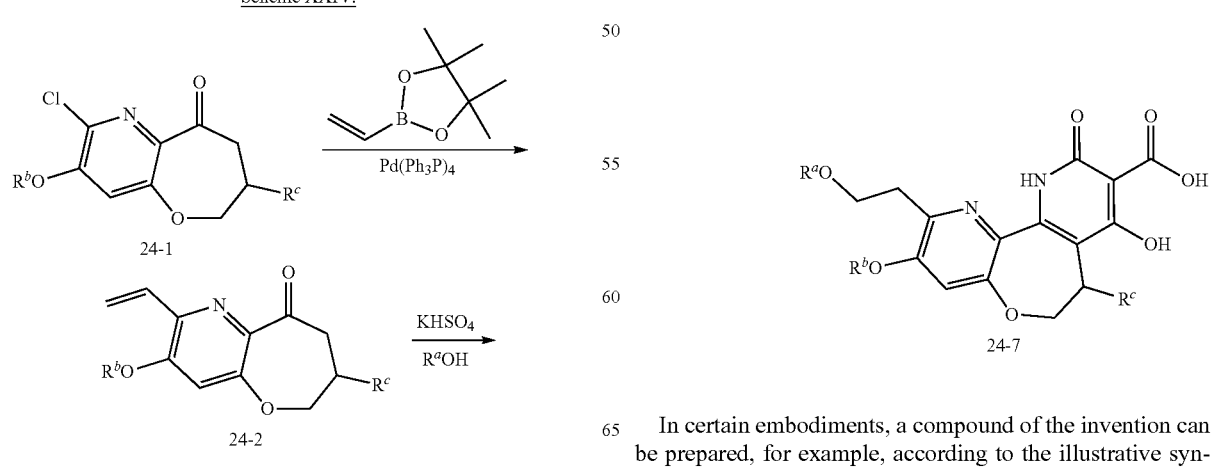
In certain embodiments, a compound of the invention can be prepared, for example, according to the illustrative synthetic methods outlined in Scheme XXV:

Scheme XXV.
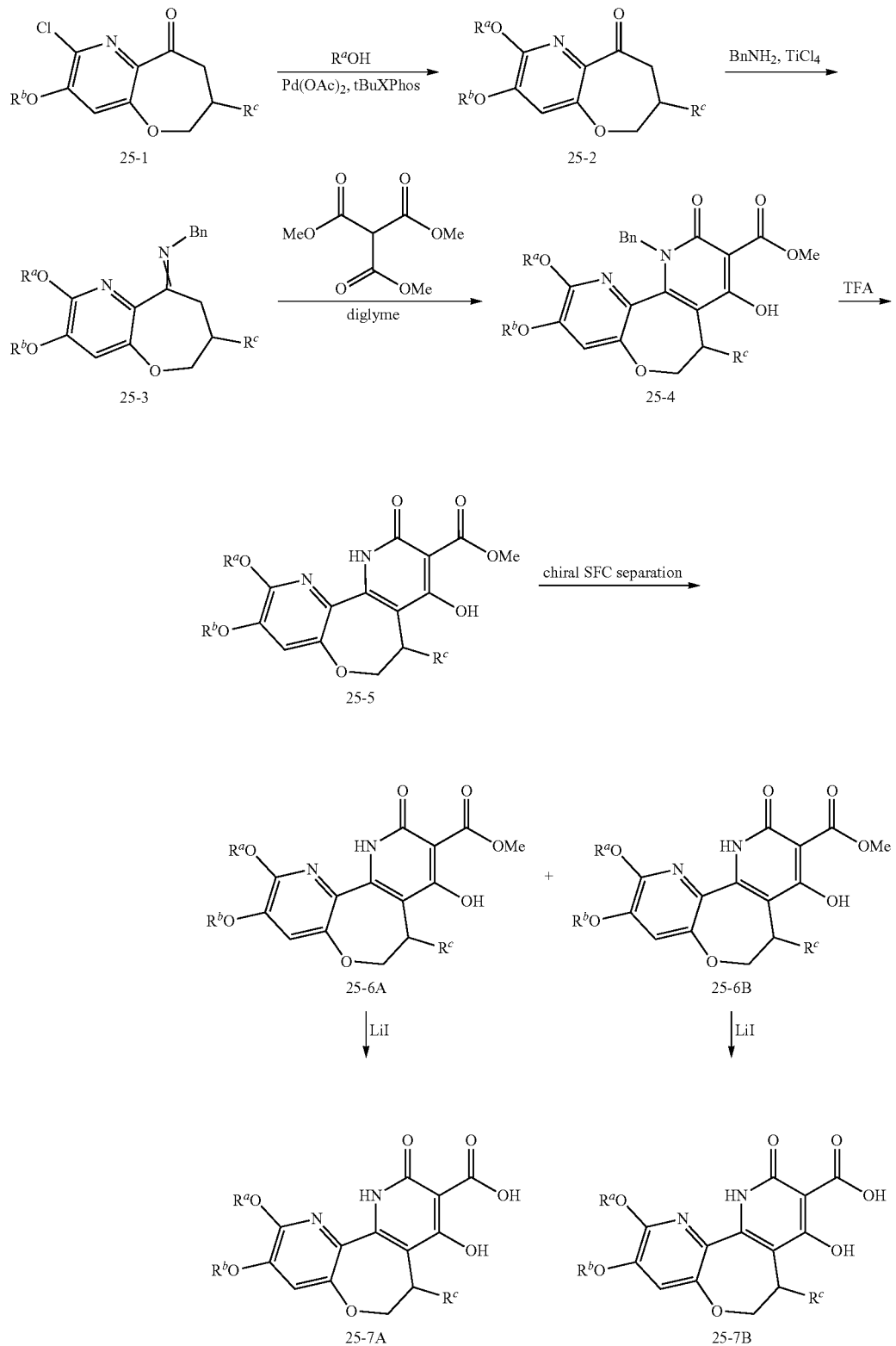
In certain embodiments, a compound of the invention can be prepared, for example, according to the illustrative synthetic methods outlined in Scheme XXVI. 26-1 can be alkylated under basic conditions to afford 26-2, which can be deprotected under reducing conditions to afford 26-3, which can be hydrolyzed to the corresponding acid 26-4.

Scheme XXVI.

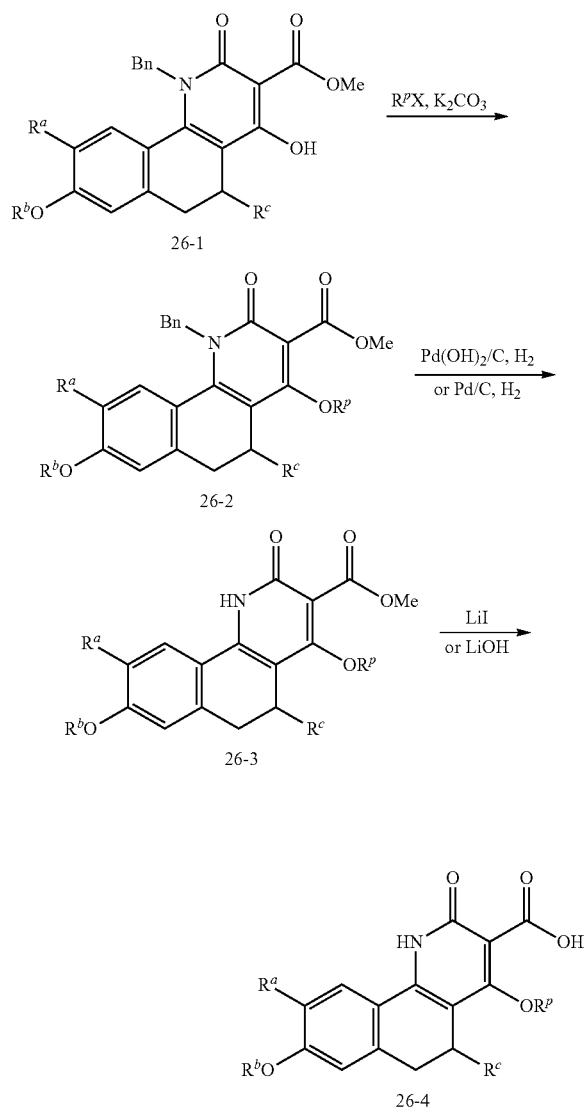

In certain embodiments, a compound of the invention can be prepared, for example, according to the illustrative synthetic methods outlined in Scheme XXVII. 27-1 can be alkylated under basic conditions to afford 27-2, which can be deprotected under reducing conditions to afford 27-3, which can be hydrolyzed to the corresponding acid 27-4.

Scheme XXVII.

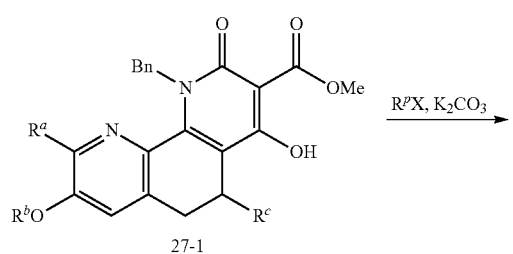

Methods

The invention provides a method of treating or preventing hepatitis virus infection in a subject. In certain embodiments, the infection comprises hepatitis B virus (HBV) infection. In yet other embodiments, the infection comprises hepatitis D virus (HDV) infection. In other embodiments, the method comprises administering to the subject in need thereof a therapeutically effective amount of at least one compound of the invention. In yet other embodiments, the compound of the invention is the only antiviral agent administered to the subject. In yet other embodiments, the at least one compound is administered to the subject in a pharmaceutically acceptable composition. In yet other embodiments, the subject is further administered at least one additional agent useful for treating the hepatitis virus infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer. In yet other embodiments, the subject is co-administered the at least one compound and the at least one additional agent. In yet other embodiments, the at least one compound and the at least one additional agent are coformulated.

The invention further provides a method of inhibiting and/or reducing HBV surface antigen (HBsAg) secretion either directly or indirectly in a subject. The invention further provides a method of reducing or minimizing levels of HBsAg in a HBV-infected subject. The invention further provides a method of reducing or minimizing levels of HBeAg in a HBV-infected subject. The invention further provides a method of reducing or minimizing levels of hepatitis B core protein in a HBV-infected subject. The invention further provides a method of reducing or minimizing levels of pg RNA in a HBV-infected subject.

In certain embodiments, the method comprises administering to the subject in need thereof a therapeutically effective amount of at least one compound of the invention. In other embodiments, the at least one compound is administered to the subject in a pharmaceutically acceptable composition. In yet other embodiments, the compound of the invention is the only antiviral agent administered to the subject. In yet other embodiments, the subject is further administered at least one additional agent useful for treating the hepatitis infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer. In yet other embodiments, the subject is co-administered the at least one compound and the at least one additional agent. In yet other embodiments, the at least one compound and the at least one additional agent are coformulated.

In certain embodiments, the subject is infected with HBV. In other embodiments, the subject is infected with HDV. In yet other embodiments, the subject is infected with HBV and HDV.

In certain embodiments, the subject is a mammal. In other embodiments, the mammal is a human.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or some combination of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalation, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically derived or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

The following procedures can be utilized in preparing and/or testing exemplary compounds of the invention.

As described herein, "enantiomer I" refers to the first enantiomer eluded from the chiral column under the specific chiral analytical conditions detailed for examples provided elsewhere herein; and "enantiomer II" refers to the second enantiomer eluded from the chiral column under the specific chiral analytical conditions detailed for examples provided elsewhere herein. Such nomenclature does not imply or impart any particular relative and/or absolute configuration for these compounds.

Example 1: 5-Isopropyl-9-methoxy-8-(3-methoxypropoxy)-2-oxo-1H,5H,6H-benzo[h]quinoline-3-carboxylic acid

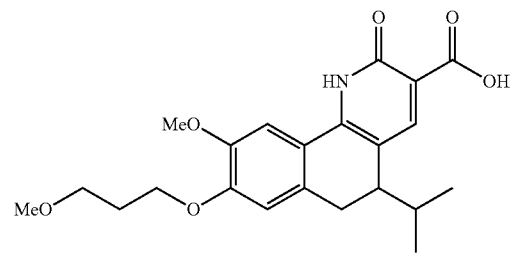 [SMILES: COCCCOc1cc2c(cc1OC)-c1[nH]c(=O)c(C(=O)O)cc1C(C(C)C)C2]

(E)-Methyl 3-((3-(benzyloxy)-4-methoxyphenyl)(hydroxy)methyl)-4-methylpent-2-enoate

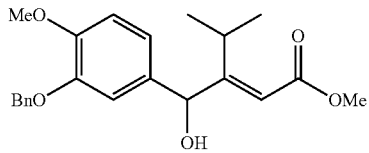 [SMILES: COC(=O)/C=C(\C(C)C)C(O)c1ccc(OC)c(OCc2ccccc2)c1]

To Mg metal (2.45 g, 101 mmol) in THF (30 mL) was added iodine (50 mg, 0.2 mmol), and the mixture was heated to 70° C. followed by the dropwise addition of 2-(benzyloxy)-4-bromo-1-methoxybenzene (30 g, 100 mmol) in THF (150 mL). The mixture was stirred for 2 h at 70° C. and then allowed to cool to room temperature and used in the next step. To a stirred solution of methyl-3-formyl-4-methylpent-2-enoate (17.5 g, 113 mmol, prepared according to the procedure by Sylvain, et al., 1987, J. Org. Chem. 52:4788) in THF (150 mL) at 0° C. was added dropwise the Grignard reagent prepared in the step above. The mixture was stirred at 0° C. for 1 h. The reaction mixture was quenched with saturated aqueous ammonium chloride solution (100 mL) and extracted with EtOAc (2×100 mL). The combined organic fractions were dried over anhydrous sodium sulfate and concentrated under vacuum. The crude oil was purified by normal phase $SiO_2$ chromatography (0 to 40% EtOAc in hexanes) to give (E)-methyl 3-((3-(benzyloxy)-4-methoxyphenyl)(hydroxy)methyl)-4-methylpent-2-enoate as a yellow oil (20 g, 53% yield). $^1$H NMR (400 MHz, $CDCl_3$) δ 7.41-7.39 (m, 2H), 7.34-7.27 (m, 3H), 6.93-6.90 (m, 1H), 6.86-6.84 (m, 2H), 6.19 (s, 1H), 5.23 (s, 1H), 5.19-5.11 (m, 2H), 3.88 (s, 3H), 3.74 (m, 3H), 3.60-3.53 (m, 1H), 1.73 (s, 1H), 1.05 (d, J=7.0 Hz, 3H), 0.66 (d, J=7.0 Hz, 3H).

Methyl 3-(3-hydroxy-4-methoxybenzyl)-4-methylpentanoate

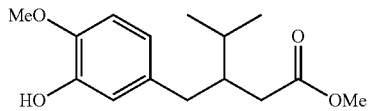

A mixture of (E)-methyl 3-((3-(benzyloxy)-4-methoxyphenyl)(hydroxy)methyl)-4-methylpent-2-enoate (20 g, 50 mmol) and palladium on carbon (10% on carbon, 2.7 g, 2.5 mmol) was stirred in MeOH (120 mL) under an atmosphere of hydrogen gas at 50 psi for 20 h. The mixture was then filtered through CELITE®, washed with MeOH (2×50 mL), and concentrated under vacuum. The crude oil was purified by normal phase $SiO_2$ chromatography (0-30% EtOAc/hexanes) to give methyl 3-(3-hydroxy-4-methoxybenzyl)-4-methylpentanoate as a colourless oil (9.7 g, 68% yield, m/z: 265 [M-H]$^-$ observed). $^1$H NMR (400 MHz, $CDCl_3$): δ 6.79-6.70 (m, 2H), 6.65-6.60 (m, 1H), 5.53 (s, 1H), 3.86 (s, 3H), 3.60 (s, 3H), 2.60-2.55 (m, 1H), 2.37-2.24 (m, 2H), 2.18-2.08 (m, 2H), 1.76-1.68 (m, 1H), 0.91-0.87 (m, 6H).

Methyl 3-(4-methoxy-3-(3-methoxypropoxy)benzyl)-4-methylpentanoate

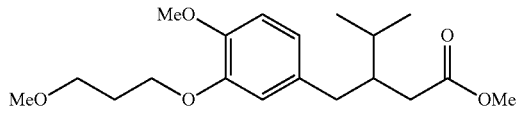 [SMILES: COCCCOc1cc(CC(CC(=O)OC)C(C)C)ccc1OC]

To a stirred solution of methyl 3-(3-hydroxy-4-methoxybenzyl)-4-methylpentanoate (9.7 g, 36 mmol) in acetonitrile (100 mL) was added anhydrous potassium carbonate (10 g, 73 mmol) followed by the dropwise addition of 1-bromo-3-methoxy propane (4.9 mL, 44 mmol) at room temperature. The resulting mixture was heated to 60° C. for 15 h. The reaction mixture was concentrated under reduced pressure, and water (150 mL) was added. The mixture was extracted with EtOAc (2×100 mL), washed with water (100 mL), saturated aqueous brine solution (100 mL), dried over anhydrous sodium sulfate, and then concentrated under reduced pressure to give methyl 3-(4-methoxy-3-(3-methoxypropoxy)benzyl)-4-methylpentanoate as yellow oil, which was used without further purification (11.8 g, 96% yield, m/z: 361 [M+Na]$^+$ observed). $^1$H NMR (400 MHz, $CDCl_3$): δ 6.78-6.68 (m, 3H), 4.10 (t, J=6.4 Hz, 2H), 3.83 (s, 3H), 3.58-3.56 (m, 5H), 3.36 (s, 3H), 2.63-2.58 (m, 1H), 2.40-2.34 (m, 1H), 2.29-2.24 (m, 1H), 2.18-2.04 (m, 4H), 1.75-1.71 (m, 1H), 0.92-0.88 (m, 6H).

3-(4-Methoxy-3-(3-methoxypropoxy)benzyl)-4-methylpentanoic acid

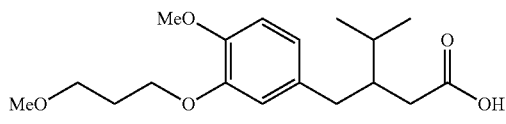 [SMILES: COCCCOc1cc(CC(CC(=O)O)C(C)C)ccc1OC]

To a stirred solution of methyl 3-(4-methoxy-3-(3-methoxypropoxy)benzyl)-4-methylpentanoate (11.8 g, 34.9 mmol) in MeOH (50 mL) was added a solution of NaOH (4.3 g, 110 mmol) in water (70 mL) dropwise at 0° C. The reaction mixture was warmed up to room temperature and stirred for 16 hours. The mixture was diluted with water (25 mL) and washed with tert-butyl methyl ether (2×50 mL). The pH of the aqueous layer was adjusted to 5 using 1N HCl and extracted with EtOAc (2×100 mL). The combined organic layers were washed with saturated brine solution (50 mL), dried over saturated sodium sulfate, and concentrated under vacuum to give 3-(4-methoxy-3-(3-methoxypropoxy)benzyl)-4-methylpentanoic acid as yellow oil, which was used without further purification (11 g, 97% yield, m/z: 323 [M-H]$^-$ observed). The crude was used in the next reaction without further purification. $^1$H NMR (400 MHz, $CDCl_3$): δ 6.78-6.69 (m, 3H), 4.10 (t, J=6.2 Hz, 2H), 3.82 (s, 3H), 3.58 (t, J=6. Hz, 2H), 3.35 (s, 3H), 2.65-2.60 (m, 1H), 2.42-2.37 (m, 1H), 3.32-2.27 (m, 1H), 2.21-2.15 (m, 1H), 2.12-2.04 (m, 3H), 1.79-1.74 (m, 1H), 0.93-0.90 (m, 6H).

3-Isopropyl-7-methoxy-6-(3-methoxypropoxy)-3,4-dihydronaphthalen-1(2H)-one

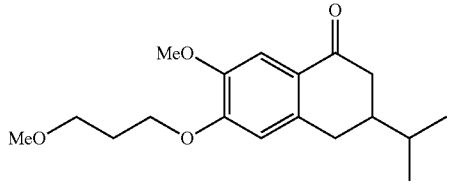 [SMILES: COCCCOc1cc2c(cc1OC)C(=O)CC(C(C)C)C2]

To 3-(4-methoxy-3-(3-methoxypropoxy)benzyl)-4-methylpentanoic acid (11 g, 34 mmol) was added polyphosphoric acid (50 g, 510 mmol). The resultant reaction mixture was heated to 60° C. for 6 h. The mixture was diluted with ice water (200 mL) and extracted with EtOAc (2×75 mL). The combined organic layers were washed with saturated aqueous sodium bicarbonate solution (100 mL), water (50 mL), saturated aqueous brine solution (50 mL), dried over anhydrous sodium sulfate and concentrated under reduced pressure. The crude was purified by normal phase $SiO_2$ chromatography (0-20% EtOAc/hexanes) to give 3-isopropyl-7-methoxy-6-(3-methoxypropoxy)-3,4-dihydronaphthalen-1(2H)-one as a yellow oil (8.3 g, 80% yield, m/z: 307 [M+H]$^+$ observed). $^1$H NMR (400 MHz, CDCl$_3$): δ 7.47 (s, 1H), 6.71 (s, 1H), 4.17 (t, J=6.8 Hz, 2H), 3.88 (s, 3H), 3.56 (t, J=6.0 Hz, 2H), 3.35 (s, 3H), 2.87-2.83 (m, 1H), 2.71-2.64 (m, 2H), 2.32-2.24 (m, 1H), 2.16-2.10 (m, 2H), 1.96-1.94 (m, 1H), 1.68-1.63 (m, 1H), 0.98-0.96 (m, 6H).

N-(tert-Butyl)-3-isopropyl-7-methoxy-6-(3-methoxypropoxy)-3,4-dihydronaphthalen-1(2H)-imine

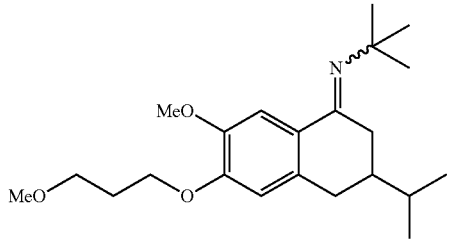 [SMILES: COCCCOc1cc2c(cc1OC)C(=NC(C)(C)C)CC(C(C)C)C2]

To a solution of 3-isopropyl-7-methoxy-6-(3-methoxypropoxy)-3,4-dihydro-2H-naphthalen-1-one (600 mg, 2 mmol) in anhydrous dichloromethane (2 mL) was added tert-butylamine (1 mL, 9.8 mmol). The solution was cooled to 0° C. Titanium tetrachloride (1M solution in dichloromethane, 2 mL, 2 mmol) was added dropwise over 15 min at 0° C. The reaction was warmed up to room temperature and stirred for 16 hours. The reaction mixture was filtered through a cotton plug and concentrated under reduced pressure to give N-(tert-butyl)-3-isopropyl-7-methoxy-6-(3-methoxypropoxy)-3,4-dihydronaphthalen-1(2H)-imine which was used without further purification (0.71 g, 100% yield, m/z: 362 [M+H]$^+$ observed).

Methyl 5-isopropyl-9-methoxy-8-(3-methoxypropoxy)-2-oxo-1,2,5,6-tetrahydrobenzo[h]quinoline-3-carboxylate

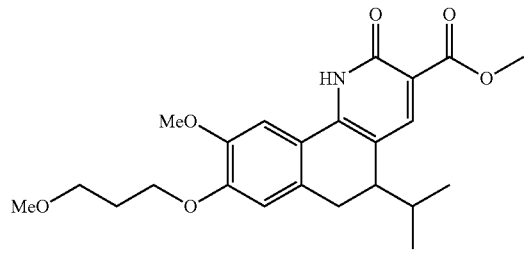 [SMILES: COCCCOc1cc2c(cc1OC)-c1[nH]c(=O)c(C(=O)OC)cc1C(C(C)C)C2]

Crude N-[(1E)-3-isopropyl-7-methoxy-6-(3-methoxypropoxy)-3,4-dihydro-2H-naphthalen-1-ylidene]-2-methylpropan-2-amine (710 mg, 1.96 mmol) and 1,3-dimethyl 2-(methoxymethylidene) propanedioate (684 mg, 3.93 mmol) were dissolved in diglyme (2 mL). The reaction was stirred at 160° C. for 3 hours and then cooled to room temperature. The reaction was diluted with EtOAc (10 mL) and washed with water (3×10 mL). The combined organics were concentrated under reduced pressure. The residue was purified by normal phase $SiO_2$ chromatography (0 to 5% methanol/dichloromethane) to afford methyl 5-isopropyl-9-methoxy-8-(3-methoxypropoxy)-2-oxo-1,2,5,6-tetrahydrobenzo[h]quinoline-3-carboxylate as a yellow foam (110 mg, 14%, m/z: 416 [M+H]$^+$ observed). $^1$H NMR (400 MHz, CDCl$_3$) δ 7.98 (s, 1H), 7.78 (s, 1H), 6.74 (s, 1H), 4.17 (td, J=6.6, 2.0 Hz, 2H), 3.97 (s, 3H), 3.92 (s, 3H), 3.57 (td, J=6.2, 1.3 Hz, 2H), 3.35 (s, 3H), 3.04-2.82 (m, 2H), 2.44 (ddd, J=8.7, 6.0, 2.8 Hz, 1H), 2.13 (p, J=6.3 Hz, 2H), 1.72-1.56 (m, 1H), 0.87 (d, J=6.6 Hz, 3H), 0.78 (d, J=6.7 Hz, 3H).

5-Isopropyl-9-methoxy-8-(3-methoxypropoxy)-2-oxo-1,2,5,6-tetrahydrobenzo[h]quinoline-3-carboxylic acid

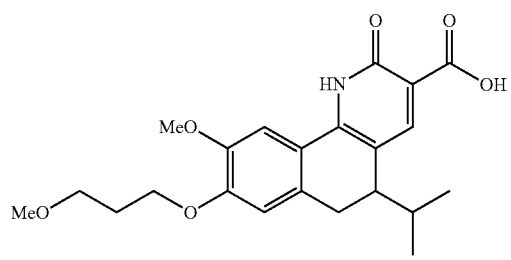

To a solution of methyl 5-isopropyl-9-methoxy-8-(3-methoxypropoxy)-2-oxo-1H,5H,6H-benzo[h]quinoline-3-carboxylate (110 mg, 0.26 mmol) in 1,4-dioxane/H$_2$O (1:1 mixture, 4 mL) was added lithium hydroxide monohydrate (22 mg, 0.53 mmol). The reaction was stirred at room temperature for 4 hours. The pH of the reaction mixture was adjusted to 5 by the addition of 1N HCl. The aqueous layer was extracted with CH$_2$Cl$_2$ (3×5 mL). The combined organic layers were concentrated under reduced pressure. The residue was purified by normal phase $SiO_2$ chromatography (0 to 6% methanol/dichloromethane) to afford 5-isopropyl-9-methoxy-8-(3-methoxypropoxy)-2-oxo-1,2,5,6-tetrahydrobenzo[h]quinoline-3-carboxylic acid as a bright yellow solid (90 mg, 84%, m/z: 402 [M+H]+ observed). ¹H NMR (400 MHz, CDCl₃) δ 13.91 (s, 1H), 12.22 (s, 1H), 8.41 (s, 1H), 7.32 (s, 1H), 6.84 (s, 1H), 4.20 (tt, J=6.2, 3.2 Hz, 2H), 3.96 (s, 3H), 3.59 (td, J=6.1, 2.0 Hz, 2H), 3.38 (s, 3H), 3.13-2.83 (m, 2H), 2.50 (ddd, J=8.1, 5.7, 2.8 Hz, 1H), 2.15 (p, J=6.3 Hz, 2H), 1.63 (m, 1H), 0.87 (d, J=6.7 Hz, 3H), 0.83 (d, J=6.8 Hz, 3H).

Example 2: 5-Isopropyl-9-methoxy-8-(3-methoxypropoxy)-2-oxo-1,2,5,6-tetrahydrobenzo[h]quinoline-3-carboxylic-acid-(single enantiomer)

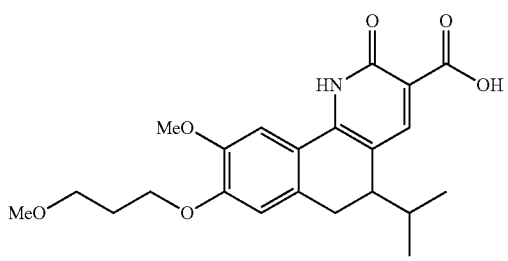 [SMILES: COCCCOc1cc2c(cc1OC)-c1[nH]c(=O)c(C(=O)O)cc1C(C(C)C)C2]

Example 3: 5-Isopropyl-9-methoxy-8-(3-methoxypropoxy)-2-oxo-1,2,5,6-tetrahydrobenzo[h]quinoline-3-carboxylic acid (single enantiomer II)

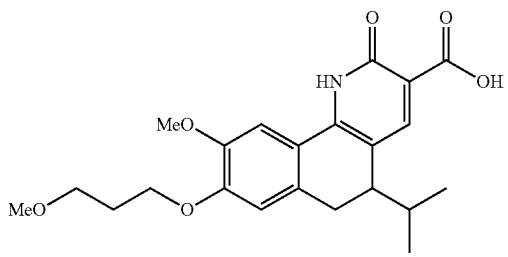 [SMILES: COCCCOc1cc2c(cc1OC)-c1[nH]c(=O)c(C(=O)O)cc1C(C(C)C)C2]

10 mg of the mixture of enantiomers was separated by SFC (supercritical fluid chromatography) on a CHIRALPACK AD column using 35% IPA (0.4% diethylamine as modifier) to give 5-isopropyl-9-methoxy-8-(3-methoxypropoxy)-2-oxo-1,2,5,6-tetrahydrobenzo[h]quinoline-3-carboxylic acid (single enantiomer I) as a bright yellow solid (faster eluting enantiomer, 1.7 mg, 17%, m/z: 402 [M+H]+ observed), and 5-isopropyl-9-methoxy-8-(3-methoxypropoxy)-2-oxo-1,2,5,6-tetrahydrobenzo[h]quinoline-3-carboxylic acid (single enantiomer II) as a bright yellow solid (slower eluting enantiomer, 2.6 mg, 26%, m/z: 402 [M+H]+ observed).

Example 2: 5-Isopropyl-9-methoxy-8-(3-methoxypropoxy)-2-oxo-1,2,5,6-tetrahydrobenzo[h]quinoline-3-carboxylic acid (single enantiomer I). m/z: 402 [M+H]+ observed. ¹H NMR (400 MHz, CDCl₃) δ 13.91 (s, 1H), 12.22 (s, 1H), 8.41 (s, 1H), 7.32 (s, 1H), 6.84 (s, 1H), 4.20 (tt, J=6.2, 3.2 Hz, 2H), 3.96 (s, 3H), 3.59 (td, J=6.1, 2.0 Hz, 2H), 3.38 (s, 3H), 3.13-2.83 (m, 2H), 2.50 (ddd, J=8.1, 5.7, 2.8 Hz, 1H), 2.15 (p, J=6.3 Hz, 2H), 1.63 (m, 1H), 0.87 (d, J=6.7 Hz, 3H), 0.83 (d, J=6.8 Hz, 3H).

Example 3: 5-Isopropyl-9-methoxy-8-(3-methoxypropoxy)-2-oxo-1,2,5,6-tetrahydrobenzo[h]quinoline-3-carboxylic acid (single enantiomer II). m/z: 402 [M+H]+ observed. ¹H NMR (400 MHz, CDCl₃) δ 13.91 (s, 1H), 12.22 (s, 1H), 8.41 (s, 1H), 7.32 (s, 1H), 6.84 (s, 1H), 4.20 (tt, J=6.2, 3.2 Hz, 2H), 3.96 (s, 3H), 3.59 (td, J=6.1, 2.0 Hz, 2H), 3.38 (s, 3H), 3.13-2.83 (m, 2H), 2.50 (ddd, J=8.1, 5.7, 2.8 Hz, 1H), 2.15 (p, J=6.3 Hz, 2H), 1.63 (m, 1H), 0.87 (d, J=6.7 Hz, 3H), 0.83 (d, J=6.8 Hz, 3H).

The following examples were prepared in a similar manner as 5-isopropyl-9-methoxy-8-(3-methoxypropoxy)-2-oxo-1,2,5,6-tetrahydrobenzo[h]quinoline-3-carboxylic acid from 3-isopropyl-7-methoxy-6-(3-methoxypropoxy)-3,4-dihydronaphthalen-1(2H)-one and an appropriate amine.

Example 4: 5-Isopropyl-9-methoxy-8-(3-methoxypropoxy)-1-methyl-2-oxo-1,2,5,6-tetrahydrobenzo[h]quinoline-3-carboxylic acid

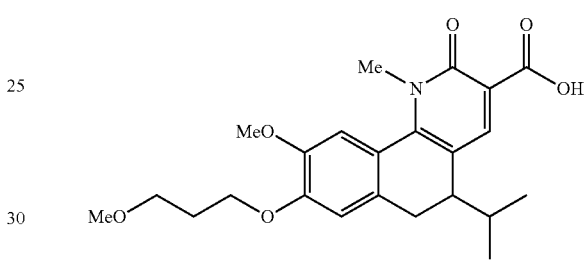

m/z: 416 [M+H]+ observed. ¹H NMR (400 MHz, CDCl₃) δ 8.28 (s, 1H), 7.08 (s, 1H), 6.84 (s, 1H), 4.25-4.09 (m, 2H), 3.87 (m, 6H), 3.56 (td, J=6.1, 0.8 Hz, 2H), 3.34 (s, 3H), 2.99-2.75 (m, 2H), 2.33 (ddd, J=8.5, 5.1, 3.1 Hz, 1H), 2.12 (p, J=6.3 Hz, 2H), 1.39-1.16 (m, 1H), 0.77 (dd, J=8.6, 6.7 Hz, 6H).

Example 5: 1-Benzyl-5-isopropyl-9-methoxy-8-(3-methoxypropoxy)-2-oxo-1,2,5,6-tetrahydrobenzo[h]quinoline-3-carboxylicacid

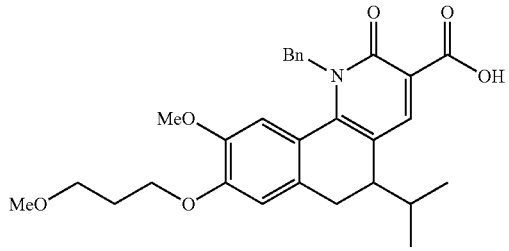 [SMILES: COCCCOc1cc2c(cc1OC)-c1c(cc(C(=O)O)c(=O)n1Cc1ccccc1)C(C(C)C)C2]

m/z: 492 [M+H]+ observed. ¹H NMR (400 MHz, CDCl₃) δ 8.44 (s, 1H), 7.44 (t, J=7.6 Hz, 2H), 7.32 (t, J=7.4 Hz, 1H), 7.22 (d, J=7.7 Hz, 2H), 6.91 (s, 1H), 6.82 (s, 1H), 5.68 (d, J=16.3 Hz, 1H), 5.32 (d, J=16.3 Hz, 1H), 4.14-4.09 (m, 1H), 3.54 (t, J=6.0 Hz, 2H), 3.34 (s, 3H), 3.03 (s, 3H), 2.96-2.78 (m, 2H), 2.40 (ddd, J=8.6, 5.1, 3.1 Hz, 1H), 2.10 (p, J=6.3 Hz, 2H), 1.75 (s, 1H), 1.25 (m, 1H), 0.85 (m, 6H).

Example 6: 5-Isopropyl-9-methoxy-8-(3-methoxypropoxy)-5-methyl-2-oxo-1,6-dihydrobenzo[h]quinoline-3-carboxylic acid

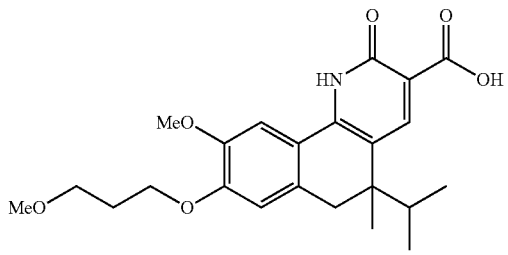 [SMILES: COCCCOc1cc2c(cc1OC)-c1[nH]c(=O)c(C(=O)O)cc1C(C)(C(C)C)C2]

1-[4-Methoxy-3-(3-methoxypropoxy)phenyl]propan-2-one

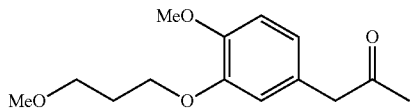 [SMILES: COCCCOc1cc(CC(C)=O)ccc1OC]

To a solution of 4-bromo-1-methoxy-2-(3-methoxypropoxy) benzene (58 g, 210 mmol) in toluene (350 mL) was added tributyltin methoxide (91 mL, 316 mmol), tri(o-tolyl)phosphine (3.9 g, 13 mmol), palladium(II) acetate (1.4 g, 6.3 mmol), and isopropenyl acetate (34 mL, 320 mmol). The reaction mixture was stirred at 100° C. for 5 hr under nitrogen. The reaction was run in 2 batches of identical scale, and each mixture was quenched with saturated aqueous KF solution (2×500 mL). The combined mixtures were stirred for 30 min at room temperature and then extracted with EtOAc (3×500 mL). The combined organic phases were washed with saturated aqueous brine solution (500 mL), dried over sodium sulfate, filtered, and concentrated under vacuum. The residue was purified by normal phase SiO$_2$ chromatography (5% to 30% EtOAc/petroleum ether) to afford 1-[4-methoxy-3-(3-methoxypropoxy) phenyl] propan-2-one as a light yellow oil (80 g, 74% yield, m/z: 253 [M+H]$^+$ observed).

Ethyl 4-[4-methoxy-3-(3-methoxypropoxy)phenyl]-2, 3-dimethyl-but-2-enoate

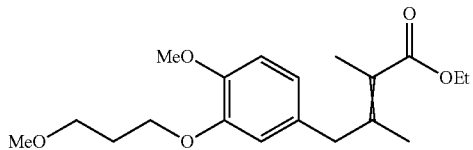 [SMILES: CCOC(=O)C(C)=C(C)Cc1ccc(OC)c(OCCCOC)c1]

To a solution of triethyl 2-phosphonopropionate (50 mL, 220 mmol) in THF (250 mL) at 0° C. was added NaH (60% in mineral oil, 8.9 g, 220 mmol) and the reaction mixture was stirred for 30 min. A solution of 1-[4-methoxy-3-(3-methoxypropoxy) phenyl] propan-2-one (47 g, 186 mmol) in THF (50 mL) was added at 0° C. The temperature was slowly raised to 30° C. and the reaction stirred for 12 h. Two identical scale batches were run and each mixture was quenched with H$_2$O (2×500 mL). The combined mixture was extracted with EtOAc (3×800 mL). The combined organic phase was washed with saturated aqueous brine solution (800 mL), dried over sodium sulfate, filtered and concentrated under vacuum. The residue was purified by normal phase SiO$_2$ chromatography (5% to 30% EtOAc/petroleum ether) to afford ethyl 4-[4-methoxy-3-(3-methoxypropoxy)phenyl]-2,3-dimethyl-but-2-enoate as a light yellow oil (108 g, 86% yield, m/z: 359 [M+Na]$^+$ observed).

4-[4-Methoxy-3-(3-methoxypropoxy)phenyl]-2,3-dimethyl-but-2-en-1-ol

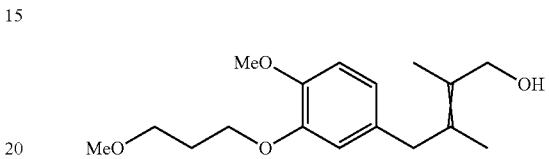

To a mixture of lithium aluminum hydride (8.1 g, 210 mmol) in THF (100 mL) at 0° C. was added a solution of ethyl 4-[4-methoxy-3-(3-methoxypropoxy)phenyl]-2,3-dimethyl-but-2-enoate (36 g, 107 mmol) in THF (50 mL) dropwise. The reaction mixture was stirred at 0° C. for 3 hr. The reaction mixture was slowly poured into water (200 mL). The resulting mixture was extracted with EtOAc (3×200 mL). The combined organic phase was washed with saturated aqueous brine solution (300 mL), dried over anhydrous sodium sulfate, filtered, and concentrated under vacuum. The residue was purified by normal phase SiO$_2$ chromatography (10% to 50% EtOAc/petroleum ether) to afford 4-[4-methoxy-3-(3-methoxypropoxy) phenyl]-2,3-dimethyl-but-2-en-1-ol as a light yellow oil (16.7 g, 54% yield, m/z: 317 [M+Na]$^+$ observed).

Ethyl 3-[[4-methoxy-3-(3-methoxypropoxy)phenyl] methyl]-3,4-dimethyl-pentanoate

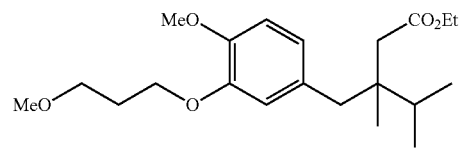 [SMILES: CCOC(=O)CC(C)(Cc1ccc(OC)c(OCCCOC)c1)C(C)C]

4-[4-methoxy-3-(3-methoxypropoxy)phenyl]-2,3-dimethyl-but-2-en-1-ol (30 g, 102 mmol), triethyl orthoacetate (93 mL, 510 mmol) and pivalic acid (3.5 mL, 31 mmol) were mixed in mesitylene (100 mL). The resultant mixture was heated at 135° C. for 36 hr. The reaction mixture was cooled to room temperature and concentrated under vacuum to afford ethyl 3-[[4-methoxy-3-(3-methoxypropoxy) phenyl]methyl]-3,4-dimethyl-pent-4-enoate as a light yellow oil that was used without further purification (47 g, >100% yield). To a solution of the above formed ethyl 3-[[4-methoxy-3-(3-methoxypropoxy) phenyl]methyl]-3,4-dimethyl-pent-4-enoate (47 g, 129 mmol) in MeOH (200 mL) was added palladium on carbon (10% on carbon, 3 g, 3 mmol) under nitrogen atmosphere. The suspension was degassed under vacuum/hydrogen purge cycle (3 times). The mixture was stirred under H$_2$ atmosphere (15 psi) at room temperature for 12 hr. The reaction mixture was filtered through CELITE® and the filter cake was washed with MeOH (3×150 mL). The filtrate was evaporated under reduced pressure. The residue was purified by normal phase SiO$_2$ chromatography (0% to 10% EtOAc/petroleum ether) to afford ethyl 3-[[4-methoxy-3-(3-methoxypropoxy)phenyl]methyl]-3,4-dimethyl-pentanoate as a light yellow oil (24 g, 51% yield, m/z: 367 [M+H]$^+$ observed).

3-[[4-Methoxy-3-(3-methoxypropoxy)phenyl]methyl]-3,4-dimethyl-pentanoic acid

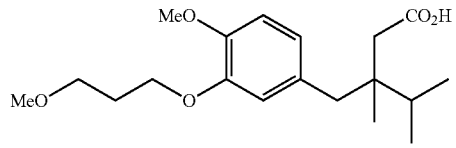 [SMILES: COCCCOc1cc(CC(C)(CC(=O)O)C(C)C)ccc1OC]

To a solution of ethyl 3-[[4-methoxy-3-(3-methoxypropoxy)phenyl]methyl]-3,4-dimethyl-pentanoate (18 g, 49 mmol) in THF/MeOH/H$_2$O (3:1:1, 100 mL) was added NaOH (19.7 g, 491 mmol). The mixture was stirred at 70° C. for 12 hr. The reaction mixture was concentrated under reduced pressure. Water (50 mL) was added to the residue and the resulting mixture was washed with EtOAc (3×35 mL). Aqueous 1N HCl solution was added to adjust the pH to 3. The mixture was then extracted with EtOAc (3×25 mL). The combined organic phase was washed with saturated aqueous brine solution (100 mL), dried over anhydrous sodium sulfate, filtered, and evaporated under reduced pressure to afford 5 g of 3-[[4-methoxy-3-(3-methoxypropoxy)phenyl]methyl]-3,4-dimethyl-pentanoic acid as a light yellow oil that was used without further purification (5 g, 30% yield, m/z: 361 [M+Na]$^+$ observed).

3-Isopropyl-7-methoxy-6-(3-methoxypropoxy)-3-methyl-tetralin-1-one

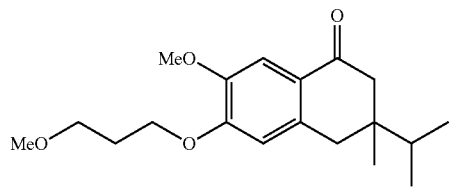 [SMILES: COCCCOc1cc2c(cc1OC)C(=O)CC(C)(C(C)C)C2]

To a solution of 3-[[4-methoxy-3-(3-methoxypropoxy)phenyl]methyl]-3,4-dimethyl-pentanoic acid (5 g, 14.8 mmol) in CH$_2$Cl$_2$ (35 mL) was added phosphorus pentachloride (3.7 g, 17.7 mmol) at 0° C. The resulting mixture was warmed up to room temperature and stirred for 4 hr. The reaction mixture was poured into H$_2$O (50 mL), and solid Na$_2$CO$_3$ was added to adjust the pH to 8. The resulting mixture was extracted with CH$_2$Cl$_2$ (3×60 mL). The combined organic phase was washed with saturated aqueous brine solution (50 mL), dried over anhydrous sodium sulfate, filtered, and evaporated under reduced pressure. The residue was purified by normal phase SiO$_2$ chromatography (5% to 50% EtOAc/petroleum ether) to afford 3-isopropyl-7-methoxy-6-(3-methoxypropoxy)-3-methyl-tetralin-1-one as a light yellow oil (2.7 g, 56% yield, m/z: 321 [M+H]$^+$ observed). $^1$H NMR (400 MHz, CDCl$_3$): δ 7.49 (s, 1H), 6.69 (s, 1H), 4.18 (t, J=6.4 Hz, 2H), 3.90 (s, 3H), 3.58 (t, J=6 Hz, 2H), 3.36 (s, 3H), 2.79 (m, 2H), 2.54-2.43 (m, 2H), 2.17-2.11 (m, 2H), 1.67-1.64 (m, 1H), 0.90 (m, 9H).

N-Benzyl-3-isopropyl-7-methoxy-6-(3-methoxypropoxy)-3-methyl-3,4-dihydronaphthalen-1(2H)-imine

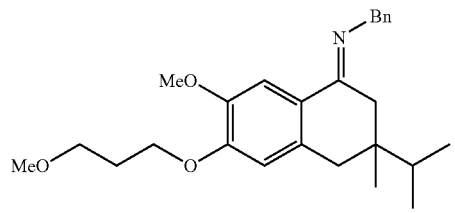 [SMILES: COCCCOc1cc2c(cc1OC)/C(=N/Cc1ccccc1)CC(C)(C(C)C)C2]

To a mixture of 3-isopropyl-7-methoxy-6-(3-methoxypropoxy)-3-methyl-tetralin-1-one (200 mg, 0.62 mmol), benzylamine (0.08 mL, 0.69 mmol) and triethylamine (0.23 mL, 1.6 mmol) in CH$_2$Cl$_2$ (2 mL) was added titanium (IV) chloride (1.0 M solution in CH$_2$Cl$_2$, 0.4 mL, 0.41 mmol) dropwise at 0° C. The reaction mixture was warmed to room temperature and stirred for 12 hr. The reaction mixture was diluted with CH$_2$Cl$_2$ (20 mL) and then poured into a mixture of H$_2$O and saturated aqueous NaHCO$_3$ solution (4:1, 25 mL) to adjust the pH to 9. The organic layer was separated and washed with H$_2$O (20 mL), dried over sodium sulfate, filtered, and evaporated under vacuum to afford N-benzyl-3-isopropyl-7-methoxy-6-(3-methoxypropoxy)-3-methyl-tetralin-1-imine as a light yellow oil that was used without further purification (250 mg, 98% yield, m/z: 410 [M+H]$^+$ observed).

Methyl 1-benzyl-5-isopropyl-9-methoxy-8-(3-methoxypropoxy)-5-methyl-2-oxo-6H-benzo[h]quinoline-3-carboxylate

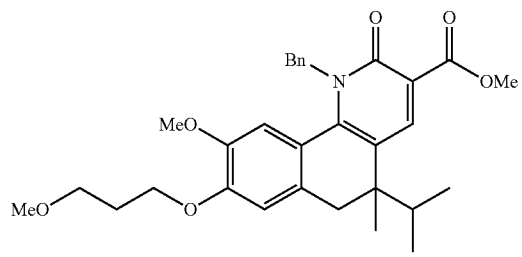 [SMILES: COCCCOc1cc2c(cc1OC)-c1c(cc(C(=O)OC)c(=O)n1Cc1ccccc1)C(C)(C(C)C)C2]

N-benzyl-3-isopropyl-7-methoxy-6-(3-methoxypropoxy)-3-methyl-tetralin-1-imine (210 mg, 0.51 mmol) and dimethyl 2-(methoxymethylene) malonate (180 mg, 1 mmol) were dissolved in diphenyl ether (2 mL) in a microwave vial. The mixture was heated at 220° C. for 15 min under microwave irradiation. The reaction mixture was purified directly by normal phase SiO$_2$ chromatography (5% to 30% EtOAc/petroleum ether; then 0% to 5% MeOH/CH$_2$Cl$_2$) to afford methyl 1-benzyl-5-isopropyl-9-methoxy-8-(3-methoxypropoxy)-5-methyl-2-oxo-6H-benzo[h]quinoline-3-carboxylate as a light yellow oil (100 mg, 38% yield, m/z: 520 [M+H]$^+$ observed).

Methyl 5-isopropyl-9-methoxy-8-(3-methoxy-propoxy)-5-methyl-2-oxo-1,6-dihydrobenzo[h]quinoline-3-carboxylate

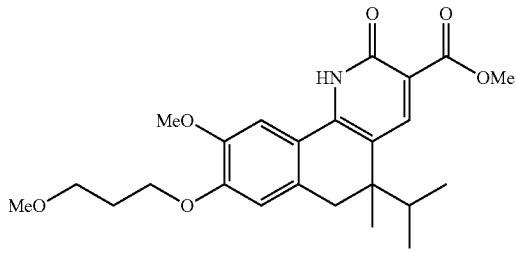 [SMILES: COCCCOc1cc2c(cc1OC)-c1[nH]c(=O)c(C(=O)OC)cc1C(C)(C(C)C)C2]

To a solution of methyl 1-benzyl-5-isopropyl-9-methoxy-8-(3-methoxypropoxy)-5-methyl-2-oxo-6H-benzo[h]quinoline-3-carboxylate (45 mg, 0.87 mmol) in MeOH (5 mL) was added palladium hydroxide on carbon (20% on carbon, 20 mg, 0.29 mmol) under nitrogen atmosphere. The suspension was degassed under vacuum/hydrogen purge cycle (3 times). The mixture was stirred under $H_2$ atmosphere (15 psi) at room temperature for 2 hr. Two identical scale reactions were run, and the combined mixture was filtered through CELITE®. The filtrate was evaporated under reduced pressure to afford methyl 5-isopropyl-9-methoxy-8-(3-methoxypropoxy)-5-methyl-2-oxo-1,6-dihydrobenzo[h]quinoline-3-carboxylate as a light yellow oil that was used directly in next step without any further purification (70 mg, 94% yield, m/z: 430 [M+H]$^+$ observed). $^1$H NMR (400 MHz, CD$_3$OD): δ 8.23 (s, 1H), 7.57 (s, 1H), 6.92 (s, 1H), 4.16-4.10 (m, 2H), 3.93 (s, 3H), 3.90 (s, 3H), 3.59 (t, J=6.4 Hz, 2H), 3.35 (s, 3H), 2.81 (m, 2H), 2.10-2.01 (m, 2H), 1.72-1.68 (m, 1H), 1.26 (s, 3H), 0.84 (d, J=6.8 Hz, 3H), 0.73 (d, J=6.8 Hz, 3H).

5-Isopropyl-9-methoxy-8-(3-methoxypropoxy)-5-methyl-2-oxo-1,6-dihydrobenzo[h]quinoline-3-carboxylic acid

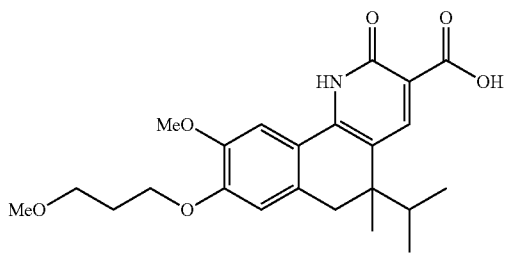 [SMILES: COCCCOc1cc2c(cc1OC)-c1[nH]c(=O)c(C(=O)O)cc1C(C)(C(C)C)C2]

To a solution of methyl 5-isopropyl-9-methoxy-8-(3-methoxypropoxy)-5-methyl-2-oxo-1,6-dihydrobenzo[h]quinoline-3-carboxylate (36 mg, 0.084 mmol) in THF/MeOH/H$_2$O (2:1:1, 4 mL) was added a solution of lithium hydroxide monohydrate (159 mg, 3.78 mmol) in THF/MeOH/H$_2$O (2:1:1, 4 mL). The mixture was stirred at room temperature for 12 hr. The reaction mixture was evaporated under reduced pressure. Water (15 mL) was added to the residue and the pH of the solution was adjusted to 3 by the addition with 1N aqueous HCl solution. The mixture was exacted with EtOAc (3×15 mL). The combined organic phase was dried over sodium sulfate, filtered and evaporated under reduced pressure. The residue was purified by reverse phase HPLC to afford to afford 5-isopropyl-9-methoxy-8-(3-methoxypropoxy)-5-methyl-2-oxo-1,6-dihydrobenzo[h]quinoline-3-carboxylic acid as a yellow solid (12 mg, 33% yield, m/z: 416 [M+H]$^+$ observed). $^1$H NMR (400 MHz, DMSO-d$_6$) δ 15.06 (bs, 1H), 13.21 (bs, 1H), 8.17 (s, 1H), 7.72 (s, 1H), 7.03 (s, 1H), 4.13-4.04 (m, 2H), 3.85 (s, 3H), 3.46 (t, J=6.4 Hz, 2H), 3.24 (s, 3H), 2.91-2.68 (m, 2H), 2.00-1.93 (m, 2H), 1.62-1.55 (m, 1H), 1.20 (s, 3H), 0.76 (d, J=6.8 Hz, 3H), 0.64 (d, J=6.8 Hz, 3H).

Example 7: 5-Isopropyl-9-methoxy-8-(3-methoxypropoxy)-5-methyl-2-oxo-1,6-dihydrobenzo[h]quinoline-3-carboxylic acid (single enantiomer I)

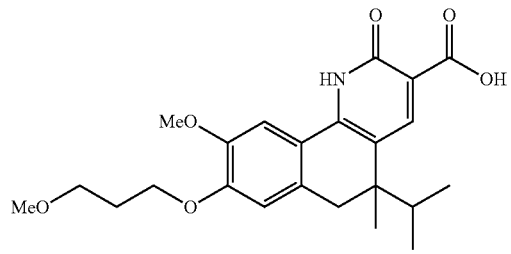 [SMILES: COCCCOc1cc2c(cc1OC)-c1[nH]c(=O)c(C(=O)O)cc1C(C)(C(C)C)C2]

Example 8: 5-Isopropyl-9-methoxy-8-(3-methoxypropoxy)-5-methyl-2-oxo-1,6-dihydrobenzo[h]quinoline-3-carboxylic acid (single enantiomer II)

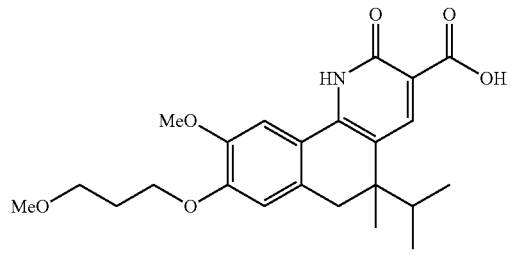 [SMILES: COCCCOc1cc2c(cc1OC)-c1[nH]c(=O)c(C(=O)O)cc1C(C)(C(C)C)C2]

5-Isopropyl-9-methoxy-8-(3-methoxypropoxy)-5-methyl-2-oxo-1,6-dihydrobenzo[h]quinoline-3-carboxylic acid (640 mg) was separated by chiral SFC (supercritical fluid chromatography) on a CHIRALPAK AD-H column using 50% IPA (0.1% NH$_4$OH modifier) to give 5-isopropyl-9-methoxy-8-(3-methoxypropoxy)-5-methyl-2-oxo-1,6-dihydrobenzo[h]quinoline-3-carboxylic acid (single enantiomer I) as a dark yellow solid (faster eluting enantiomer, 227 mg, 35% yield, m/z: 416 [M+H]$^+$ observed) and impure 5-isopropyl-9-methoxy-8-(3-methoxypropoxy)-5-methyl-2-oxo-1,6-dihydrobenzo[h]quinoline-3-carboxylic acid (slower eluting enantiomer, 230 mg), which was further purified by reverse phase HPLC to give 5-isopropyl-9-methoxy-8-(3-methoxypropoxy)-5-methyl-2-oxo-1,6-dihydrobenzo[h]quinoline-3-carboxylic acid (single enantiomer II) as a yellow solid (slower eluting enantiomer, 180 mg, 28% yield, m/z: 416 [M+H]$^+$ observed).

Example 7: 5-Isopropyl-9-methoxy-8-(3-methoxypropoxy)-5-methyl-2-oxo-1,6-dihydrobenzo[h]quinoline-3-carboxylic acid (single enantiomer I). m/z: 416 [M+H]$^+$ observed). $^1$H NMR (400 MHz, DMSO-d$_6$) δ 15.06 (bs, 1H), 13.21 (bs, 1H), 8.17 (s, 1H), 7.72 (s, 1H), 7.03 (s, 1H), 4.13-4.04 (m, 2H), 3.85 (s, 3H), 3.46 (t, J=6.4 Hz, 2H), 3.24 (s, 3H), 2.91-2.68 (m, 2H), 2.00-1.93 (m, 2H), 1.62-1.55 (m, 1H), 1.20 (s, 3H), 0.76 (d, J=6.8 Hz, 3H), 0.64 (d, J=6.8 Hz, 3H).

Example 8: 5-Isopropyl-9-methoxy-8-(3-methoxypropoxy)-5-methyl-2-oxo-1,6-dihydrobenzo[h]quinoline-3-carboxylic acid (single enantiomer II). m/z: 416 [M+H]+ observed. ¹H NMR (400 MHz, DMSO-d₆) δ 15.06 (bs, 1H), 13.21 (bs, 1H), 8.17 (s, 1H), 7.72 (s, 1H), 7.03 (s, 1H), 4.13-4.04 (m, 2H), 3.85 (s, 3H), 3.46 (t, J=6.4 Hz, 2H), 3.24 (s, 3H), 2.91-2.68 (m, 2H), 2.00-1.93 (m, 2H), 1.62-1.55 (m, 1H), 1.20 (s, 3H), 0.76 (d, J=6.8 Hz, 3H), 0.64 (d, J=6.8 Hz, 3H).

The following examples were prepared in a similar manner as 5-isopropyl-9-methoxy-8-(3-methoxypropoxy)-5-methyl-2-oxo-1,6-dihydrobenzo[h]quinoline-3-carboxylic acid from isopropenyl acetate and an appropriate bromobenzene.

Example 9: 9-Chloro-5-isopropyl-8-(3-methoxypropoxy)-5-methyl-2-oxo-1,6-dihydrobenzo[h]quinoline-3-carboxylic acid

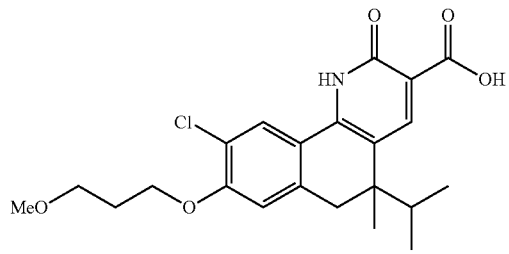 [SMILES: COCCCOc1cc2c(cc1Cl)-c1[nH]c(=O)c(C(=O)O)cc1C(C)(C(C)C)C2]

m/z: 420,422 [M+H]+ observed. ¹H NMR (400 MHz, DMSO-d₆) δ 15.27 (bs, 1H), 13.19 (bs, 1H), 8.21 (s, 1H), 8.16 (s, 1H), 7.24 (s, 1H), 4.22-4.16 (m, 2H), 3.50 (t, J=6.4 Hz, 2H), 3.25 (s, 3H), 2.99-2.73 (m, 2H), 2.02-1.96 (m, 2H), 1.59-1.52 (m, 1H), 1.21 (s, 3H), 0.77 (d, J=6.8 Hz, 3H), 0.77 (d, J=7.2 Hz, 3H).

Example 10: 9-Chloro-5-isopropyl-8-(3-methoxypropoxy)-5-methyl-2-oxo-1,6-dihydrobenzo[h]quinoline-3-carboxylic acid (single enantiomer I)

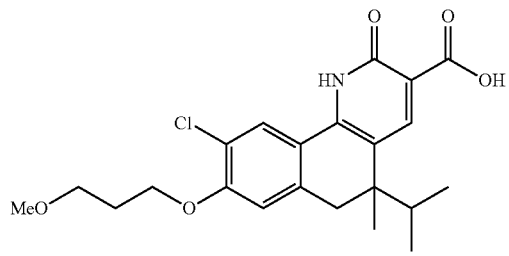

m/z: 420,422 [M+H]+ observed. ¹H NMR (400 MHz, DMSO-d₆) δ 15.27 (bs, 1H), 13.19 (bs, 1H), 8.21 (s, 1H), 8.16 (s, 1H), 7.24 (s, 1H), 4.22-4.16 (m, 2H), 3.50 (t, J=6.4 Hz, 2H), 3.25 (s, 3H), 2.99-2.73 (m, 2H), 2.02-1.96 (m, 2H), 1.59-1.52 (m, 1H), 1.21 (s, 3H), 0.77 (d, J=6.8 Hz, 3H), 0.77 (d, J=7.2 Hz, 3H).

Example 11: 9-Chloro-5-isopropyl-8-(3-methoxypropoxy)-5-methyl-2-oxo-1,6-dihydrobenzo[h]quinoline-3-carboxylic acid (single enantiomer II)

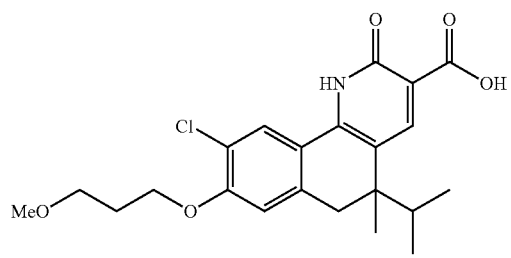 [SMILES: COCCCOc1cc2c(cc1Cl)-c1[nH]c(=O)c(C(=O)O)cc1C(C)(C(C)C)C2]

m/z: 420, 422 [M+H]+ observed. ¹H NMR (400 MHz, DMSO-d₆) δ 15.27 (bs, 1H), 13.19 (bs, 1H), 8.21 (s, 1H), 8.16 (s, 1H), 7.24 (s, 1H), 4.22-4.16 (m, 2H), 3.50 (t, J=6.4 Hz, 2H), 3.25 (s, 3H), 2.99-2.73 (m, 2H), 2.02-1.96 (m, 2H), 1.59-1.52 (m, 1H), 1.21 (s, 3H), 0.77 (d, J=6.8 Hz, 3H), 0.77 (d, J=7.2 Hz, 3H).

Example 12: 5-Isopropyl-2,9-dimethoxy-8-(3-methoxypropoxy)-5,6-dihydrobenzo[h]quinoline-3-carboxylicacid

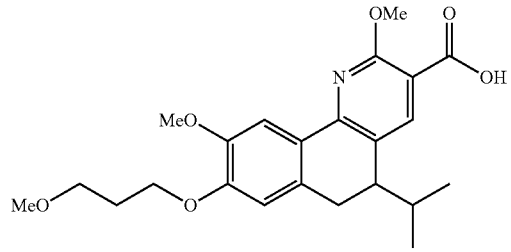 [SMILES: COCCCOc1cc2c(cc1OC)-c1nc(OC)c(C(=O)O)cc1C(C(C)C)C2]

Methyl 5-Isopropyl-2,9-dimethoxy-8-(3-methoxypropoxy)-5,6-dihydrobenzo[h]quinoline-3-carboxylate

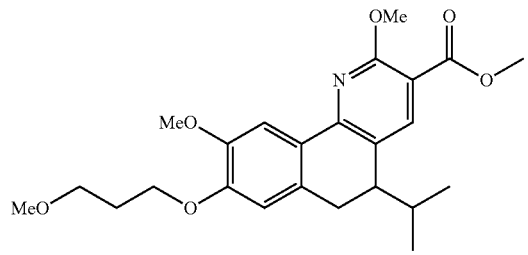 [SMILES: COCCCOc1cc2c(cc1OC)-c1nc(OC)c(C(=O)OC)cc1C(C(C)C)C2]

To a solution of methyl 5-isopropyl-9-methoxy-8-(3-methoxypropoxy)-2-oxo-1,2,5,6-tetrahydrobenzo[h]quinoline-3-carboxylate (35 mg, 0.084 mmol) and silver carbonate (47 mg, 0.17 mmol) in toluene (2 mL) was added iodomethane (0.02 mL, 0.34 mmol). The reaction mixture was heated to 110° C. in a microwave reactor for 2 hours. The reaction was cooled to room temperature, diluted with EtOAc (5 mL), and extracted with water (3×5 mL). The combined organic phase was dried with sodium sulfate, and the solvent was concentrated under reduced pressure to give methyl 5-isopropyl-2,9-dimethoxy-8-(3-methoxypropoxy)-5,6-dihydrobenzo[h]quinoline-3-carboxylate which was used without further purification (40 mg, >100% yield, m/z: 430 [M+H]⁺ observed).

5-Isopropyl-2,9-dimethoxy-8-(3-methoxypropoxy)-5,6-dihydrobenzo[h]quinoline-3-carboxylic acid

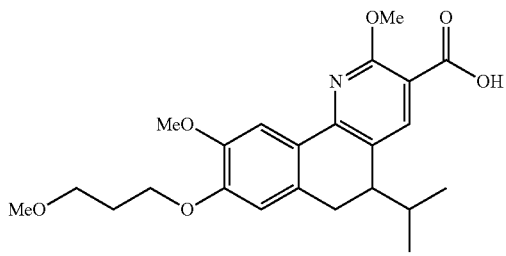 [SMILES: COCCCOc1cc2c(cc1OC)-c1nc(OC)c(C(=O)O)cc1C(C(C)C)C2]

To a solution of methyl 5-isopropyl-2,9-dimethoxy-8-(3-methoxypropoxy)-5,6-dihydrobenzo[h]quinoline-3-carboxylate (45 mg, 0.1 mmol) in 1,4-dioxane/H₂O (1:1 mixture, 2 mL) was added lithium hydroxide monohydrate (9 mg, 0.2 mmol). The reaction was stirred at room temperature for 4 hours. The pH of the reaction mixture was adjusted to 5 by the addition of 1N HCl. The mixture was extracted with CH₂Cl₂ (3×5 mL), and the combined organic layers were concentrated under reduced pressure. The residue was purified by reverse phase HPLC to afford 5-isopropyl-2,9-dimethoxy-8-(3-methoxypropoxy)-5,6-dihydrobenzo[h]quinoline-3-carboxylic acid as a yellow solid (9 mg, 21% yield, m/z: 416 [M+H]⁺ observed). ¹H NMR (400 MHz, CDCl₃) δ 8.19 (d, J=1.1 Hz, 1H), 7.78 (d, J=1.0 Hz, 1H), 6.77 (s, 1H), 4.28 (t, J=0.9 Hz, 3H), 4.21-4.13 (m, 2H), 3.95 (d, J=1.0 Hz, 3H), 3.71-3.55 (m, 2H), 3.44-3.33 (m, 3H), 3.10-2.84 (m, 2H), 2.68-2.50 (m, 1H), 2.23-2.09 (m, 2H), 1.70 (dt, J=13.7, 6.8 Hz, 1H), 0.88 (dd, J=6.7, 1.0 Hz, 3H), 0.82-0.72 (m, 3H).

Example 13: 4-Chloro-5-isopropyl-9-methoxy-8-(3-methoxypropoxy)-2-oxo-1,2,5,6-tetrahydrobenzo[h]quinoline-3-carboxylic acid

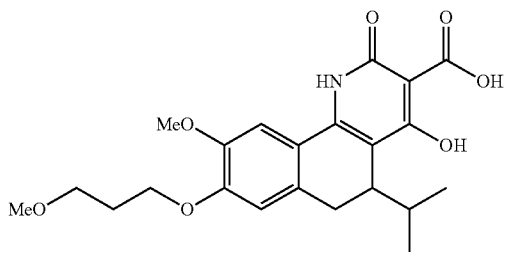

Methyl 1-benzyl-4-hydroxy-5-isopropyl-9-methoxy-8-(3-methoxypropoxy)-2-oxo-1,2,5,6-tetrahydrobenzo[h]quinoline-3-carboxylate

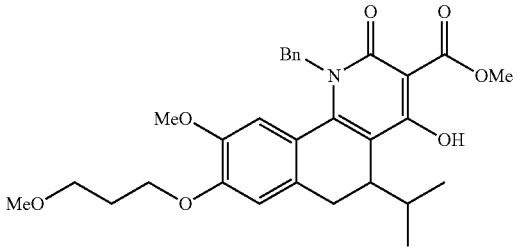

N-benzyl-3-isopropyl-7-methoxy-6-(3-methoxypropoxy) tetralin-1-imine (1 g, 2.53 mmol) and trimethyl methanetricarboxylate (1.44 g, 7.6 mmol) were dissolved in diglyme (10 mL). The reaction mixture was stirred at 180° C. in a microwave reactor for 30 minutes. Ethyl acetate (20 mL), followed by H₂O (30 mL) were added to the reaction mixture. The separated organic layer was washed with H₂O (2×20 mL), saturated aqueous brine solution (2×20 mL), dried over anhydrous sodium sulfate and concentrated under reduced pressure. The crude residue was purified by normal phase SiO₂ chromatography (0 to 70% EtOAc/hexanes) to give methyl 1-benzyl-4-hydroxy-5-isopropyl-9-methoxy-8-(3-methoxypropoxy)-2-oxo-1,2,5,6-tetrahydrobenzo[h]quinoline-3-carboxylate as a yellow oil (560 mg, 42% yield, m/z: 522 [M+H]⁺ observed).

Methyl 4-hydroxy-5-isopropyl-9-methoxy-8-(3-methoxypropoxy)-2-oxo-1,2,5,6-tetrahydrobenzo[h]quinoline-3-carboxylate

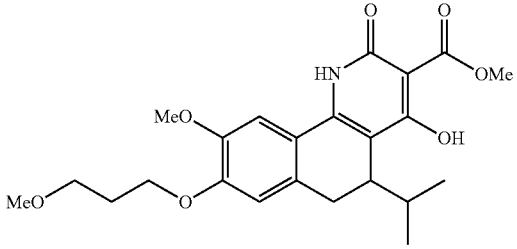

Methyl 1-benzyl-4-hydroxy-5-isopropyl-9-methoxy-8-(3-methoxypropoxy)-2-oxo-5,6-dihydrobenzo[h]quinoline-3-carboxylate (100 mg, 0.19 mmol) and palladium hydroxide (20% on carbon, 38 mg, 0.03 mmol) were dissolved in methanol (2 mL). A H₂ balloon was applied and the reaction was stirred at room temperature for 16 h. The crude reaction mixture was filtered through CELITE®, concentrated under reduced pressure to give methyl 4-hydroxy-5-isopropyl-9-methoxy-8-(3-methoxypropoxy)-2-oxo-1,2,5,6-tetrahydrobenzo[h]quinoline-3-carboxylate, which was used in the next step without further purification (80 mg, 97% yield, m/z: 432 [M+H]⁺ observed). ¹H NMR (400 MHz, CDCl₃) δ 7.41 (s, 1H), 6.79 (s, 1H), 4.19 (td, J=6.5, 5.1 Hz, 2H), 3.98 (d, J=4.5 Hz, 6H), 3.64-3.52 (m, 3H), 3.36 (s, 3H), 2.98-2.87 (m, 3H), 2.14 (p, J=6.3 Hz, 2H), 1.77-1.51 (m, 1H), 0.83 (dd, J=10.5, 6.7 Hz, 6H).

4-Hydroxy-5-isopropyl-9-methoxy-8-(3-methoxypropoxy)-2-oxo-1,2,5,6-tetrahydrobenzo[h]quinoline-3-carboxylicacid

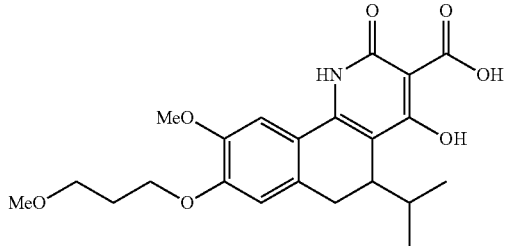

Methyl 4-hydroxy-5-isopropyl-9-methoxy-8-(3-methoxypropoxy)-2-oxo-5,6-dihydro-1H-benzo[h]quinoline-3-carboxylate (80 mg, 0.19 mmol) and lithium iodide (50 mg, 0.37 mmol) were dissolved in EtOAc and stirred at 60° C. for 4 hours. Aqueous 1N HCl (2 mL) was added to the reaction and stirred for 5 min. The separated organic layer was washed with H$_2$O (2×2 mL), saturated aqueous brine solution (2×2 mL) and concentrated under reduced pressure. The residue was purified with reverse phase HPLC to give 4-hydroxy-5-isopropyl-9-methoxy-8-(3-methoxypropoxy)-2-oxo-1,2,5,6-tetrahydrobenzo[h]quinoline-3-carboxylic acid as a yellow foam (19 mg, 25% yield, m/z: 418 [M+H]$^+$ observed). $^1$H NMR (400 MHz, CDCl$_3$) δ 13.79 (s, 1H), 10.56 (s, 1H), 7.15 (s, 1H), 6.83 (s, 1H), 4.29-4.11 (m, 2H), 3.95 (s, 3H), 3.59 (td, J=6.1, 1.4 Hz, 2H), 3.37 (s, 3H), 2.94 (s, 3H), 2.15 (p, J=6.3 Hz, 2H), 1.72-1.53 (m, 1H), 0.83 (dd, J=9.3, 6.7 Hz, 6H).

The following examples were prepared in a similar manner as 4-hydroxy-5-isopropyl-9-methoxy-8-(3-methoxypropoxy)-2-oxo-1,2,5,6-tetrahydrobenzo[h]quinoline-3-carboxylic acid from N-benzyl-7-chloro-3-isopropyl-6-(3-methoxypropoxy)-3-methyl-3,4-dihydronaphthalen-1(2H)-imine and trimethyl methanetricarboxylate.

Example 14: 9-Chloro-4-hydroxy-5-isopropyl-8-(3-methoxypropoxy)-5-methyl-2-oxo-1,2,5,6-tetrahydrobenzo[h]quinoline-3-carboxylic acid

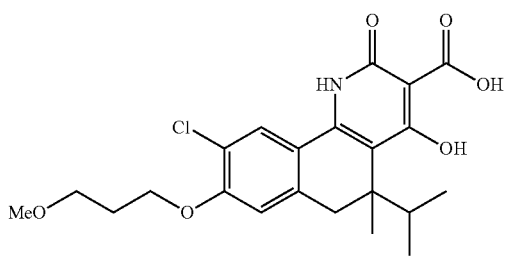 [SMILES: COCCCOc1cc2c(cc1Cl)-c1[nH]c(=O)c(C(=O)O)c(O)c1C(C)(C(C)C)C2]

m/z: 436 [M+H]$^+$ observed. $^1$H NMR (400 MHz, DMSO-d$_6$) δ 14.76 (br s, 1H), 8.10 (s, 1H), 7.21 (s, 1H), 4.22-4.14 (m, 2H), 3.50 (t, J=6 Hz, 2H), 3.26 (s, 3H), 2.93-2.73 (m, 2H), 2.03-1.88 (m, 3H), 1.38 (s, 3H), 0.81 (d, J=6.8 Hz, 3H), 0.71-0.66 (d, J=6.8 Hz, 3H).

Example 15: 9-Chloro-4-hydroxy-5-isopropyl-8-(3-methoxypropoxy)-5-methyl-2-oxo-1,2,5,6-tetrahydrobenzo[h]quinoline-3-carboxylic acid (single enantiomer I)

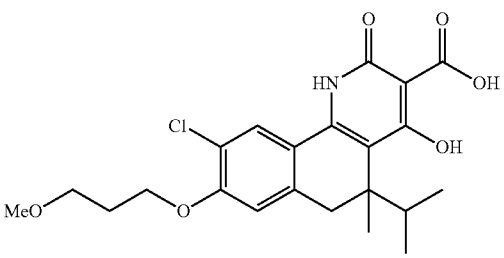 [SMILES: COCCCOc1cc2c(cc1Cl)-c1[nH]c(=O)c(C(=O)O)c(O)c1C(C)(C(C)C)C2]

m/z: 436 [M+H]$^+$ observed. $^1$H NMR (400 MHz, DMSO-d$_6$) δ 14.76 (br s, 1H), 8.10 (s, 1H), 7.21 (s, 1H), 4.22-4.14 (m, 2H), 3.50 (t, J=6 Hz, 2H), 3.26 (s, 3H), 2.93-2.73 (m, 2H), 2.03-1.88 (m, 3H), 1.38 (s, 3H), 0.81 (d, J=6.8 Hz, 3H), 0.71-0.66 (d, J=6.8 Hz, 3H).

Example 16: 9-Chloro-4-hydroxy-5-isopropyl-8-(3-methoxypropoxy)-5-methyl-2-oxo-1,2,5,6-tetrahydrobenzo[h]quinoline-3-carboxylic acid (single enantiomer II)

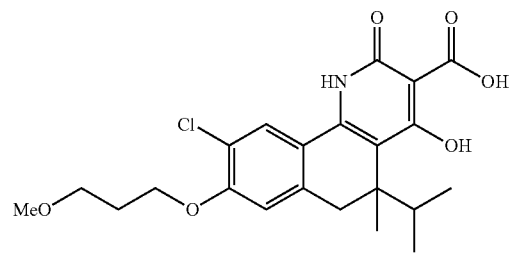 [SMILES: COCCCOc1cc2c(cc1Cl)-c1[nH]c(=O)c(C(=O)O)c(O)c1C(C)(C(C)C)C2]

m/z: 436 [M+H]$^+$ observed. $^1$H NMR (400 MHz, DMSO-d$_6$) δ 14.76 (br s, 1H), 8.10 (s, 1H), 7.21 (s, 1H), 4.22-4.14 (m, 2H), 3.50 (t, J=6 Hz, 2H), 3.26 (s, 3H), 2.93-2.73 (m, 2H), 2.03-1.88 (m, 3H), 1.38 (s, 3H), 0.81 (d, J=6.8 Hz, 3H), 0.71-0.66 (d, J=6.8 Hz, 3H).

Example 17: 4-Fluoro-5-isopropyl-9-methoxy-8-(3-methoxypropoxy)-2-oxo-1,2,5,6-tetrahydrobenzo[h]quinoline-3-carboxylic acid

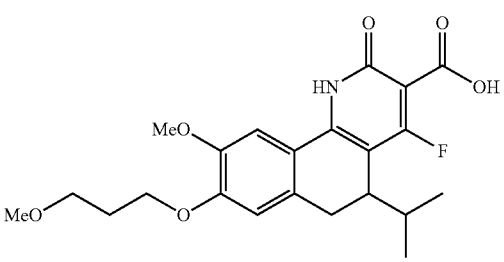

Methyl 1-benzyl-5-isopropyl-9-methoxy-8-(3-methoxypropoxy)-2-oxo-4-(((trifluoromethyl)sulfonyl)oxy)-1,2,5,6-tetrahydrobenzo[h]quinoline-3-carboxylate

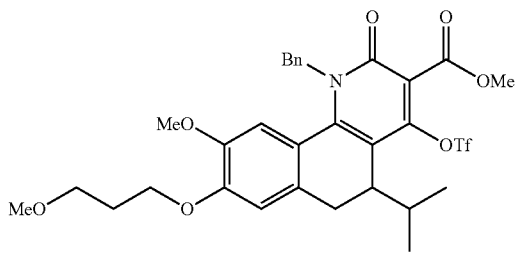 [SMILES: COCCCOc1cc2c(cc1OC)-c1c(c(OS(=O)(=O)C(F)(F)F)c(C(=O)OC)c(=O)n1Cc1ccccc1)C(C(C)C)C2]

A solution of methyl 1-benzyl-4-hydroxy-5-isopropyl-9-methoxy-8-(3-methoxypropoxy)-2-oxo-5,6-dihydrobenzo[h]quinoline-3-carboxylate (260 mg, 0.50 mmol) and triethylamine (0.21 mL, 1.50 mmol) in anhydrous CH$_2$Cl$_2$ (5 mL) was cooled to 0° C. Trifluoromethanesulfonic anhydride (1M solution in CH$_2$Cl$_2$, 0.75 mL, 0.75 mmol) was added dropwise at 0° C. The reaction mixture was warmed up to room temperature and stirred for 1 hour. The reaction was quenched with saturated aqueous sodium bicarbonate solution (1 mL), washed with H$_2$O (1 mL), saturated aqueous brine solution (1 mL), dried over anhydrous sodium sulfate and concentrated under reduced pressure to give methyl 1-benzyl-5-isopropyl-9-methoxy-8-(3-methoxypropoxy)-2-oxo-4-(((trifluoromethyl)sulfonyl)oxy)-1,2,5,6-tetrahydrobenzo[h]quinoline-3-carboxylate which was used in the next step without further purification (110 mg, 34% yield, m/z: 654 [M+H]$^+$ observed).

Methyl 1-benzyl-4-chloro-5-isopropyl-9-methoxy-8-(3-methoxypropoxy)-2-oxo-1,2,5,6-tetrahydrobenzo[h]quinoline-3-carboxylate

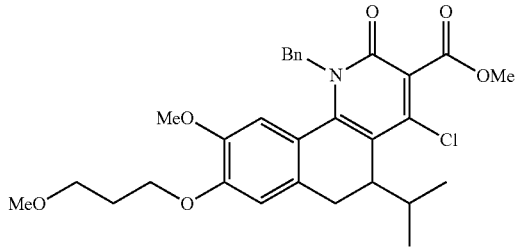 [SMILES: COCCCOc1cc2c(cc1OC)-c1c(c(Cl)c(C(=O)OC)c(=O)n1Cc1ccccc1)C(C(C)C)C2]

To a solution of methyl 1-benzyl-5-isopropyl-9-methoxy-8-(3-methoxypropoxy)-2-oxo-4-(((trifluoromethyl)sulfonyl)oxy)-1,2,5,6-tetrahydrobenzo[h]quinoline-3-carboxylate (110 mg, 0.17 mmol) and triethylamine (0.03 mL, 0.2 mmol) in CH$_2$Cl$_2$ (2 mL) was added oxalyl chloride (0.37 mL, 4.22 mmol) at room temperature. The reaction mixture was stirred at room temperature for 3 days. Saturated aqueous sodium bicarbonate solution (1 mL) was added. The separated organic layer was dried over sodium sulfate and concentrated under reduced pressure. The residue was purified via normal phase SiO$_2$ chromatography (0-5% MeOH/CH$_2$Cl$_2$) to give methyl 1-benzyl-4-chloro-5-isopropyl-9-methoxy-8-(3-methoxypropoxy)-2-oxo-1,2,5,6-tetrahydrobenzo[h]quinoline-3-carboxylate as a yellow solid (70 mg, 77% yield, m/z: 540 [M+H]$^+$ observed).

Methyl 1-benzyl-4-fluoro-5-isopropyl-9-methoxy-8-(3-methoxypropoxy)-2-oxo-1,2,5,6-tetrahydrobenzo[h]quinoline-3-carboxylate

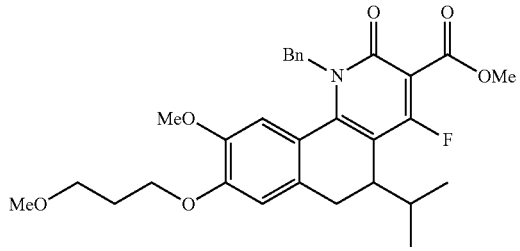

A solution of methyl 1-benzyl-4-chloro-5-isopropyl-9-methoxy-8-(3-methoxypropoxy)-2-oxo-5,6-dihydrobenzo[h]quinoline-3-carboxylate (70 mg, 0.13 mmol) and tetramethylammonium fluoride (36 mg, 0.39 mmol) in DMF (1 mL) was stirred at 40° C. for 24 hours. The reaction mixture was filtered through a syringe filter and purified by reverse phase HPLC to give methyl 1-benzyl-4-fluoro-5-isopropyl-9-methoxy-8-(3-methoxypropoxy)-2-oxo-1,2,5,6-tetrahydrobenzo[h]quinoline-3-carboxylate as a yellow foam (10 mg, 15% yield, m/z: 524 [M+H]$^+$ observed).

Methyl 4-fluoro-5-isopropyl-9-methoxy-8-(3-methoxypropoxy)-2-oxo-1,2,5,6-tetrahydrobenzo[h]quinoline-3-carboxylate

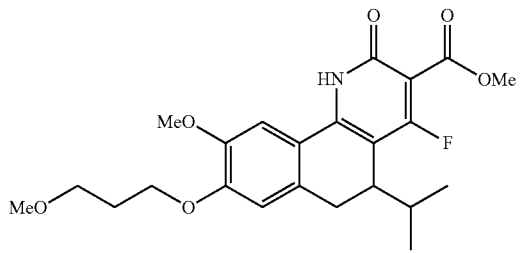 [SMILES: COCCCOc1cc2c(cc1OC)-c1[nH]c(=O)c(C(=O)OC)c(F)c1C(C(C)C)C2]

Methyl 1-benzyl-4-fluoro-5-isopropyl-9-methoxy-8-(3-methoxypropoxy)-2-oxo-5,6-dihydrobenzo[h]quinoline-3-carboxylate (10 mg, 0.02 mmol) and palladium hydroxide (20% on carbon, 20 mg, 0.015 mmol) were dissolved in MeOH (2 mL). A H$_2$ balloon was applied and the reaction mixture stirred for 30 min. The catalyst was filtered off through a syringe filter and the reaction mixture concentrated under reduced pressure to give methyl 4-fluoro-5-isopropyl-9-methoxy-8-(3-methoxypropoxy)-2-oxo-1,2,5,6-tetrahydrobenzo[h]quinoline-3-carboxylate without further purification (5 mg, 60% yield, m/z: 434 [M+H]$^+$ observed).

4-Fluoro-5-isopropyl-9-methoxy-8-(3-methoxy-propoxy)-2-oxo-1,2,5,6-tetrahydrobenzo[h]quinoline-3-carboxylic acid

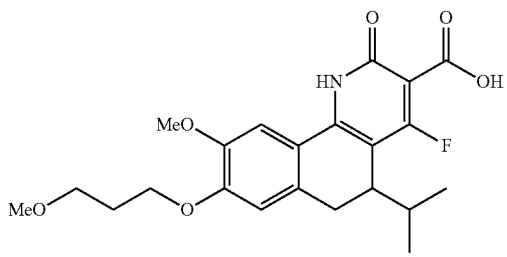

Methyl 4-fluoro-5-isopropyl-9-methoxy-8-(3-methoxypropoxy)-2-oxo-5,6-dihydro-1H-benzo[h]quinoline-3-carboxylate (5 mg, 0.01 mmol) and lithium hydroxide monohydrate (1 mg, 0.02 mmol) were dissolved in 1,4-dioxane/H$_2$O (1:1, 1 mL). The reaction mixture was stirred at room temperature for 16 h. The organic solvent was removed under reduced pressure and the residual aqueous phase was acidified to pH=5 with 1N HCl (1 mL). The aqueous phase was extracted with CH$_2$Cl$_2$ (3×3 mL). The organic layer was dried over anhydrous sodium sulfate and concentrated under reduced pressure. The residue was purified via normal phase SiO$_2$ chromatography (0-7% MeOH/CH$_2$Cl$_2$) to give 4-fluoro-5-isopropyl-9-methoxy-8-(3-methoxypropoxy)-2-oxo-1,2,5,6-tetrahydrobenzo[h]quinoline-3-carboxylic acid as a yellow foam (1.6 mg, 33% yield, m/z: 420 [M+H]$^+$ observed). $^1$H NMR (400 MHz, CDCl$_3$) δ 7.15 (s, 1H), 6.83 (s, 1H), 4.20 (q, J=6.2 Hz, 2H), 3.95 (s, 3H), 3.59 (td, J=6.1, 1.7 Hz, 2H), 3.37 (s, 3H), 2.98-2.87 (m, 3H), 2.14 (q, J=6.0 Hz, 2H), 1.68-1.66 (m, 1H), 0.89-0.83 (m, 6H).

Example 18: 1-Benzyl-4-hydroxy-5-isopropyl-9-methoxy-8-(3-methoxypropoxy)-2-oxo-1,2,5,6-tetrahydrobenzo[h]quinoline-3-carboxylic acid

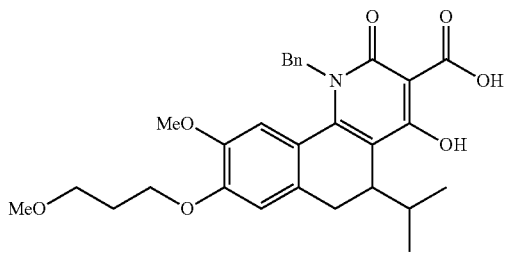 [SMILES: COCCCOc1cc2c(cc1OC)-c1c(c(O)c(C(=O)O)c(=O)n1Cc1ccccc1)C(C(C)C)C2]

A solution of methyl 1-benzyl-4-hydroxy-5-isopropyl-9-methoxy-8-(3-methoxypropoxy)-2-oxo-1,2,5,6-tetrahydrobenzo[h]quinoline-3-carboxylate (80 mg, 0.15 mmol) and lithium iodide (50 mg, 0.37 mmol) in EtOAc (3 mL) was stirred at 60° C. for 4 hours. Aqueous 1N HCl (2 mL) was added to the reaction and stirred for 5 min. The separated organic layer was washed with H$_2$O (2×2 mL), saturated aqueous brine solution (2×2 mL), dried over anhydrous sodium sulfate and concentrated under reduced pressure. The residue was purified by reverse phase HPLC to give 1-benzyl-4-hydroxy-5-isopropyl-9-methoxy-8-(3-methoxypropoxy)-2-oxo-1,2,5,6-tetrahydrobenzo[h]quinoline-3-carboxylic acid as a yellow foam (19 mg, 24.6% yield, m/z: 508 [M+H]$^+$ observed). $^1$H NMR (400 MHz, CDCl$_3$) (13.90 (s, 1H), 7.43 (t, J=7.6 Hz, 2H), 7.37-7.27 (m, 1H), 7.25-7.19 (m, 2H), 6.91 (s, 1H), 6.80 (s, 1H), 5.57 (d, J=16.6 Hz, 1H), 5.25 (t, J=18.0 Hz, 1H), 4.15 (qt, J=9.5, 6.5 Hz, 2H), 3.55 (t, J=6.0 Hz, 2H), 3.35 (s, 3H), 3.09-2.91 (m, 4H), 2.84 (dd, J=6.6, 3.6 Hz, 2H), 2.10 (p, J=6.3 Hz, 2H), 1.38-1.19 (m, 1H), 0.85 (d, J=6.8 Hz, 3H), 0.79 (d, J=6.6 Hz, 3H).

Example 19: 2-Chloro-4-hydroxy-5-isopropyl-9-methoxy-8-(3-methoxypropoxy)-5,6-dihydrobenzo[h]quinoline-3-carboxylicacid

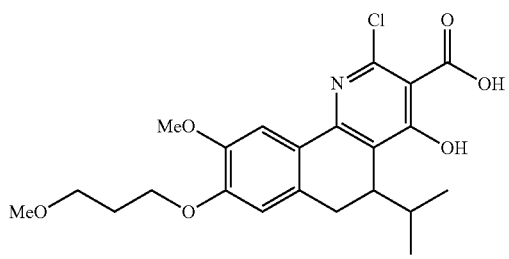

Methyl 1-benzyl-4-((tert-butoxycarbonyl)oxy)-5-isopropyl-9-methoxy-8-(3-methoxypropoxy)-2-oxo-1,2,5,6-tetrahydrobenzo[h]quinoline-3-carboxylate

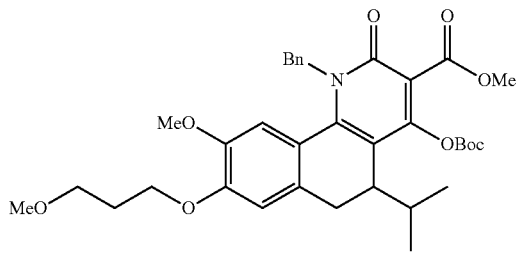

A solution of methyl 1-benzyl-4-hydroxy-5-isopropyl-9-methoxy-8-(3-methoxypropoxy)-2-oxo-5,6-dihydrobenzo[h]quinoline-3-carboxylate (90 mg, 0.17 mmol), di-tert-butyl dicarbonate (45 mg, 0.21 mmol), triethylamine (0.02 mL, 0.17 mmol) and 4-dimethylaminopyridine (2 mg, 0.02 mmol) in CH$_2$Cl$_2$ was stirred at room temperature for 30 minutes. The reaction was quenched by the addition of H$_2$O (1 mL) and extracted with CH$_2$Cl$_2$ (3×2 mL). The combined organic layer was dried over anhydrous sodium sulfate and concentrated under reduced pressure to give methyl 1-benzyl-4-((tert-butoxycarbonyl)oxy)-5-isopropyl-9-methoxy-8-(3-methoxypropoxy)-2-oxo-1,2,5,6-tetrahydrobenzo[h]quinoline-3-carboxylate which was used in the next step without further purification (110 mg, >100% yield, m/z: 622 [M+H]$^+$ observed).

113

Methyl 4-((tert-butoxycarbonyl)oxy)-5-isopropyl-9-methoxy-8-(3-methoxypropoxy)-2-oxo-1,2,5,6-tetrahydrobenzo[h]quinoline-3-carboxylate

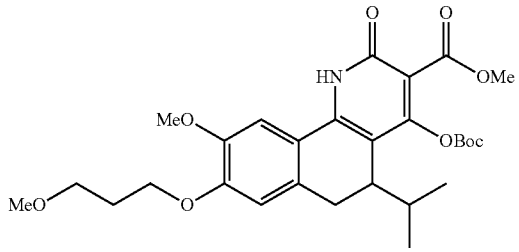

Methyl 1-benzyl-4-tert-butoxycarbonyloxy-5-isopropyl-9-methoxy-8-(3-methoxypropoxy)-2-oxo-5,6-dihydrobenzo[h]quinoline-3-carboxylate (110 mg, 0.18 mmol) and palladium hydroxide (20% on carbon, 20 mg, 0.015 mmol) were dissolved in MeOH (2 mL). A $H_2$ balloon was applied and the reaction mixture for 1 h. The catalyst was filtered off via a syringe filter and the reaction mixture concentrated under reduced pressure to give methyl 4-((tert-butoxycarbonyl)oxy)-5-isopropyl-9-methoxy-8-(3-methoxypropoxy)-2-oxo-1,2,5,6-tetrahydrobenzo[h]quinoline-3-carboxylate which was used in the next step without further purification (110 mg, >100% yield, m/z: 532 [M+H]+ observed).

Methyl 4-((tert-butoxycarbonyl)oxy)-5-isopropyl-9-methoxy-8-(3-methoxypropoxy)-2-(((trifluoromethyl)sulfonyl)oxy)-5,6-dihydrobenzo[h]quinoline-3-carboxylate

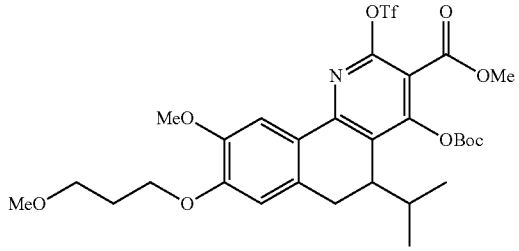

Methyl 4-tert-butoxy carbonyloxy-5-isopropyl-9-methoxy-8-(3-methoxypropoxy)-2-oxo-5,6-dihydro-1H-benzo[h]quinoline-3-carboxylate (110 mg, 0.21 mmol) and triethylamine (0.09 mL, 0.62 mmol) were dissolved in $CH_2Cl_2$ (3 mL). Trifluoromethanesulfonic anhydride (1M solution in $CH_2Cl_2$, 0.25 mL, 0.25 mmol) was added dropwise at 0° C. and stirred for 20 min. The reaction was quenched by adding saturated aqueous sodium bicarbonate solution (1 mL) and extracted with $CH_2Cl_2$ (3×3 mL). The combined organic phase was dried over anhydrous sodium sulfate and concentrated under reduced pressure to give methyl 4-((tert-butoxycarbonyl)oxy)-5-isopropyl-9-methoxy-8-(3-methoxypropoxy)-2-(((trifluoromethyl)sulfonyl)oxy)-5,6-dihydrobenzo[h]quinoline-3-carboxylate which was used in the next step without further purification (140 mg, >100% yield, m/z: 664 [M+H]+ observed).

114

Methyl 2-chloro-4-hydroxy-5-isopropyl-9-methoxy-8-(3-methoxypropoxy)-5,6-dihydrobenzo[h]quinoline-3-carboxylate

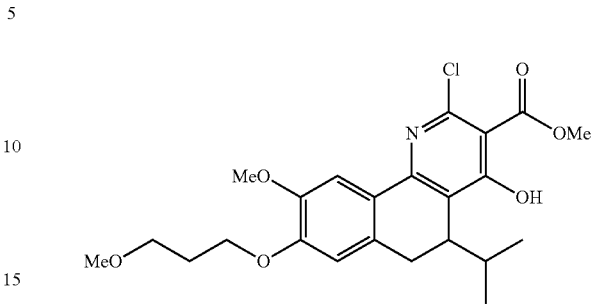

Methyl 4-tert-butoxycarbonyloxy-5-isopropyl-9-methoxy-8-(3-methoxypropoxy)-2-(p-tolylsulfonyloxy)-5,6-dihydrobenzo[h]quinoline-3-carboxylate (140 mg, 0.20 mmol) and HCl (4N solution in 1,4-dioxane, 0.05 mL, 0.20 mmol) were dissolved in EtOAc (3 mL). The reaction mixture was stirred at 0° C. for 2 h. The mixture was concentrated under reduced pressure to give methyl 2-chloro-4-hydroxy-5-isopropyl-9-methoxy-8-(3-methoxypropoxy)-5,6-dihydrobenzo[h]quinoline-3-carboxylate which was used in the next step without further purification (35 mg, 37% yield, m/z: 450 [M+H]+ observed).

2-Chloro-4-hydroxy-5-isopropyl-9-methoxy-8-(3-methoxypropoxy)-5,6-dihydrobenzo[h]quinoline-3-carboxylic acid

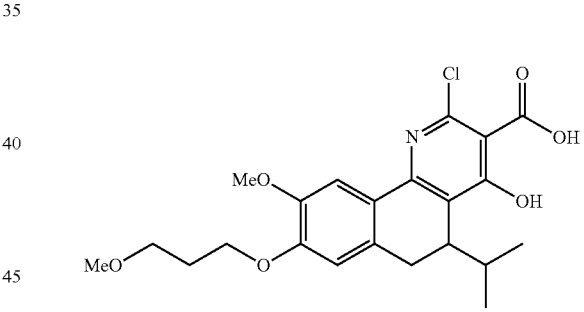

Methyl 2-chloro-4-hydroxy-5-isopropyl-9-methoxy-8-(3-methoxypropoxy)-5,6-dihydrobenzo[h]quinoline-3-carboxylate (35 mg, 0.08 mmol) and lithium iodide (62 mg, 0.47 mmol) were dissolved in EtOAc (3 mL) and stirred at 80° C. for 3 days. The reaction mixture was diluted with $H_2O$ (4 mL), washed with saturated aqueous brine solution (2×2 mL), dried over anhydrous sodium sulfate and concentrated under reduced pressure. The residue was purified by reverse phase HPLC to give 2-chloro-4-hydroxy-5-isopropyl-9-methoxy-8-(3-methoxypropoxy)-5,6-dihydrobenzo[h]quinoline-3-carboxylic acid as a yellow foam (16 mg, 47%, m/z: 436 [M+H]+ observed). 1H NMR (400 MHz, $CDCl_3$) (7.63 (s, 1H), 6.70 (s, 1H), 4.27-4.08 (m, 2H), 3.95 (s, 3H), 3.82 (dt, J=10.0, 6.2 Hz, 1H), 3.64 (dt, J=10.4, 5.4 Hz, 1H), 3.44 (s, 3H), 3.04 (dt, J=7.9, 4.0 Hz, 1H), 2.86 (d, J=4.0 Hz, 2H), 2.17 (p, J=6.1 Hz, 2H), 1.59 (dt, J=14.0, 7.0 Hz, 1H), 0.77 (dd, J=6.7, 1.8 Hz, 6H).

Example 20: 4-Chloro-5-isopropyl-9-methoxy-8-(3-methoxypropoxy)-2-oxo-1,2,5,6-tetrahydrobenzo[h]quinoline-3-carboxylic acid

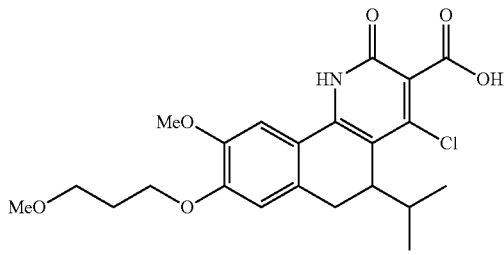

Methyl 4-hydroxy-5-isopropyl-9-methoxy-8-(3-methoxypropoxy)-2-oxo-1,2,5,6-tetrahydrobenzo[h]quinoline-3-carboxylate

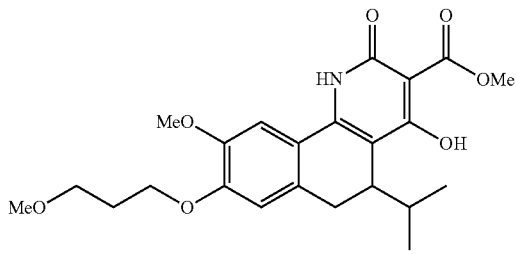 [SMILES: COCCCOc1cc2c(cc1OC)-c1[nH]c(=O)c(C(=O)OC)c(O)c1C(C(C)C)C2]

Methyl 1-benzyl-4-hydroxy-5-isopropyl-9-methoxy-8-(3-methoxypropoxy)-2-oxo-5,6-dihydrobenzo[h]quinoline-3-carboxylate (100 mg, 0.19 mmol) and palladium hydroxide (20% on carbon, 38 mg, 0.03 mmol) were dissolved in methanol (2 mL). A H$_2$ balloon was applied and the reaction was stirred at room temperature for 16 h. The crude reaction mixture was filtered through CELITE®, concentrated under reduced pressure to give methyl 4-hydroxy-5-isopropyl-9-methoxy-8-(3-methoxypropoxy)-2-oxo-1,2,5,6-tetrahydrobenzo[h]quinoline-3-carboxylate which was used in the next step without further purification (80 mg, 97% yield, m/z: 432 [M+H]$^+$ observed). $^1$H NMR (400 MHz, CDCl$_3$) (7.41 (s, 1H), 6.79 (s, 1H), 4.19 (td, J=6.5, 5.1 Hz, 2H), 3.98 (d, J=4.5 Hz, 6H), 3.64-3.52 (m, 3H), 3.36 (s, 3H), 2.98-2.87 (m, 3H), 2.14 (p, J=6.3 Hz, 2H), 1.77-1.51 (m, 1H), 0.83 (dd, J=10.5, 6.7 Hz, 6H).

Methyl 4-chloro-5-isopropyl-9-methoxy-8-(3-methoxypropoxy)-2-oxo-1,2,5,6-tetrahydrobenzo[h]quinoline-3-carboxylate

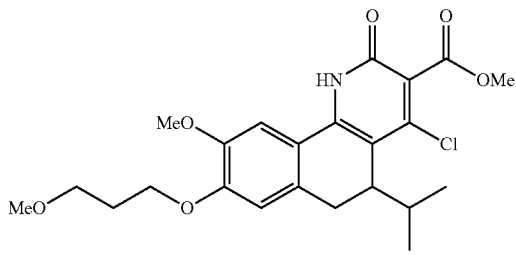 [SMILES: COCCCOc1cc2c(cc1OC)-c1[nH]c(=O)c(C(=O)OC)c(Cl)c1C(C(C)C)C2]

To a solution of methyl 4-hydroxy-5-isopropyl-9-methoxy-8-(3-methoxypropoxy)-2-oxo-5,6-dihydro-1H-benzo[h]quinoline-3-carboxylate (8 mg, 0.02 mmol) and triethylamine (13 uL, 0.09 mmol) in dichloromethane (2 mL) was added oxalyl chloride (16 uL, 0.19 mmol) at room temperature and stirred for 48 h. Saturated aqueous sodium bicarbonate solution (1 mL) was added to quench the reaction. The layers were separated. The aqueous layer was extracted with CH$_2$Cl$_2$ (3×2 mL). The combined organic phase was dried over anhydrous sodium sulfate and concentrated under reduced pressure. The residue was purified by reverse phase HPLC to give methyl 4-chloro-5-isopropyl-9-methoxy-8-(3-methoxypropoxy)-2-oxo-1,2,5,6-tetrahydrobenzo[h]quinoline-3-carboxylate as a yellow foam (8 mg, 95% yield, m/z: 450 [M+H]$^+$ observed). $^1$H NMR (400 MHz, CDCl$_3$) δ 7.47 (s, 1H), 6.79 (s, 1H), 4.27-4.11 (m, 2H), 3.98 (s, 3H), 3.95 (s, 3H), 3.58 (td, J=6.1, 1.7 Hz, 2H), 3.37 (s, 3H), 2.97 (dd, J=19.8, 5.4 Hz, 3H), 2.14 (q, J=6.3 Hz, 2H), 1.69 (dt, J=13.6, 6.9 Hz, 1H), 0.90 (d, J=6.9 Hz, 3H), 0.76 (d, J=6.7 Hz, 3H).

4-Chloro-5-isopropyl-9-methoxy-8-(3-methoxypropoxy)-2-oxo-1,2,5,6-tetrahydrobenzo[h]quinoline-3-carboxylic acid

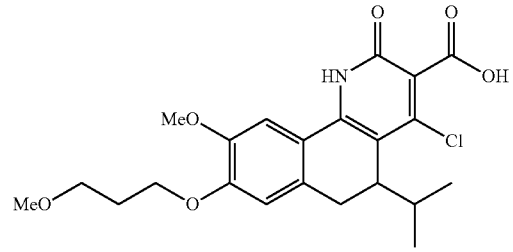

Methyl 4-chloro-5-isopropyl-9-methoxy-8-(3-methoxypropoxy)-2-oxo-5,6-dihydro-1H-benzo[h]quinoline-3-carboxylate (8 mg, 0.02 mmol) was dissolved in THF/MeOH/H$_2$O (1:1:1, 3 mL). Lithium hydroxide monohydrate (7.5 mg, 0.18 mmol) was added and the reaction was stirred at 65° C. for 5 days. The organic solvent was removed under reduced pressure and the residual aqueous phase was acidified to pH=5 with 1N HCl (1 mL). The aqueous phase was extracted with CH$_2$Cl$_2$ (3×3 mL). The combined organic phase was dried over anhydrous sodium sulfate and concentrated under reduced pressure to give 4-chloro-5-isopropyl-9-methoxy-8-(3-methoxypropoxy)-2-oxo-1,2,5,6-tetrahydrobenzo[h]quinoline-3-carboxylic acid as a yellow foam (2.4 mg, 31% yield, m/z: 436 [M+H]$^+$ observed). $^1$H NMR (400 MHz, CDCl$_3$) δ 7.23 (s, 1H), 6.83 (s, 1H), 4.20 (q, J=6.3 Hz, 2H), 3.95 (s, 3H), 3.65 (t, J=5.9 Hz, 1H), 3.59 (td, J=6.1, 1.6 Hz, 2H), 3.37 (s, 3H), 2.99 (d, J=3.9 Hz, 2H), 2.24-2.04 (m, 2H), 1.68-1.66 (m, 1H), 0.91 (d, J=6.9 Hz, 3H), 0.75 (d, J=6.7 Hz, 3H).

Example 21: 2,4-Dichloro-5-isopropyl-9-methoxy-8-(3-methoxypropoxy)-5,6-dihydrobenzo[h]quinoline-3-carboxylic acid

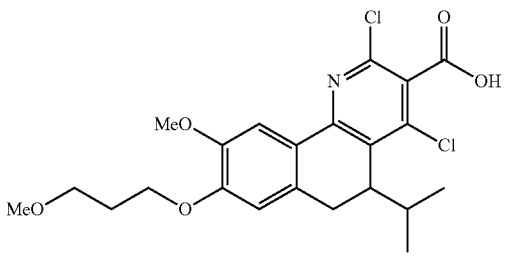 [SMILES: COCCCOc1cc2c(cc1OC)-c1nc(Cl)c(C(=O)O)c(Cl)c1C(C(C)C)C2]

Methyl 5-isopropyl-9-methoxy-8-(3-methoxypropoxy)-2,4-bis(((trifluoromethyl)sulfonyl)oxy)-5,6-dihydrobenzo[h]quinoline-3-carboxylate

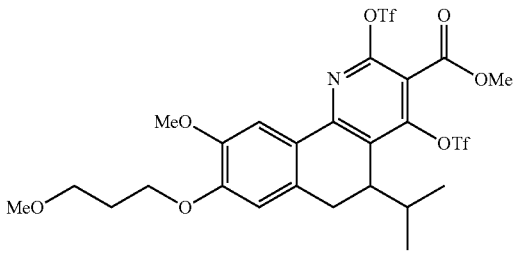 [SMILES: COCCCOc1cc2c(cc1OC)-c1nc(OS(=O)(=O)C(F)(F)F)c(C(=O)OC)c(OS(=O)(=O)C(F)(F)F)c1C(C(C)C)C2]

Methyl 4-hydroxy-5-isopropyl-9-methoxy-8-(3-methoxypropoxy)-2-oxo-5,6-dihydro-1H-benzo[h]quinoline-3-carboxylate (150 mg, 0.35 mmol) and triethylamine (0.24 mL, 1.74 mmol) were dissolved in CH$_2$Cl$_2$ (3 mL). Trifluoromethanesulfonic anhydride (1M dichloromethane solution, 1.0 mL, 1.04 mmol) was added dropwise at 0° C. and stirred for 20 min. The reaction mixture was quenched by adding saturated aqueous sodium bicarbonate solution (1 mL). The reaction mixture was extracted with CH$_2$C$_2$ (3×3 mL). The combined organic layer was dried over anhydrous sodium sulfate and concentrated under reduced pressure to give methyl 5-isopropyl-9-methoxy-8-(3-methoxypropoxy)-2,4-bis(((trifluoromethyl)sulfonyl)oxy)-5,6-dihydrobenzo[h]quinoline-3-carboxylate which was used in the next step without further purification (120 mg, 50% yield, m/z: 696 [M+H]$^+$ observed).

Methyl 2,4-dichloro-5-isopropyl-9-methoxy-8-(3-methoxypropoxy)-5,6-dihydrobenzo[h]quinoline-3-carboxylate

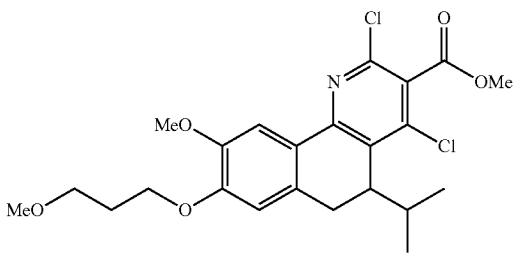 [SMILES: COCCCOc1cc2c(cc1OC)-c1nc(Cl)c(C(=O)OC)c(Cl)c1C(C(C)C)C2]

Methyl 5-isopropyl-9-methoxy-8-(3-methoxypropoxy)-2,4-bis(trifluoromethylsulfonyloxy)-5,6-dihydrobenzo[h]quinoline-3-carboxylate (120 mg, 0.17 mmol) and HCl (4N in 1,4-dioxane, 0.43 mL, 1.73 mmol) were dissolved in EtOAc (3 mL). The reaction mixture was stirred at 80° C. for 3 days. The solvent was removed under reduced pressure to give methyl 2,4-dichloro-5-isopropyl-9-methoxy-8-(3-methoxypropoxy)-5,6-dihydrobenzo[h]quinoline-3-carboxylate which was used in the next step without further purification (15 mg, 20% yield, m/z: 468 [M+H]$^+$ observed).

2,4-Dichloro-5-isopropyl-9-methoxy-8-(3-methoxypropoxy)-5,6-dihydrobenzo[h]quinoline-3-carboxylic acid

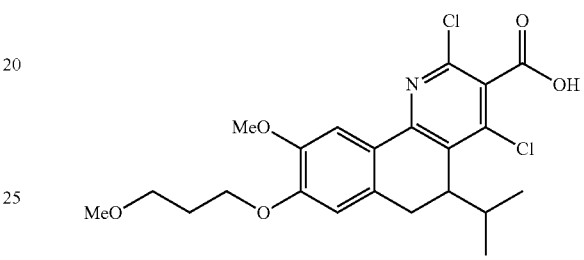

Lithium hydroxide monohydrate (3 mg, 0.06 mmol) and methyl 2,4-dichloro-5-isopropyl-9-methoxy-8-(3-methoxypropoxy)-5,6-dihydrobenzo[h]quinoline-3-carboxylate (15.0 mg, 0.03 mmol) were dissolved in 1,4-dioxane/H$_2$O (1:1, 2 mL). The reaction was stirred at room temperature for 16 h. Aqueous 1N HCl solution (1 mL) was added to the reaction mixture and stirred for 1 minute. The mixture was extracted with CH$_2$Cl$_2$ (3×3 mL). The organic layer was concentrated under reduced pressure. The residue was purified by normal phase SiO$_2$ chromatography (0-10% MeOH/CH$_2$Cl$_2$) to give 2,4-dichloro-5-isopropyl-9-methoxy-8-(3-methoxypropoxy)-5,6-dihydrobenzo[h]quinoline-3-carboxylic acid as a yellow foam (7 mg, 48% yield, m/z: 455 [M+H]$^+$ observed). $^1$H NMR (400 MHz, CD$_3$OD) δ 7.77-7.73 (m, 1H), 6.85 (d, J=8.7 Hz, 1H), 4.12 (tt, J=6.3, 3.2 Hz, 2H), 3.91 (s, 3H), 3.62-3.58 (m, 2H), 3.35 (s, 3H), 3.17 (ddd, J=7.6, 5.7, 1.9 Hz, 1H), 3.06-2.84 (m, 3H), 2.09-2.01 (m, 2H), 0.93-0.77 (m, 6H).

Example 22: 4-Hydroxy-5-isopropyl-9-methoxy-8-(3-methoxypropoxy)-5,6-dihydrobenzo[h]quinolin-2(1H)-one

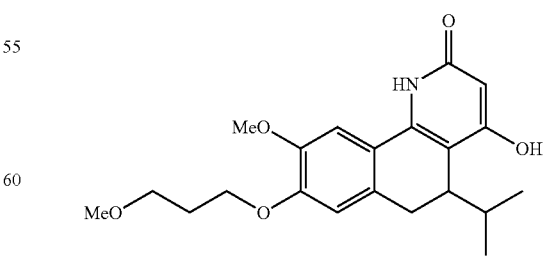

Methyl 4-hydroxy-5-isopropyl-9-methoxy-8-(3-methoxypropoxy)-2-oxo-5,6-dihydro-1H-benzo[h]quinoline-3-carboxylate (110 mg, 0.25 mmol) and lithium hydroxide monohydrate (21 mg, 0.5 mmol) were dissolved in 1,4-dioxane/H$_2$O (3 mL, 2:1). The reaction mixture was stirred at 50° C. for 16 h. Aqueous 1N HCl (1 mL) was added to the reaction and stirred for 5 min. The reaction mixture was extracted with EtOAc (3×2 mL) and concentrated under reduced pressure. The residue was purified via normal phase SiO$_2$ chromatography (0-7% MeOH/CH$_2$Cl$_2$) to give 4-hydroxy-5-isopropyl-9-methoxy-8-(3-methoxypropoxy)-5,6-dihydrobenzo[h]quinolin-2(1H)-one as a yellow solid (9 mg, 9%, m/z: 374 [M+H]$^+$ observed). $^1$H NMR (400 MHz, CDCl$_3$) δ 7.26-7.19 (s, 1H), 6.70 (s, 1H), 6.09 (s, 1H), 4.23-4.03 (m, 2H), 3.94 (s, 3H), 3.59 (ddd, J=21.3, 11.4, 6.3 Hz, 2H), 3.38 (s, 3H), 2.79 (s, 3H), 2.10 (dd, J=9.2, 3.2 Hz, 2H), 1.51 (d, J=12.1 Hz, 1H), 0.87-0.66 (m, 6H).

Example 23: 2-Chloro-5-isopropyl-9-methoxy-8-(3-methoxypropoxy)-5,6-dihydrobenzo[h]quinoline-3-carboxylic acid

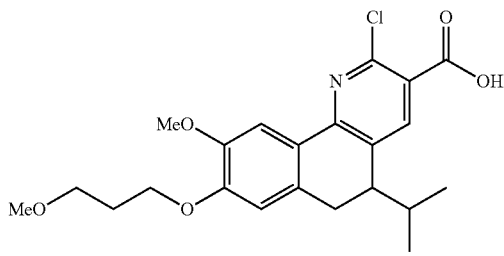 [SMILES: COCCCOc1cc2c(cc1OC)-c1nc(Cl)c(C(=O)O)cc1C(C(C)C)C2]

Methyl 5-isopropyl-9-methoxy-8-(3-methoxypropoxy)-2-(((trifluoromethyl)sulfonyl)oxy)-5,6-dihydrobenzo[h]quinoline-3-carboxylate

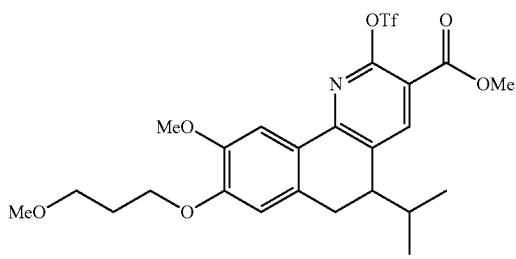 [SMILES: COCCCOc1cc2c(cc1OC)-c1nc(OS(=O)(=O)C(F)(F)F)c(C(=O)OC)cc1C(C(C)C)C2]

Methyl 5-isopropyl-9-methoxy-8-(3-methoxypropoxy)-2-oxo-5,6-dihydro-1H-benzo[h]quinoline-3-carboxylate (140 mg, 0.34 mmol) and triethylamine (0.14 mL, 1.0 mmol) were dissolved in CH$_2$Cl$_2$ (3 mL). Trifluoromethanesulfonic anhydride (1M solution in CH$_2$Cl$_2$, 0.5 mL, 0.5 mmol) was added dropwise at 0° C. and stirred for 10 min. The reaction was quenched with saturated aqueous sodium bicarbonate solution (1 mL). The reaction was extracted with CH$_2$Cl$_2$ (3×3 mL). The combined organic phase was dried over anhydrous sodium sulfate and concentrated under reduced pressure to give methyl 5-isopropyl-9-methoxy-8-(3-methoxypropoxy)-2-(((trifluoromethyl)sulfonyl)oxy)-5,6-dihydrobenzo[h]quinoline-3-carboxylate which was used in next step without further purification (90 mg, 49% yield, m/z: 548 [M+H]$^+$ observed).

Methyl 2-chloro-5-isopropyl-9-methoxy-8-(3-methoxypropoxy)-5,6-dihydrobenzo[h]quinoline-3-carboxylate

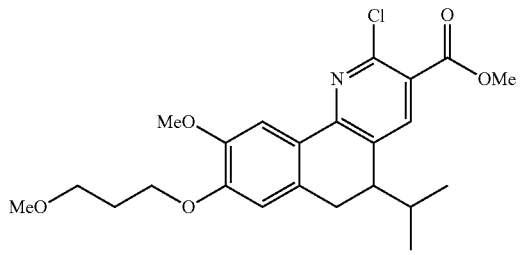 [SMILES: COCCCOc1cc2c(cc1OC)-c1nc(Cl)c(C(=O)OC)cc1C(C(C)C)C2]

Methyl 5-isopropyl-9-methoxy-8-(3-methoxypropoxy)-2-(trifluoromethylsulfonyloxy)-5,6-dihydrobenzo[h]quinoline-3-carboxylate (90 mg, 0.16 mmol) and hydrogen chloride (4N solution in 1,4-dioxane, 0.21 mL, 0.82 mmol) were dissolved in EtOAc (4 mL). The reaction was stirred at 70° C. for 16 h. The reaction mixture was concentrated under reduced pressure to give methyl 2-chloro-5-isopropyl-9-methoxy-8-(3-methoxypropoxy)-5,6-dihydrobenzo[h]quinoline-3-carboxylate which was used in next step without further purification (40 mg, 71% yield, m/z: 434 [M+H]$^+$ observed).

2-Chloro-5-isopropyl-9-methoxy-8-(3-methoxypropoxy)-5,6-dihydrobenzo[h]quinoline-3-carboxylic acid

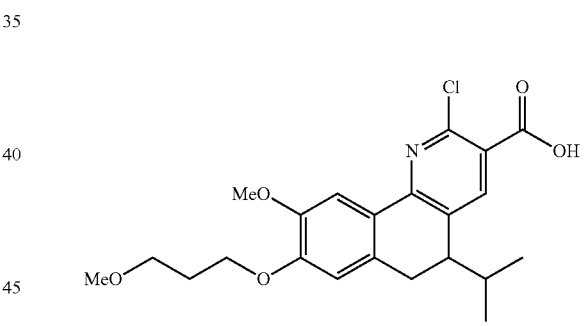

Lithium hydroxide monohydrate (6 mg, 0.14 mmol) and methyl 2-chloro-5-isopropyl-9-methoxy-8-(3-methoxypropoxy)-5,6-dihydrobenzo[h]quinoline-3-carboxylate (40.0 mg, 0.09 mmol) were dissolved in 1,4-dioxane/H$_2$O (1:1, 2 mL). The reaction mixture was stirred at room temperature for 1 h. Aqueous 1N HCl solution (1 mL) was added to the solution and stirred for 1 minute. The reaction was extracted with CH$_2$Cl$_2$ (3×3 mL). The combined organic layer was concentrated under reduced pressure. The residue was purified by normal phase SiO$_2$ chromatography (0-6% MeOH/CH$_2$Cl$_2$) (38 mg, 98% yield, m/z: 420 [M+H]$^+$ observed). $^1$H NMR (400 MHz, CDCl$_3$) δ 8.04 (s, 1H), 7.78 (s, 1H), 6.74 (s, 1H), 4.18 (t, J=6.5 Hz, 2H), 3.98 (s, 3H), 3.61 (t, J=6.0 Hz, 2H), 3.38 (s, 3H), 3.11-2.81 (m, 2H), 2.65-2.47 (m, 1H), 2.22-2.07 (m, 3H), 0.89 (d, J=6.7 Hz, 3H), 0.78 (d, J=6.8 Hz, 3H).

Example 24: 9-Chloro-5-isopropyl-8-(3-methoxypropoxy)-2-oxo-1,2,5,6-tetrahydro-1,10-phenanthroline-3-carboxylic acid

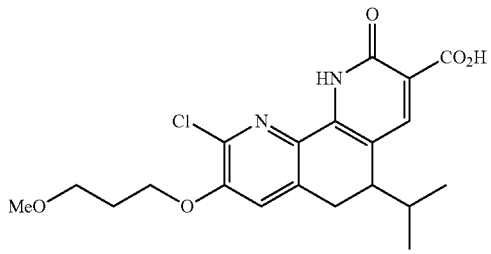 [SMILES: COCCCOc1cc2c(nc1Cl)-c1[nH]c(=O)c(C(=O)O)cc1C(C(C)C)C2]

6-Isopropyl-3-nitro-5,6,7,8-tetrahydroquinolin-2-ol

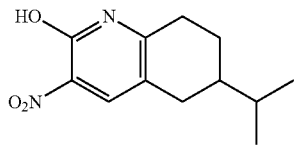 [SMILES: CC(C)C1CCc2nc(O)c([N+](=O)[O-])cc2C1]

To a solution of NaOH (4.07 g, 101.7 mmol) in H$_2$O (150 mL) was added 2-(hydroxymethylene)-4-isopropylcyclohexan-1-one (16.3 g, 97.0 mmol, synthesized by the procedure described in the PCt Patent Appl. Publ. No. WO2006098961). To the clear yellow solution was added aqueous piperidinium acetate solution [15 mL, synthesized by mixing glacial acetic acid (5.2 mL), piperidine (9 mL) and H$_2$O (12.5 mL)]. The resulting solution was stirred at 100° C. for 5 min. Nitro acetamide (10.1 g, 97 mmol, synthesized by the procedure described in the patent WO2016176460) was then added portion-wise over 20 min. The reaction mixture was then stirred at 100° C. for 3 h and then cooled to room temperature. The mixture was extracted with CH$_2$Cl$_2$ (2×100 mL). The organic phase was dried over anhydrous sodium sulfate and evaporated in vacuum. The dark red residue was triturated with EtOAc (25 mL) and allowed to slurry for 30 min with stirring. The resulting yellow solid was collected by filtration and dried under vacuum to give 6-isopropyl-3-nitro-5,6,7,8-tetrahydroquinolin-2-ol as a yellow solid (8.2 g, 36%, m/z: 237 [M+H]$^+$ observed). $^1$H NMR (300 MHz, CDCl$_3$): δ 7.97 (s, 1H), 3.15-3.08 (m, 1H), 2.98-2.86 (m, 2H), 2.58 (dd, J=18, 9 Hz, 1H), 2.12-2.06 (m, 1H), 1.70-1.50 (m, 3H), 1.01 (dd, J=7.5, 3 Hz, 6H).

2-Chloro-6-isopropyl-3-nitro-5,6,7,8-tetrahydroquinoline

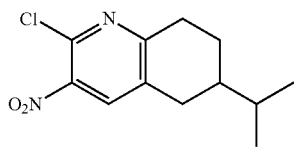 [SMILES: CC(C)C1CCc2nc(Cl)c([N+](=O)[O-])cc2C1]

A mixture of 6-isopropyl-3-nitro-5,6,7,8-tetrahydroquinolin-2-ol (14.2 g, 60.1 mmol) and phosphorous(V) oxychloride (90 mL, 962 mmol) was stirred at 100° C. for 2 h. The excess phosphorous(V) oxychloride was removed under reduced pressure and the residue was poured into ice water (100 mL) and stirred for 15 minutes. The mixture was adjusted to pH 7 using aqueous 1N NaOH solution and extracted with EtOAc (2×100 mL). The combined organic phase was washed with H$_2$O (200 mL), dried over anhydrous sodium sulfate and evaporated in vacuum. The residue was purified by normal phase SiO$_2$ chromatography (0 to 20% EtOAc/hexanes) to give 2-chloro-6-isopropyl-3-nitro-5,6,7,8-tetrahydroquinoline as a yellow oil (14.3 g, 93%, m/z: 255 [M+H]$^+$ observed).

2-Chloro-6-isopropyl-5,6,7,8-tetrahydroquinolin-3-amine

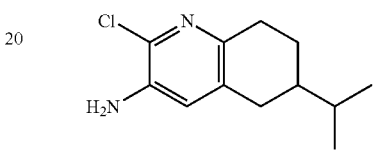

To a stirred solution of 2-chloro-6-isopropyl-3-nitro-5,6,7,8-tetrahydroquinoline (7.23 g, 28.5 mmol) in ethanol (100 mL) was added glacial acetic acid (60 mL) followed by the addition of iron powder (11.3 g, 202 mmol), and the mixture was stirred at room temperature for 24 h. The reaction mixture was concentrated in vacuum and the resulting residue was treated with EtOAc (100 mL) and saturated aqueous sodium bicarbonate solution (100 mL). The mixture was stirred for 30 min and then filtered through CELITE®. The mixture was washed with EtOAc (100 mL), the combined organic phase was washed with saturated aqueous brine solution (100 mL), dried over anhydrous sodium sulfate and concentrated under reduced pressure. The residue was purified by normal phase SiO$_2$ chromatography (0 to 20% EtOAc/hexanes) to give 2-chloro-6-isopropyl-5,6,7,8-tetrahydroquinolin-3-amine as white solid (6.2 g, 97%, m/z: 225 [M+H]$^+$ observed). $^1$H NMR (300 MHz, DMSO-d$_6$): δ 6.83 (s, 1H), 5.17 (s, 2H), 2.64-2.58 (m, 3H), 2.41-2.32 (m, 1H), 1.89-1.86 (m, 1H), 1.58-1.52 (m, 1H), 1.43-1.30 (m, 2H), 0.92 (d, J=6.0 Hz, 6H).

2-Chloro-6-isopropyl-5,6,7,8-tetrahydroquinolin-3-ol

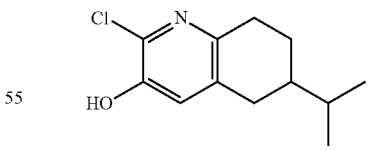

To a stirred solution of 2-chloro-6-isopropyl-5,6,7,8-tetrahydroquinolin-3-amine (2.0 g, 8.92 mmol) in trifluoroacetic acid (20 mL) at 0° C. was added a pre-made solution of sodium nitrite (1.22 g, 17.7 mmol) in H$_2$O (8 mL) dropwise and the mixture was stirred for 1 h. The ice bath was removed, and the mixture was stirred at room temperature for 30 min. The mixture was then heated at 70° C. in a pre-heated oil bath for 40 min. The reaction mixture was concentrated under reduced pressure and the residue was treated with saturated aqueous sodium bicarbonate solution (100 mL) and EtOAc (100 mL). The mixture was stirred for 30 min and then the layers were separated. The aqueous layer was extracted with EtOAc (50 mL). The combined organic phase was washed with saturated aqueous brine solution (100 mL), dried over anhydrous sodium sulfate and concentrated in vacuum. The residue was triturated with $CH_2Cl_2$ (10 mL), the resulting solid was collected by filtration and washed with $CH_2Cl_2$ (3 mL) to give 2-chloro-6-isopropyl-5,6,7,8-tetrahydroquinolin-3-ol as a yellow solid (1.15 g). The mother liquor was concentrated in vacuum and purified by normal phase $SiO_2$ chromatography (0 to 40% EtOAc/hexanes) to give additional 2-chloro-6-isopropyl-5,6,7,8-tetrahydroquinolin-3-ol as an off-white solid (0.166 g, combined yield 1.32 g, 66%, m/z: 226 [M+H]$^+$ observed). $^1$H NMR (300 MHz, CDCl$_3$): δ 6.99 (s, 1H), 2.95-2.87 (m, 1H), 2.81-2.68 (m, 2H), 2.50-2.41 (m, 1H), 2.04-1.95 (m, 1H), 1.34 (bs, 1H), 1.65-1.55 (m, 1H), 1.53-1.40 (m, 2H), 0.95 (d, J=6.0 Hz, 6H).

2-Chloro-6-isopropyl-3-(3-methoxypropoxy)-5,6,7,8-tetrahydroquinoline

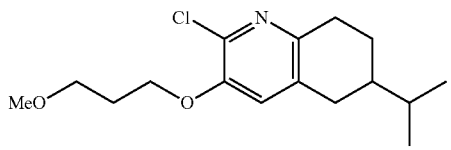 [SMILES: COCCCOc1cc2c(nc1Cl)CCC(C(C)C)C2]

To a stirred solution of 2-chloro-6-isopropyl-5,6,7,8-tetrahydroquinolin-3-ol (1.31 g, 5.82 mmol) in acetonitrile (60 mL) was added anhydrous potassium carbonate (2.41 g, 17.4 mmol) followed by 1-bromo-3-methoxypropane (1.3 mL, 11.6 mmol) and the mixture was stirred at 60° C. for 20 h. The reaction mixture was then cooled, poured into ice cold water (100 mL) and extracted with EtOAc (2×100 mL). The EtOAc layer was then washed with saturated aqueous brine solution (100 mL), dried over anhydrous sodium sulfate and concentrated in vacuum. The crude oil was purified by normal phase $SiO_2$ chromatography (0 to 30% EtOAc/hexanes) to give 2-chloro-6-isopropyl-3-(3-methoxypropoxy)-5,6,7,8-tetrahydroquinoline as a yellow oil (1.37 g, 80%, m/z: 298 [M+H]$^+$ observed). $^1$H NMR (300 MHz, CDCl$_3$): δ 6.94 (s, 1H), 4.10 (t, J=6.0 Hz, 2H), 3.60 (t, J=6.0 Hz, 2H), 3.37 (s, 3H), 2.98-2.90 (m, 1H), 2.84-2.71 (m, 2H), 2.54-2.45 (m, 1H), 2.13-2.02 (m, 2H), 2.01-1.97 (m, 1H), 1.65-1.53 (m, 1H), 1.51-1.42 (m, 2H), 0.97 (dd, J=6.0 Hz & 3.0 Hz, 6H).

2-Chloro-6-isopropyl-3-(3-methoxypropoxy)-6,7-dihydroquinolin-8(5H)-one oxime

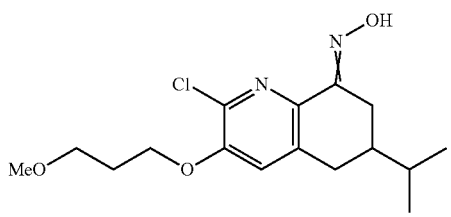 [SMILES: COCCCOc1cc2c(nc1Cl)C(=NO)CC(C(C)C)C2]

A solution of 2-chloro-6-isopropyl-3-(3-methoxypropoxy)-5,6,7,8-tetrahydroquinoline (1.0 g, 3.3 mmol) and diisopropylamine (1.4 mL, 10.0 mmol) in dry tert-butyl methyl ether (50 mL) was stirred for 15 min at room temperature under an argon atmosphere The solution was then cooled to −78° C. and a solution of n-butyllithium (2.5M in hexanes, 4 mL, 10.0 mmol) was added rapidly. The temperature of the cooling bath was then allowed to increase to −40° C. over 1 h and maintained at −40° C. for 2 additional hours. The dark red mixture was cooled to −78° C. and cannulated into a pre-cooled solution of isoamyl nitrite (2.2 mL, 16.7 mmol) in dry tert-butyl methyl ether (50 mL) at −78° C. The temperature of the cooling bath was gradually increased to room temperature over 1 h. The reaction was diluted with H$_2$O (20 mL), extracted with EtOAc (50 mL), washed with saturated aqueous brine solution (50 mL), dried over anhydrous sodium sulfate and concentrated in vacuum. The crude oil was purified by normal phase $SiO_2$ chromatography (0 to 70% EtOAc/hexanes) to give a mixture of isomers of 2-chloro-6-isopropyl-3-(3-methoxypropoxy)-6,7-dihydroquinolin-8(5H)-one oxime as a yellow solid (0.44 g, 40%, m/z: 327 [M+H]$^+$ observed).

2-Chloro-6-isopropyl-3-(3-methoxypropoxy)-6,7-dihydroquinolin-8(5H)-one

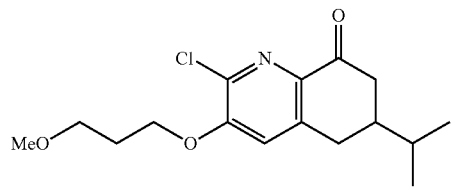 [SMILES: COCCCOc1cc2c(nc1Cl)C(=O)CC(C(C)C)C2]

A solution of 2-chloro-6-isopropyl-3-(3-methoxypropoxy)-6,7-dihydroquinolin-8(5H)-one oxime (0.24 g, 0.74 mmol) and glyoxylic acid (50% solution in water, 15.0 mL) was stirred at room temperature for 24 h. The reaction mixture was poured into ice cold water (10 mL) and neutralized with 10% aqueous NaOH solution. The mixture was extracted with EtOAc (2×25 mL), washed with saturated aqueous brine solution (15 mL), dried over anhydrous sodium sulfate and concentrated in vacuum. The crude oil was purified by normal phase $SiO_2$ chromatography (0 to 80% EtOAc/hexanes) to give 2-chloro-6-isopropyl-3-(3-methoxypropoxy)-6,7-dihydroquinolin-8(5H)-one as a yellow oil (0.18 g, 78%, m/z: 312 [M+H]$^+$ observed). $^1$H NMR (400 MHz, CDCl$_3$): δ 7.06 (s, 1H), 4.22 (t, J=8.0 Hz, 2H), 3.61 (t, J=8.0 Hz, 2H), 3.38 (s, 3H), 2.98-2.79 (m, 3H), 2.46-2.39 (dd, J=12, 9 Hz, 1H), 2.19-2.13 (m, 2H), 2.09-2.03 (m, 1H), 1.74-1.67 (m, 1H), 1.02 (d, J=8.0 Hz, 6H).

N-Benzyl-2-chloro-6-isopropyl-3-(3-methoxypropoxy)-6,7-dihydroquinolin-8(5H)-imine

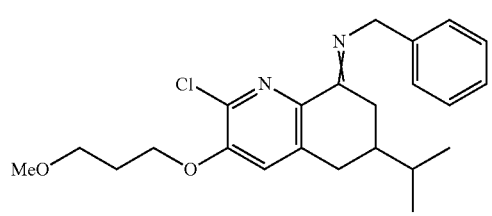 [SMILES: COCCCOc1cc2c(nc1Cl)C(=NCc1ccccc1)CC(C(C)C)C2]

To a stirred solution of 2-chloro-6-isopropyl-3-(3-methoxypropoxy)-6,7-dihydroquinolin-8(5H)-one (0.3 g, 0.96 mmol) and benzyl amine (0.16 mL, 1.45 mmol) in CH$_2$Cl$_2$ (30 mL) at 0° C. was added titanium tetrachloride (1.0M solution in CH$_2$Cl$_2$, 1.2 mL, 1.15 mmol) and the mixture allowed to stir at room temperature for 24 h. The reaction mixture was then cooled to 0° C., treated with saturated aqueous sodium bicarbonate solution (50 mL) and stirred for an additional 15 min. Following separation of the organic phase, the aqueous layer was further extracted with CH$_2$Cl$_2$ (25 mL). The combined organic phase was dried over anhydrous sodium sulfate and concentrated under vacuum to give N-benzyl-2-chloro-6-isopropyl-3-(3-methoxypropoxy)-6,7-dihydroquinolin-8(5H)-imine as an yellow oil, which was used without further purification (0.35 g, 91%, m/z: 401 [M+H]$^+$ observed).

Methyl 1-benzyl-9-chloro-5-isopropyl-8-(3-methoxypropoxy)-2-oxo-1,2,5,6-tetrahydro-1,10-phenanthroline-3-carboxylate

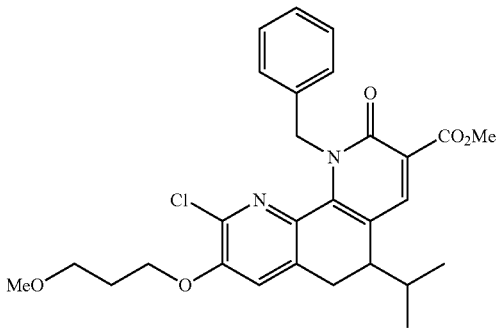 [SMILES: COCCCOc1cc2c(nc1Cl)-c1c(cc(C(=O)OC)c(=O)n1Cc1ccccc1)C(C(C)C)C2]

A mixture of N-benzyl-2-chloro-6-isopropyl-3-(3-methoxypropoxy)-6,7-dihydroquinolin-8(5H)-imine (0.35 g, 0.87 mmol) and 1,3-dimethyl-2-(methoxymethylidene)propanedioate (0.457 g, 2.62 mmol) in diphenyl ether (3 mL) was heated at 220° C. in a microwave reactor for 45 min. The mixture was purified by normal phase SiO$_2$ chromatography (0-70% EtOAc/hexanes) to give methyl 1-benzyl-9-chloro-5-isopropyl-8-(3-methoxypropoxy)-2-oxo-1,2,5,6-tetrahydro-1,10-phenanthroline-3-carboxylate as a yellow oil (0.062 g, 14%, m/z: 511 [M+H]$^+$ observed). $^1$H NMR (300 MHz, CDCl$_3$): δ 8.07 (s, 1H), 7.28 (s, 1H), 7.15-7.00 (m, 5H), 6.38 (q, 2H), 4.20-4.13 (m, 2H), 3.95 (s, 3H), 3.60 (t, J=6.0 Hz, 2H), 3.37 (s, 3H), 2.96-2.79 (m, 2H), 2.37-2.33 (m, 1H), 2.17-2.08 (m, 2H), 1.46-1.39 (m, 1H), 0.85 (d, J=6.0 Hz, 6H).

Methyl 9-chloro-5-isopropyl-8-(3-methoxypropoxy)-2-oxo-1,2,5,6-tetrahydro-1,10-phenanthroline-3-carboxylate

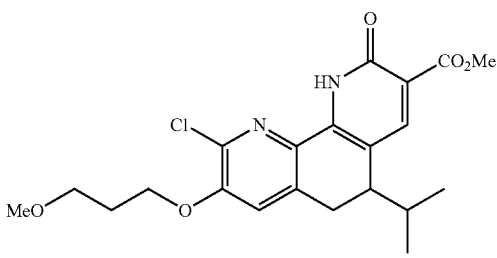 [SMILES: COCCCOc1cc2c(nc1Cl)-c1[nH]c(=O)c(C(=O)OC)cc1C(C(C)C)C2]

A mixture of methyl 1-benzyl-9-chloro-5-isopropyl-8-(3-methoxypropoxy)-2-oxo-1,2,5,6-tetrahydro-1,10-phenanthroline-3-carboxylate (0.062 g, 0.12 mmol) and trifluoroacetic acid (3 mL) was heated at 90° C. in a microwave reactor for 3 days. The trifluoroacetic acid was removed under reduced pressure and the residue was treated with aqueous saturated sodium bicarbonate solution (10 mL). The mixture was then extracted with EtOAc (2×15 mL). The combined organic phase was dried over anhydrous sodium sulfate and concentrated in vacuum. The crude oil was triturated with methanol (1 mL) to give methyl 9-chloro-5-isopropyl-8-(3-methoxypropoxy)-2-oxo-1,2,5,6-tetrahydro-1,10-phenanthroline-3-carboxylate as a white solid which was collected by filtration (27 mg). The mother liquor was concentrated in vacuum and purified by normal phase SiO$_2$ chromatography (0-100% EtOAc/hexanes) to give methyl 9-chloro-5-isopropyl-8-(3-methoxypropoxy)-2-oxo-1,2,5,6-tetrahydro-1,10-phenanthroline-3-carboxylate as a yellow solid (15 mg, combined yield 42 mg, 82%, m/z: 421 [M+H]$^+$ observed). $^1$H NMR (300 MHz, CDCl$_3$): δ 10.14 (bs, 1H), 8.17 (s, 1H), 7.11 (s, 1H), 4.22 (t, J=6.0 Hz, 2H), 3.95 (s, 3.62, 3H) (t, J=6.0 Hz, 2H), 3.38 (s, 3H), 3.18-3.13 (m, 1H), 3.04-2.97 (m, 1H), 2.66-2.63 (m, 1H), 2.20-2.12 (m, 2H), 1.80-1.75 (m, 1H), 0.90 (d, J=9.0 Hz, 3H), 0.86 (d, J=6.0 Hz, 3H).

9-Chloro-5-isopropyl-8-(3-methoxypropoxy)-2-oxo-1,2,5,6-tetrahydro-1,10-phenanthroline-3-carboxylic acid

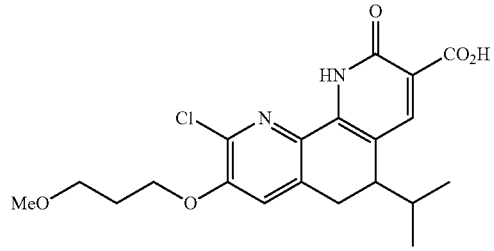

To a solution of methyl 9-chloro-5-isopropyl-8-(3-methoxypropoxy)-2-oxo-1,2,5,6-tetrahydro-1,10-phenanthroline-3-carboxylate (30 mg, 0.07 mmol) in THF (2 mL) was added a solution of lithium hydroxide (8 mg, 0.35 mmol) in H$_2$O (1 mL) and the mixture was stirred at room temperature for 15 h. The solvent was removed under reduced pressure, the resulting residue was diluted with H$_2$O (2 mL) and the pH of the aqueous layer was adjusted to 5 using 1N HCl. The mixture was then extracted with EtOAc (2×3 mL). The combined organic phase was dried over anhydrous sodium sulfate, dried over anhydrous sodium sulfate and concentrated in vacuum. The crude residue was triturated with methanol (1 mL) to give 9-chloro-5-isopropyl-8-(3-methoxypropoxy)-2-oxo-1,2,5,6-tetrahydro-1,10-phenanthroline-3-carboxylic acid as a yellow solid which was collected by filtration and air dried (18 mg, 62%, m/z: 407 [M+H]$^+$ observed). $^1$H NMR (300 MHz, CDCl$_3$): δ 15.18 (s, 1H), 10.65 (s, 1H), 8.44 (s, 1H), 7.16 (s, 1H), 4.24 (t, J=6.0 Hz, 2H), 3.62 (t, J=6.0 Hz, 2H), 3.39 (s, 3H), 3.25-3.17 (m, 1H), 3.08-3.02 (m, 1H), 2.77-2.73 (m, 1H), 2.21-2.13 (m, 2H), 1.86-1.79 (m, 1H), 0.91 (d, J=9.0 Hz, 3H), 0.87 (d, J=9.0 Hz, 3H).

The following examples were prepared in a similar manner as 9-chloro-5-isopropyl-8-(3-methoxypropoxy)-2-oxo- 1,2,5,6-tetrahydro-1,10-phenanthroline-3-carboxylic acid from 2-chloro-6-isopropyl-3-(3-methoxypropoxy)-6,7-dihydroquinolin-8(5H)-one and an appropriate amine.

Example 25: 9-Chloro-5-isopropyl-8-(3-methoxypropoxy)-1-methyl-2-oxo-1,2,5,6-tetrahydro-1,10-phenanthroline-3-carboxylic acid

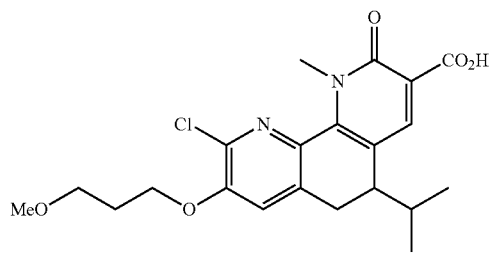 [SMILES: COCCCOc1cc2c(nc1Cl)-c1c(cc(C(=O)O)c(=O)n1C)C(C(C)C)C2]

m/z: 421 [M+H]$^+$ observed. $^1$H NMR (400 MHz, CDCl$_3$): δ 14.80 (s, 1H), 8.37 (s, 1H), 7.18 (s, 1H), 4.28-4.25 (m, 2H), 4.09 (s, 3H), 3.64 (t, J=8.0 Hz, 2H), 3.40 (s, 3H), 3.13-2.96 (m, 2H), 2.60-2.50 (m, 1H), 2.20-2.17 (m, 2H), 1.60-1.48 (m, 1H), 0.85 (t, J=8.0 Hz, 6H).

Example 26: 9-Chloro-4-hydroxy-5-isopropyl-8-(3-methoxypropoxy)-2-oxo-1,2,5,6-tetrahydro-1,10-phenanthroline-3-carboxylic acid

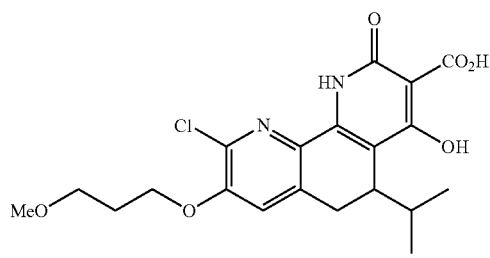 [SMILES: COCCCOc1cc2c(nc1Cl)-c1[nH]c(=O)c(C(=O)O)c(O)c1C(C(C)C)C2]

N-Benzyl-2-chloro-6-isopropyl-3-(3-methoxypropoxy)-6,7-dihydroquinolin-8(5H)-imine

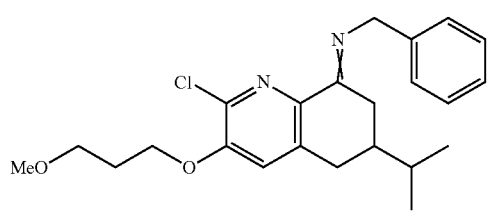 [SMILES: COCCCOc1cc2c(nc1Cl)C(=NCc1ccccc1)CC(C(C)C)C2]

To a stirred solution of 2-chloro-6-isopropyl-3-(3-methoxypropoxy)-6,7-dihydroquinolin-8(5H)-one (0.25 g, 0.80 mmol) and benzylamine (0.13 mL, 1.21 mmol) in CH$_2$Cl$_2$ (30 mL) at 0° C. was added dropwise titanium tetrachloride (1M solution in CH$_2$Cl$_2$, 1 mL, 0.96 mmol) and the mixture was allowed to stir at room temperature for 24 h. The reaction mixture was cooled to 0° C. and treated with saturated aqueous sodium bicarbonate solution (50 mL) and stirred further for 15 min. Following separation of the organic phase, the aqueous layer was further extracted with CH$_2$Cl$_2$ (2×25 mL). The combined organic phase was dried over anhydrous sodium sulfate and concentrated in vacuum to give N-benzyl-2-chloro-6-isopropyl-3-(3-methoxypropoxy)-6,7-dihydroquinolin-8(5H)-imine as a yellow oil that was used without further purification (0.34 g, >100% yield, m/z: 401 [M+H]$^+$ observed).

Methyl 1-benzyl-9-chloro-4-hydroxy-5-isopropyl-8-(3-methoxypropoxy)-2-oxo-1,2,5,6-tetrahydro-1,10-phenanthroline-3-carboxylate

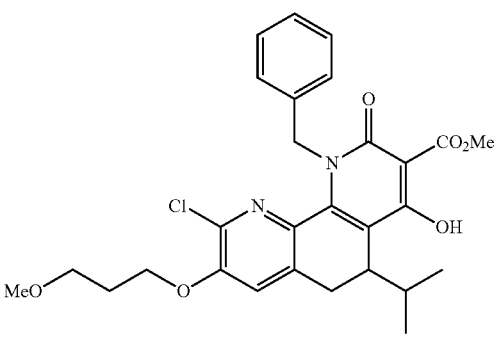 [SMILES: COCCCOc1cc2c(nc1Cl)-c1c(c(O)c(C(=O)OC)c(=O)n1Cc1ccccc1)C(C(C)C)C2]

A mixture of N-benzyl-2-chloro-6-isopropyl-3-(3-methoxypropoxy)-6,7-dihydroquinolin-8(5H)-imine (0.34 g, 0.85 mmol) and trimethyl methanetricarboxylate (0.491 g, 2.50 mmol) in diglyme (3 mL) was heated at 180° C. in a microwave reactor for 45 min. The reaction mixture was concentrated under reduced pressure and the residue purified by normal phase SiO$_2$ chromatography (0-70% EtOAc/hexanes) to give methyl 1-benzyl-9-chloro-4-hydroxy-5-isopropyl-8-(3-methoxypropoxy)-2-oxo-1,2,5,6-tetrahydro-1,10-phenanthroline-3-carboxylate as a yellow oil (0.12 g, 27%, m/z: 527 [M+H]$^+$ observed). $^1$H NMR (300 MHz, CDCl$_3$): δ 13.80 (s, 1H), 7.28 (s, 1H), 7.16-6.98 (m, 5H), 6.30-6.10 (m, 2H), 4.20-4.11 (m, 2H), 4.02 (s, 3H), 3.59 (t, J=6.0 Hz, 2H), 3.37 (s, 3H), 3.01-2.96 (m, 1H), 2.89-2.75 (m, 2H), 2.16-2.08 (m, 2H), 1.42-1.37 (m, 1H), 0.84 (d, J=6.0 Hz, 3H), 0.78 (d, J=6.0 Hz, 3H).

Methyl 9-chloro-4-hydroxy-5-isopropyl-8-(3-methoxypropoxy)-2-oxo-1,2,5,6-tetrahydro-1,10-phenanthroline-3-carboxylate

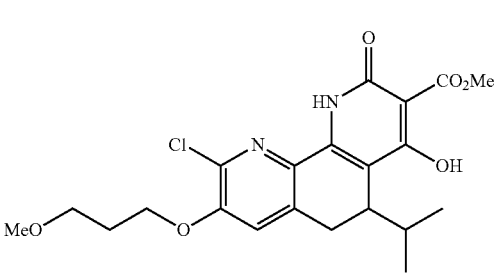 [SMILES: COCCCOc1cc2c(nc1Cl)-c1[nH]c(=O)c(C(=O)OC)c(O)c1C(C(C)C)C2]

A mixture of methyl 1-benzyl-9-chloro-4-hydroxy-5-isopropyl-8-(3-methoxypropoxy)-2-oxo-1,2,5,6-tetrahydro-1,10-phenanthroline-3-carboxylate (0.12 g, 0.23 mmol) and trifluoroacetic acid (3 mL) was heated at 90° C. in a microwave reactor for 56 h. The reaction mixture was concentrated under reduced pressure and the residue was treated with saturated aqueous sodium bicarbonate solution (10 mL). The mixture was extracted with EtOAc (2×15 mL), the combined organic phase was dried over anhydrous sodium sulfate and concentrated in vacuum. The crude oil was purified by normal phase SiO₂ chromatography (0-100% EtOAc/hexanes) to give methyl 9-chloro-4-hydroxy-5-isopropyl-8-(3-methoxypropoxy)-2-oxo-1,2,5,6-tetrahydro-1,10-phenanthroline-3-carboxylate as a yellow oil (0.064 g, 67, m/z: 437 [M+H]⁺ observed).

9-Chloro-4-hydroxy-5-isopropyl-8-(3-methoxypropoxy)-2-oxo-1,2,5,6-tetrahydro-1,10-phenanthroline-3-carboxylicacid

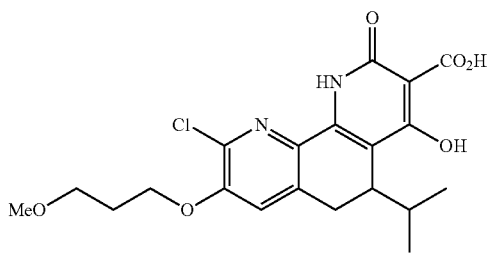

A mixture of methyl 9-chloro-4-hydroxy-5-isopropyl-8-(3-methoxypropoxy)-2-oxo-1,2,5,6-tetrahydro-1,10-phenanthroline-3-carboxylate (0.064 g, 0.15 mmol) and lithium iodide (0.058 g, 0.43 mmol) in anhydrous EtOAc (3 mL) was heated at 60° C. for 4 h. The reaction mixture was cooled and diluted with EtOAc (15 mL) and washed with water (15 mL). The organic phase was then dried over anhydrous sodium sulfate and concentrated in vacuum. The crude solid was purified by normal phase SiO₂ chromatography (0-100% EtOAc/hexanes) to give 9-chloro-4-hydroxy-5-isopropyl-8-(3-methoxypropoxy)-2-oxo-1,2,5,6-tetrahydro-1,10-phenanthroline-3-carboxylic acid as an off-white solid (30 mg, 49%, m/z: 423 [M+H]⁺ observed). ¹H NMR (300 MHz, CDCl₃): δ 15.12 (s, 1H), 14.00 (s, 1H), 10.05 (s, 1H), 7.15 (s, 1H), 4.24 (t, J=6.0 Hz, 2H), 3.62 (t, J=6.0 Hz, 2H), 3.39 (s, 3H), 3.14-3.04 (m, 3H), 2.21-2.13 (m, 2H), 1.87-1.72 (m, 1H), 0.94 (d, J=6.0 Hz, 3H), 0.78 (d, J=9.0 Hz, 3H).

Example 27: 9-Chloro-4-hydroxy-5-isopropyl-8-(3-methoxypropoxy)-2-oxo-1,2,5,6-tetrahydro-1,10-phenanthroline-3-carboxylic acid (single enantiomer I)

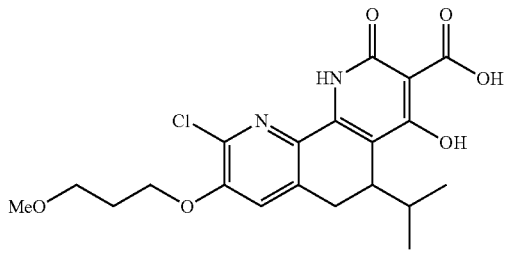 [SMILES: COCCCOc1cc2c(nc1Cl)-c1[nH]c(=O)c(C(=O)O)c(O)c1C(C(C)C)C2]

Example 28: 9-Chloro-4-hydroxy-5-isopropyl-8-(3-methoxypropoxy)-2-oxo-1,2,5,6-tetrahydro-1,10-phenanthroline-3-carboxylic acid (single enantiomer II)

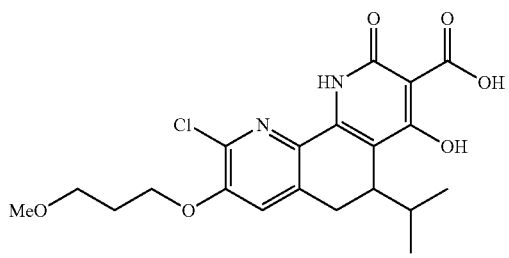 [SMILES: COCCCOc1cc2c(nc1Cl)-c1[nH]c(=O)c(C(=O)O)c(O)c1C(C(C)C)C2]

21 mg of the mixture of enantiomers was separated by chiral HPLC on a CHIRALPACK AY-H column using 0-25% EtOH (0.2% TFA as modifier)/n-hexane to give 9-chloro-4-hydroxy-5-isopropyl-8-(3-methoxypropoxy)-2-oxo-1,2,5,6-tetrahydro-1,10-phenanthroline-3-carboxylic acid (single enantiomer I) as an off-white solid (faster eluting enantiomer, 6.8 mg, 32%, m/z: 423 [M+H]+ observed), and 9-chloro-4-hydroxy-5-isopropyl-8-(3-methoxypropoxy)-2-oxo-1,2,5,6-tetrahydro-1,10-phenanthroline-3-carboxylic acid (single enantiomer II) as a yellow solid (slower eluting enantiomer, 10.6 mg, 48%, m/z: 423 [M+H]+ observed).

Example 27: 9-Chloro-4-hydroxy-5-isopropyl-8-(3-methoxypropoxy)-2-oxo-1,2,5,6-tetrahydro-1,10-phenanthroline-3-carboxylic acid (single enantiomer I). m/z: 423 [M+H]⁺ observed). ¹H NMR (300 MHz, CDCl₃): δ 15.12 (s, 1H), 14.00 (s, 1H), 10.05 (s, 1H), 7.15 (s, 1H), 4.24 (t, J=6.0 Hz, 2H), 3.62 (t, J=6.0 Hz, 2H), 3.39 (s, 3H), 3.14-3.04 (m, 3H), 2.21-2.13 (m, 2H), 1.87-1.72 (m, 1H), 0.94 (d, J=6.0 Hz, 3H), 0.78 (d, J=9.0 Hz, 3H).

Example 28: 9-Chloro-4-hydroxy-5-isopropyl-8-(3-methoxypropoxy)-2-oxo-1,2,5,6-tetrahydro-1,10-phenanthroline-3-carboxylic acid (single enantiomer II). m/z: 423 [M+H]⁺ observed). ¹H NMR (300 MHz, CDCl₃): δ 15.12 (s, 1H), 14.00 (s, 1H), 10.05 (s, 1H), 7.15 (s, 1H), 4.24 (t, J=6.0 Hz, 2H), 3.62 (t, J=6.0 Hz, 2H), 3.39 (s, 3H), 3.14-3.04 (m, 3H), 2.21-2.13 (m, 2H), 1.87-1.72 (m, 1H), 0.94 (d, J=6.0 Hz, 3H), 0.78 (d, J=9.0 Hz, 3H).

The following examples were prepared in a similar manner as 9-chloro-4-hydroxy-5-isopropyl-8-(3-methoxypropoxy)-2-oxo-1,2,5,6-tetrahydro-1,10-phenanthroline-3-carboxylic acid from (Z)-4-(tert-butyl)-2-(hydroxymethylene)cyclohexan-1-one and an appropriate amine.

Example 29: 5-(tert-Butyl)-9-chloro-4-hydroxy-8-(3-methoxypropoxy)-2-oxo-1,2,5,6-tetrahydro-1,10-phenanthroline-3-carboxylic acid

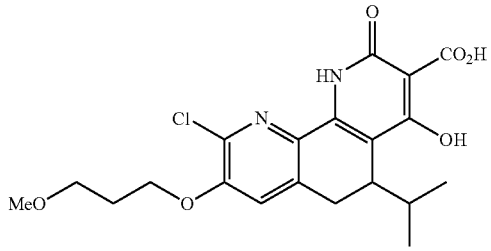 [SMILES: COCCCOc1cc2c(nc1Cl)-c1[nH]c(=O)c(C(=O)O)c(O)c1C(C(C)C)C2]

m/z: 437 [M+H]+ observed. ¹H NMR (300 MHz, CDCl₃): δ 10.23 (s, 1H), 7.11 (s, 1H), 4.21 (q, J=6.2 Hz, 2H), 3.62 (t, J=5.9 Hz, 2H), 3.38 (s, 3H), 3.19-3.04 (m, 3H), 2.15 (p, J=6.1 Hz, 2H), 0.80 (s, 9H).

The following examples were prepared in a similar manner as 9-chloro-4-hydroxy-5-isopropyl-8-(3-methoxypropoxy)-2-oxo-1,2,5,6-tetrahydro-1,10-phenanthroline-3-carboxylic acid from 3-isopropyl-7-methoxy-6-(3-methoxypropoxy)-3-methyl-3,4-dihydronaphthalen-1(2H)-one and an appropriate amine.

Example 30: 4-Hydroxy-5-isopropyl-9-methoxy-8-(3-methoxypropoxy)-5-methyl-2-oxo-1,2,5,6-tetrahydrobenzo[h]quinoline-3-carboxylic acid

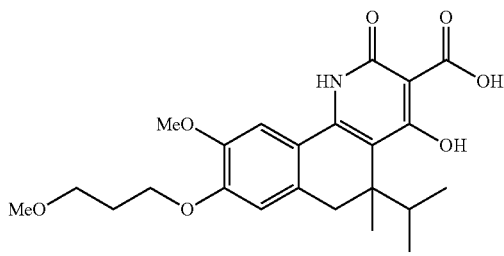 [SMILES: COCCCOc1cc2c(cc1OC)-c1[nH]c(=O)c(C(=O)O)c(O)c1C(C)(C(C)C)C2]

m/z: 432 [M+H]+ observed. ¹H NMR (400 MHz, DMSO-d₆) δ 14.62 (bs, 1H), 12.68 (bs, 1H), 7.58 (s, 1H), 6.98 (s, 1H), 4.10-4.04 (m, 2H), 3.84 (s, 3H), 3.46 (t, J=6 Hz, 2H), 3.24 (s, 3H), 2.84-2.67 (m, 2H), 1.99-1.88 (m, 3H), 1.36 (s, 3H), 0.80 (d, J=6.8 Hz, 3H), 0.67 (d, J=6.8 Hz, 3H).

Example 31: 4-Hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer I)

Example 32: 4-Hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer II)

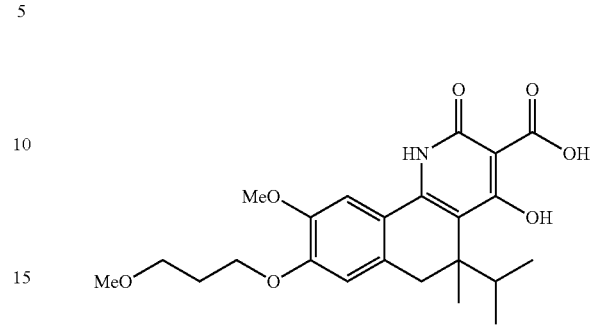

A mixture of enantiomers (500 mg) was separated by chiral SFC (supercritical fluid chromatography) on a CHIRALPACK AD-H column using 46% IPA (0.1% NH₄OH modifier) to give 4-hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer I) as a dark yellow solid (faster eluting enantiomer, 117 mg, 23%, m/z: 432 [M+H]+ observed), and 4-hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer II) as a light yellow solid (slower eluting enantiomer, 123 mg, 25%, m/z: 432 [M+H]+ observed).

Example 31: 4-Hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer I). m/z: 432 [M+H]+ observed. ¹H NMR (400 MHz, DMSO-d₆) δ 14.62 (bs, 1H), 12.68 (bs, 1H), 7.58 (s, 1H), 6.98 (s, 1H), 4.10-4.04 (m, 2H), 3.84 (s, 3H), 3.46 (t, J=6 Hz, 2H), 3.24 (s, 3H), 2.84-2.67 (m, 2H), 1.99-1.88 (m, 3H), 1.36 (s, 3H), 0.80 (d, J=6.8 Hz, 3H), 0.67 (d, J=6.8 Hz, 3H).

Example 32: 4-Hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer II). m/z: 432 [M+H]+ observed. ¹H NMR (400 MHz, DMSO-d₆) δ 14.62 (bs, 1H), 12.68 (bs, 1H), 7.58 (s, 1H), 6.98 (s, 1H), 4.10-4.04 (m, 2H), 3.84 (s, 3H), 3.46 (t, J=6 Hz, 2H), 3.24 (s, 3H), 2.84-2.67 (m, 2H), 1.99-1.88 (m, 3H), 1.36 (s, 3H), 0.80 (d, J=6.8 Hz, 3H), 0.67 (d, J=6.8 Hz, 3H).

Example 33: 4-Hydroxy-5-isopropyl-9-methoxy-8-(3-methoxypropoxy)-2-oxo-1,2,5,6-tetrahydro-1,10-phenanthroline-3-carboxylic acid

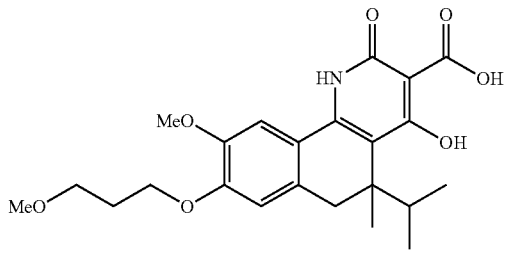 [SMILES: COCCCOc1cc2c(cc1OC)-c1[nH]c(=O)c(C(=O)O)c(O)c1C(C)(C(C)C)C2]

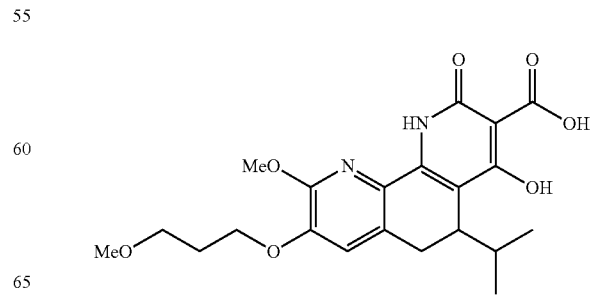

Methyl 1-benzyl-4-hydroxy-5-isopropyl-9-methoxy-8-(3-methoxypropoxy)-2-oxo-1,2,5,6-tetrahydro-1,10-phenanthroline-3-carboxylate

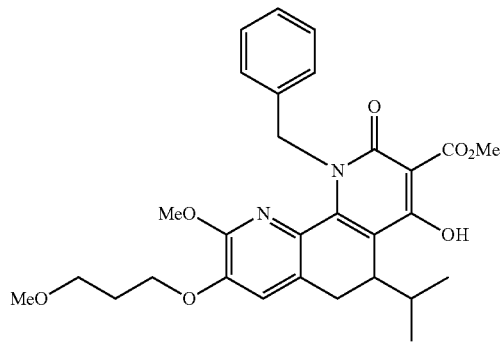 [SMILES: COCCCOc1cc2c(nc1OC)-c1c(c(O)c(C(=O)OC)c(=O)n1Cc1ccccc1)C(C(C)C)C2]

Methyl 1-benzyl-9-chloro-4-hydroxy-5-isopropyl-8-(3-methoxypropoxy)-2-oxo-5,6-dihydro-1,10-phenanthroline-3-carboxylate (40 mg, 0.08 mmol) and potassium carbonate (42 mg, 0.3 mmol) were dissolved in 1,4-dioxane (1 mL) in a microwave vial. The mixture was purged with $N_2$ for 5 minutes. Anhydrous methanol (0.06 mL, 1.52 mmol) was added to the reaction, followed by Xantphos Pd G3 catalyst (7.2 mg, 0.01 mmol). The vial was purged with $N_2$, sealed and stirred at 110° C. for 2 hours. The reaction was cooled to room temperature and diluted with EtOAc (3 mL), followed by $H_2O$ (2 mL). The combined organic phase was concentrated under vacuum. The crude material was purified via normal phase $SiO_2$ chromatography (0-10% MeOH/$CH_2Cl_2$) to give methyl 1-benzyl-4-hydroxy-5-isopropyl-9-methoxy-8-(3-methoxypropoxy)-2-oxo-1,2,5,6-tetrahydro-1,10-phenanthroline-3-carboxylate as a yellow foam (20 mg, 50% yield, m/z: 523 [M+H]$^+$ observed).

1-Benzyl-4-hydroxy-5-isopropyl-9-methoxy-8-(3-methoxypropoxy)-2-oxo-1,2,5,6-tetrahydro-1,10-phenanthroline-3-carboxylic acid

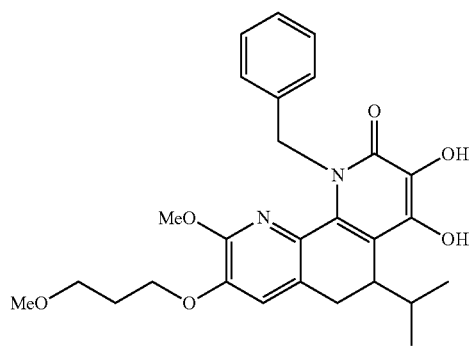 [SMILES: COCCCOc1cc2c(nc1OC)-c1c(c(O)c(O)c(=O)n1Cc1ccccc1)C(C(C)C)C2]

A solution of methyl 1-benzyl-4-hydroxy-5-isopropyl-9-methoxy-8-(3-methoxypropoxy)-2-oxo-5,6-dihydro-1,10-phenanthroline-3-carboxylate (15 mg, 0.03 mmol) and lithium iodide (11 mg, 0.09 mmol) in EtOAc (1 mL) was heated to 65° C. for 30 minutes. The reaction mixture was cooled to room temperature and $H_2O$ (1 mL) was added. The mixture was extracted with EtOAc (3×1 mL). The combined organic layer was dried over anhydrous sodium sulfate and concentrated under vacuum to give 1-benzyl-4-hydroxy-5-isopropyl-9-methoxy-8-(3-methoxypropoxy)-2-oxo-1,2,5,6-tetrahydro-1,10-phenanthroline-3-carboxylic acid which was used in the next step without further purification (10 mg, 69% yield, m/z: 509 [M+H]$^+$ observed).

4-Hydroxy-5-isopropyl-9-methoxy-8-(3-methoxypropoxy)-2-oxo-1,2,5,6-tetrahydro-1,10-phenanthroline-3-carboxylic acid

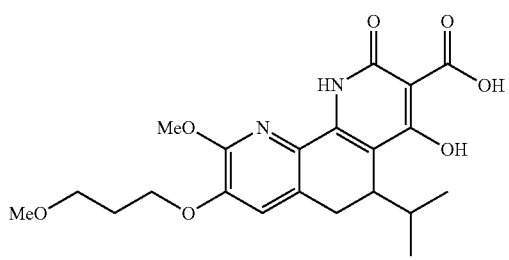 [SMILES: COCCCOc1cc2c(nc1OC)-c1[nH]c(=O)c(C(=O)O)c(O)c1C(C(C)C)C2]

1-Benzyl-4-hydroxy-5-isopropyl-9-methoxy-8-(3-methoxypropoxy)-2-oxo-5,6-dihydro-1,10-phenanthroline-3-carboxylic acid (10 mg, 0.02 mmol) and palladium hydroxide (20% on carbon, 10 mg, 0.07 mmol) were dissolved in methanol (2 mL). A $H_2$ balloon was applied and the reaction was stirred at room temperature for 4 hours. The catalyst was removed by filtering the reaction mixture through a syringe filter. The solvent was removed under reduced pressure. The residue was purified by reverse phase HPLC to give 4-hydroxy-5-isopropyl-9-methoxy-8-(3-methoxypropoxy)-2-oxo-1,2,5,6-tetrahydro-1,10-phenanthroline-3-carboxylic acid as a light-yellow foam (0.70 mg, 8.5% yield, m/z: 419 [M+H]$^+$ observed). $^1$H NMR (400 MHz, CDCl$_3$) δ 6.97 (s, 1H), 4.18 (td, J=6.5, 3.0 Hz, 2H), 4.06 (s, 3H), 3.58 (t, J=5.9 Hz, 2H), 3.37 (s, 3H), 3.06-2.91 (m, 3H), 2.15 (p, J=6.3 Hz, 2H), 1.80 (dt, J=13.3, 6.6 Hz, 1H), 0.91 (d, J=6.8 Hz, 3H), 0.78 (d, J=6.7 Hz, 3H).

Example 34: 4-Hydroxy-5-isopropyl-9-methoxy-8-(3-methoxypropoxy)-2-oxo-1,2,5,6-tetrahydro-1,10-phenanthroline-3-carboxylic acid (single enantiomer I)

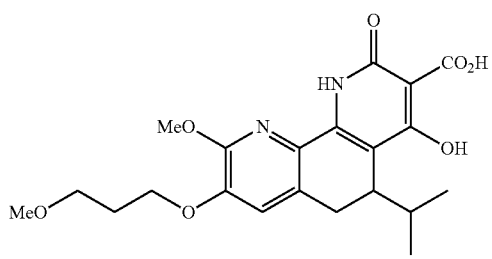 [SMILES: COCCCOc1cc2c(nc1OC)-c1[nH]c(=O)c(C(=O)O)c(O)c1C(C(C)C)C2]

Example 35: 4-Hydroxy-5-isopropyl-9-methoxy-8-(3-methoxypropoxy)-2-oxo-1,2,5,6-tetrahydro-1,10-phenanthroline-3-carboxylic acid (single enantiomer II)

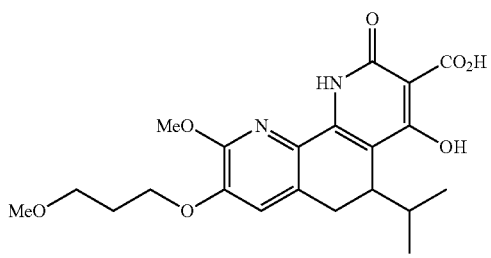 [SMILES: COCCCOc1cc2c(nc1OC)-c1[nH]c(=O)c(C(=O)O)c(O)c1C(C(C)C)C2]

Methyl 4-hydroxy-5-isopropyl-9-methoxy-8-(3-methoxypropoxy)-2-oxo-1,2,5,6-tetrahydro-1,10-phenanthroline-3-carboxylate

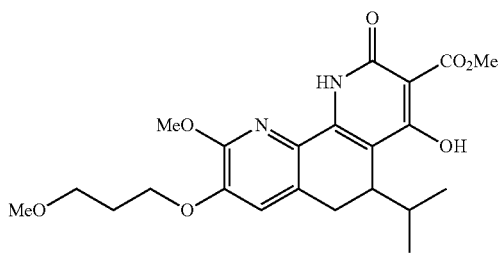 [SMILES: COCCCOc1cc2c(nc1OC)-c1[nH]c(=O)c(C(=O)OC)c(O)c1C(C(C)C)C2]

To a mixture of methyl 1-benzyl-4-hydroxy-5-isopropyl-9-methoxy-8-(3-methoxypropoxy)-2-oxo-1,2,5,6-tetrahydro-1,10-phenanthroline-3-carboxylate (1 g, 1.91 mmol) in MeOH (30 mL) was added palladium hydroxide on carbon (20 wt. % loading, 15 g, 1.34 mmol). The suspension was degassed by using vacuum and purging with hydrogen gas (repeat cycle 2 times). The mixture was stirred under an atmosphere of hydrogen gas at 15 psi for 1 h. The reaction mixture was filtered through CELITE®, washed with MeOH (2×20 mL) and concentrated under reduced pressure. The crude was purified by normal phase SiO$_2$ chromatography (30-100% EtOAc/petroleum ether) to afford methyl 4-hydroxy-5-isopropyl-9-methoxy-8-(3-methoxypropoxy)-2-oxo-1,2,5,6-tetrahydro-1,10-phenanthroline-3-carboxylate as a light green solid (0.45 g, 54% yield, 433 [M+H]$^+$ observed). $^1$H NMR (400 MHz, CDCl$_3$): δ 13.87 (s, 1H), 9.45 (s, 1H), 6.96 (s, 1H), 4.20-4.15 (t, J=3.6 Hz, 2H), 4.08 (s, 3H), 4.01 (s, 3H), 3.60-3.57 (t, J=6.4 Hz, 2H), 3.37 (s, 3H), 3.07-2.91 (m, 3H), 2.18-2.12 (m, 2H), 1.81-1.75 (m, 1H), 0.92-0.91 (d, J=6.8 Hz, 3H), 0.79-0.77 (d, J=6.4 Hz, 3H).

A mixture of enantiomers (450 mg) was separated by SFC (supercritical fluid chromatography) on a DAICEL CHIRALCEL OD-H column using 50% MeOH (0.1% NH$_4$OH modifier) to give methyl 4-hydroxy-5-isopropyl-9-methoxy-8-(3-methoxypropoxy)-2-oxo-1,2,5,6-tetrahydro-1,10-phenanthroline-3-carboxylate (single enantiomer I) as a yellow solid (faster eluting enantiomer, 180 mg, 40% yield, m/z: 433 [M+H]+ observed), and methyl 5-(tert-butyl)-11-(difluoromethoxy)-4-hydroxy-2-oxo-1,2,5,6-tetrahydroindolo[1,2-h][1,7]naphthyridine-3-carboxylate (single enantiomer II) as a yellow solid (slower eluting enantiomer, 160 mg, 36% yield, m/z: 433 [M+H]+ observed).

Example 34: 4-Hydroxy-5-isopropyl-9-methoxy-8-(3-methoxypropoxy)-2-oxo-1,2,5,6-tetrahydro-1,10-phenanthroline-3-carboxylic acid (single enantiomer I)

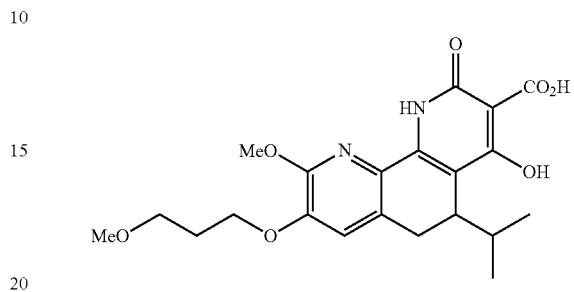

To a solution of methyl 5-(tert-butyl)-11-(difluoromethoxy)-4-hydroxy-2-oxo-1,2,5,6-tetrahydroindolo[1,2-h][1,7]naphthyridine-3-carboxylate (enantiomer I) (180 mg, 0.42 mmol) in EtOAc (5 mL) was added lithium iodide (111 mg, 0.42 mmol) under a nitrogen atmosphere. The mixture was stirred at 60° C. for 4 h. The contents of the flask were cooled to rt, H$_2$O (10 mL) was added and the mixture extracted with EtOAc (2×10 mL). The combined organic phase was washed with saturated aqueous brine solution (10 mL), dried with anhydrous sodium sulfate, filtered and concentrated in vacuum. The reaction mixture was purified by reverse phase HPLC to give 4-hydroxy-5-isopropyl-9-methoxy-8-(3-methoxypropoxy)-2-oxo-1,2,5,6-tetrahydro-1,10-phenanthroline-3-carboxylic acid (enantiomer I) as a yellow solid (95 mg, 55% yield, m/z: 419 [M+H]$^+$ observed). $^1$H NMR (400 MHz, CDCl$_3$): δ 15.13 (s, 1H), 13.90 (s, 1H), 9.81 (s, 1H), 6.99 (s, 1H), 4.21-4.17 (m, 2H), 4.07 (s, 3H), 3.60-3.57 (t, J=6 Hz, 2H), 3.38 (s, 3H), 3.10-2.95 (m, 3H), 2.17-2.14 (m, 2H), 1.84-1.78 (m, 1H), 0.93-0.92 (d, J=6.8 Hz, 3H), 0.80-0.79 (d, J=6.8 Hz, 3H).

Example 35: 4-Hydroxy-5-isopropyl-9-methoxy-8-(3-methoxypropoxy)-2-oxo-1,2,5,6-tetrahydro-1,10-phenanthroline-3-carboxylic acid (single enantiomer II)

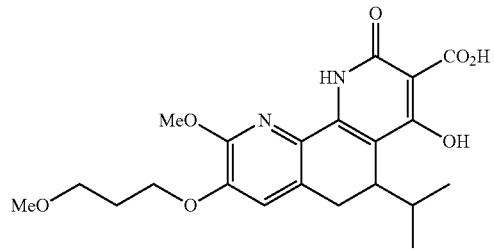 [SMILES: COCCCOc1cc2c(nc1OC)-c1[nH]c(=O)c(C(=O)O)c(O)c1C(C(C)C)C2]

To a solution of methyl 5-(tert-butyl)-11-(difluoromethoxy)-4-hydroxy-2-oxo-1,2,5,6-tetrahydroindolo[1,2-h][1,7]naphthyridine-3-carboxylate (enantiomer I) (160 mg, 0.37 mmol) in EtOAc (5 mL) was added lithium iodide (99 mg, 0.74 mmol) under a nitrogen atmosphere. The mixture was stirred at 60° C. for 4 h. The contents of the flask were cooled to rt, H$_2$O (10 mL) was added and the mixture extracted with EtOAc (2×10 mL). The combined organic phase was washed with saturated aqueous brine solution (10 mL), dried with anhydrous sodium sulfate, filtered and concentrated in vacuum. The reaction mixture was purified by reverse phase HPLC to give 4-hydroxy-5-isopropyl-9-methoxy-8-(3-methoxypropoxy)-2-oxo-1,2,5,6-tetrahydro-1,10-phenanthroline-3-carboxylic acid (enantiomer I) as a yellow solid (62 mg, 39% yield, m/z: 419 [M+H]+ observed). $^1$H NMR (400 MHz, CDCl$_3$): δ 15.13 (s, 1H), 13.90 (s, 1H), 9.81 (s, 1H), 6.99 (s, 1H), 4.21-4.17 (m, 2H), 4.07 (s, 3H), 3.60-3.57 (t, J=6 Hz, 2H), 3.38 (s, 3H), 3.10-2.95 (m, 3H), 2.17-2.14 (m, 2H), 1.84-1.78 (m, 1H), 0.93-0.92 (d, J=6.8 Hz, 3H), 0.80-0.79 (d, J=6.8 Hz, 3H).

Example 36: 5-(tert-Butyl)-4-hydroxy-9-methoxy-8-(3-methoxypropoxy)-2-oxo-1,2,5,6-tetrahydro-1,10-phenanthroline-3-carboxylicacid

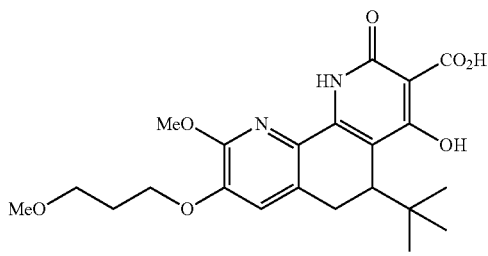

N-Benzyl-6-(tert-butyl)-2-chloro-3-(3-methoxypropoxy)-6,7-dihydroquinolin-8(5H)-imine

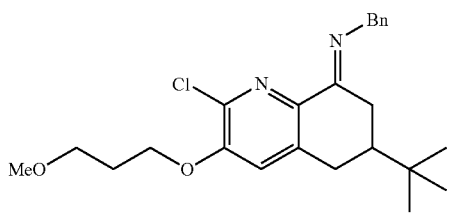 [SMILES: COCCCOc1cc2c(nc1Cl)/C(=N/Cc1ccccc1)CC(C(C)(C)C)C2]

Titanium (IV) isopropoxide (3.2 mL, 10.7 mmol) was added to a suspension of 6-tert-butyl-2-chloro-3-(3-methoxypropoxy)-6,7-dihydro-5H-quinolin-8-one (1 g, 3.06 mmol) and benzylamine (0.5 mL, 4.6 mmol) in THF (4 mL) in a microwave flask. The mixture was heated to 95° C. for 30 minutes in a microwave reactor. The reaction was cooled to rt, quenched with H$_2$O (10 mL) and extracted with CH$_2$Cl$_2$ (3×20 mL). The combined organic phase was filtered through CELITE®, dried over anhydrous sodium sulfate and concentrated in vacuum to give N-benzyl-6-(tert-butyl)-2-chloro-3-(3-methoxypropoxy)-6,7-dihydroquinolin-8(5H)-imine as a yellow solid, which was used without further purification (1.27 g, 100% yield, m/z: 415 [M+H]+ observed).

Methyl 1-benzyl-5-(tert-butyl)-9-chloro-4-hydroxy-8-(3-methoxypropoxy)-2-oxo-1,2,5,6-tetrahydro-1,10-phenanthroline-3-carboxylate

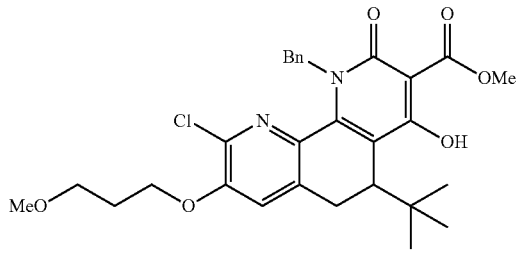 [SMILES: COCCCOc1cc2c(nc1Cl)-c1c(c(O)c(C(=O)OC)c(=O)n1Cc1ccccc1)C(C(C)(C)C)C2]

A mixture of N-benzyl-6-(tert-butyl)-2-chloro-3-(3-methoxypropoxy)-6,7-dihydroquinolin-8(5H)-imine (1.27 g, 3.06 mmol) and trimethyl methanetricarboxylate (1.75 g, 9.18 mmol) in diglyme (10 mL) was heated to 185° C. in a microwave reactor for 1 h. EtOAc (40 mL) was added and the organic phase was washed with H$_2$O (3×50 mL), followed by saturated aqueous brine solution (20 mL). The combined organic phase was concentrated in vacuum. The crude product was purified by normal phase SiO$_2$ chromatography (0-50% EtOAc/hexanes) to give methyl 1-benzyl-5-(tert-butyl)-9-chloro-4-hydroxy-8-(3-methoxypropoxy)-2-oxo-1,2,5,6-tetrahydro-1,10-phenanthroline-3-carboxylate as light yellow foam (0.96 g, 58% yield, m/z: 541 [M+H]+ observed).

Methyl 1-benzyl-5-(tert-butyl)-4-hydroxy-9-methoxy-8-(3-methoxypropoxy)-2-oxo-1,2,5,6-tetrahydro-1,10-phenanthroline-3-carboxylate

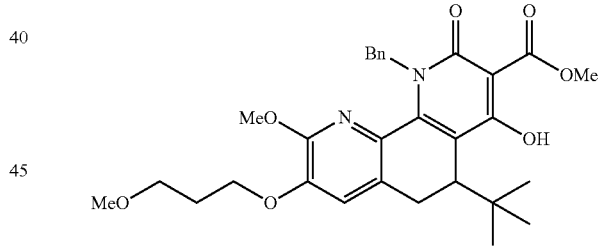

A solution of methyl 1-benzyl-5-tert-butyl-9-chloro-4-hydroxy-8-(3-methoxypropoxy)-2-oxo-5,6-dihydro-1,10-phenanthroline-3-carboxylate (0.92 g, 1.7 mmol) and potassium carbonate (0.94 g, 6.8 mmol) in dioxane (10 mL) in a microwave vial was purged with nitrogen gas for 5 minutes. Anhydrous methanol (0.37 mL, 34.0 mmol) was added to the reaction, followed by Xantphos Pd G3 (161 mg, 0.17 mmol). The vial was sealed and heated thermally to 110° C. for 2 h. The reaction mixture was cooled to rt, diluted with EtOAc (30 mL) and washed with H$_2$O (3×20 mL). The combined organic phase was washed with saturated aqueous brine solution (20 mL), dried over anhydrous sodium sulfate and concentrated in vacuum. The crude product was purified by normal phase SiO$_2$ chromatography (0-50% EtOAc/hexanes) to give methyl 1-benzyl-5-(tert-butyl)-4-hydroxy-9-methoxy-8-(3-methoxypropoxy)-2-oxo-1,2,5,6-tetrahydro-1,10-phenanthroline-3-carboxylate as a yellow solid (0.5 g, 55% yield, m/z: 537 [M+H]+ observed).

Methyl 5-(tert-butyl)-4-hydroxy-9-methoxy-8-(3-methoxypropoxy)-2-oxo-1,2,5,6-tetrahydro-1,10-phenanthroline-3-carboxylate

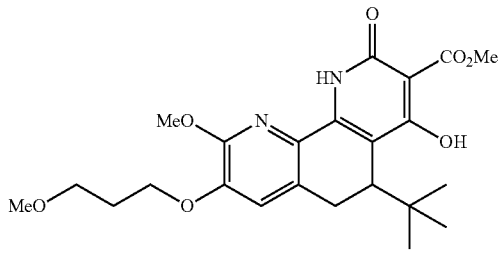 [SMILES: COCCCOc1cc2c(nc1OC)-c1[nH]c(=O)c(C(=O)OC)c(O)c1C(C(C)(C)C)C2]

A solution of methyl 1-benzyl-5-tert-butyl-4-hydroxy-9-methoxy-8-(3-methoxypropoxy)-2-oxo-5,6-dihydro-1,10-phenanthroline-3-carboxylate (10 mg, 0.19 mmol) and palladium hydroxide on carbon (20 wt. % loading on carbon, 26 mg, 0.04 mmol) in MeOH (3 mL) was purged with hydrogen gas. The reaction was stirred at rt for 16 h under an atmosphere of hydrogen. The reaction mixture was filtered through CELITE® and washed with MeOH (15 mL). The solvent was removed under vacuum to give methyl 5-(tert-butyl)-4-hydroxy-9-methoxy-8-(3-methoxypropoxy)-2-oxo-1,2,5,6-tetrahydro-1,10-phenanthroline-3-carboxylate as a yellow solid, which was used in the next step without further purification (75 mg, 90% yield, m/z: 447 [M+H]$^+$ observed).

5-(tert-Butyl)-4-hydroxy-9-methoxy-8-(3-methoxypropoxy)-2-oxo-1,2,5,6-tetrahydro-1,10-phenanthroline-3-carboxylic acid

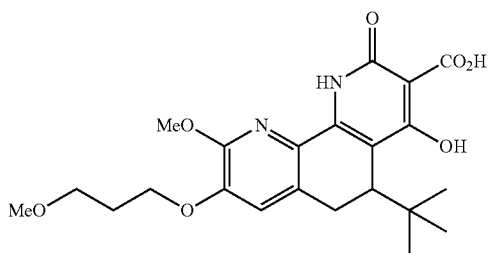 [SMILES: COCCCOc1cc2c(nc1OC)-c1[nH]c(=O)c(C(=O)O)c(O)c1C(C(C)(C)C)C2]

A solution of methyl 5-tert-butyl-4-hydroxy-9-methoxy-8-(3-methoxypropoxy)-2-oxo-5,6-dihydro-1H-1,10-phenanthroline-3-carboxylate (75 mg, 0.17 mmol) and lithium iodide (33 mg, 0.25 mmol) in EtOAc (4 mL) was stirred at 55° C. for 4 h. The reaction mixture was cooled to rt and the organic layer was washed with H$_2$O (3×3 mL). The combined organic phase was concentrated under reduced pressure. The crude product was purified by normal phase SiO$_2$ chromatography (0-50% EtOAc/hexanes) to give 5-(tert-butyl)-4-hydroxy-9-methoxy-8-(3-methoxypropoxy)-2-oxo-1,2,5,6-tetrahydro-1,10-phenanthroline-3-carboxylic acid as a yellow solid (30 mg, 41% yield, m/z: 433 [M+H]$^+$ observed). $^1$H NMR (300 MHz, CDCl$_3$): δ 6.95 (s, 1H), 4.17 (td, J=6.5, 4.9 Hz, 2H), 4.08 (s, 3H), 3.62-3.55 (m, 2H), 3.38 (s, 3H), 3.14-3.03 (m, 3H), 2.15 (p, J=6.2 Hz, 2H), 0.80 (s, 9H).

Example 37: 5-(tert-Butyl)-4-hydroxy-9-methoxy-8-(3-methoxypropoxy)-2-oxo-1,2,5,6-tetrahydro-1,10-phenanthroline-3-carboxylic acid (single enantiomer I)

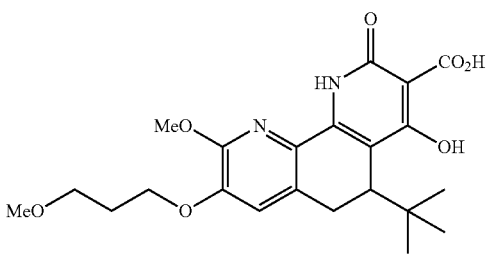 [SMILES: COCCCOc1cc2c(nc1OC)-c1[nH]c(=O)c(C(=O)O)c(O)c1C(C(C)(C)C)C2]

Example 38: 5-(tert-Butyl)-4-hydroxy-9-methoxy-8-(3-methoxypropoxy)-2-oxo-1,2,5,6-tetrahydro-1,10-phenanthroline-3-carboxylic acid (single enantiomer II)

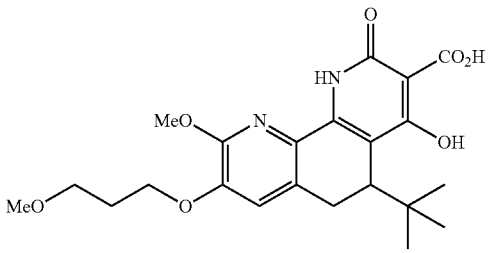 [SMILES: COCCCOc1cc2c(nc1OC)-c1[nH]c(=O)c(C(=O)O)c(O)c1C(C(C)(C)C)C2]

10 mg of the mixture of enantiomers was separated by chiral SFC (supercritical fluid chromatography) on a CHIRALPACK IG column using 35% IPA (0.4% diethylamine modifier) to give 5-(tert-butyl)-4-hydroxy-9-methoxy-8-(3-methoxypropoxy)-2-oxo-1,2,5,6-tetrahydro-1,10-phenanthroline-3-carboxylic acid (single enantiomer I) as a yellow solid (faster eluting enantiomer, 3.6 mg, 36% yield, m/z: 433 [M+H]$^+$ observed), and 5-(tert-butyl)-4-hydroxy-9-methoxy-8-(3-methoxypropoxy)-2-oxo-1,2,5,6-tetrahydro-1,10-phenanthroline-3-carboxylic acid (single enantiomer II) as a yellow solid (slower eluting enantiomer, 38 mg, 38% yield, m/z: 433 [M+H]$^+$ observed).

Example 37: 5-(tert-butyl)-4-hydroxy-9-methoxy-8-(3-methoxypropoxy)-2-oxo-1,2,5,6-tetrahydro-1,10-phenanthroline-3-carboxylic acid (single enantiomer I). m/z: 433 [M+H]$^+$ observed. $^1$H NMR (300 MHz, CDCl$_3$): δ 6.95 (s, 1H), 4.17 (td, J=6.5, 4.9 Hz, 2H), 4.08 (s, 3H), 3.62-3.55 (m, 2H), 3.38 (s, 3H), 3.14-3.03 (m, 3H), 2.15 (p, J=6.2 Hz, 2H), 0.80 (s, 9H).

Example 38: 5-(tert-butyl)-4-hydroxy-9-methoxy-8-(3-methoxypropoxy)-2-oxo-1,2,5,6-tetrahydro-1,10-phenanthroline-3-carboxylic acid (single enantiomer II). m/z: 433 [M+H]$^+$ observed. $^1$H NMR (300 MHz, CDCl$_3$): δ 6.95 (s, 1H), 4.17 (td, J=6.5, 4.9 Hz, 2H), 4.08 (s, 3H), 3.62-3.55 (m, 2H), 3.38 (s, 3H), 3.14-3.03 (m, 3H), 2.15 (p, J=6.2 Hz, 2H), 0.80 (s, 9H).

The following examples were prepared in a similar manner as 5-(tert-butyl)-4-hydroxy-9-methoxy-8-(3-methoxypropoxy)-2-oxo-1,2,5,6-tetrahydro-1,10-phenanthroline-3-carboxylic acid from methyl 9-chloro-4-hydroxy-5- isopropyl-8-(3-methoxypropoxy)-2-oxo-1,2,5,6-tetrahydro-1,10-phenanthroline-3-carboxylate and an appropriate alcohol:

Example 39: 9-Ethoxy-4-hydroxy-5-isopropyl-8-(3-methoxypropoxy)-2-oxo-1,2,5,6-tetrahydro-1,10-phenanthroline-3-carboxylicacid

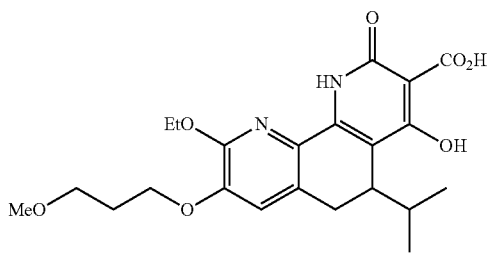

m/z: 433 [M+H]⁺ observed. ¹H NMR (300 MHz, CDCl₃): δ 9.78 (s, 1H), 6.96 (s, 1H), 4.47 (qd, J=7.1, 2.2 Hz, 2H), 4.17 (td, J=6.5, 2.6 Hz, 2H), 3.58 (t, J=5.9 Hz, 2H), 3.37 (s, 3H), 3.16-2.83 (m, 3H), 2.20-2.09 (m, 2H), 1.88-1.68 (m, 1H), 1.47 (t, J=7.1 Hz, 3H), 0.91 (d, J=6.8 Hz, 3H), 0.78 (d, J=6.7 Hz, 3H).

Example 40: 9-Ethoxy-4-hydroxy-5-isopropyl-8-(3-methoxypropoxy)-2-oxo-1,2,5,6-tetrahydro-1,10-phenanthroline-3-carboxylic acid (single enantiomer I)

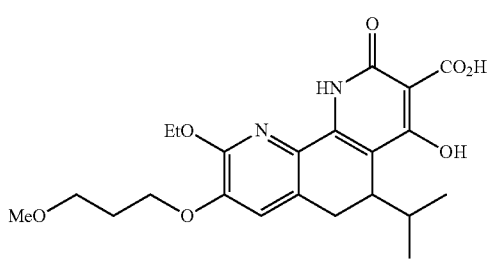

m/z: 433 [M+H]⁺ observed. ¹H NMR (300 MHz, CDCl₃): δ 9.78 (s, 1H), 6.96 (s, 1H), 4.47 (qd, J=7.1, 2.2 Hz, 2H), 4.17 (td, J=6.5, 2.6 Hz, 2H), 3.58 (t, J=5.9 Hz, 2H), 3.37 (s, 3H), 3.16-2.83 (m, 3H), 2.20-2.09 (m, 2H), 1.88-1.68 (m, 1H), 1.47 (t, J=7.1 Hz, 3H), 0.91 (d, J=6.8 Hz, 3H), 0.78 (d, J=6.7 Hz, 3H).

Example 41: 9-Ethoxy-4-hydroxy-5-isopropyl-8-(3-methoxypropoxy)-2-oxo-1,2,5,6-tetrahydro-1,10-phenanthroline-3-carboxylic acid (single enantiomer II)

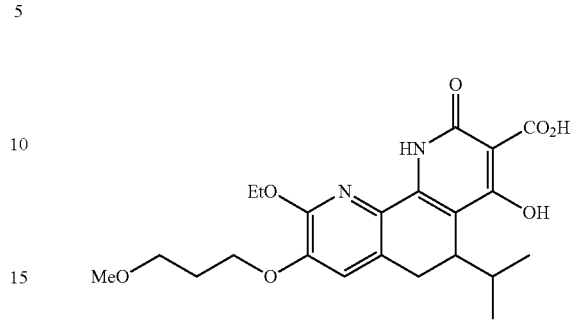

m/z: 433 [M+H]⁺ observed. ¹H NMR (300 MHz, CDCl₃): δ 9.78 (s, 1H), 6.96 (s, 1H), 4.47 (qd, J=7.1, 2.2 Hz, 2H), 4.17 (td, J=6.5, 2.6 Hz, 2H), 3.58 (t, J=5.9 Hz, 2H), 3.37 (s, 3H), 3.16-2.83 (m, 3H), 2.20-2.09 (m, 2H), 1.88-1.68 (m, 1H), 1.47 (t, J=7.1 Hz, 3H), 0.91 (d, J=6.8 Hz, 3H), 0.78 (d, J=6.7 Hz, 3H).

Example 42: 9-(2,2-Difluoroethoxy)-4-hydroxy-5-isopropyl-8-(3-methoxypropoxy)-2-oxo-1,2,5,6-tetrahydro-10-phenanthroline-3-carboxylic acid

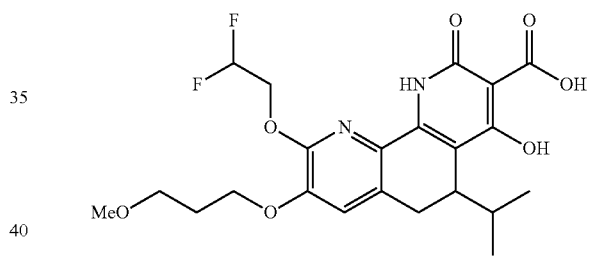

m/z: 469 [M+H]⁺ observed. ¹H NMR (300 MHz, CDCl₃): δ 15.08 (bs, 1H), 13.92 (s, 1H), 9.73 (bs, 1H), 7.05 (s, 1H), 6.19 (t, J=54.0 Hz, 1H), 4.64 (td, J=12.0 Hz, 3.0 Hz, 2H), 4.20 (t, J=12.0 Hz, 2H), 3.59 (t, J=6.0 Hz, 2H), 3.38 (s, 3H), 3.12-2.97 (m, 3H), 2.19-2.11 (m, 2H), 1.82-1.78 (m, 1H), 0.93 (d, J=6.0 Hz, 3H), 0.80 (d, J=6.0 Hz, 3H).

Example 43: 5-Isopropyl-9-methoxy-8-(3-methoxypropoxy)-2-oxo-1,2,5,6-tetrahydro-1,10-phenanthroline-3-carboxylic acid

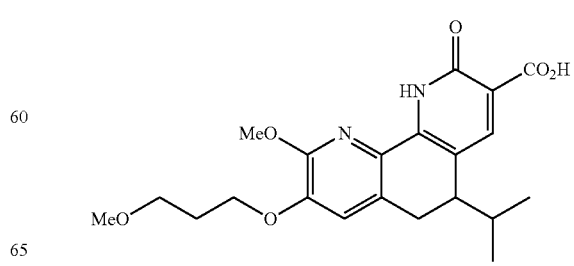

Methyl 1-benzyl-5-isopropyl-9-methoxy-8-(3-methoxypropoxy)-2-oxo-1,2,5,6-tetrahydro-1,10-phenanthroline-3-carboxylate

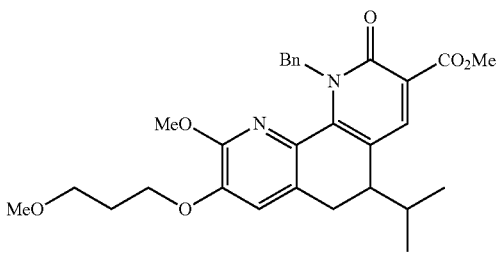 [SMILES: COCCCOc1cc2c(nc1OC)-c1c(cc(C(=O)OC)c(=O)n1Cc1ccccc1)C(C(C)C)C2]

A solution of methyl 1-benzyl-9-chloro-5-isopropyl-8-(3-methoxypropoxy)-2-oxo-5,6-dihydro-1,10-phenanthroline-3-carboxylate (130 mg, 0.25 mmol) and potassium carbonate (140 mg, 1 mmol) in 1,4-dioxane (4 mL) in a microwave vial was purged with nitrogen for 5 minutes. Anhydrous methanol (200 uL, 5.1 mmol) was added to the reaction, followed by Xantphos Pd G3 (24 mg, 0.03 mmol). The vial was sealed and heated thermally to 110° C. for 2 h. The reaction mixture was cooled to rt, diluted with EtOAc (20 mL) and washed with H$_2$O (3×20 mL). The combined organic phase was dried with anhydrous sodium sulfate, filtered and concentrated under reduced pressure. The crude product was purified by normal phase SiO$_2$ chromatography (0-50% EtOAc/hexanes) to afford methyl 1-benzyl-5-isopropyl-9-methoxy-8-(3-methoxypropoxy)-2-oxo-1,2,5,6-tetrahydro-1,10-phenanthroline-3-carboxylate as a yellow solid (61 mg, 47% yield, m/z: 507 [M+H]$^+$ observed).

Methyl 5-isopropyl-9-methoxy-8-(3-methoxypropoxy)-2-oxo-1,2,5,6-tetrahydro-1,10-phenanthroline-3-carboxylate

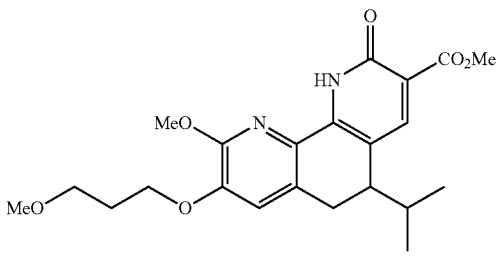 [SMILES: COCCCOc1cc2c(nc1OC)-c1[nH]c(=O)c(C(=O)OC)cc1C(C(C)C)C2]

A solution of methyl 1-benzyl-5-isopropyl-9-methoxy-8-(3-methoxypropoxy)-2-oxo-5,6-dihydro-1,10-phenanthroline-3-carboxylate (50 mg, 0.1 mmol) and palladium hydroxide on carbon (20 wt. % loading on carbon, 14 mg, 0.02 mmol) in methanol (3 mL) was purged with hydrogen gas for 2 min. The reaction mixture was stirred under an atmosphere of hydrogen at rt for 16 h. The mixture was filtered through CELITE®, washed with MeOH (2×10 mL) and concentrated under reduced pressure to afford methyl 5-isopropyl-9-methoxy-8-(3-methoxypropoxy)-2-oxo-1,2,5,6-tetrahydro-1,10-phenanthroline-3-carboxylate as a yellow solid, which was used in the next step without further purification (41 mg, 100% yield, m/z: 417 [M+H]$^+$ observed).

5-Isopropyl-9-methoxy-8-(3-methoxypropoxy)-2-oxo-1,2,5,6-tetrahydro-1,10-phenanthroline-3-carboxylicacid

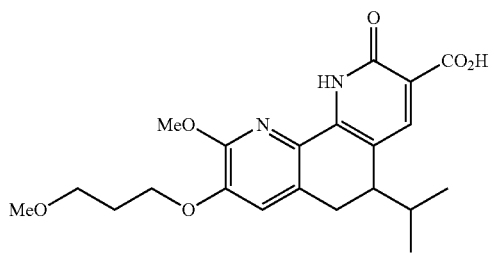 [SMILES: COCCCOc1cc2c(nc1OC)-c1[nH]c(=O)c(C(=O)O)cc1C(C(C)C)C2]

A solution of methyl 5-isopropyl-9-methoxy-8-(3-methoxypropoxy)-2-oxo-5,6-dihydro-1H-1,10-phenanthroline-3-carboxylate (41 mg, 0.1 mmol) and lithium hydroxide monohydrate (5 mg, 0.11 mmol) in 1,4-dioxane/water (2:1, 3 mL) was stirred at rt for 2 h. The solvent was removed under reduced pressure. H$_2$O (1 mL) was added to the mixture, followed by 1N HCl to adjust the pH to 5. The resulting yellow solid was collected by filtration, re-dissolved in CH$_2$Cl$_2$ and purified by normal phase SiO$_2$ chromatography (0-4% MeOH/CH$_2$Cl$_2$) to afford 5-isopropyl-9-methoxy-8-(3-methoxypropoxy)-2-oxo-1,2,5,6-tetrahydro-1,10-phenanthroline-3-carboxylic acid as a bright yellow solid (21 mg, 54% yield, m/z: 403 [M+H]$^+$ observed). $^1$H NMR (300 MHz, CDCl$_3$): δ 10.39 (s, 1H), 8.39 (d, J=0.5 Hz, 1H), 7.04-6.91 (m, 1H), 4.17 (td, J=6.5, 1.4 Hz, 2H), 4.06 (s, 3H), 3.61-3.51 (m, 2H), 3.35 (s, 3H), 3.21-2.88 (m, 2H), 2.67 (td, J=7.0, 3.2 Hz, 1H), 2.23-2.06 (m, 2H), 1.91-1.73 (m, 1H), 0.84 (dd, J=11.9, 6.7 Hz, 6H).

Example 44: 5-Isopropyl-9-methoxy-8-(3-methoxypropoxy)-2-oxo-1,2,5,6-tetrahydro-1,10-phenanthroline-3-carboxylic acid (single enantiomer I)

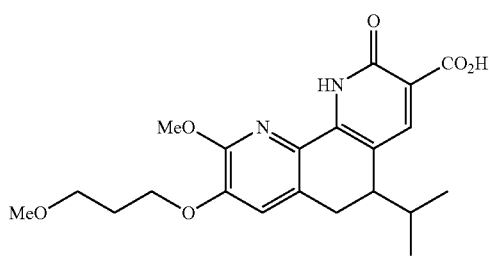 [SMILES: COCCCOc1cc2c(nc1OC)-c1[nH]c(=O)c(C(=O)O)cc1C(C(C)C)C2]

Example 45: 5-Isopropyl-9-methoxy-8-(3-methoxypropoxy)-2-oxo-1,2,5,6-tetrahydro-1,10-phenanthroline-3-carboxylic acid (single enantiomer II)

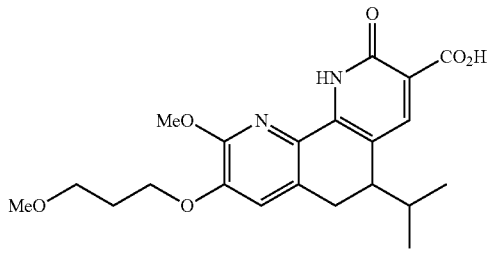

A mixture of enantiomers (18 mg) was separated by chiral SFC (supercritical fluid chromatography) on a CHIRAL-PACK AD column using 30% IPA to give 5-isopropyl-9-methoxy-8-(3-methoxypropoxy)-2-oxo-1,2,5,6-tetrahydro-1,10-phenanthroline-3-carboxylic acid (single enantiomer I) as a yellow solid (faster eluting enantiomer, 8 mg, 44% yield, m/z: 403 [M+H]$^+$ observed) and 5-isopropyl-9-methoxy-8-(3-methoxypropoxy)-2-oxo-1,2,5,6-tetrahydro-1,10-phenanthroline-3-carboxylic acid (single enantiomer II) as a yellow solid (slower eluting enantiomer, 7 mg, 39% yield, m/z: 403 [M+H]$^+$ observed).

Example 44: 5-Isopropyl-9-methoxy-8-(3-methoxypropoxy)-2-oxo-1,2,5,6-tetrahydro-1,10-phenanthroline-3-carboxylic acid (single enantiomer I). m/z: 403 [M+H]$^+$ observed. $^1$H NMR (300 MHz, CDCl$_3$): δ 10.39 (s, 1H), 8.39 (d, J=0.5 Hz, 1H), 7.04-6.91 (m, 1H), 4.17 (td, J=6.5, 1.4 Hz, 2H), 4.06 (s, 3H), 3.61-3.51 (m, 2H), 3.35 (s, 3H), 3.21-2.88 (m, 2H), 2.67 (td, J=7.0, 3.2 Hz, 1H), 2.23-2.06 (m, 2H), 1.91-1.73 (m, 1H), 0.84 (dd, J=11.9, 6.7 Hz, 6H).

Example 45: 5-Isopropyl-9-methoxy-8-(3-methoxypropoxy)-2-oxo-1,2,5,6-tetrahydro-1,10-phenanthroline-3-carboxylic acid (single enantiomer II). m/z: 403 [M+H]$^+$ observed. $^1$H NMR (300 MHz, CDCl$_3$): δ 10.39 (s, 1H), 8.39 (d, J=0.5 Hz, 1H), 7.04-6.91 (m, 1H), 4.17 (td, J=6.5, 1.4 Hz, 2H), 4.06 (s, 3H), 3.61-3.51 (m, 2H), 3.35 (s, 3H), 3.21-2.88 (m, 2H), 2.67 (td, J=7.0, 3.2 Hz, 1H), 2.23-2.06 (m, 2H), 1.91-1.73 (m, 1H), 0.84 (dd, J=11.9, 6.7 Hz, 6H).

The following examples were prepared in a similar manner as 5-isopropyl-9-methoxy-8-(3-methoxypropoxy)-2-oxo-1,2,5,6-tetrahydro-1,10-phenanthroline-3-carboxylic acid from methyl 1-benzyl-5-(tert-butyl)-9-chloro-8-(3-methoxypropoxy)-2-oxo-1,2,5,6-tetrahydro-1,10-phenanthroline-3-carboxylate and an appropriate alcohol:

Example 46: 5-(tert-Butyl)-9-methoxy-8-(3-methoxypropoxy)-2-oxo-1,2,5,6-tetrahydro-1,10-phenanthroline-3-carboxylicacid

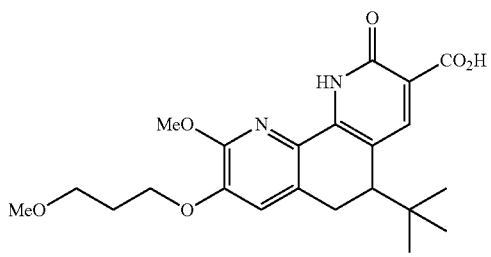 [SMILES: COCCCOc1cc2c(nc1OC)-c1[nH]c(=O)c(C(=O)O)cc1C(C(C)(C)C)C2]

m/z: 417 [M+H]$^+$ observed. $^1$H NMR (300 MHz, CDCl$_3$): δ 10.36 (s, 1H), 8.38 (s, 1H), 6.96 (d, J=0.7 Hz, 1H), 4.18 (td, J=6.5, 3.1 Hz, 2H), 4.06 (s, 3H), 3.60-3.52 (m, 2H), 3.36 (s, 3H), 3.28-3.05 (m, 2H), 2.64 (dd, J=7.8, 1.5 Hz, 1H), 2.16-2.10 (m, 2H), 0.80 (s, 9H).

Example 47: 5-(tert-Butyl)-9-methoxy-8-(3-methoxypropoxy)-2-oxo-1,2,5,6-tetrahydro-1,10-phenanthroline-3-carboxylic acid (single enantiomer I)

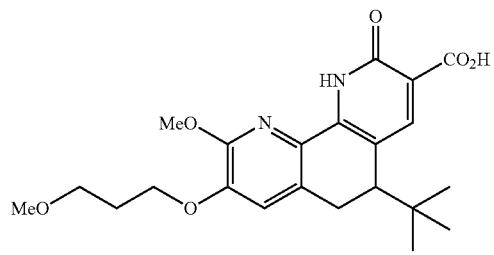 [SMILES: COCCCOc1cc2c(nc1OC)-c1[nH]c(=O)c(C(=O)O)cc1C(C(C)(C)C)C2]

Example 48: 5-(tert-Butyl)-9-methoxy-8-(3-methoxypropoxy)-2-oxo-1,2,5,6-tetrahydro-1,10-phenanthroline-3-carboxylic acid (single enantiomer II)

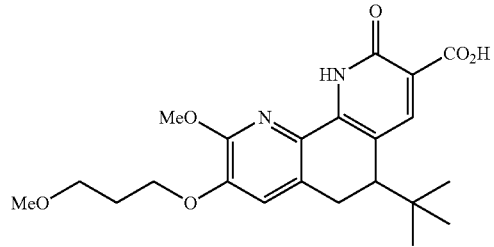

A mixture of enantiomers (18 mg) was separated by chiral SFC (supercritical fluid chromatography) on a CHIRAL-PACK AD column using 30% methanol/acetonitrile (1:1) to give 5-(tert-butyl)-9-methoxy-8-(3-methoxypropoxy)-2-oxo-1,2,5,6-tetrahydro-1,10-phenanthroline-3-carboxylic acid (single enantiomer I) as a yellow solid (faster eluting enantiomer, 5.5 mg, 31% yield, m/z: 417 [M+H]$^+$ observed) and 5-(tert-butyl)-9-methoxy-8-(3-methoxypropoxy)-2-oxo-1,2,5,6-tetrahydro-1,10-phenanthroline-3-carboxylic acid (single enantiomer II) as a yellow solid (slower eluting enantiomer, 5.5 mg, 31%, m/z: 417 [M+H]$^+$ observed).

Example 47: 5-(tert-Butyl)-9-methoxy-8-(3-methoxypropoxy)-2-oxo-1,2,5,6-tetrahydro-1,10-phenanthroline-3-carboxylic acid (single enantiomer I). m/z: 417 [M+H]$^+$ observed. $^1$H NMR (300 MHz, CDCl$_3$): δ 10.36 (s, 1H), 8.38 (s, 1H), 6.96 (d, J=0.7 Hz, 1H), 4.18 (td, J=6.5, 3.1 Hz, 2H), 4.06 (s, 3H), 3.60-3.52 (m, 2H), 3.36 (s, 3H), 3.28-3.05 (m, 2H), 2.64 (dd, J=7.8, 1.5 Hz, 1H), 2.16-2.10 (m, 2H), 0.80 (s, 9H).

Example 48: 5-(tert-Butyl)-9-methoxy-8-(3-methoxypropoxy)-2-oxo-1,2,5,6-tetrahydro-1,10-phenanthroline-3-carboxylic acid (single enantiomer II). m/z: 417 [M+H]$^+$ observed. $^1$H NMR (300 MHz, CDCl$_3$): δ 10.36 (s, 1H), 8.38 (s, 1H), 6.96 (d, J=0.7 Hz, 1H), 4.18 (td, J=6.5, 3.1 Hz, 2H), 4.06 (s, 3H), 3.60-3.52 (m, 2H), 3.36 (s, 3H), 3.28-3.05 (m, 2H), 2.64 (dd, J=7.8, 1.5 Hz, 1H), 2.16-2.10 (m, 2H), 0.80 (s, 9H).

Example 49: 9-Cyclopropyl-4-hydroxy-5-isopropyl-8-(3-methoxypropoxy)-2-oxo-1,2,5,6-tetrahydro-1,10-phenanthroline-3-carboxylicacid

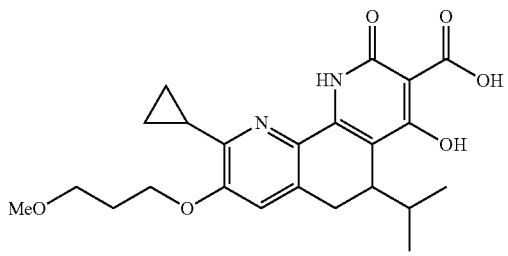 [SMILES: COCCCOc1cc2c(nc1C1CC1)-c1[nH]c(=O)c(C(=O)O)c(O)c1C(C(C)C)C2]

Methyl 1-benzyl-9-cyclopropyl-4-hydroxy-5-isopropyl-8-(3-methoxypropoxy)-2-oxo-1,2,5,6-tetrahydro-1,10-phenanthroline-3-carboxylate

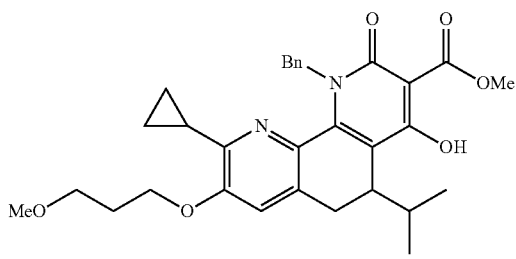 [SMILES: COCCCOc1cc2c(nc1C1CC1)-c1c(c(O)c(C(=O)OC)c(=O)n1Cc1ccccc1)C(C(C)C)C2]

A mixture of methyl 1-benzyl-9-chloro-4-hydroxy-5-isopropyl-8-(3-methoxypropoxy)-2-oxo-1,2,5,6-tetrahydro-1,10-phenanthroline-3-carboxylate (300 mg, 0.56 mmol) and potassium carbonate (236 mg, 1.7 mmol) in 1,4-dioxane (5 mL) was purged with argon gas for 10 min. Cyclopropylboronic acid (195 mg, 2.27 mmol) and [1,1'-bis(di-tert-butylphosphino)ferrocene)dichloropalladium (II)] (74 mg, 0.11 mmol) were added and the mixture further purged with argon gas for 10 min. The reaction vessel was then sealed and heated in a microwave reactor at 90° C. for 2 h. The mixture was cooled to rt and quenched with H$_2$O (10 mL). The resulting mixture was extracted with EtOAc (2×15 mL). The combined organic phase was dried over anhydrous sodium sulfate and concentrated in vacuum. The crude oil was purified by normal phase SiO$_2$ chromatography (0 to 70% EtOAc/hexanes) to give methyl 1-benzyl-9-cyclopropyl-4-hydroxy-5-isopropyl-8-(3-methoxypropoxy)-2-oxo-1,2,5,6-tetrahydro-1,10-phenanthroline-3-carboxylate as a yellow solid (105 mg, 35% yield, m/z: 533 [M+H]$^+$ observed).

Methyl 9-cyclopropyl-4-hydroxy-5-isopropyl-8-(3-methoxypropoxy)-2-oxo-1,2,5,6-tetrahydro-1,10-phenanthroline-3-carboxylate

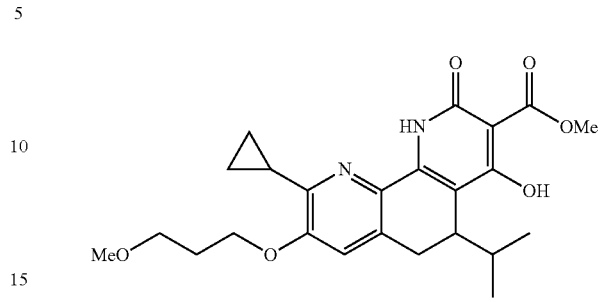

Methyl 4-hydroxy-5-isopropyl-8-(3-methoxypropoxy)-2-oxo-9-propyl-1,2,5,6-tetrahydro-1,10-phenanthroline-3-carboxylate

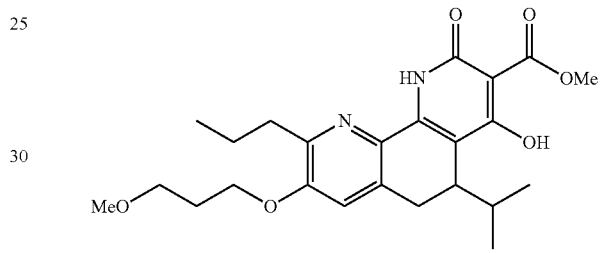

A mixture of methyl 1-benzyl-9-cyclopropyl-4-hydroxy-5-isopropyl-8-(3-methoxypropoxy)-2-oxo-1,2,5,6-tetrahydro-1,10-phenanthroline-3-carboxylate (105 mg, 0.2 mmol) and palladium on carbon (10% on carbon, 32 mg, 0.3 mmol) in methanol (5 mL) was stirred at rt for 15 h under an atmosphere of hydrogen gas. The reaction mixture was then filtered through CELITE® and washed with MeOH (2×10 mL). The combined organic phase was concentrated under reduced pressure. The crude oil was purified by normal phase SiO$_2$ chromatography (40% EtOAc/hexanes) to give methyl 4-hydroxy-5-isopropyl-8-(3-methoxypropoxy)-2-oxo-9-propyl-1,2,5,6-tetrahydro-1,10-phenanthroline-3-carboxylate as a yellow syrup (faster eluting compound, 20 mg, 23%, m/z: 445 [M+H]$^+$ observed). $^1$H NMR (300 MHz, CDCl$_3$): δ 13.86 (s, 1H), 9.83 (bs, 1H), 6.96 (s, 1H), 4.12 (t, J=6.0 Hz, 2H), 4.01 (s, 3H), 3.59 (t, J=6.0 Hz, 2H), 3.38 (s, 3H), 3.05-2.95 (m, 3H), 2.78 (td, J=6.0 Hz, 3 Hz, 2H), 2.14-2.10 (m, 2H), 1.77-1.70 (m, 3H), 0.99 (t, J=9.0 Hz, 3H), 0.91 (d, J=6.0 Hz, 3H), 0.77 (d, J=6.0 Hz, 3H) and methyl 9-cyclopropyl-4-hydroxy-5-isopropyl-8-(3-methoxypropoxy)-2-oxo-1,2,5,6-tetrahydro-1,10-phenanthroline-3-carboxylate as a yellow syrup (slower eluting compound, 55 mg, 63%, m/z: 443 [M+H]$^+$ observed). $^1$H NMR (300 MHz, CDCl$_3$): δ 13.86 (s, 1H), 9.52 (bs, 1H), 6.95 (s, 1H), 4.19-4.14 (m, 2H), 4.01 (s, 3H), 3.62 (t, J=6.0 Hz, 2H), 3.39 (s, 3H), 3.08-2.93 (m, 3H), 2.51-2.46 (m, 1H), 2.20-2.11 (m, 2H), 1.78-1.67 (m, 1H), 1.15-1.11 (m, 2H), 1.05-1.00 (m, 2H), 0.90 (d, J=9.0 Hz, 3H), 0.77 (d, J=6.0 Hz, 3H).

9-Cyclopropyl-4-hydroxy-5-isopropyl-8-(3-methoxypropoxy)-2-oxo-1,2,5,6-tetrahydro-1,10-phenanthroline-3-carboxylic acid

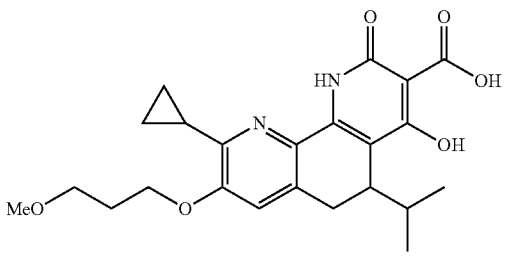 [SMILES: COCCCOc1cc2c(nc1C1CC1)-c1[nH]c(=O)c(C(=O)O)c(O)c1C(C(C)C)C2]

A mixture of methyl 9-cyclopropyl-4-hydroxy-5-isopropyl-8-(3-methoxypropoxy)-2-oxo-1,2,5,6-tetrahydro-1,10-phenanthroline-3-carboxylate (55 mg, 0.12 mmol) and lithium iodide (49 mg, 0.37 mmol) in anhydrous EtOAc (3 mL) was heated at 60° C. for 3 h. The reaction mixture was cooled to rt, diluted with EtOAc (10 mL) and treated with glacial acetic acid (3 drops). The organic layer was washed with H$_2$O (10 mL), saturated aqueous brine solution (10 mL), dried over anhydrous sodium sulfate and concentrated in vacuum. The crude solid was purified by reverse phase HPLC to give 9-cyclopropyl-4-hydroxy-5-isopropyl-8-(3-methoxypropoxy)-2-oxo-1,2,5,6-tetrahydro-1,10-phenanthroline-3-carboxylic acid as a light yellow solid (35 mg, 66% yield, m/z: 429 [M+H]$^+$ observed). $^1$H NMR (300 MHz, CDCl$_3$): δ 15.21 (bs, 1H), 13.91 (s, 1H), 9.92 (bs, 1H), 6.98 (s, 1H), 4.19 (t, J=6.0 Hz, 2H), 3.62 (t, J=6.0 Hz, 2H), 3.40 (s, 3H), 3.12-2.97 (m, 3H), 2.52-2.46 (m, 1H), 2.21-2.13 (m, 2H), 1.81-1.75 (m, 1H), 1.10-1.04 (m, 4H), 0.92 (d, J=6.0 Hz, 3H), 0.79 (d, J=6.0 Hz, 3H).

Example 50: 4-Hydroxy-5-isopropyl-8-(3-methoxypropoxy)-2-oxo-9-propyl-1,2,5,6-tetrahydro-1,10-phenanthroline-3-carboxylic acid

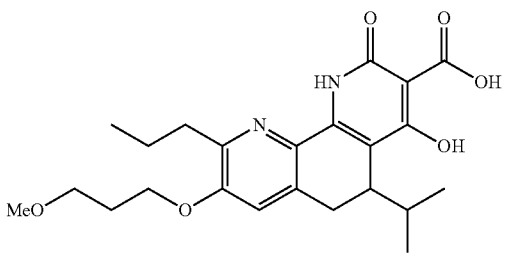 [SMILES: CCCc1nc2c(cc1OCCCOC)CC(C(C)C)c1c-2[nH]c(=O)c(C(=O)O)c1O]

A mixture of methyl 4-hydroxy-5-isopropyl-8-(3-methoxypropoxy)-2-oxo-9-propyl-1,2,5,6-tetrahydro-1,10-phenanthroline-3-carboxylate (20 mg, 0.045 mmol) and lithium iodide (18 mg, 0.13 mmol) in anhydrous EtOAc (2 mL) was heated at 60° C. for 3 h. The reaction mixture was cooled, diluted with EtOAc (5 mL) and treated with glacial acetic acid (2 drops). The organic layer was washed with H$_2$O (5 mL), saturated aqueous brine solution (5 mL) solution, dried over anhydrous sodium sulfate and concentrated in vacuum. The crude solid was triturated with methanol (1 mL) to give 4-hydroxy-5-isopropyl-8-(3-methoxypropoxy)-2-oxo-9-propyl-1,2,5,6-tetrahydro-1,10-phenanthroline-3-carboxylic acid as a light yellow solid (14 mg, 73% yield, m/z: 431 [M+H]$^+$ observed). $^1$H NMR (300 MHz, CDCl$_3$): δ 15.26 (bs, 1H), 13.92 (s, 1H), 10.21 (bs, 1H), 7.00 (s, 1H), 4.15 (t, J=6.0 Hz, 2H), 3.60 (t, J=6.0 Hz, 2H), 3.39 (s, 3H), 3.14-2.99 (m, 3H), 2.82-2.77 (m, 2H), 2.14-2.10 (m, 2H), 1.77-1.70 (m, 3H), 0.99 (t, J=6.0 Hz, 3H), 0.91 (d, J=6.0 Hz, 3H), 0.77 (d, J=6.0 Hz, 3H).

Example 51: 4-Hydroxy-5-isopropyl-9-((2-methoxyethyl)amino)-8-(3-methoxypropoxy)-2-oxo-1,2,5,6-tetrahydro-1,10-phenanthroline-3-carboxylicacid

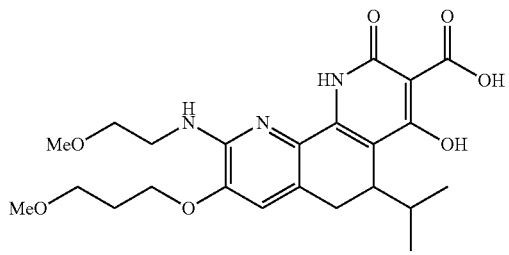 [SMILES: COCCCOc1cc2c(nc1NCCOC)-c1[nH]c(=O)c(C(=O)O)c(O)c1C(C(C)C)C2]

1-Benzyl-4-hydroxy-5-isopropyl-9-((2-methoxyethyl)amino)-8-(3-methoxypropoxy)-2-oxo-1,2,5,6-tetrahydro-1,10-phenanthroline-3-carboxylicacid

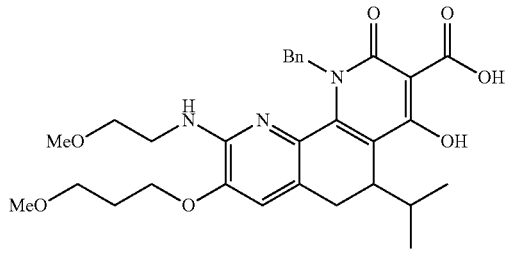 [SMILES: COCCCOc1cc2c(nc1NCCOC)-c1c(c(O)c(C(=O)O)c(=O)n1Cc1ccccc1)C(C(C)C)C2]

1-Benzyl-4-hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide

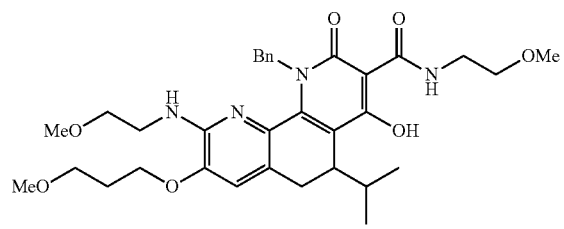 [SMILES: COCCCOc1cc2c(nc1NCCOC)-c1c(c(O)c(C(=O)NCCOC)c(=O)n1Cc1ccccc1)C(C(C)C)C2]

A mixture of methyl 1-benzyl-9-chloro-4-hydroxy-5-isopropyl-8-(3-methoxypropoxy)-2-oxo-1,2,5,6-tetrahydro-1,10-phenanthroline-3-carboxylate (200 mg, 0.38 mmol) and 2-methoxyethylamine (0.07 mL, 0.75 mmol) in 1,4-dioxane (10 mL) was degassed with argon for 10 min. Sodium tert-butoxide (109 mg, 1.13 mmol) and BrettPhos Pd G3 (34 mg, 0.038 mmol) were added and the mixture was degassed with argon for 5 min. The reaction vessel was then sealed and stirred at 100° C. for 16 h. The mixture was cooled to rt, quenched with H₂O (10 mL) and extracted with EtOAc (2×15 mL). The combined organic layer was dried over anhydrous sodium sulfate and concentrated in vacuum. The crude oil was purified by normal phase SiO₂ chromatography (40% EtOAc/hexanes) to give 1-benzyl-4-hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide as a yellow syrup (faster eluting compound, 40 mg, 17% yield, m/z: 609 [M+H]⁺ observed). ¹H NMR (400 MHz, CDCl₃): δ 16.18 (s, 1H), 10.48 (bs, 1H), 7.23-7.06 (m, 5H), 6.68 (s, 1H), 5.99 (d, J=15 Hz, 1H), 5.06 (bs, 1H), 4.12-4.06 (m, 2H), 3.61-3.53 (m, 7H), 3.34 (s, 6H), 3.30 (s, 3H), 3.20-3.17 (m, 2H), 2.95-2.85 (m, 3H), 2.68-2.64 (d, J=14.6 Hz, 1H), 2.10-2.04 (m, 2H), 1.53-1.49 (m, 2H), 0.86 (d, J=6.7 Hz, 3H), 0.79 (d, J=6.5 Hz, 3H) and 1-benzyl-4-hydroxy-5-isopropyl-9-((2-methoxyethyl)amino)-8-(3-methoxypropoxy)-2-oxo-1,2,5,6-tetrahydro-1,10-phenanthroline-3-carboxylic acid as a yellow syrup (slower eluting compound, 30 mg, 14% yield, m/z: 552 [M+H]⁺ observed). ¹H NMR (400 MHz, CDCl₃): δ 16.43 (s, 1H), 10.47 (bs, 1H), 7.21-6.99 (m, 5H), 6.79 (s, 1H), 6.07 (bs, 1H), 5.49 (bs, 1H), 4.15-4.08 (m, 2H), 3.62-3.59 (m, 2H), 3.57-3.54 (m, 4H), 3.38 (s, 3H), 3.35 (s, 3H), 3.30-2.94 (m, 1H), 2.83-2.78 (m, 1H), 2.71-2.67 (m, 1H), 2.13-2.07 (m, 2H), 1.43-1.41 (m, 2H), 0.84 (d, J=6.7 Hz, 3H), 0.76 (d, J=6.6 Hz, 3H).

4-Hydroxy-5-isopropyl-9-((2-methoxyethyl)amino)-8-(3-methoxypropoxy)-2-oxo-1,2,5,6-tetrahydro-1,10-phenanthroline-3-carboxylicacid

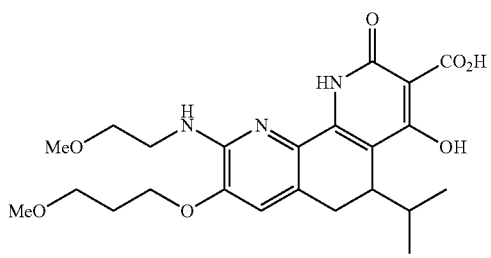 [SMILES: COCCCOc1cc2c(nc1NCCOC)-c1[nH]c(=O)c(C(=O)O)c(O)c1C(C(C)C)C2]

A mixture of 1-benzyl-4-hydroxy-5-isopropyl-9-((2-methoxyethyl)amino)-8-(3-methoxypropoxy)-2-oxo-1,2,5,6-tetrahydro-1,10-phenanthroline-3-carboxylic acid (50 mg, 0.09 mmol) and palladium on carbon (10% on carbon, 10 mg, 0.009 mmol) in methanol (10 mL) was stirred at rt for 20 h under an atmosphere of hydrogen gas. The reaction mixture was then filtered through Celite® and washed with methanol (2×10 mL). The combined organic layer was concentrated under reduced pressure. The crude mixture was purified by reverse phase HPLC to give 4-hydroxy-5-isopropyl-9-((2-methoxyethyl)amino)-8-(3-methoxypropoxy)-2-oxo-1,2,5,6-tetrahydro-1,10-phenanthroline-3-carboxylic acid as a yellow solid (19 mg, 45% yield, m/z: 462 [M+H]⁺ observed). ¹H NMR (300 MHz, CDCl₃): δ 11.47 (bs, 1H), 10.01 (s, 1H), 6.79 (s, 1H), 4.17 (m, 2H), 3.64-3.53 (m, 6H), 3.38 (s, 3H), 3.30 (s, 3H), 3.01-2.96 (m, 2H), 2.83-2.78 (m, 1H), 2.21-2.15 (m, 2H), 1.79-1.77 (m, 1H), 0.91-0.88 (d, J=9.0 Hz, 3H), 0.82-0.79 (d, J=9.0 Hz, 3H).

Example 52: 4-Hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide

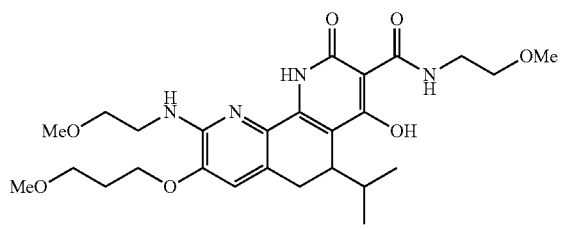 [SMILES: COCCCOc1cc2c(nc1NCCOC)-c1[nH]c(=O)c(C(=O)NCCOC)c(O)c1C(C(C)C)C2]

A mixture of 1-benzyl-4-hydroxy-5-isopropyl-N-(2-methoxyethyl)-9-((2-methoxyethyl) amino)-8-(3-methoxypropoxy)-2-oxo-1,2,5,6-tetrahydro-1,10-phenanthroline-3-carboxamide (50 mg, 0.08 mmol) and palladium on carbon (10% on carbon, 20 mg, 0.19 mmol) in methanol (10 ml) was stirred at rt for 16 h under an atmosphere of hydrogen gas. The reaction mixture was then filtered through Celite® and washed with methanol (2×10 mL). The combined organic phase was concentrated under reduced pressure. The crude oil was purified by normal phase SiO₂ chromatography (40% EtOAc/hexanes) to give 4-hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide as a yellow syrup (25 mg, 59% yield, m/z: 519 [M+H]±observed). ¹H NMR (400 MHz, CDCl₃): δ 16.16 (s, 1H), 10.38 (bs, 1H), 9.63 (bs, 1H), 6.70 (s, 1H), 5.33 (bs, 1H), 4.15-4.11 (m, 2H), 3.69-6.67 (m, 2H), 3.63-6.54 (m, 8H), 3.41 (s, 6H), 3.36 (s, 3H), 3.00-2.93 (m, 2H), 2.84-2.80 (m, 1H), 2.13-2.07 (m, 2H), 1.80-1.78 (m, 1H), 0.89 (d, J=6.8 Hz, 3H), 0.76 (d, J=6.7 Hz, 3H).

The following examples were prepared in a similar manner as 4-hydroxy-5-isopropyl-9-((2-methoxyethyl)amino)-8-(3-methoxypropoxy)-2-oxo-1,2,5,6-tetrahydro-1,10-phenanthroline-3-carboxylic acid from methyl 1-benzyl-9-chloro-4-hydroxy-5-isopropyl-8-(3-methoxypropoxy)-2-oxo-1,2,5,6-tetrahydro-1,10-phenanthroline-3-carboxylate and an appropriate amine.

Example 53: 4-Hydroxy-5-isopropyl-8-(3-methoxypropoxy)-9-(methylamino)-2-oxo-1,2,5,6-tetrahydro-1,10-phenanthroline-3-carboxylic acid

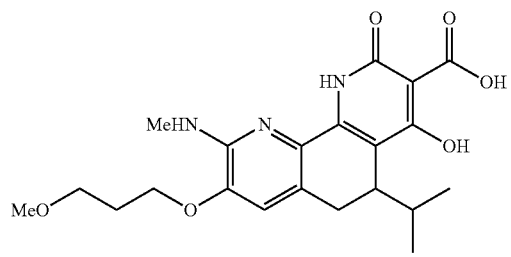 [SMILES: CNc1nc2c(cc1OCCCOC)CC(C(C)C)c1c-2[nH]c(=O)c(C(=O)O)c1O]

m/z: 418 [M+H]⁺ observed. ¹H NMR (300 MHz, CDCl₃): δ 13.76 (bs, 1H), 6.72 (s, 1H), 4.18 (m, 2H), 3.63 (t, J=6.0 Hz, 2H), 3.42 (s, 3H), 3.12 (s, 3H) 3.09-2.99 (m, 2H), 2.91-2.86 (m, 1H), 2.17-2.11 (m, 3H), 1.86-1.77 (m, 1H), 0.91 (d, J=6.0 Hz, 3H), 0.82 (d, J=6.0 Hz, 3H).

Example 54: 9-(Dimethylamino)-4-hydroxy-5-isopropyl-8-(3-methoxypropoxy)-2-oxo-1,2,5,6-tetrahydro-1,10-phenanthroline-3-carboxylic acid

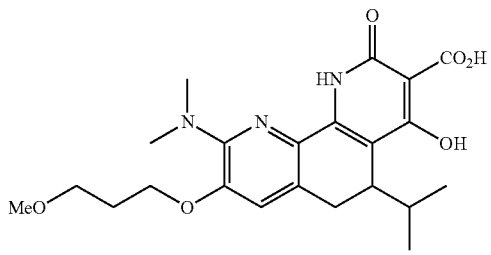

m/z: 432 [M+H]$^+$ observed. $^1$H NMR (300 MHz, DMSO-d$_6$): δ 15.25 (bs, 1H), 13.86 (s, 1H), 9.93 (bs, 1H), 6.89 (s, 1H), 4.16 (t, J=6.0 Hz, 2H), 3.61 (t, J=6.0 Hz, 2H), 3.39 (s, 3H), 3.07 (s, 6H), 3.03-2.90 (m, 3H), 2.21-2.13 (m, 2H), 1.85-1.75 (m, 1H), 0.92 (d, J=6.0 Hz, 3H), 0.82-0.81 (d, J=6.0 Hz, 3H).

Example 55: 5-Isopropyl-8-(3-methoxypropoxy)-9-(methylamino)-2-oxo-1,2,5,6-tetrahydro-1,10-phenanthroline-3-carboxylic acid

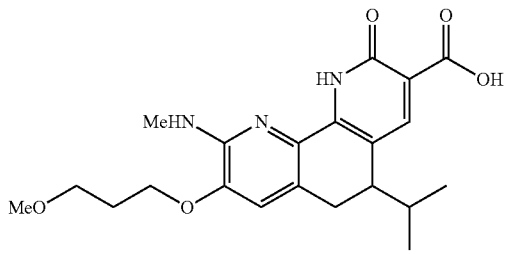 [SMILES: CNc1nc2c(cc1OCCCOC)CC(C(C)C)c1cc(C(=O)O)c(=O)[nH]c1-2]

m/z: 402 [M+H]$^+$ observed. $^1$H NMR (300 MHz, CDCl$_3$): δ 14.37 (s, 1H), 10.56 (bs, 1H), 8.39 (s, 1H), 6.73 (s, 1H), 5.16 (d, J=6.0 Hz, 1H), 4.18 (t, J=6.0 Hz, 2H), 3.58 (t, J=6.0 Hz, 2H), 3.39 (s, 3H), 3.12-3.04 (m, 4H), 2.87 (dd, J=15.0 Hz, 3 Hz, 1H), 2.67-2.62 (m, 1H), 2.17-2.09 (m, 2H), 1.88-1.82 (m, 1H), 0.87 (t, J=6.0 Hz, 6H).

Example 56: 9-Cyclopropyl-5-isopropyl-8-(3-methoxypropoxy)-2-oxo-1,2,5,6-tetrahydro-1,10-phenanthroline-3-carboxylic acid

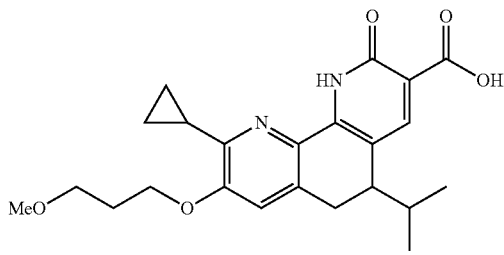 [SMILES: COCCCOc1cc2c(nc1C1CC1)-c1[nH]c(=O)c(C(=O)O)cc1C(C(C)C)C2]

m/z: 413 [M+H]$^+$ observed. $^1$H NMR (400 MHz, CDCl$_3$): δ 14.26 (bs, 1H), 10.42 (bs, 1H), 8.40 (s, 1H), 6.97 (s, 1H), 4.17 (m, 2H), 3.60 (m, 2H), 3.38 (s, 3H), 3.14-3.12 (m, 1H), 2.99-2.95 (m, 1H), 2.66 (m, 1H), 2.50 (m, 1H), 2.15 (m, 2H), 1.77 (m, 1H), 1.06 (m, 4H), 0.87 (m, 6H).

Example 57: 4-Hydroxy-5-isopropyl-9-methoxy-8-(3-methoxypropoxy)-3-(1H-1,2,4-triazol-5-yl)-5,6-dihydrobenzo[h]quinolin-2(1H)-one

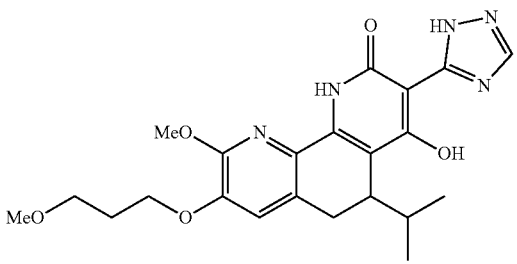

1-Benzyl-4-hydroxy-5-isopropyl-9-methoxy-8-(3-methoxypropoxy)-3-(1H-1,2,4-triazol-5-yl)-5,6-dihydrobenzo[h]quinolin-2(H)-one

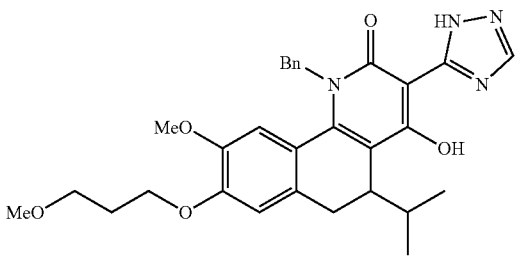 [SMILES: COCCCOc1cc2c(cc1OC)-c1c(c(O)c(-c3ncn[nH]3)c(=O)n1Cc1ccccc1)C(C(C)C)C2]

To a solution of 1-benzyl-4-hydroxy-5-isopropyl-9-methoxy-8-(3-methoxypropoxy)-2-oxo-5,6-dihydrobenzo[h]quinoline-3-carboxylic acid (120 mg, 0.24 mmol) in CH$_2$Cl$_2$ (3 mL) at 0° C. was added phosphorus pentachloride (59 mg, 0.28 mmol) and the reaction was stirred for 30 minutes. Ammonium hydroxide (28-30% in H$_2$O, 0.07 mL, 0.52 mmol) was added and the reaction stirred at rt overnight. Water (5 mL) was added and the layers separated. The organic phase was dried over sodium sulfate and concentrated under vacuum. The crude amide product was dissolved in N,N-dimethylformamide dimethyl acetal (1 mL) and stirred at 90° C. for 30 min. The N,N-dimethylformamide dimethyl acetal was removed under vacuum. Glacial acetic acid (2 mL) was added to reaction mixture followed by hydrazine monohydride (59 mg, 1.2 mmol). The reaction was stirred at 95° C. for 30 minutes. The acetic acid was removed under vacuum. The residue was purified by normal phase SiO$_2$ chromatography (0% to 5% MeOH/CH$_2$Cl$_2$) to afford 1-benzyl-4-hydroxy-5-isopropyl-9-methoxy-8-(3-methoxypropoxy)-3-(1H-1,2,4-triazol-5-yl)-5,6-dihydrobenzo[h]quinolin-2-one as a yellow solid (5 mg, 4% yield, m/z: 531 [M+H]$^+$ observed).

4-Hydroxy-5-isopropyl-9-methoxy-8-(3-methoxypropoxy)-3-(H-1,2,4-triazol-5-yl)-5,6-dihydrobenzo[h]quinolin-2(1H)-one

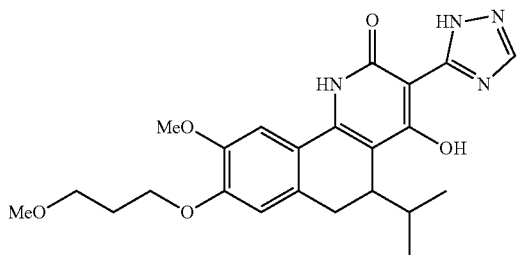 [SMILES: COCCCOc1cc2c(cc1OC)-c1[nH]c(=O)c(-c3ncn[nH]3)c(O)c1C(C(C)C)C2]

1-benzyl-4-hydroxy-5-isopropyl-9-methoxy-8-(3-methoxypropoxy)-3-(1H-1,2,4-triazol-5-yl)-5,6-dihydrobenzo[h]quinolin-2-one, (5 mg, 0.01 mmol) and palladium hydroxide (20% on carbon, 5 mg, 0.007 mmol) were dissolved in MeOH (3 mL). A hydrogen balloon was applied to the reaction. The reaction was stirred at room temperature for 16 h. The reaction solution was filtered through CELITE®, washed with MeOH (2×3 mL) and concentrated under vacuum. The crude product was purified by normal phase SiO$_2$ chromatography (0% to 5% MeOH/CH$_2$Cl$_2$) to afford 4-hydroxy-5-isopropyl-9-methoxy-8-(3-methoxypropoxy)-3-(1H-1,2,4-triazol-5-yl)-5,6-dihydrobenzo[h]quinolin-2(1H)-one (1 mg, 17% yield, m/z: 441 [M+H]$^+$ observed). $^1$H NMR (400 MHz, CDCl$_3$) δ 8.00 (s, 1H), 7.20 (qt, J=1.2, 0.7 Hz, 1H), 6.80 (s, 1H), 4.16 (dtd, J=15.9, 9.4, 6.5 Hz, 2H), 3.89 (s, 3H), 3.59 (td, J=6.2, 1.4 Hz, 2H), 3.38 (s, 3H), 3.05-2.86 (m, 3H), 2.14 (p, J=6.3 Hz, 2H), 1.64 (d, J=7.1 Hz, 1H), 0.85 (dd, J=19.1, 6.8 Hz, 6H).

Example 58: 4-Hydroxy-5-isopropyl-9-methoxy-8-(3-methoxypropoxy)-2-oxo-1,2,5,6-tetrahydrobenzo[h]quinoline-3-carboxamide

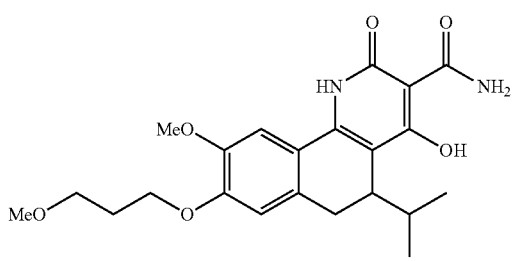 [SMILES: COCCCOc1cc2c(cc1OC)-c1[nH]c(=O)c(C(N)=O)c(O)c1C(C(C)C)C2]

1-Benzyl-4-hydroxy-5-isopropyl-9-methoxy-8-(3-methoxypropoxy)-2-oxo-1,2,5,6-tetrahydrobenzo[h]quinoline-3-carboxamide

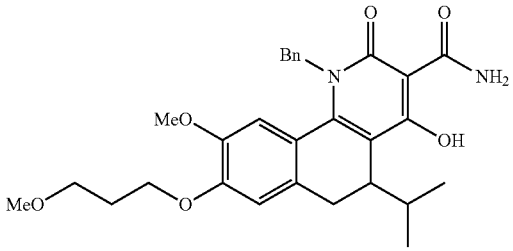 [SMILES: COCCCOc1cc2c(cc1OC)-c1c(c(O)c(C(N)=O)c(=O)n1Cc1ccccc1)C(C(C)C)C2]

To a solution of methyl 1-benzyl-4-hydroxy-5-isopropyl-9-methoxy-8-(3-methoxypropoxy)-2-oxo-1,2,5,6-tetrahydrobenzo[h]quinoline-3-carboxylate (100 mg, 0.19 mmol) in MeOH (3 mL) was added ammonia (7N solution in methanol, 0.28 mL, 2 mmol). The reaction was heated at 60° C. for 24 h. The solvent was removed under vacuum to give 1-benzyl-4-hydroxy-5-isopropyl-9-methoxy-8-(3-methoxypropoxy)-2-oxo-1,2,5,6-tetrahydrobenzo[h]quinoline-3-carboxamide as a yellow solid, which was used in the next step without further purifications (100 mg, >100% yield, m/z: 507 [M+H]$^+$ observed).

4-Hydroxy-5-isopropyl-9-methoxy-8-(3-methoxypropoxy)-2-oxo-1,2,5,6-tetrahydrobenzo[h]quinoline-3-carboxamide

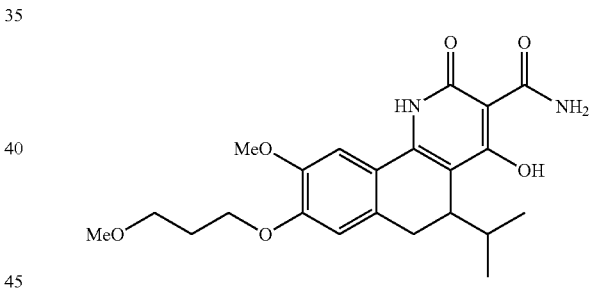

A mixture of 1-benzyl-4-hydroxy-5-isopropyl-9-methoxy-8-(3-methoxypropoxy)-2-oxo-1,2,5,6-tetrahydrobenzo[h]quinoline-3-carboxamide (10 mg, 0.02 mmol) and palladium hydroxide on carbon (20% on carbon, 10 mg, 0.015 mmol) in methanol (3 mL) was stirred at rt for 16 h under an atmosphere of hydrogen gas. The reaction solution was filtered through Celite®. The solvent was removed under vacuum. The crude mixture was purified by reverse phase HPLC to afford 4-hydroxy-5-isopropyl-9-methoxy-8-(3-methoxypropoxy)-2-oxo-1,2,5,6-tetrahydrobenzo[h]quinoline-3-carboxamide as a white solid (2.6 mg, 31% yield, m/z: 417 [M+H]$^+$ observed). $^1$H NMR (400 MHz, CDCl$_3$) δ 10.66 (s, 1H), 9.66 (d, J=5.0 Hz, 1H), 7.24 (ddq, J=1.5, 0.4 Hz, 1H), 6.81 (s, 1H), 4.25-4.11 (m, 2H), 3.93 (s, 3H), 3.59 (t, J=6.0 Hz, 2H), 3.37 (s, 3H), 2.92 (d, J=6.1 Hz, 3H), 2.14 (p, J=6.3 Hz, 2H), 1.60 (tt, J=6.8, 3.8 Hz, 1H), 0.83 (dd, J=20.5, 6.7 Hz, 6H).

The following examples were prepared in a similar manner as 4-hydroxy-5-isopropyl-9-methoxy-8-(3-methoxypropoxy)-2-oxo-1,2,5,6-tetrahydrobenzo[h]quinoline-3-carboxamide from methyl 1-benzyl-5-(tert-butyl)-4-hydroxy-9- methoxy-8-(3-methoxypropoxy)-2-oxo-1,2,5,6-tetrahydro-1,10-phenanthroline-3-carboxylate and an appropriate amine.

Example 59: 5-(tert-Butyl)-4-hydroxy-9-methoxy-8-(3-methoxypropoxy)-2-oxo-1,2,5,6-tetrahydro-1,10-phenanthroline-3-carboxamide

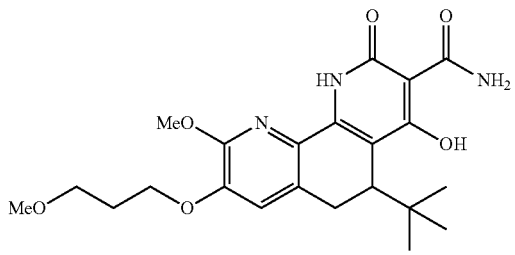 [SMILES: COCCCOc1cc2c(nc1OC)-c1[nH]c(=O)c(C(N)=O)c(O)c1C(C(C)(C)C)C2]

m/z: 432 [M+H]⁺ observed, $^1$H NMR (400 MHz, CDCl$_3$) δ 9.86 (s, 1H), 9.55 (s, 1H), 6.94 (s, 1H), 5.71 (s, 2H), 4.16 (td, J=6.5, 3.9 Hz, 2H), 4.05 (s, 3H), 3.57 (t, J=5.9 Hz, 2H), 3.36 (s, 3H), 3.09-2.98 (m, 3H), 2.14-2.05 (m, 2H), 0.80 (s, 9H).

Example 60: 5-(tert-Butyl)-4-hydroxy-9-methoxy-8-(3-methoxypropoxy)-2-oxo-1,2,5,6-tetrahydro-1,10-phenanthroline-3-carboxamide (single enantiomer I)

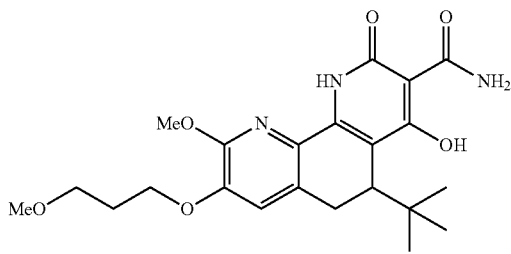 [SMILES: COCCCOc1cc2c(nc1OC)-c1[nH]c(=O)c(C(N)=O)c(O)c1C(C(C)(C)C)C2]

m/z: 432 [M+H]⁺ observed $^1$H NMR (400 MHz, CDCl$_3$) δ 9.86 (s, 1H), 9.55 (s, 1H), 6.94 (s, 1H), 5.71 (s, 2H), 4.16 (td, J=6.5, 3.9 Hz, 2H), 4.05 (s, 3H), 3.57 (t, J=5.9 Hz, 2H), 3.36 (s, 3H), 3.09-2.98 (m, 3H), 2.14-2.05 (m, 2H), 0.80 (s, 9H).

Example 61: 5-(tert-Butyl)-4-hydroxy-9-methoxy-8-(3-methoxypropoxy)-2-oxo-1,2,5,6-tetrahydro-1,10-phenanthroline-3-carboxamide (single enantiomer II)

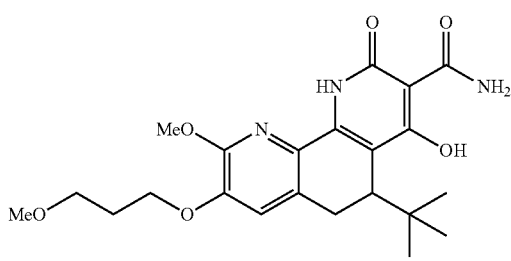 [SMILES: COCCCOc1cc2c(nc1OC)-c1[nH]c(=O)c(C(N)=O)c(O)c1C(C(C)(C)C)C2]

m/z: 432 [M+H]⁺ observed, H NMR (400 MHz, CDCl$_3$) δ 9.86 (s, 1H), 9.55 (s, 1H), 6.94 (s, 1H), 5.71 (s, 2H), 4.16 (td, J=6.5, 3.9 Hz, 2H), 4.05 (s, 3H), 3.57 (t, J=5.9 Hz, 2H), 3.36 (s, 3H), 3.09-2.98 (m, 3H), 2.14-2.05 (m, 2H), 0.80 (s, 9H).

Example 62: 5-(tert-Butyl)-9-methoxy-8-(3-methoxypropoxy)-2-oxo-1,2,5,6-tetrahydro-1,10-phenanthroline-3-carboxamide

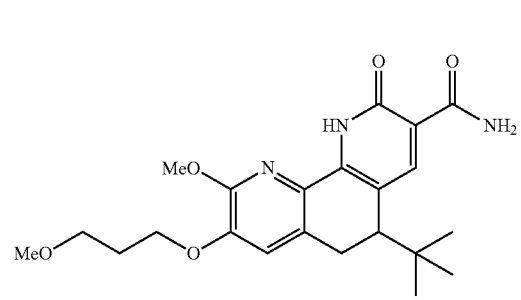 [SMILES: COCCCOc1cc2c(nc1OC)-c1[nH]c(=O)c(C(N)=O)cc1C(C(C)(C)C)C2]

m/z: 416 [M+H]⁺ observed. $^1$H NMR (400 MHz, CDCl$_3$) δ 10.09 (s, 1H), 9.45 (bs, 1H), 8.42 (s, 1H), 6.94 (s, 1H), 5.79 (s, 1H), 4.16 (td, J=6.6, 2.9 Hz, 2H), 4.06 (d, J=1.0 Hz, 3H), 3.57 (t, J=5.9 Hz, 2H), 3.36 (d, J=1.0 Hz, 3H), 3.25-2.98 (m, 2H), 2.62 (dd, J=8.0, 1.4 Hz, 1H), 2.13 (p, J=6.0 Hz, 2H), 0.80 (s, 9H).

Example 63: 5-(tert-Butyl)-4-hydroxy-9-methoxy-8-(3-methoxypropoxy)-N-methyl-2-oxo-1,2,5,6-tetrahydro-1,10-phenanthroline-3-carboxamide

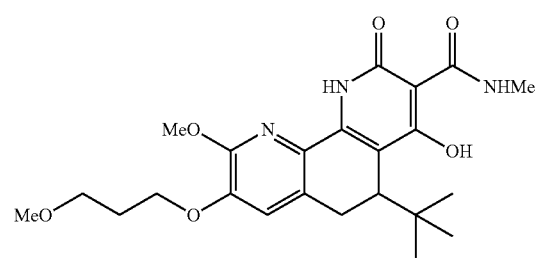 [SMILES: CNC(=O)c1c(O)c2c([nH]c1=O)-c1nc(OC)c(OCCCOC)cc1CC2C(C)(C)C]

m/z: 446 [M+H]⁺ observed. $^1$H NMR (400 MHz, CDCl$_3$) δ 10.05 (bs, 1H), 9.54 (s, 1H), 6.94 (s, 1H), 4.15 (td, J=6.5, 4.0 Hz, 2H), 4.06 (s, 3H), 3.60-3.52 (m, 2H), 3.36 (s, 3H), 3.04-2.96 (m, 4H), 2.19-2.07 (m, 5H), 0.79 (s, 9H).

Example 64: 5-(tert-Butyl)-9-methoxy-8-(3-methoxypropoxy)-N,N,4-trimethyl-2-oxo-1,2,5,6-tetrahydro-1,10-phenanthroline-3-carboxamide

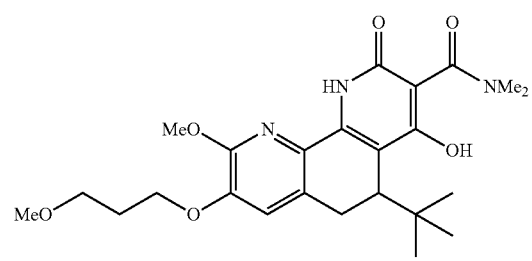 [SMILES: COCCCOc1cc2c(nc1OC)-c1[nH]c(=O)c(C(=O)N(C)C)c(O)c1C(C(C)(C)C)C2]

m/z: 460 [M+H]+ observed. ¹H NMR (400 MHz, CDCl₃) δ 12.85 (s, 1H), 9.46 (s, 1H), 6.93 (s, 1H), 4.15 (td, J=6.5, 3.7 Hz, 2H), 4.04 (s, 3H), 3.62-3.52 (m, 2H), 3.36 (s, 3H), 3.12 (s, 6H), 3.09-2.96 (m, 3H), 2.12 (q, J=6.2 Hz, 2H), 0.80 (s, 9H).

Example 65: 5-(tert-Butyl)-N,4-dihydroxy-9-methoxy-8-(3-methoxypropoxy)-2-oxo-1,2,5,6-tetrahydro-1,10-phenanthroline-3-carboxamide

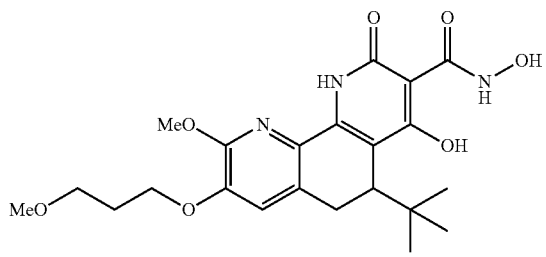 [SMILES: COCCCOc1cc2c(nc1OC)-c1[nH]c(=O)c(C(=O)NO)c(O)c1C(C(C)(C)C)C2]

1-Benzyl-5-(tert-butyl)-N,4-dihydroxy-9-methoxy-8-(3-methoxypropoxy)-2-oxo-1,2,5,6-tetrahydro-1,10-phenanthroline-3-carboxamide

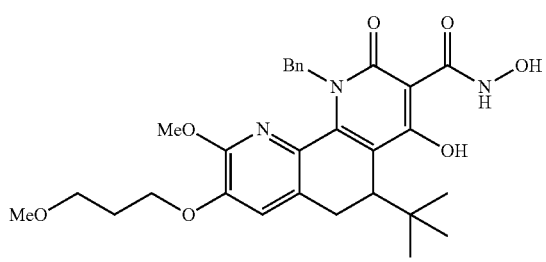 [SMILES: COCCCOc1cc2c(nc1OC)-c1c(c(O)c(C(=O)NO)c(=O)n1Cc1ccccc1)C(C(C)(C)C)C2]

To a solution of methyl 1-benzyl-5-(tert-butyl)-4-hydroxy-9-methoxy-8-(3-methoxypropoxy)-2-oxo-1,2,5,6-tetrahydro-1,10-phenanthroline-3-carboxylate (45 mg, 0.08 mmol) in MeOH/CH₂Cl₂ (2:1 mixture, 2.4 mL) at rt was added dropwise a mixture of hydroxylamine (28 mg, 0.84 mmol) in MeOH (1 mL). The reaction mixture was heated to 60° C. for 24 h. The mixture was cooled to rt and concentrated under vacuum to afford 1-benzyl-5-(tert-butyl)-N,4-dihydroxy-9-methoxy-8-(3-methoxypropoxy)-2-oxo-1,2,5,6-tetrahydro-1,10-phenanthroline-3-carboxamide as a yellow solid that was used without further purification (33 mg; 73% yield, m/z: 538 [M+H]+ observed).

5-(tert-Butyl)-N,4-dihydroxy-9-methoxy-8-(3-methoxypropoxy)-2-oxo-1,2,5,6-tetrahydro-1,10-phenanthroline-3-carboxamide

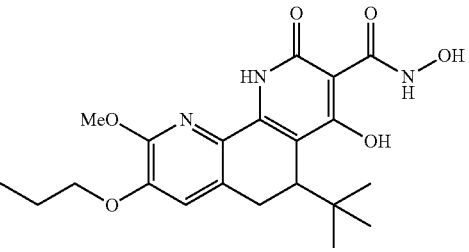

A solution of 1-benzyl-5-(tert-butyl)-N,4-dihydroxy-9-methoxy-8-(3-methoxypropoxy)-2-oxo-1,2,5,6-tetrahydro-1,10-phenanthroline-3-carboxamide (33 mg, 0.06 mmol) and palladium hydroxide (10% on carbon, 28 mg, 0.02 mmol) in MeOH (3 mL) was sparged with hydrogen gas. The reaction was stirred at rt for 16 h under an atmosphere of hydrogen. The reaction mixture was filtered through CELITE® and washed with MeOH (5 mL). The solvent was removed under vacuum to give 5-(tert-butyl)-N,4-dihydroxy-9-methoxy-8-(3-methoxypropoxy)-2-oxo-1,2,5,6-tetrahydro-1,10-phenanthroline-3-carboxamide as a yellow solid (16 mg, 58% yield, m/z: 448 [M+H]+ observed). ¹H NMR (400 MHz, CDCl₃): 12.14 (s, 1H), 9.72 (s, 1H), 7.97 (s, 1H), 6.94 (s, 1H), 4.17 (td, J=6.5, 1.4 Hz, 2H), 4.05 (s, 3H), 3.58 (t, J=5.9 Hz, 2H), 3.37 (s, 3H), 3.07-3.00 (m, 3H), 2.14 (t, J=6.1 Hz, 2H), 0.79 (s, 9H).

The following examples were prepared in a similar manner as 5-(tert-butyl)-N,4-dihydroxy-9-methoxy-8-(3-methoxypropoxy)-2-oxo-1,2,5,6-tetrahydro-1,10-phenanthroline-3-carboxamide from methyl 1-benzyl-4-hydroxy-5-isopropyl-9-methoxy-8-(3-methoxypropoxy)-2-oxo-1,2,5,6-tetrahydrobenzo[h]quinoline-3-carboxylate and an appropriate amine.

Example 66: N,4-Dihydroxy-5-isopropyl-9-methoxy-8-(3-methoxypropoxy)-2-oxo-1,2,5,6-tetrahydrobenzo[h]quinoline-3-carboxamide

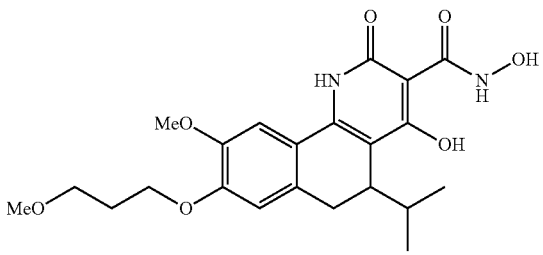 [SMILES: COCCCOc1cc2c(cc1OC)-c1[nH]c(=O)c(C(=O)NO)c(O)c1C(C(C)C)C2]

m/z: 433 [M+H]+ observed. ¹H NMR (400 MHz, CDCl₃): δ 12.01 (s, 1H), 11.26 (s, 1H), 8.9 (bs, 1H), 7.38 (s, 1H), 6.81 (s, 1H), 4.20 (t, J=6.5 Hz, 2H), 3.91 (s, 3H), 3.60 (t, J=6.0 Hz, 2H), 3.38 (s, 3H), 2.95-2.84 (m, 3H), 2.15 (p, J=6.2 Hz, 2H), 1.64-1.54 (m, 1H), 0.80 (dd, J=12.9, 6.7 Hz, 6H).

Example 67: 5-(tert-Butyl)-N-hydroxy-9-methoxy-8-(3-methoxypropoxy)-2-oxo-1,2,5,6-tetrahydro-1,10-phenanthroline-3-carboxamide

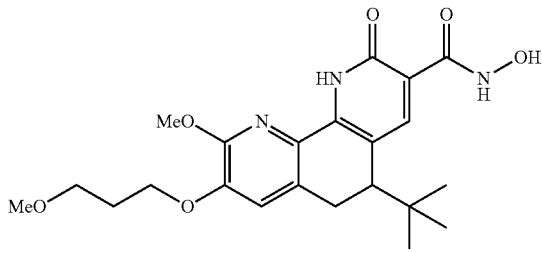 [SMILES: COCCCOc1cc2c(nc1OC)-c1[nH]c(=O)c(C(=O)NO)cc1C(C(C)(C)C)C2]

m/z: 432 [M+H]$^+$ observed. $^1$H NMR (400 MHz, CDCl$_3$) δ 12.01 (s, 1H), 10.15 (s, 1H), 8.33 (s, 1H), 6.94 (s, 1H), 4.16 (td, J=6.5, 2.9 Hz, 2H), 4.05 (s, 3H), 3.57 (t, J=5.9 Hz, 2H), 3.36 (d, J=0.5 Hz, 3H), 3.17-3.00 (m, 2H), 2.66-2.58 (m, 1H), 2.17-2.10 (m, 2H), 0.80 (s, 9H).

Example 68: 5-(tert-Butyl)-2,4-dichloro-9-methoxy-8-(3-methoxypropoxy)-5,6-dihydro-1,10-phenanthroline-3-carboxylicacid

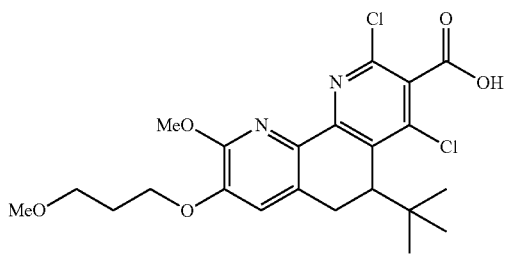 [SMILES: COCCCOc1cc2c(nc1OC)-c1nc(Cl)c(C(=O)O)c(Cl)c1C(C(C)(C)C)C2]

Methyl 5-(tert-butyl)-9-methoxy-8-(3-methoxypropoxy)-2,4-bis(((trifluoromethyl) sulfonyl)oxy)-5,6-dihydro-1,10-phenanthroline-3-carboxylate

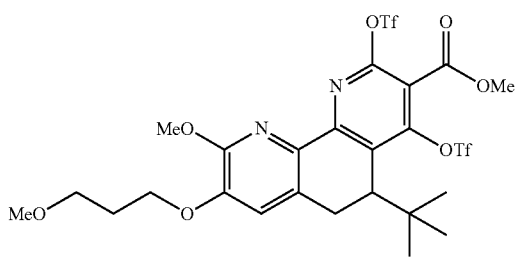 [SMILES: COCCCOc1cc2c(nc1OC)-c1nc(OS(=O)(=O)C(F)(F)F)c(C(=O)OC)c(OS(=O)(=O)C(F)(F)F)c1C(C(C)(C)C)C2]

To a solution of methyl 5-tert-butyl-4-hydroxy-9-methoxy-8-(3-methoxypropoxy)-2-oxo-5,6-dihydro-1H-1,10-phenanthroline-3-carboxylate (83 mg, 0.19 mmol) and triethylamine (0.13 mL, 0.93 mmol) in CH$_2$Cl$_2$ (4 mL) at 0° C. was added trifluoromethylsulfonyl trifluoromethanesulfonate (0.56 mL, 0.56 mmol) dropwise. The reaction was stirred at 0° C. for 30 minutes. Saturated aqueous sodium bicarbonate solution (2 mL) was added to quench the reaction. The aqueous phase was washed with CH$_2$Cl$_2$ (3×4 mL). The combined organic phase was dried over anhydrous sodium sulfate, filtered and concentrated under vacuum to give methyl 5-(tert-butyl)-9-methoxy-8-(3-methoxypropoxy)-2,4-bis(((trifluoromethyl)sulfonyl)oxy)-5,6-dihydro-1,10-phenanthroline-3-carboxylate as a yellow oil, which was used in the next step without further purifications (130 mg, 98% yield, m/z: 711 [M+H]$^+$ observed).

5-(tert-Butyl)-2,4-dichloro-9-methoxy-8-(3-methoxypropoxy)-5,6-dihydro-1,10-phenanthroline-3-carboxylicacid

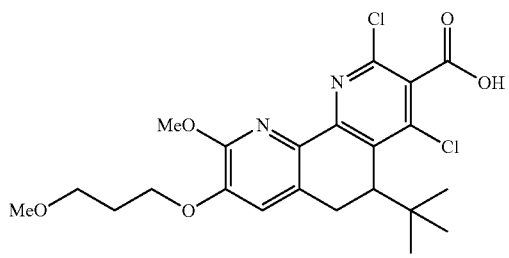

To a solution of methyl 5-tert-butyl-9-methoxy-8-(3-methoxypropoxy)-2,4-bis(trifluoromethylsulfonyloxy)-5,6-dihydro-1,10-phenanthroline-3-carboxylate (130 mg, 0.18 mmol) in 1,4-dioxane (2 mL) was added hydrogen chloride (4N solution in dioxane, 0.9 mL, 3.6 mmol). The reaction mixture was heated to 100° C. in a seal tube for 5 days. The reaction was cooled to rt and the solvent was removed under vacuum. The crude material was purified by reverse phase HPLC to afford 5-(tert-butyl)-2,4-dichloro-9-methoxy-8-(3-methoxypropoxy)-5,6-dihydro-1,10-phenanthroline-3-carboxylic acid as a yellow solid (2.9 mg, 4% yield, m/z: 469 [M+H]$^+$ observed). $^1$H NMR (400 MHz, CDCl$_3$) δ 6.56 (s, 1H), 4.11 (q, J=6.3 Hz, 2H), 3.99 (d, J=1.5 Hz, 3H), 3.58 (q, J=11.2, 8.5 Hz, 2H), 3.36 (d, J=1.7 Hz, 3H), 3.25 (dd, J=6.8, 1.8 Hz, 1H), 3.04-2.81 (m, 2H), 2.21-2.09 (m, 2H), 0.86 (s, 9H).

Example 69: (S)-10-Chloro-5-isopropyl-9-(3-methoxypropoxy)-2-oxo-1,2,5,6-tetrahydrobenzo[2,3]oxepino[4,5-b]pyridine-3-carboxylicacid

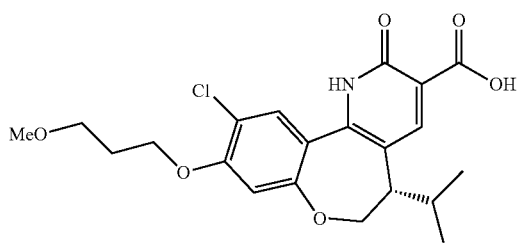 [SMILES: COCCCOc1cc2c(cc1Cl)-c1[nH]c(=O)c(C(=O)O)cc1[C@H](C(C)C)CO2]

tert-Butyl(R)-3-((R)-4-benzyl-2-oxooxazolidine-3-carbonyl)-4-methylpentanoate

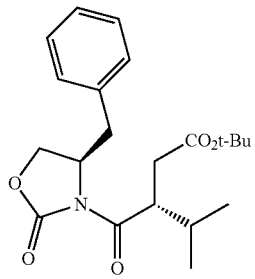 [SMILES: CC(C)[C@@H](CC(=O)OC(C)(C)C)C(=O)N1C(=O)OC[C@H]1Cc1ccccc1]

To a solution of (R)-4-benzyl-3-(3-methylbutanoyl)oxazolidin-2-one (20 g, 76 mmol) in freshly distilled THF (400 mL) was added dropwise lithium diisopropylamide (2 M in THF, 50 mL, 100 mmol) at −70° C. under nitrogen and stirred for 1 h. Then tert-butyl bromoacetate (51 mL, 352 mmol) was added to the reaction mixture at −70° C. under nitrogen. The reaction was warmed to rt and stirred for 15 h. The reaction was quenched by saturated aqueous ammonium chloride solution (500 mL) and extracted with EtOAc (2×300 mL). The combined organic layers were washed with 1N aqueous HCl solution (2×200 mL), saturated aqueous sodium bicarbonate (2×300 mL), dried over anhydrous sodium sulfate, filtered and concentrated in vacuo. The residue was purified by normal phase SiO$_2$ chromatography (0-5% EtOAc/petroleum ether) to give tert-butyl(R)-3-((R)-4-benzyl-2-oxooxazolidine-3-carbonyl)-4-methylpentanoate as a white solid (27 g, 93% yield, m/z: 320 [M−(tert-Butyl)+H]$^+$ observed).

(R)-4-(tert-Butoxy)-2-isopropyl-4-oxobutanoic acid

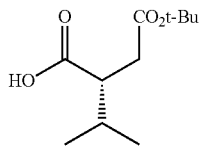

To a solution of tert-butyl(R)-3-((R)-4-benzyl-2-oxooxazolidine-3-carbonyl)-4-methylpentanoate (15 g, 40 mmol) in THF/H$_2$O (7:2, 900 mL) was added hydrogen peroxide (30% in water, 65 mL, 676 mmol) dropwise at 0° C. Lithium hydroxide monohydrate (2.7 g, 64 mmol) was added in three portions at 0° C. The mixture was stirred at 20° C. for 4 h. The reaction (combined with another 12 g batch) was quenched with saturated aqueous sodium sulphite solution (400 mL). After stirring for 10 minutes, the solution was extracted with MTBE (2×200 mL). The aqueous layer was acidified with 1N aqueous HCl solution to adjust the pH to 2, then extracted with CH$_2$Cl$_2$ (3×150 mL). The combined organic layer was dried over anhydrous sodium sulfate, filtered and concentrated in vacuo. The residue was purified by normal phase SiO$_2$ chromatography (10% EtOAc/petroleum ether) to give (R)-4-(tert-butoxy)-2-isopropyl-4-oxobutanoic acid as a yellow oil (16 g combined for 2 batches, m/z: 215 [M−H]$^−$ observed).

tert-Butyl(R)-3-(hydroxymethyl)-4-methylpentanoate

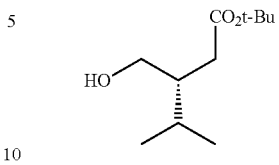

To a mixture of (R)-4-(tert-butoxy)-2-isopropyl-4-oxobutanoic acid (10 g, 46 mmol) in tetrahydrofuran (50 mL) was added dropwise borane-dimethylsulfide (10 M solution in tetrahydrofuran, 5.3 mL, 53 mmol) at 0° C. under nitrogen. The mixture was stirred at rt for 16 h. The reaction was carefully quenched with H$_2$O (30 mL) at 0° C. Solid potassium carbonate (10 g) was added and the mixture was stirred for 10 minutes. The aqueous layer was extracted with EtOAc (3×100 mL). The combined organic layers were washed with saturated aqueous brine solution (2×100 mL), dried over anhydrous sodium sulfate, filtered and concentrated under reduced pressure. The residue was purified by normal phase SiO$_2$ chromatography (0-15% EtOAc/petroleum ether) to give tert-butyl(R)-3-(hydroxymethyl)-4-methylpentanoate as a yellow oil (7 g, 74% yield).

2-(4-Chloro-3-(3-methoxypropoxy)phenyl)-4,4,5,5-tetramethyl-1,3,2-dioxaborolane

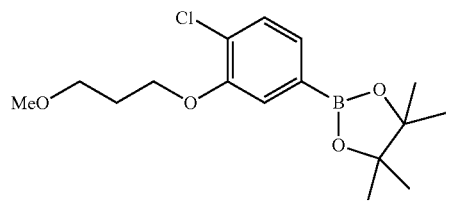 [SMILES: COCCCOc1cc(B2OC(C)(C)C(C)(C)O2)ccc1Cl]

To a mixture of 4-bromo-1-chloro-2-(3-methoxypropoxy)benzene (20 g, 71 mmol), bis(pinacolato)diboron (20 g, 78 mmol) and potassium acetate (14 g, 143 mmol) in 1,4-dioxane (320 mL) was added [1,1′-bis(diphenylphosphino)ferrocene]dichloropalladium(II) (1:1 complex with dichloromethane, 5.8 g, 7.2 mmol) under nitrogen. The reaction mixture was heated to 100° C. for 16 h. The reaction mixture was poured into H$_2$O (500 mL) and extracted with EtOAc (3×1 L). The combined organic phase was dried over anhydrous sodium sulfate, filtered and concentrated in vacuum to give 2-(4-chloro-3-(3-methoxypropoxy)phenyl)-4,4,5,5-tetramethyl-1,3,2-dioxaborolane as a black-brown oil, which was used in the next step without further purification (25 g, 98% yield, m/z: 327 [M+H]$^+$ observed).

4-Chloro-3-(3-methoxypropoxy)phenol

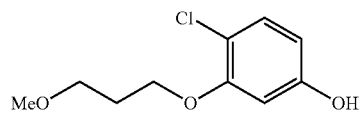 [SMILES: COCCCOc1cc(O)ccc1Cl]

To a mixture of 2-(4-chloro-3-(3-methoxypropoxy)phenyl)-4,4,5,5-tetramethyl-1,3,2-dioxaborolane (20 g, 61 mmol) in tetrahydrofuran (150 mL) was added hydrogen peroxide (30% solution in water, 12 mL, 122 mmol) and sodium hydroxide (2 M solution in water, 61 mL, 122 mmol) in three portions at 0° C. under nitrogen. The mixture was stirred at rt for 4 h. The mixture was acidified with 1 N HCl solution to adjust the pH to 4, then extracted with EtOAc (3×200 mL). The combined organic layers were washed with saturated aqueous brine solution (200 mL), dried over sodium sulfate, filtered and concentrated under reduced pressure. The residue was purified by normal phase $SiO_2$ chromatography (5-50% EtOAc/petroleum ether) to give 4-chloro-3-(3-methoxypropoxy)phenol as a yellow oil (7.0 g, 52% yield, m/z: 217 [M+H]$^+$ observed).

tert-Butyl(R)-3-((4-chloro-3-(3-methoxypropoxy)phenoxy)methyl)-4-methylpentanoate

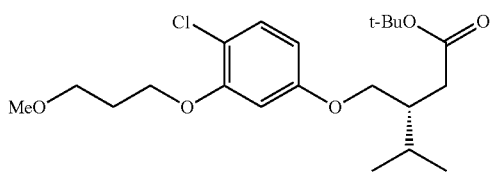 [SMILES: COCCCOc1cc(OC[C@H](CC(=O)OC(C)(C)C)C(C)C)ccc1Cl]

To a mixture of 4-chloro-3-(3-methoxypropoxy)phenol (4.1 g, 19 mmol) and tert-butyl(R)-3-(hydroxymethyl)-4-methylpentanoate (5.0 g, 24 mmol) in tetrahydrofuran (50 mL) was added triphenylphosphine (6.5 g, 25 mmol), followed by diisopropyl azodicarboxylate (5.0 g, 25 mmol, 4.8 mL) in portions at 0° C. under nitrogen. The mixture was stirred at 40° C. for 16 h. The reaction mixture cooled to rt, diluted with water (100 mL) and extracted with EtOAc (2×100 mL). The combined organic layers were washed with saturated aqueous brine solution (100 mL), dried over sodium sulfate, filtered and concentrated under reduced pressure. The residue was purified by normal phase $SiO_2$ chromatography (0-50% EtOAc/petroleum ether) to give tert-butyl(R)-3-((4-chloro-3-(3-methoxypropoxy)phenoxy)methyl)-4-methylpentanoate as a colorless oil (5.0 g, 55% yield, m/z: 345 [M-(tert-Butyl)+H]$^+$ observed).

(R)-3-((4-Chloro-3-(3-methoxypropoxy)phenoxy)methyl)-4-methylpentanoic acid

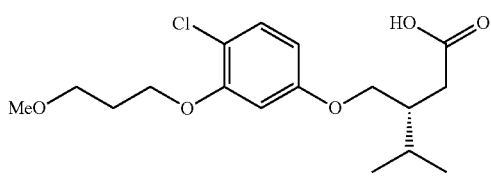 [SMILES: COCCCOc1cc(OC[C@H](CC(=O)O)C(C)C)ccc1Cl]

To a mixture of tert-butyl(R)-3-((4-chloro-3-(3-methoxypropoxy)phenoxy)methyl)-4-methylpentanoate (2.0 g, 5 mmol) in $CH_2Cl_2$ (20 mL) was added trifluoroacetic acid (2.5 mL) and the reaction mixture was stirred at 15° C. for 16 h. The reaction mixture was concentrated under reduced pressure to give (R)-3-((4-chloro-3-(3-methoxypropoxy)phenoxy)methyl)-4-methylpentanoic acid as a brown oil, which was used in the next step without further purification (2.0 g, >100% yield, m/z: 345 [M+H]$^+$ observed).

(R)-7-Chloro-8-hydroxy-3-isopropyl-3,4-dihydrobenzo[b]oxepin-5(2H)-one

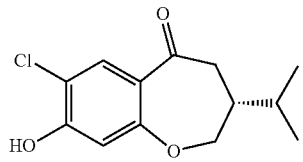 [SMILES: CC(C)[C@@H]1COc2cc(O)c(Cl)cc2C(=O)C1]

Thionyl chloride (2.07 g, 17.40 mmol, 1.26 mL) was added dropwise to a mixture of (R)-3-((4-chloro-3-(3-methoxypropoxy)phenoxy)methyl)-4-methylpentanoic acid (2.0 g, 5.8 mmol) in $CH_2Cl_2$ (20 mL). The mixture was stirred at rt for 16 h. The reaction mixture was concentrated under reduced pressure to give (R)-3-((4-chloro-3-(3-methoxypropoxy)phenoxy)methyl)-4-methylpentanoyl chloride as a brown oil, which was used in the next step without further purification (2.1 g, 99% yield).

To a mixture of (R)-3-((4-chloro-3-(3-methoxypropoxy)phenoxy)methyl)-4-methylpentanoyl chloride (3.3 g, 9.1 mmol) in $CH_2Cl_2$ (30 mL) was added aluminum trichloride (2.4 g, 18 mmol) in three portions. The mixture was stirred at rt for 4 h, then quenched with H2O (50 mL) at 0° C. and extracted with $CH_2Cl_2$ (3×100 mL). The combined organic layers were washed with saturated aqueous brine solution (2×100 mL), dried over sodium sulfate, filtered and concentrated under reduced pressure to give (R)-7-chloro-8-hydroxy-3-isopropyl-3,4-dihydrobenzo[b]oxepin-5(2H)-one as a yellow oil, which was used in the next step without further purification (2.0 g, 85% yield, m/z: 255 [M+H]$^+$ observed).

(R)—N-Benzyl-7-chloro-3-isopropyl-8-(3-methoxypropoxy)-3,4-dihydrobenzo[b]oxepin-5(2H)-imine

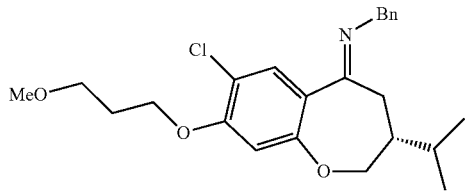 [SMILES: COCCCOc1cc2c(cc1Cl)/C(=N/Cc1ccccc1)C[C@H](C(C)C)CO2]

To a mixture of (R)-7-chloro-8-hydroxy-3-isopropyl-3,4-dihydrobenzo[b]oxepin-5(2H)-one (2.0 g, 7.8 mmol) and 1-bromo-3-methoxy-propane (1.2 g, 7.8 mmol) in acetonitrile (30 mL) was added potassium carbonate (3.26 g, 23.6 mmol). The mixture was stirred at rt for 16 h. The reaction mixture was diluted with $H_2O$ (50 mL) and extracted with EtOAc (3×50 mL). The combined organic layers were washed with saturated aqueous brine solution (50 mL), dried over sodium sulfate, filtered and concentrated under reduced pressure. The residue was purified by normal phase $SiO_2$ chromatography (0-50% EtOAc/petroleum ether) to give (R)-7-chloro-3-isopropyl-8-(3-methoxypropoxy)-3,4-dihydrobenzo[b]oxepin-5(2H)-one as a brown oil, which was used in the next step without further purification (1.5 g, 58% yield). Titanium (IV) chloride solution (1 M solution in dichloromethane, 2.3 mL, 2.3 mmol) was added dropwise to a mixture of (R)-7-chloro-3-isopropyl-8-(3-methoxypropoxy)-3,4-dihydrobenzo[b]oxepin-5(2H)-one (1.2 g, 3.6 mmol), benzylamine (0.43 mL, 3.92 mmol) and triethylamine (1.3 mL, 9.26 mmol) in CH$_2$Cl$_2$ (1 mL) at 0° C. The mixture was gradually warmed to rt and stirred for 16 h. The reaction mixture was diluted with saturated sodium bicarbonate solution (5 mL) and extracted with CH$_2$Cl$_2$ (2×10 mL). The combined organic layers were dried over sodium sulfate, filtered and concentrated under reduced pressure to give (R)—N-benzyl-7-chloro-3-isopropyl-8-(3-methoxypropoxy)-3,4-dihydrobenzo[b]oxepin-5(2H)-imine as a brown solid, which was used in the next step without further purification (1.74 g, 54% yield, m/z: 416 [M+H]$^+$ observed).

Methyl (S)-10-chloro-5-isopropyl-9-(3-methoxypropoxy)-2-oxo-1,2,5,6-tetrahydrobenzo[2,3]oxepino[4,5-b]pyridine-3-carboxylate

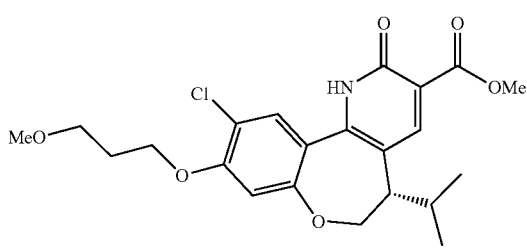 [SMILES: COCCCOc1cc2c(cc1Cl)-c1[nH]c(=O)c(C(=O)OC)cc1[C@H](C(C)C)CO2]

A mixture of (R)—N-benzyl-7-chloro-3-isopropyl-8-(3-methoxypropoxy)-3,4-dihydrobenzo[b]oxepin-5(2H)-imine (1.74 g, 4.18 mmol) and dimethyl 2-(meth oxymethylene)propanedioate (1.46 g, 8.37 mmol) in Ph$_2$O (20 mL) was stirred at 220° C. for 15 minutes. The reaction mixture was purified directly by normal phase SiO$_2$ chromatography (50% EtOAc/petroleum ether then 9% MeOH/CH$_2$Cl$_2$) to give methyl (S)-1-benzyl-10-chloro-5-isopropyl-9-(3-methoxypropoxy)-2-oxo-1,2,5,6-tetrahydrobenzo[2,3]oxepino[4,5-b]pyridine-3-carboxylate as a brown oil and was used in the next step without purification (650 mg, 29% yield).

To a solution of methyl (S)-1-benzyl-10-chloro-5-isopropyl-9-(3-methoxypropoxy)-2-oxo-1,2,5,6-tetrahydrobenzo[2,3]oxepino[4,5-b]pyridine-3-carboxylate (650 mg, 1.24 mmol) in tetrahydrofuran (10 mL) was added palladium hydroxide (20% on carbon, 860 mg, 0.83 mmol). The mixture was stirred under hydrogen (15 psi) at rt for 15 minutes. The reaction mixture was filtered, washed with MeOH (3×10 mL) and concentrated under reduced pressure. The residue was purified by purified by reverse phase HPLC to give methyl (S)-10-chloro-5-isopropyl-9-(3-methoxypropoxy)-2-oxo-1,2,5,6-tetrahydrobenzo[2,3]oxepino[4,5-b]pyridine-3-carboxylate as a purple solid (50 mg, 9% yield, m/z: 436 [M+H]$^+$ observed).

(S)-10-Chloro-5-isopropyl-9-(3-methoxypropoxy)-2-oxo-1,2,5,6-tetrahydrobenzo[2,3]oxepino[4,5-b]pyridine-3-carboxylicacid

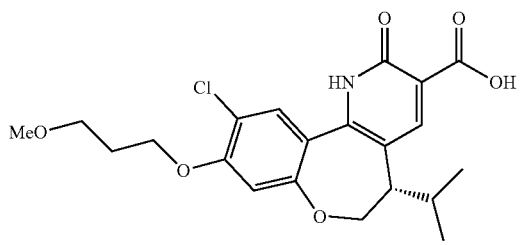 [SMILES: COCCCOc1cc2c(cc1Cl)-c1[nH]c(=O)c(C(=O)O)cc1[C@H](C(C)C)CO2]

To a mixture of methyl (S)-10-chloro-5-isopropyl-9-(3-methoxypropoxy)-2-oxo-1,2,5,6-tetrahydrobenzo[2,3]oxepino[4,5-b]pyridine-3-carboxylate (20 mg, 45 umol) in methanol/water (1:1, 1 mL) was added lithium hydroxide monohydrate (19 mg, 460 umol) in one portion. The mixture was stirred at rt for 16 h. The mixture was acidified with 1 M HCl solution to adjust the pH to 2 and extracted with EtOAc (3×10 mL). The combined organic layers were dried over sodium sulfate, filtered and concentrated under reduced pressure. The residue was purified by purified by reverse phase HPLC to give (S)-10-chloro-5-isopropyl-9-(3-methoxypropoxy)-2-oxo-1,2,5,6-tetrahydrobenzo[2,3]oxepino[4,5-b]pyridine-3-carboxylic acid as a yellow solid (11 mg, 56% yield, m/z: 422 [M+H]$^+$ observed). $^1$H NMR (400 MHz, CDCl$_3$): δ 13.53 (s, 1H), 12.21 (s, 1H), 8.38 (s, 1H), 7.64 (s, 1H), 6.70 (s, 1H), 4.61-4.57 (m, 1H), 4.48-4.45 (m, 1H), 4.19-4.16 (t, J=6 Hz, 2H), 3.64-3.61 (t, J=6 Hz, 2H), 3.39 (s, 3H), 2.58-2.54 (m, 1H), 2.18-2.12 (m, 2H), 1.95-1.88 (m, 1H), 1.07-1.05 (d, J=6.4 Hz, 3H), 0.85-0.83 (d, J=6.4 Hz, 3H).

Example 70: (S)-10-Chloro-4-hydroxy-5-isopropyl-9-(3-methoxypropoxy)-2-oxo-1,2,5,6-tetrahydrobenzo[2,3]oxepino[4,5-b]pyridine-3-carboxylic acid

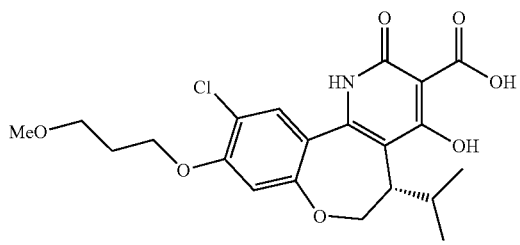 [SMILES: COCCCOc1cc2c(cc1Cl)-c1[nH]c(=O)c(C(=O)O)c(O)c1[C@H](C(C)C)CO2]

Methyl (S)-1-benzyl-10-chloro-4-hydroxy-5-isopropyl-9-(3-methoxypropoxy)-2-oxo-1,2,5,6-tetrahydrobenzo[2,3]oxepino[4,5-b]pyridine-3-carboxylate

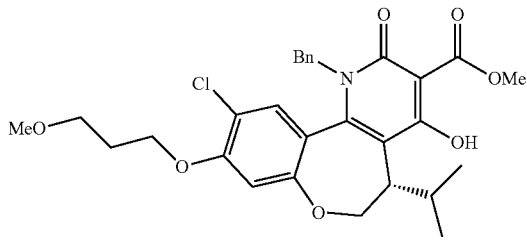 [SMILES: COCCCOc1cc2c(cc1Cl)-c1c(c(O)c(C(=O)OC)c(=O)n1Cc1ccccc1)[C@H](C(C)C)CO2]

A mixture of (R)—N-benzyl-7-chloro-3-isopropyl-8-(3-methoxypropoxy)-3,4-dihydrobenzo[b]oxepin-5(2H)-imine (1.2 g, 2.9 mmol) and trimethyl methanetricarboxylate (1.1 g, 5.8 mmol) in Ph$_2$O (5 mL) was stirred at 220° C. for 30 min under nitrogen. The mixture was cooled to rt and purified by normal phase SiO$_2$ chromatography (10-100% EtOAc/petroleum ether) to give methyl (5S)-1-benzyl-10-chloro-4-hydroxy-5-isopropyl-9-(3-methoxypropoxy)-2-oxo-5,6-dihydro-[1]benzoxepino[5,4-b]pyridine-3-carboxylate as a yellow solid (400 mg, 19% yield, m/z: 542 [M+H]$^+$ observed). $^1$H NMR (400 MHz, DMSO-d$_6$): δ 13.54 (s, 1H), 7.40 (s, 1H), 7.26-7.25 (m, 2H), 7.23-7.20 (m, 1H), 6.98 (s, 1H), 6.93-6.91 (d, J=7.2 Hz, 2H), 5.25-5.21 (m, 1H), 5.13-5.09 (m, 1H), 4.50-4.42 (m, 2H), 4.17-4.08 (m, 2H), 3.85 (s, 3H), 3.51-3.46 (m, 2H), 3.24 (s, 3H), 3.03-2.99 (m, 1H), 1.99-1.93 (m, 2H), 0.79-0.78 (d, J=6 Hz, 3H), 0.67-0.63 (m, 1H), 0.53-0.51 (d, J=6.4 Hz, 3H).

Methyl (S)-10-chloro-4-hydroxy-5-isopropyl-9-(3-methoxypropoxy)-2-oxo-1,2,5,6-tetrahydrobenzo[2,3]oxpino[4,5-b]pyridine-3-carboxylate

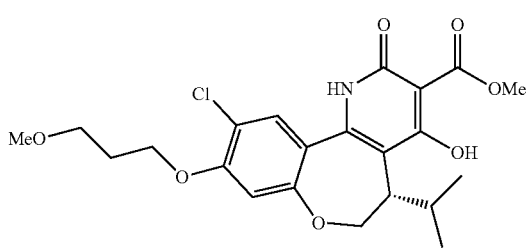 [SMILES: COCCCOc1cc2c(cc1Cl)-c1[nH]c(=O)c(C(=O)OC)c(O)c1[C@H](C(C)C)CO2]

To a solution of methyl (5S)-1-benzyl-10-chloro-4-hydroxy-5-isopropyl-9-(3-methoxypropoxy)-2-oxo-5,6-dihydro-[1]benzoxepino[5,4-b]pyridine-3-carboxylate (400 mg, 0.74 mmol) in EtOH (5 mL) was added palladium hydroxide (10% on carbon, 0.1 g) under hydrogen. The suspension was degassed under vacuum and purged with hydrogen (cycle repeated three times). The mixture was stirred under hydrogen (15 psi) at rt for 6 h. The mixture was filtered and washed with EtOAc (2×30 mL). The filtrate was concentrated under reduced pressure. The residue was purified by preparative normal phase SiO$_2$ chromatography (50% petroleum ether/EtOAc) to give methyl (S)-10-chloro-4-hydroxy-5-isopropyl-9-(3-methoxypropoxy)-2-oxo-1,2,5,6-tetrahydrobenzo[2,3]oxepino[4,5-b]pyridine-3-carboxylate as a yellow solid (200 mg, 50% yield). $^1$H NMR (400 MHz, CDCl$_3$): δ 13.93 (s, 1H), 10.43 (s, 1H), 7.60 (s, 1H), 6.61-6.59 (m, 1H), 4.68-4.65 (m, 1H), 4.38-4.35 (m, 1H), 4.16-4.14 (m, 2H), 3.96 (s, 3H), 3.62-3.60 (m, 2H), 3.59 (s, 3H), 3.37-3.21 (m, 1H), 2.14-2.11 (m, 2H), 1.66-1.62 (m, 1H), 1.07-1.05 (d, J=6.4 Hz, 3H), 0.79-0.77 (d, J=6.4 Hz, 3H).

(S)-10-Chloro-4-hydroxy-5-isopropyl-9-(3-methoxypropoxy)-2-oxo-1,2,5,6-tetrahydrobenzo[2,3]oxepino[4,5-b]pyridine-3-carboxylicacid

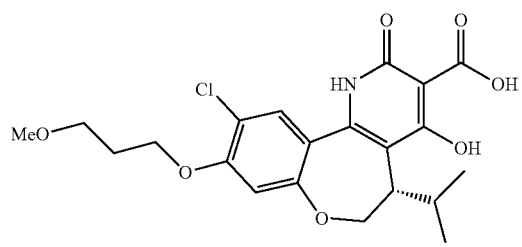 [SMILES: COCCCOc1cc2c(cc1Cl)-c1[nH]c(=O)c(C(=O)O)c(O)c1[C@H](C(C)C)CO2]

To a mixture of methyl (S)-10-chloro-4-hydroxy-5-isopropyl-9-(3-methoxypropoxy)-2-oxo-1,2,5,6-tetrahydrobenzo[2,3]oxepino[4,5-b]pyridine-3-carboxylate (200 mg, 0.443 mmol) in EtOAc (5 mL) was added lithium iodide (118.47 mg, 0.885 mmol) under nitrogen. The mixture was stirred at 60° C. for 4 h. The reaction mixture was cooled to rt, diluted with H$_2$O (15 mL) and extracted with EtOAc (2×10 mL). The combined organic phase was washed with saturated aqueous brine solution (20 mL), dried with anhydrous sodium sulfate, filtered and concentrated under reduced pressure. The residue was purified by reverse phase HPLC to give (S)-10-chloro-4-hydroxy-5-isopropyl-9-(3-methoxypropoxy)-2-oxo-1,2,5,6-tetrahydrobenzo[2,3]oxepino[4,5-b]pyridine-3-carboxylic acid as a light yellow solid (90 mg, 44% yield, m/z: 436 [M−H]$^-$ observed). $^1$H NMR (400 MHz, DMSO-d$_6$): δ 14.38 (s, 1H), 12.77 (s, 1H), 7.82 (s, 1H), 6.82 (s, 1H), 4.66-4.62 (m, 1H), 4.42-4.40 (m, 1H), 4.52-4.10 (m, 2H), 3.51-3.48 (t, J=6 Hz, 2H), 3.25 (s, 3H), 3.12-3.08 (m, 1H), 2.01-1.95 (m, 2H), 1.50-1.44 (m, 1H), 0.99-0.97 (d, J=6.4 Hz, 3H), 0.66-0.65 (d, J=6.4 Hz, 3H).

Example 71: (S)-4-Hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylicacid

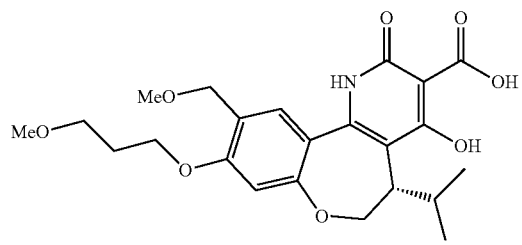 [SMILES: COCCCOc1cc2c(cc1COC)-c1[nH]c(=O)c(C(=O)O)c(O)c1[C@H](C(C)C)CO2]

(R)-3-Isopropyl-7-(methoxymethyl)-8-(3-methoxypropoxy)-3,4-dihydrobenzo[b]oxepin-5(2H)-one

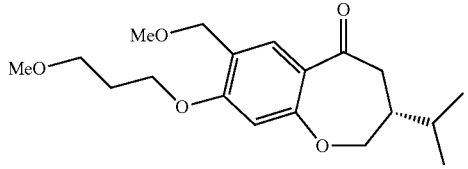 [SMILES: COCCCOc1cc2c(cc1COC)C(=O)C[C@H](C(C)C)CO2]

To a mixture of (3R)-7-chloro-3-isopropyl-8-(3-methoxypropoxy)-3,4-dihydro-2H-1-benzoxepin-5-one (2.1 g, 6.4 mmol) and potassium trifluoro(methoxymethyl)borate (1.46 g, 9.64 mmol) in 1,4-dioxane:water (10:1, 22 mL) was added RuPhos (1.20 g, 2.57 mmol), tris(dibenzylideneacetone)dipalladium(0) (1.18 g, 1.29 mmol) and sodium carbonate (1.70 g, 16 mmol) in one portion under nitrogen. The mixture was stirred at 120° C. for 16 h. The mixture was cooled to rt, H$_2$O (30 mL) was added and the aqueous phase was extracted with EtOAc (2×20 mL). The combined organic phase was washed with saturated aqueous brine solution (30 mL), dried with anhydrous sodium sulfate, filtered and concentrated in vacuum. The residue was purified by normal phase SiO$_2$ chromatography (0-15% EtOAc/petroleum ether) to give (R)-3-isopropyl-7-(methoxymethyl)-8-(3-methoxypropoxy)-3,4-dihydrobenzo[b]oxepin-5(2H)-one as a yellow oil (0.7 g, 32% yield, m/z: 337 [M+H]$^+$ observed).

(R)—N-Benzyl-3-isopropyl-7-(methoxymethyl)-8-(3-methoxypropoxy)-3,4-dihydrobenzo[b]oxepin-5(2H)-imine

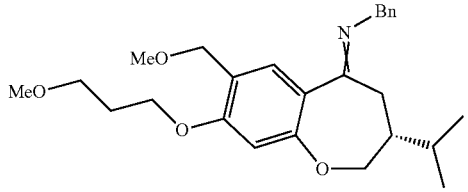 [SMILES: COCCCOc1cc2c(cc1COC)C(=NCc1ccccc1)C[C@H](C(C)C)CO2]

To a mixture of (R)-3-isopropyl-7-(methoxymethyl)-8-(3-methoxypropoxy)-3,4-dihydrobenzo[b]oxepin-5(2H)-one (500 mg, 1.5 mmol) and benzylamine (0.2 mL, 1.6 mmol) in CH$_2$Cl$_2$ (7 mL) was added triethylamine (0.5 mL, 3.86 mmol) under nitrogen. Then a solution of titanium (IV) chloride (1 M solution in dichloromethane, 1 mL, 0.966 mmol) in CH$_2$Cl$_2$ (3 mL) was added at 0° C. for 30 min, then stirred at rt for 16 h. To the mixture was added saturated aqueous sodium bicarbonate to adjust the pH to 8 and the mixture was extracted with CH$_2$Cl$_2$ (2×30 mL). The combined organic phase was washed with saturated aqueous brine solution (50 mL), dried over anhydrous sodium sulfate, filtered and concentrated in vacuo to give (R)—N-benzyl-3-isopropyl-7-(methoxymethyl)-8-(3-methoxypropoxy)-3,4-dihydrobenzo[b]oxepin-5(2H)-imine as a yellow oil, which was used in the next step without further purification (500 mg, 78% yield, m/z: 426 [M+H]$^+$ observed).

Methyl (S)-1-benzyl-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylate

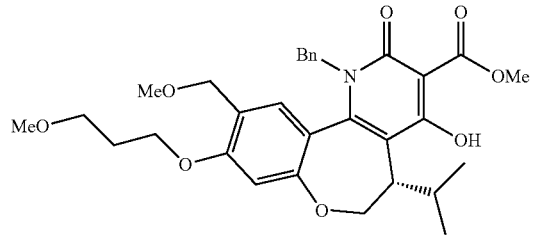 [SMILES: COCCCOc1cc2c(cc1COC)-c1c(c(O)c(C(=O)OC)c(=O)n1Cc1ccccc1)[C@H](C(C)C)CO2]

A mixture of (R,E)-N-benzyl-3-isopropyl-7-(methoxymethyl)-8-(3-methoxypropoxy)-3,4-dihydrobenzo[b]oxepin-5(2H)-imine (500 mg, 1.2 mmol) and trimethyl methanetricarboxylate (446 mg, 2.35 mmol) in Ph$_2$O (5 mL) was stirred at 220° C. for 15 min under nitrogen. The mixture was cooled to rt and purified by normal phase SiO$_2$ chromatography (0-25% EtOAc/petroleum ether) to give methyl (S)-1-benzyl-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylate as a yellow oil (100 mg, 10% yield, m/z: 552 [M+H]$^+$ observed).

Methyl (S)-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylate

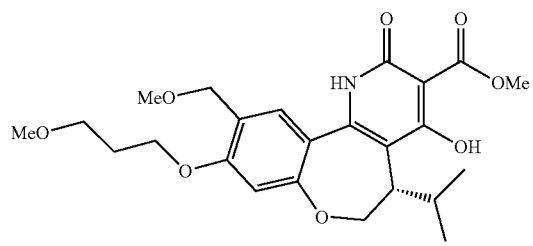 [SMILES: COCCCOc1cc2c(cc1COC)-c1[nH]c(=O)c(C(=O)OC)c(O)c1[C@H](C(C)C)CO2]

To a solution of methyl (S)-1-benzyl-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylate (100 mg, 0.181 mmol) in EtOH (5 mL) was added palladium hydroxide (10% on carbon, 0.1 g, 0.096 mmol) under hydrogen. The suspension was degassed under vacuum and purged with hydrogen (cycle repeated three times), then stirred under hydrogen (15 psi) at rt for 6 h. The mixture was filtered and washed with EtOAc (2×30 mL). The filtrate was concentrated under reduced pressure. The residue was purified by normal phase SiO$_2$ chromatography (50% petroleum ether/EtOAc) to give methyl (5S)-4-hydroxy-5-isopropyl-10-(methoxymethyl)-9-(3-methoxypropoxy)-2-oxo-5,6-dihydro-1H-[1]benzoxepino[5,4-b]pyridine-3-carboxylate as a yellow solid (40 mg, 47% yield, m/z: 462 [M+H]$^+$ observed).

(S)-4-Hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylic acid

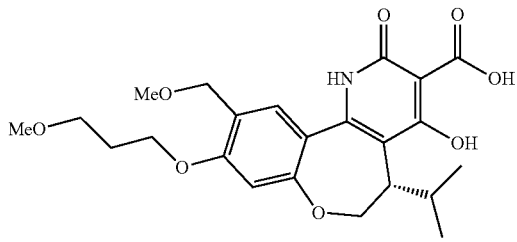 [SMILES: COCCCOc1cc2c(cc1COC)-c1[nH]c(=O)c(C(=O)O)c(O)c1[C@H](C(C)C)CO2]

To a mixture of methyl (5S)-4-hydroxy-5-isopropyl-10-(methoxymethyl)-9-(3-methoxypropoxy)-2-oxo-5,6-dihydro-1H-[1]benzoxepino[5,4-b]pyridine-3-carboxylate (15 mg, 0.032 mmol) in EtOAc (3 mL) was added lithium iodide (8.70 mg, 0.065 mmol) in one portion under nitrogen. The mixture was stirred at 60° C. for 4 h. To the mixture (combined with another 40 mg batch) was added 1M HCl solution to adjust the pH to 4. The aqueous phase was separated and extracted with EtOAc (2×20 mL). The combined organic phase was washed with saturated aqueous brine solution (20 mL), dried with anhydrous sodium sulfate, filtered and concentrated under reduced pressure. The residue was purified by reverse phase HPLC to give (S)-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylic acid as a white solid (30 mg, 57% yield, m/z: 448 [M+H]±observed). $^1$H NMR (400 MHz, DMSO-$d_6$): δ 14.05 (s, 1H), 12.77 (s, 1H), 7.53 (s, 1H), 6.69 (s, 1H), 4.64-4.61 (m, 1H), 4.47-4.41 (m, 1H), 4.38-4.33 (m, 2H), 4.09-4.04 (m, 2H), 3.50-3.47 (t, J=6.4 Hz, 2H), 3.34 (s, 3H), 3.25 (s, 3H), 3.10-3.06 (m, 1H), 1.99-1.92 (m, 2H), 1.47-1.39 (m, 1H), 0.97-0.95 (d, J=6.4 Hz, 3H), 0.63-0.62 (d, J=6.8 Hz, 3H).

The following examples were prepared in a similar manner as (S)-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylic acid from (3R)-7-chloro-3-isopropyl-8-(3-methoxypropoxy)-3,4-dihydro-2H-1-benzoxepin-5-one and an appropriate organoboron species.

Example 72: (S)-4-Hydroxy-5-isopropyl-10-(2-methoxyethyl)-9-(3-methoxypropoxy)-2-oxo-1,2,5,6-tetrahydrobenzo[2,3]oxepino[4,5-b]pyridine-3-carboxylic acid

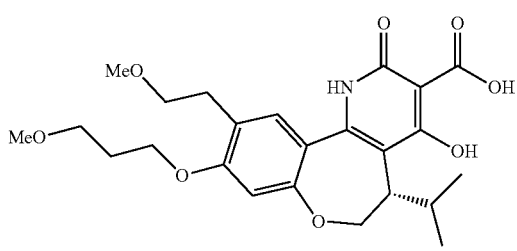 [SMILES: COCCCOc1cc2c(cc1CCOC)-c1[nH]c(=O)c(C(=O)O)c(O)c1[C@H](C(C)C)CO2]

m/z: 460 [M−H]$^−$ observed. $^1$H NMR (400 MHz, DMSO-$d_6$): δ 14.15 (s, 1H), 12.68 (s, 1H), 7.47 (s, 1H), 6.63 (s, 1H), 4.63-4.60 (m, 1H), 4.40-4.36 (m, 1H), 4.09-4.03 (m, 3H), 3.57-3.44 (m, 3H), 3.26-3.25 (m, 5H), 3.10-3.07 (m, 1H), 2.82-2.73 (m, 3H), 2.00-1.94 (m, 2H), 1.51-1.41 (m, 1H), 0.98-0.96 (d, J=6.4 Hz, 3H), 0.65-0.63 (d, J=6.8 Hz, 3H).

Example 73: 9-Methoxy-8-(3-methoxypropoxy)-2-oxo-2,6-dihydro-1H-spiro[benzo[h]quinoline-5,1′-cyclohexane]-3-carboxylic acid

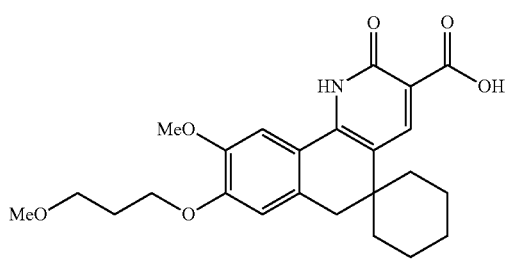 [SMILES: COCCCOc1cc2c(cc1OC)-c1[nH]c(=O)c(C(=O)O)cc1C1(CCCCC1)C2]

3-(4-Methoxy-3-(3-methoxypropoxy)benzyl)cyclohex-2-en-1-one

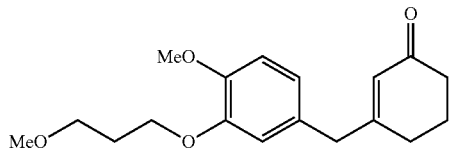 [SMILES: COCCCOc1cc(CC2=CC(=O)CCC2)ccc1OC]

To a mixture of 4-bromo-1-methoxy-2-(3-methoxypropoxy)benzene (40 g, 145 mmol) and 3-methylcyclohex-2-en-1-one (66 mL, 581 mmol) in DMF (180 mL) was added triphenylphosphine (3.81 g, 14.5 mmol), cesium carbonate (56.8 g, 174 mmol) and palladium acetate (1.63 g, 7.27 mmol). The mixture was stirred at 80° C. for 16 h. The reaction was cooled to rt, H$_2$O (600 mL) was added and the mixture extracted with EtOAc (3×400 mL). The combined organic phase was washed with saturated aqueous brine solution (2×200 mL), dried with anhydrous sodium sulfate, filtered and concentrated under reduced pressure. The residue was purified by normal phase SiO$_2$ chromatography (0-10% EtOAc/petroleum ether) to give 3-(4-methoxy-3-(3-methoxypropoxy)benzyl)cyclohex-2-en-1-one as a yellow oil (25 g, 56% yield). $^1$H NMR (400 MHz, CDCl$_3$): δ 6.82-6.80 (m, 1H), 6.70-6.65 (m, 2H), 5.89-5.87 (m, 1H), 4.20-3.90 (m, 2H), 3.85 (s, 3H), 3.57 (m, 2H), 3.36 (m, 5H), 2.38-2.35 (m, 2H), 2.27-2.24 (m, 2H), 2.12-2.08 (m, 2H), 1.83 (m, 2H).

3-(4-Methoxy-3-(3-methoxypropoxy)benzyl)cyclohex-2-en-1-ol

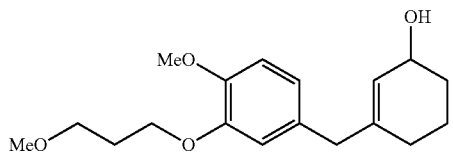 [SMILES: COCCCOc1cc(CC2=CC(O)CCC2)ccc1OC]

Lithium aluminum hydride (2.3 g, 62.4 mmol) was added portion wise to a mixture of 3-(4-methoxy-3-(3-methoxypropoxy)benzyl)cyclohex-2-en-1-one (9.5 g, 31 mmol) in THF (90 mL) at −40° C. under nitrogen. The mixture was stirred at −40° C. for 2 hours. The reaction was quenched with careful addition of H₂O (50 mL). The aqueous phase was extracted with EtOAc (3×50 mL). The combined organic phase was washed with saturated aqueous brine solution (2×20 mL), dried with anhydrous sodium sulfate, filtered and concentrated under reduced pressure. The residue was purified by normal phase $SiO_2$ chromatography (0-50% EtOAc/petroleum ether) to give 3-(4-methoxy-3-(3-methoxypropoxy)benzyl)cyclohex-2-en-1-ol as a yellow oil (15 g, 78% yield, m/z: 329 [M+Na]⁺ observed).

Ethyl 2-(1-(4-methoxy-3-(3-methoxypropoxy)benzyl)cyclohex-2-en-1-yl)acetate

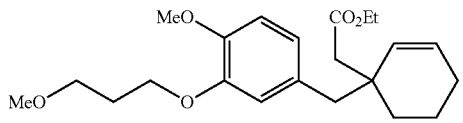 [SMILES: CCOC(=O)CC1(Cc2ccc(OC)c(OCCCOC)c2)C=CCCC1]

To a mixture of 3-(4-methoxy-3-(3-methoxypropoxy)benzyl)cyclohex-2-en-1-ol (13 g, 42.4 mmol) and 1,1,1-triethoxyethane (78 mL, 424 mmol) in mesitylene (40 mL) was added pivalic acid (1.5 mL, 12.7 mmol) in one portion under nitrogen. The mixture was stirred at 135° C. for 12 h. The reaction mixture was combined with a second 2 g batch. The combined reaction mixture was concentrated under reduced pressure to give ethyl 2-(1-(4-methoxy-3-(3-methoxypropoxy)benzyl)cyclohex-2-en-1-yl)acetate as a yellow oil, which was used in the next step without further purification (20 g, m/z: 377 [M+H]⁺ observed).

6'-Methoxy-7'-(3-methoxypropoxy)-1'H-spiro[cyclohexane-1,2'-naphthalen]-4'(3'H)-one

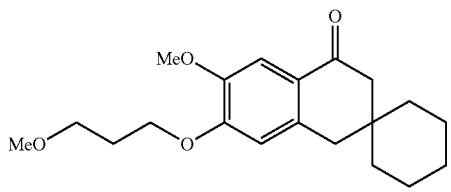 [SMILES: COCCCOc1cc2c(cc1OC)C(=O)CC1(CCCCC1)C2]

To a mixture of ethyl 2-(1-(4-methoxy-3-(3-methoxypropoxy)benzyl)cyclohex-2-en-1-yl)acetate (10 g, 26.5 mmol) in MeOH (200 mL) was added palladium (10% on carbon, 3 g, 2.65 mmol) in one portion under hydrogen. The mixture was stirred under hydrogen (15 psi) at rt for 2 h. The reaction mixture was combined with a second 10 g batch. The reaction mixture was filtered through Celite® and washed with EtOAc (100 mL). Water (100 mL) was added and the mixture extracted with EtOAc (2×100 mL). The combined organic phase was washed with saturated aqueous brine solution (2×500 mL), dried with anhydrous sodium sulfate, filtered and concentrated under reduced pressure. The residue was purified by normal phase $SiO_2$ chromatography (0-5% EtOAc/petroleum ether) to give ethyl 2-(1-(4-methoxy-3-(3-methoxypropoxy)benzyl)cyclohexyl)acetate as a yellow oil, which was used in the next step without further purification (6.0 g, 30% yield).

Sodium hydroxide (6.34 g, 158 mmol) was added to a mixture of ethyl 2-(1-(4-methoxy-3-(3-methoxypropoxy)benzyl)cyclohexyl)acetate (6.0 g, 15 mmol) in MeOH/THF/H₂O (3:1.5:1 mixture, 25 mL). The reaction was stirred at 70° C. for 2 h. H₂O (30 mL) was added and the aqueous phase was extracted with MTBE (2×20 mL). Aqueous 1M HCl solution was added to adjust the pH to 3 then the mixture was extracted with EtOAc (2×40 mL). The combined organic phase was washed with saturated aqueous brine solution (20 mL), dried with anhydrous sodium sulfate, filtered and concentrated under reduced pressure to give 2-(1-(4-methoxy-3-(3-methoxypropoxy)benzyl)cyclohexyl)acetic acid as a white solid, which was used in the next step without further purification (2.4 g, 46% yield).

Phosphorous pentachloride (1.71 g, 8.22 mmol) was added in one portion to a cooled mixture of 2-(1-(4-methoxy-3-(3-methoxypropoxy)benzyl)cyclohexyl)acetic acid (2.4 g, 6.8 mmol) in CH₂Cl₂ (20 mL) and the mixture was stirred at rt for 5 h under nitrogen. H₂O (10 mL) was added and the mixture was extracted with CH₂Cl₂ (2×20 mL). The combined organic phase was washed with saturated aqueous brine solution (2×10 mL), dried with anhydrous sodium sulfate, filtered and concentrated under reduced pressure. The residue was purified by reverse phase HPLC to give 6'-methoxy-7'-(3-methoxypropoxy)-1'H-spiro[cyclohexane-1,2'-naphthalen]-4'(3'H)-one as a white solid (460 mg, 24% yield). ¹H NMR (400 MHz, CDCl₃): δ 7.48 (s, 1H), 6.69 (s, 1H), 4.19 (t, J=6.4 Hz, 2H), 3.89 (s, 3H), 3.58 (t, J=6 Hz, 2H), 3.37 (s, 3H), 2.81 (s, 2H), 2.52 (s, 2H), 2.18-2.12 (m, 2H), 1.47-1.42 (m, 10H).

N-Benzyl-6'-methoxy-7'-(3-methoxypropoxy)-1'H-spiro[cyclohexane-1,2'-naphthalen]-4'(3'H)-imine

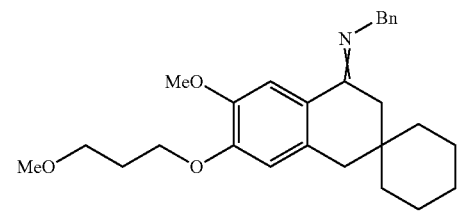 [SMILES: COCCCOc1cc2c(cc1OC)C(=NCc1ccccc1)CC1(CCCCC1)C2]

To a mixture of 6'-methoxy-7'-(3-methoxypropoxy)-1'H-spiro[cyclohexane-1,2'-naphthalen]-4'(3'H)-one (360 mg, 1.08 mmol) and benzylamine (0.13 mL, 1.25 mmol) in CH₂Cl₂ (4 mL) was added triethylamine (0.4 mL, 2.84 mmol) under nitrogen. Titanium (IV) chloride (1 M solution in dichloromethane, 0.7 mL, 0.704 mmol) was added at 0° C. for 30 minutes, then the mixture was warmed to rt and stirred for 16 h. Saturated sodium bicarbonate solution was added to adjust the pH to 8 and the mixture was extracted with CH₂Cl₂ (2×20 mL). The combined organic phase was washed with saturated aqueous brine solution (20 mL), dried over anhydrous sodium sulfate, filtered and concentrated under reduced pressure to give N-benzyl-6'-methoxy-7'-(3-methoxypropoxy)-1'H-spiro[cyclohexane-1,2'-naphthalen]-4'(3'H)-imine as a yellow solid, which was used in the next step without further purification (600 mg, >100% yield, m/z: 422 [M+H]±observed).

Methyl 1-benzyl-9-methoxy-8-(3-methoxypropoxy)-2-oxo-2,6-dihydro-1H-spiro[benzo[h]quinoline-5,1'-cyclohexane]-3-carboxylate

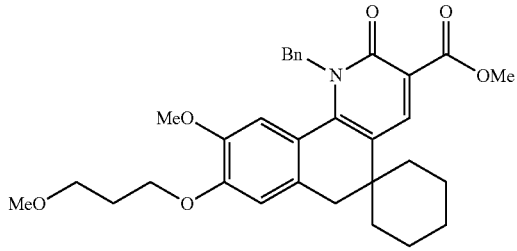 [SMILES: COCCCOc1cc2c(cc1OC)-c1c(cc(C(=O)OC)c(=O)n1Cc1ccccc1)C1(CCCCC1)C2]

A mixture of N-benzyl-6'-methoxy-7'-(3-methoxypropoxy)-1'H-spiro[cyclohexane-1,2'-naphthalen]-4'(3'H)-imine (600 mg, 1.42 mmol) and dimethyl 2-(methoxymethylene)malonate (496 mg, 2.85 mmol) in Ph$_2$O (4 mL) was stirred at 220° C. for 15 minutes under nitrogen. The mixture was cooled to rt. The residue was purified by normal phase SiO$_2$ chromatography (100% petroleum ether then 9% MeOH/CH$_2$Cl$_2$) to give methyl 1-benzyl-9-methoxy-8-(3-methoxypropoxy)-2-oxo-2,6-dihydro-1H-spiro[benzo[h]quinoline-5,1'-cyclohexane]-3-carboxylate as a yellow solid (250 mg, 33% yield, m/z: 532 [M+H]$^+$ observed).

Methyl 9-methoxy-8-(3-methoxypropoxy)-2-oxo-2,6-dihydro-1H-spiro[benzo[h]quinoline-5,1'-cyclohexane]-3-carboxylate

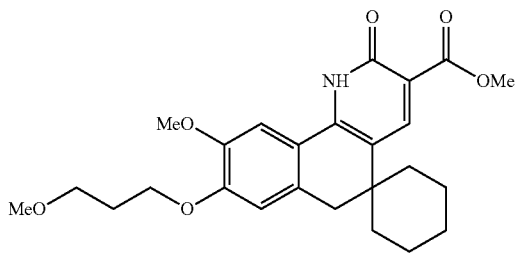 [SMILES: COCCCOc1cc2c(cc1OC)-c1[nH]c(=O)c(C(=O)OC)cc1C1(CCCCC1)C2]

To a solution of methyl 1-benzyl-9-methoxy-8-(3-methoxypropoxy)-2-oxo-2,6-dihydro-1H-spiro[benzo[h]quinoline-5,1'-cyclohexane]-3-carboxylate (250 mg, 0.47 mmol) in MeOH (5 mL) was added palladium hydroxide (20% on carbon, 83 mg, 0.16 mmol). The suspension was degassed under vacuum and purged with hydrogen (cycle repeated three times). The mixture was stirred under hydrogen (15 psi) at rt for 2 h. The mixture was filtered and washed with EtOAc (2×30 mL). The filtrate was concentrated under reduced pressure to give methyl 9-methoxy-8-(3-methoxypropoxy)-2-oxo-2,6-dihydro-1H-spiro[benzo[h]quinoline-5,1'-cyclohexane]-3-carboxylate as a yellow solid, which was used in the next step without further purification (130 mg, m/z: 442 [M+H]$^+$ observed). 9-Methoxy-8-(3-methoxypropoxy)-2-oxo-2,6-dihydro-1H-spiro[benzo[h]quinoline-5,1'-cyclohexane]-3-carboxylic acid:

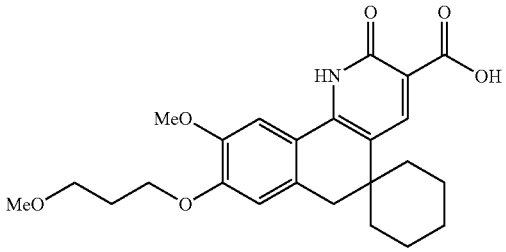

To a mixture of methyl 9-methoxy-8-(3-methoxypropoxy)-2-oxo-2,6-dihydro-1H-spiro[benzo[h]quinoline-5,1'-cyclohexane]-3-carboxylate (130 mg, 0.29 mmol) in THF/H$_2$O (1:1 mixture, 4 mL) was added lithium hydroxide monohydrate (62 mg, 1.5 mmol) in one portion at 15° C. The mixture was stirred at 15° C. for 16 h. 1M HCl solution was added to adjust the pH to 3. The mixture was extracted with EtOAc (2×20 mL). The combined organic phase was washed with saturated aqueous brine solution (20 mL), dried with anhydrous sodium sulfate, filtered and concentrated under reduced pressure. The residue was purified by reverse phase HPLC to give 9-methoxy-8-(3-methoxypropoxy)-2-oxo-2,6-dihydro-1H-spiro[benzo[h]quinoline-5,1'-cyclohexane]-3-carboxylic acid as a yellow solid (24 mg, 20% yield, m/z: 428 [M+H]±observed). $^1$H NMR (400 MHz, DMSO-d$_6$): δ 14.93 (s, 1H), 13.20 (s, 1H), 8.36 (s, 1H), 7.73 (s, 1H), 7.10 (s, 1H), 4.10 (t, J=6.4 Hz, 2H), 3.86 (s, 3H), 3.48 (t, J=6.4 Hz, 2H), 3.25 (s, 3H), 2.91 (s, 2H), 2.01-1.92 (m, 2H), 1.69-1.66 (m, 1H), 1.53-1.49 (m, 8H), 1.26-1.22 (m, 1H).

Example 74: 2-Chloro-8-hydroxy-7-isopropyl-3-(3-methoxypropoxy)-10-oxo-6,7,10,11-tetrahydrooxepino[3,2-b:4,5-b']dipyridine-9-carboxylic acid

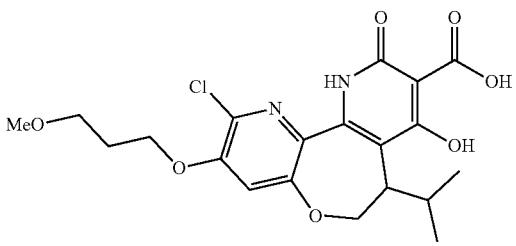 [SMILES: COCCCOc1cc2c(nc1Cl)-c1[nH]c(=O)c(C(=O)O)c(O)c1C(C(C)C)CO2]

Ethyl 2-isopropylpent-4-enoate

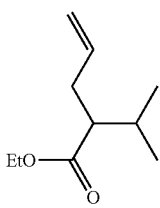

To a solution of diisopropylamine (8.55 g, 84.5 mmol) in THF (100 mL) at −78° C. was added dropwise n-butyl-lithium (2.5 M solution in hexanes, 33.2 mL, 83 mmol) and the mixture was stirred for 15 minutes. Ethyl 3-methylbutanoate (11.6 mL, 76.8 mmol) was slowly added and the stirring was continued at −78° C. for additional 15 minutes. Allyl bromide (8 mL, 92 mmol) was added and the reaction mixture was warmed to rt and stirred for 15 h. The reaction was quenched with saturated aqueous ammonium chloride solution (100 mL) and extracted with EtOAc (3×100 mL). The organic layer was washed with saturated aqueous brine solution (2×200 mL), dried over anhydrous sodium sulfate, filtered and concentrated under reduced pressure. The residue was purified by normal phase $SiO_2$ chromatography (0-10% EtOAc/petroleum ether) to give ethyl 2-isopropylpent-4-enoate as a yellow oil (12 g, 91% yield). $^1H$ NMR (400 MHz, $CDCl_3$, 5.78-5.74 (m, 1H), 5.06-4.95 (m, 2H), 4.12-4.08 (m, 2H), 2.30-2.27 (m, 3H), 1.87 (m, 1H), 1.26-1.21 (m, 3H), 0.95-0.90 (m, 6H).

2-Isopropylpent-4-en-1-ol

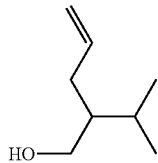

To a mixture of lithium aluminum hydride (5.88 g, 155 mmol) in THF (150 mL) was added dropwise a solution of ethyl 2-isopropylpent-4-enoate (17.6 g, 103 mmol) in THF (50 mL) at 0° C. The reaction was stirred at 0° C. for 1 h. $H_2O$ (30 mL) was carefully added dropwise until no more gas evolution was observed. Then, more water (100 mL) was added and stirring was continued at rt for 30 minutes. The reaction mixture was filtered through Celite®, washed with THF (300 mL) and concentrated under reduced pressure. The residue was purified by normal phase $SiO_2$ chromatography (0-15% EtOAc/petroleum ether) to give 2-isopropylpent-4-en-1-ol as a colorless oil (9.0 g, 67% yield). $^1H$ NMR (400 MHz, $CDCl_3$): δ 5.89-5.83 (m, 1H), 5.11-5.02 (m, 2H), 3.64-3.62 (m, 2H), 2.20-2.05 (m, 2H), 1.83-1.82 (m, 1H), 1.32-1.26 (m, 2H), 0.95-0.92 (m, 6H).

2-Chloro-6-iodo-5-((2-isopropylpent-4-en-1-yl)oxy)-3-(3-methoxypropoxy)pyridine

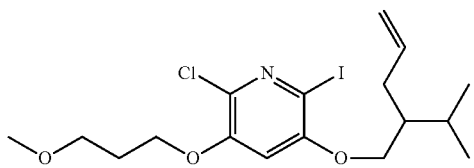 [SMILES: C=CCC(COc1cc(OCCCOC)c(Cl)nc1I)C(C)C]

To a solution of 6-chloro-2-iodo-5-(3-methoxypropoxy) pyridin-3-ol (10 g, 29 mmol, prepared according to WO2018085619) and 2-isopropylpent-4-en-1-ol (3.81 g, 29.7 mmol) in THF (100 mL) was added triphenyl phosphine (9.16 g, 34.9 mmol), followed by diisopropyl azodicarboxylate (6.3 mL, 32 mmol) at 0° C. Then the reaction was heated to 40° C. for 12 h. The reaction was cooled to rt, quenched with $H_2O$ (100 mL) and extracted with EtOAc (3×100 mL). The combined organic phase was washed with saturated aqueous brine solution (2×300 mL), dried over anhydrous sodium sulfate, filtered and concentrated under reduced pressure. The residue was purified by normal phase $SiO_2$ chromatography (0-15% EtOAc/petroleum ether) to give 2-chloro-6-iodo-5-(2-isopropylpent-4-enoxy)-3-(3-methoxypropoxy)pyridine as a colorless oil (10.8 g, 81% yield). $^1H$ NMR (400 MHz, $CDCl_3$): δ 6.65 (s, 1H), 5.84-5.80 (m, 1H), 5.10-5.01 (m, 2H), 4.14-4.11 (m, 2H), 3.94 (d, J=5.2 Hz, 2H), 3.64-3.56 (m, 2H), 3.35 (s, 3H), 2.31-2.09 (m, 4H), 1.99-1.73 (m, 2H), 1.01-0.97 (m, 6H).

2-Chloro-7-isopropyl-3-(3-methoxypropoxy)-9-methylene-6,7,8,9-tetrahydrooxepino[3,2-b]pyridine

To a mixture of 2-chloro-6-iodo-5-(2-isopropylpent-4-enoxy)-3-(3-methoxypropoxy)pyridine (8.4 g, 18 mmol) in DMF (80 mL) was added potassium acetate (3.63 g, 37.0 mmol), ethylenebis(diphenylphosphine) (1.48 g, 3.70 mmol) and palladium (II) acetate (416 mg, 1.85 mmol). The reaction was heated to 100° C. for 12 h. The reaction was cooled to rt, diluted with $H_2O$ (150 mL) and extracted with EtOAc (3×100 mL). The organic layer was washed with saturated aqueous brine solution (3×200 mL), dried over sodium sulfate, filtered and concentrated under reduced pressure. The residue was purified by normal phase $SiO_2$ chromatography (0-20% EtOAc/petroleum ether) to give 2-chloro-7-isopropyl-3-(3-methoxypropoxy)-9-methylene-6,7,8,9-tetrahydrooxepino[3,2-b]pyridine as a yellow oil (3.5 g, 58% yield).

2-Chloro-7-isopropyl-3-(3-methoxypropoxy)-7,8-dihydrooxepino[3,2-b]pyridin-9(6H)-one

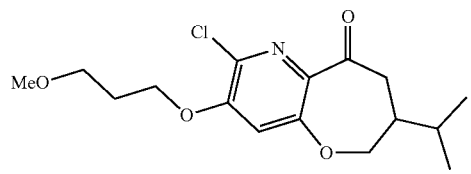 [SMILES: COCCCOc1cc2c(nc1Cl)C(=O)CC(C(C)C)CO2]

2-Chloro-7-isopropyl-3-(3-methoxypropoxy)-9-methylene-6,7,8,9-tetrahydrooxepino[3,2-b]pyridine (3.5 g, 10.7 mmol) was dissolved in $CH_2Cl_2$ (30 mL) and cooled to −78° C. While stirring, ozone gas (50 psi) was bubbled through the mixture for 20 minutes. The residual ozone was removed by purging with oxygen gas. The solution was stirred for 5 minutes at −78° C. before dimethylsulfide (7.9 mL, 107 mmol) was added dropwise. The mixture was stirred at −78° C. for 10 minutes and then warmed up to rt and stirred for additional for 15 h. The reaction mixture was concentrated under reduced pressure. The residue was combined with another 1 g batch and purified by normal phase $SiO_2$ chromatography (0-25% EtOAc/petroleum ether) to give 2-chloro-7-isopropyl-3-(3-methoxypropoxy)-7,8-dihydrooxepino[3,2-b]pyridin-9(6H)-one as a light yellow solid (1.2 g, 80% yield). $^1H$ NMR (400 MHz, $CDCl_3$): δ 6.92 (s, 1H), 4.22-4.14 (m, 4H), 3.61-3.58 (m, 2H), 3.37 (s, 3H), 2.92-2.86 (m, 2H), 2.17-2.13 (m, 3H), 1.84-1.82 (m, 1H), 1.03-0.98 (m, 6H).

N-Benzyl-2-chloro-7-isopropyl-3-(3-methoxypropoxy)-7,8-dihydrooxepino[3,2-b]pyridin-9(6H)-imine

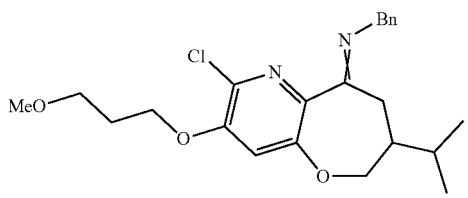 [SMILES: COCCCOc1cc2c(nc1Cl)C(=NCc1ccccc1)CC(C(C)C)CO2]

To a mixture of 2-chloro-7-isopropyl-3-(3-methoxypropoxy)-7,8-dihydrooxepino[3,2-b]pyridin-9(6H)-one (1.2 g, 3.7 mmol) and benzylamine (0.4 mL, 4.0 mmol) in CH$_2$Cl$_2$ (12 mL) was added triethylamine (2.2 mL, 15.8 mmol). Titanium (IV) chloride (1 M solution in dichloromethane, 2.4 mL, 2.4 mmol) in CH$_2$Cl$_2$ was added dropwise at 0° C. and the reaction was stirred for 30 minutes. The mixture was warmed to rt and stirred for 16 h. The contents of the flask were diluted with CH$_2$Cl$_2$ (30 mL) and H$_2$O (30 mL). The mixture was basified with saturated aqueous sodium bicarbonate solution to adjust the pH to 9. The organic layer was separated, washed with H$_2$O (2×50 mL), dried over anhydrous sodium sulfate, filtered and concentrated under reduced pressure to give N-benzyl-2-chloro-7-isopropyl-3-(3-methoxypropoxy)-7,8-dihydrooxepino[3,2-b]pyridin-9(6H)-imine as a yellow oil, which was used in the next step without further purification (1.54 g, 100% yield).

Methyl 11-benzyl-2-chloro-8-hydroxy-7-isopropyl-3-(3-methoxypropoxy)-10-oxo-6,7,10,11-tetrahydrooxepino[3,2-b:4,5-b']dipyridine-9-carboxylate

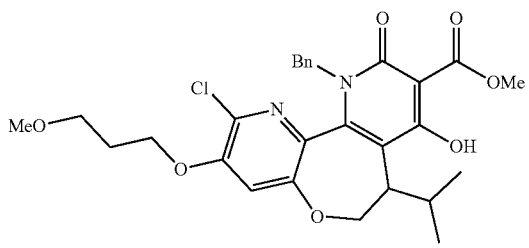 [SMILES: COCCCOc1cc2c(nc1Cl)-c1c(c(O)c(C(=O)OC)c(=O)n1Cc1ccccc1)C(C(C)C)CO2]

The mixture of N-benzyl-2-chloro-7-isopropyl-3-(3-methoxypropoxy)-7,8-dihydrooxepino[3,2-b]pyridin-9(6H)-imine (1.54 g, 3.69 mmol) and trimethyl methanetricarboxylate (1.4 g, 7.4 mmol) in Ph$_2$O (3 mL) was heated to 220° C. for 30 minutes. After cooling to rt, the reaction mixture was purified directly by normal phase SiO$_2$ chromatography (0-100% EtOAc/petroleum ether) and then further purified by reverse phase HPLC to give methyl 11-benzyl-2-chloro-8-hydroxy-7-isopropyl-3-(3-methoxypropoxy)-10-oxo-6,7,10,11-tetrahydrooxepino[3,2-b:4,5-b']dipyridine-9-carboxylate as a light red solid (0.28 g, 13% yield). $^1$H NMR (400 MHz, CDCl$_3$): δ 14.01 (s, 1H), 7.28-7.07 (m, 3H), 6.83 (d, J=6.0 Hz, 2H), 6.74 (s, 1H), 6.03 (m, 1H), 5.32-5.28 (m, 1H), 4.51-4.47 (m, 2H), 4.16-4.09 (m, 2H), 4.04 (s, 3H), 3.63-3.60 (m, 2H), 3.59 (s, 3H), 3.39 (s, 1H), 2.16-2.10 (m, 2H), 0.92-0.68 (m, 7H).

Methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate

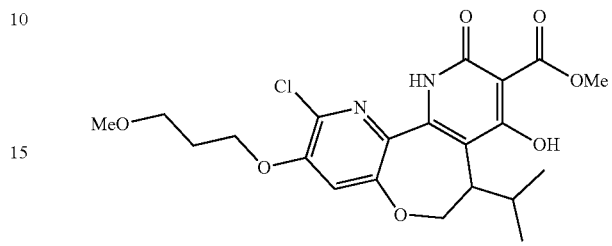

A mixture of methyl 11-benzyl-2-chloro-8-hydroxy-7-isopropyl-3-(3-methoxypropoxy)-10-oxo-6,7,10,11-tetrahydrooxepino[3,2-b:4,5-b']dipyridine-9-carboxylate (0.21 g, 0.39 mmol) in trifluoracetic acid (20 mL) was stirred at 100° C. for 16 h. The reaction cooled to rt and concentrated under vacuum. Saturated aqueous sodium bicarbonate solution was added to adjust the pH to 8 and extracted with EtOAc (3×20 mL). The combined organic phase was dried over anhydrous sodium sulfate, filtered and concentrated under reduced pressure. The residue was purified by normal phase SiO$_2$ chromatography (0-100% EtOAc/petroleum ether) to give methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate as a light yellow solid (0.14 g, 79% yield). $^1$H NMR (400 MHz, CDCl$_3$): δ 13.97 (s, 1H), 10.42 (s, 1H), 6.85 (s, 1H), 4.68-4.09 (m, 4H), 3.94 (s, 3H), 3.87 (d, J=12 Hz, 1H), 3.53-3.29 (m, 6H), 2.09-2.03 (m, 2H), 1.01 (d, J=6.4 Hz, 3H), 0.82 (d, J=6.8 Hz, 3H).

2-Chloro-8-hydroxy-7-isopropyl-3-(3-methoxypropoxy)-10-oxo-6,7,10,11-tetrahydrooxepino[3,2-b:4,5-b']dipyridine-9-carboxylicacid

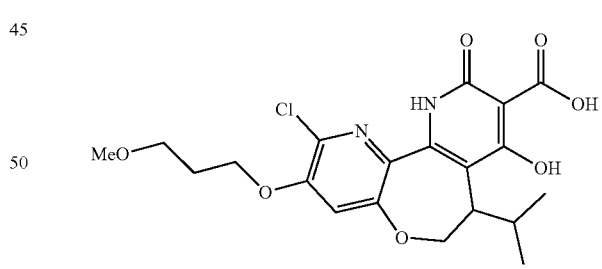

A mixture of methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate (130 mg, 0.287 mmol) in EtOAc (10 mL) and lithium iodide (77 mg, 0.57 mmol) was stirred at 60° C. for 4 h. After cooling to rt, the reaction was diluted with EtOAc (10 mL) and washed with H$_2$O (2×10 mL). The organic layer was dried over anhydrous sodium sulfate, filtered and concentrated under reduced pressure to give 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid as a light yellow solid (130 mg, 99% yield, m/z: 439 [M+H]$^+$ observed). $^1$H NMR (400 MHz, CDCl₃): δ 15.18 (s, 1H), 14.02 (s, 1H), 10.90 (s, 1H), 6.89 (s, 1H), 4.81-4.77 (dd, J=12, 4.8 Hz, 1H), 4.15-4.08 (m, 2H), 3.85 (d, J=12 Hz, 1H), 3.53-3.50 (m, 2H), 3.31-3.28 (m, 4H), 2.10-2.04 (m, 2H), 1.67-1.58 (m, 1H), 1.03 (d, J=6.8 Hz, 3H), 0.83 (d, J=6.8 Hz, 3H).

Example 75: 2-Chloro-8-hydroxy-7-isopropyl-3-(3-methoxypropoxy)-10-oxo-6,7,10,11-tetrahydrooxepino[3,2-b:4,5-b']dipyridine-9-carboxylic acid (single enantiomer I)

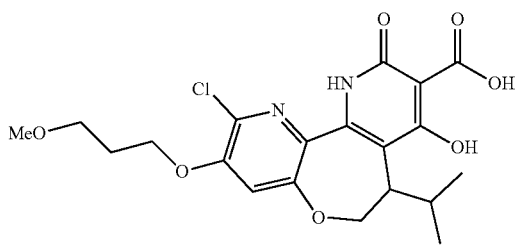 [SMILES: COCCCOc1cc2c(nc1Cl)-c1[nH]c(=O)c(C(=O)O)c(O)c1C(C(C)C)CO2]

Example 76: 2-Chloro-8-hydroxy-7-isopropyl-3-(3-methoxypropoxy)-10-oxo-6,7,10,11-tetrahydrooxepino[3,2-b:4,5-b']dipyridine-9-carboxylic acid (single enantiomer II)

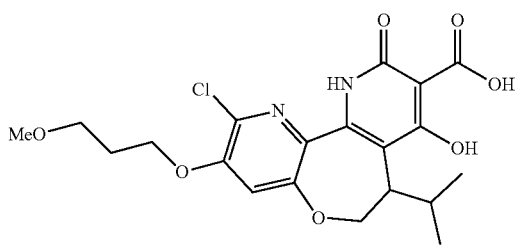 [SMILES: COCCCOc1cc2c(nc1Cl)-c1[nH]c(=O)c(C(=O)O)c(O)c1C(C(C)C)CO2]

Methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate (580 mg) was separated by SFC (supercritical fluid chromatography) on a CHIRALCEL OD-H using 50% EtOH (0.1% aq. NH₃) as a modifier to give methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate as a light-yellow solid (single enantiomer I, faster eluting enantiomer, 0.277 g, 45% yield, ¹H NMR (400 MHz, CDCl₃): δ 13.97 (s, 1H), 10.42 (s, 1H), 6.85 (s, 1H), 4.68-4.09 (m, 4H), 3.94 (s, 3H), 3.87 (d, J=12 Hz, 1H), 3.53-3.29 (m, 6H), 2.09-2.03 (m, 2H), 1.01 (d, J=6.4 Hz, 3H), 0.82 (d, J=6.8 Hz, 3H). and methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate as a light-yellow solid (single enantiomer II, slower eluting enantiomer, 0.334 g, 56% yield, ¹H NMR (400 MHz, CDCl₃): δ 13.97 (s, 1H), 10.42 (s, 1H), 6.85 (s, 1H), 4.68-4.09 (m, 4H), 3.94 (s, 3H), 3.87 (d, J=12 Hz, 1H), 3.53-3.29 (m, 6H), 2.09-2.03 (m, 2H), 1.01 (d, J=6.4 Hz, 3H), 0.82 (d, J=6.8 Hz, 3H).

Example 75: 2-Chloro-8-hydroxy-7-isopropyl-3-(3-methoxypropoxy)-10-oxo-6,7,10,11-tetrahydrooxepino[3,2-b:4,5-b']dipyridine-9-carboxylic acid (single enantiomer I)

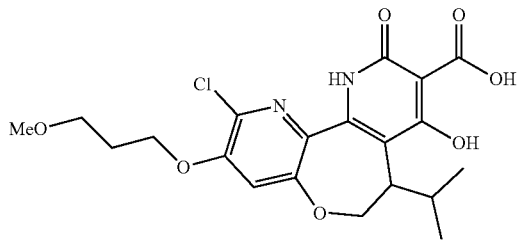 [SMILES: COCCCOc1cc2c(nc1Cl)-c1[nH]c(=O)c(C(=O)O)c(O)c1C(C(C)C)CO2]

To the solution of methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate (single enantiomer II, slower eluting enantiomer, 334 mg, 0.74 mmol) in EtOAc (10 mL) was added lithium iodide (197 mg, 1.5 mmol) and the mixture was stirred at 60° C. for 4 h. After cooling to rt, the reaction was diluted with EtOAc (30 mL) and washed with H₂O (2×30 mL). The combined organic phase was dried over anhydrous sodium sulfate, filtered and concentrated under vacuum. The residue purified by purified by reverse phase HPLC to give 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid as a light yellow solid (97 mg, 30% yield, m/z: 439 [M+H]⁺ observed). ¹H NMR (400 MHz, CDCl₃): δ 15.18 (s, 1H), 14.02 (s, 1H), 10.90 (s, 1H), 6.89 (s, 1H), 4.81-4.77 (dd, J=12, 4.8 Hz, 1H), 4.15-4.08 (m, 2H), 3.85 (d, J=12 Hz, 1H), 3.53-3.50 (m, 2H), 3.31-3.28 (m, 4H), 2.10-2.04 (m, 2H), 1.67-1.58 (m, 1H), 1.03 (d, J=6.8 Hz, 3H), 0.83 (d, J=6.8 Hz, 3H).

Example 76: 2-Chloro-8-hydroxy-7-isopropyl-3-(3-methoxypropoxy)-10-oxo-6,7,10,11-tetrahydrooxepino[3,2-b:4,5-b']dipyridine-9-carboxylic acid (single enantiomer II)

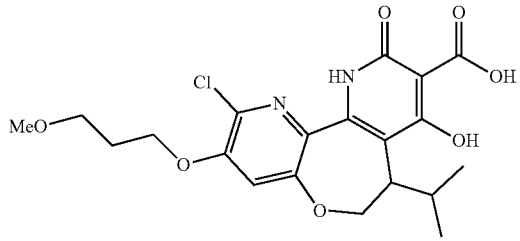 [SMILES: COCCCOc1cc2c(nc1Cl)-c1[nH]c(=O)c(C(=O)O)c(O)c1C(C(C)C)CO2]

To the solution of methyl 2-chloro-8-hydroxy-7-isopropyl-3-(3-methoxypropoxy)-10-oxo-6,7,10,11-tetrahydrooxepino[3,2-b:4,5-b']dipyridine-9-carboxylate (single enantiomer I, faster eluting enantiomer, 277 mg, 0.611 mmol) in EtOAc (10 mL) was added lithium iodide (164 mg, 1.22 mmol). The mixture was stirred at 60° C. for 4 h. After cooling to rt, the reaction was diluted with EtOAc (20 mL) and washed with H₂O (2×20 mL). The combined organic phase was dried over anhydrous sodium sulfate, filtered and concentrated under vacuum. The residue was purified by reverse phase HPLC to give 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid as a light-yellow solid (97 mg, 35% yield, m/z: 439 [M+H] observed). $^1$H NMR (400 MHz, CDCl$_3$): δ 15.18 (s, 1H), 14.02 (s, 1H), 10.90 (s, 1H), 6.89 (s, 1H), 4.81-4.77 (dd, J=12, 4.8 Hz, 1H), 4.15-4.08 (m, 2H), 3.85 (d, J=12 Hz, 1H), 3.53-3.50 (m, 2H), 3.31-3.28 (m, 4H), 2.10-2.04 (m, 2H), 1.67-1.58 (m, 1H), 1.03 (d, J=6.8 Hz, 3H), 0.83 (d, J=6.8 Hz, 3H).

The following examples were prepared in a similar manner as 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid from 6-chloro-2-iodo-5-(3-methoxypropoxy)pyridin-3-ol and an appropriate alcohol.

Example 77: 7-(tert-Butyl)-2-chloro-8-hydroxy-3-(3-methoxypropoxy)-10-oxo-6,7,10,11-tetrahydrooxepino[3,2-b:4,5-b']dipyridine-9-carboxylic acid (single enantiomer I)

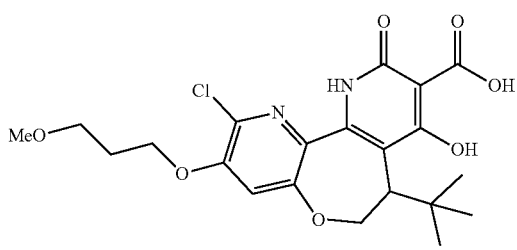 [SMILES: COCCCOc1cc2c(nc1Cl)-c1[nH]c(=O)c(C(=O)O)c(O)c1C(C(C)(C)C)CO2]

m/z: 453 [M+H]$^+$ observed. $^1$H NMR (400 MHz, DMSO-d$_6$): δ 15.32 (s, 1H), 14.23 (s, 1H), 11.17 (s, 1H), 7.40 (s, 1H) 4.96-4.92 (m, 1H) 4.26-4.23 (m, 2H) 4.06-4.03 (m, 1H) 3.50-3.47 (m, 2H) 3.42-3.41 (m, 1H) 3.25 (s, 3H) 2.01-1.98 (m, 2H) 0.90 (s, 9H).

Example 78: 7-(tert-Butyl)-2-chloro-8-hydroxy-3-(3-methoxypropoxy)-10-oxo-6,7,10,11-tetrahydrooxepino[3,2-b:4,5-b']dipyridine-9-carboxylicacid (single enantiomer II)

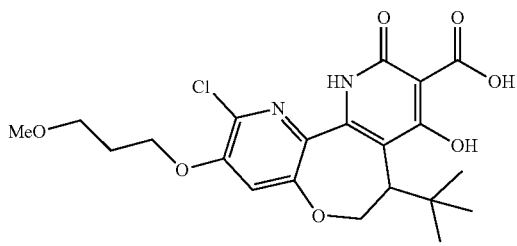 [SMILES: COCCCOc1cc2c(nc1Cl)-c1[nH]c(=O)c(C(=O)O)c(O)c1C(C(C)(C)C)CO2]

m/z: 453 [M+H]$^+$ observed. $^1$H NMR (400 MHz, DMSO-d$_6$): δ 15.32 (s, 1H), 14.23 (s, 1H), 11.17 (s, 1H), 7.40 (s, 1H) 4.96-4.92 (m, 1H) 4.26-4.23 (m, 2H) 4.06-4.03 (m, 1H) 3.50-3.47 (m, 2H) 3.42-3.41 (m, 1H) 3.25 (s, 3H) 2.01-1.98 (m, 2H) 0.90 (s, 9H).

Example 79: 8-Hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylic acid

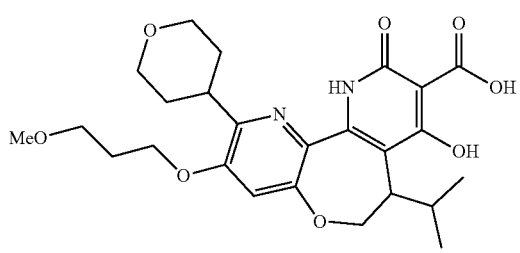 [SMILES: COCCCOc1cc2c(nc1C1CCOCC1)-c1[nH]c(=O)c(C(=O)O)c(O)c1C(C(C)C)CO2]

2-(3,6-Dihydro-2H-pyran-4-yl)-7-isopropyl-3-(3-methoxypropoxy)-7,8-dihydrooxepino[3,2-b]pyridin-9(6H)-one

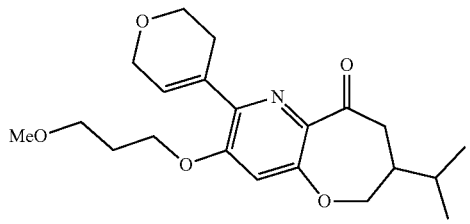 [SMILES: COCCCOc1cc2c(nc1C1=CCOCC1)C(=O)CC(C(C)C)CO2]

To a mixture of 2-chloro-7-isopropyl-3-(3-methoxypropoxy)-7,8-dihydrooxepino[3,2-b]pyridin-9(6H)-one (500 mg, 1.53 mmol), 2-(3,6-dihydro-2H-pyran-4-yl)-4,4,5,5-tetramethyl-1,3,2-dioxaborolane (384.5 mg, 1.83 mmol) in 1,4-dioxane (7.5 mL) and saturated aqueous sodium carbonate solution (2.5 mL) was added tetrakis(triphenylphosphine)palladium(0) (88 mg, 0.76 mmol) in one portion under nitrogen. The mixture was stirred at 100° C. for 16 h. The reaction mixture was filtered and washed with EtOAc (50 mL). Water (30 mL) was added to the filtrate. The organic phase was separated and the aqueous phase was extracted with EtOAc (2×10 mL). The combined organic phase was washed with saturated aqueous brine solution (30 mL), dried with anhydrous sodium sulfate, filtered and concentrated under reduced pressure. The residue was purified by normal phase SiO$_2$ chromatography (0-50% EtOAc/petroleum ether) to give 2-(3,6-dihydro-2H-pyran-4-yl)-7-isopropyl-3-(3-methoxypropoxy)-7,8-dihydrooxepino[3,2-b]pyridin-9(6H)-one as a yellow solid (350 mg, 61% yield, m/z: 376 [M+H]$^+$ observed).

187

N-Benzyl-2-(3,6-dihydro-2H-pyran-4-yl)-7-isopropyl-3-(3-methoxypropoxy)-7,8-dihydrooxepino[3,2-b]pyridin-9(6H)-imine

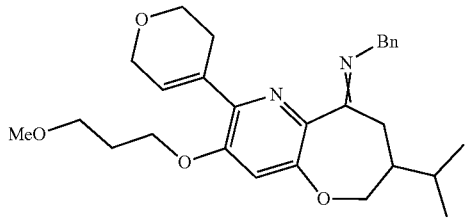 [SMILES: COCCCOc1cc2c(nc1C1=CCOCC1)C(=NCc1ccccc1)CC(C(C)C)CO2]

To a mixture of 2-(3,6-dihydro-2H-pyran-4-yl)-7-isopropyl-3-(3-methoxypropoxy)-7,8-dihydrooxepino[3,2-b]pyridin-9(6H)-one (520 mg, 1.38 mmol) and benzylamine (0.2 mL, 1.52 mmol) in CH$_2$Cl$_2$ (8 mL) was added triethylamine (0.5 mL, 3.60 mmol) under nitrogen. A solution of titanium (IV) chloride (1 M solution in dichloromethane, 0.90 mL) in CH$_2$Cl$_2$ (2 mL) was added dropwise at 0° C. over 30 min, then stirred at rt for 16 h. The mixture was diluted with saturated aqueous sodium bicarbonate solution (20 mL), filtered and extracted with CH$_2$Cl$_2$ (2×20 mL). The combined organic phase was washed with saturated aqueous brine solution (10 mL), dried over anhydrous sodium sulfate, filtered and concentrated under reduced pressure to give N-benzyl-2-(3,6-dihydro-2H-pyran-4-yl)-7-isopropyl-3-(3-methoxypropoxy)-7,8-dihydrooxepino[3,2-b]pyridin-9(6H)-imine as a yellow oil, which was used in the next step without further purification (600 mg, 93% yield, m/z: 465 [M+H]$^+$ observed).

Methyl 11-benzyl-2-(3,6-dihydro-2H-pyran-4-yl)-8-hydroxy-7-isopropyl-3-(3-methoxypropoxy)-10-oxo-6,7,10,11-tetrahydrooxepino[3,2-b:4,5-b']dipyridine-9-carboxylate

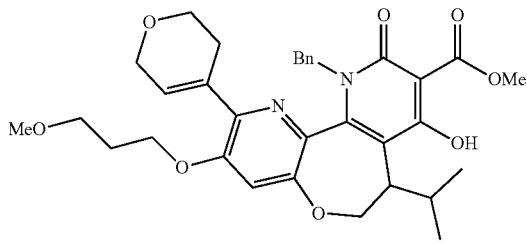 [SMILES: COCCCOc1cc2c(nc1C1=CCOCC1)-c1c(c(O)c(C(=O)OC)c(=O)n1Cc1ccccc1)C(C(C)C)CO2]

A mixture of N-benzyl-2-(3,6-dihydro-2H-pyran-4-yl)-7-isopropyl-3-(3-methoxypropoxy)-7,8-dihydrooxepino[3,2-b]pyridin-9(6H)-imine (600 mg, 1.29 mmol), trimethyl methanetricarboxylate (491 mg, 2.58 mmol) in Ph$_2$O (3 mL) was degassed under vacuum and purged with nitrogen gas (cycle repeated 3 times). The mixture was stirred at 220° C. for 15 min under nitrogen atmosphere. The mixture was cooled to rt and purified directly by normal phase SiO$_2$ chromatography (0-50% EtOAc/petroleum ether) to give methyl 11-benzyl-2-(3,6-dihydro-2H-pyran-4-yl)-8-hydroxy-7-isopropyl-3-(3-methoxypropoxy)-10-oxo-6,7,10,11-tetrahydrooxepino[3,2-b:4,5-b']dipyridine-9-carboxylate as a yellow oil (430 mg, 56% yield, m/z: 591 [M+H]$^+$ observed).

188

Methyl 8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylate

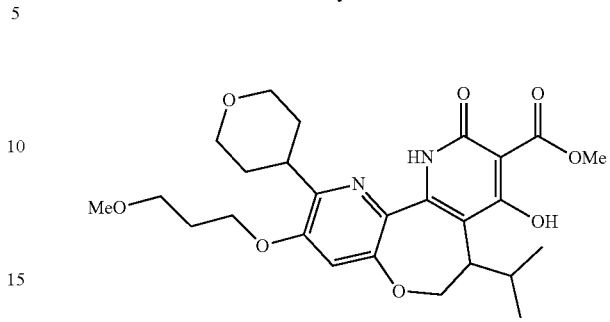

To a solution of methyl 11-benzyl-2-(3,6-dihydro-2H-pyran-4-yl)-8-hydroxy-7-isopropyl-3-(3-methoxypropoxy)-10-oxo-6,7,10,11-tetrahydrooxepino[3,2-b:4,5-b']dipyridine-9-carboxylate (430 mg, 0.73 mmol) in EtOH (10 mL) was added palladium hydroxide (10% on carbon, 1 g, 0.94 mmol). The suspension was degassed and purged with hydrogen 3 times. The mixture was stirred under hydrogen (15 Psi) at rt for 6 h. The mixture was filtered, washed EtOH (50 mL) and concentrated under reduced pressure. The residue was purified by normal phase SiO$_2$ chromatography (15:1 CH$_2$Cl$_2$:MeOH) to give methyl 8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b'] dipyridine-9-carboxylate as a yellow solid (120 mg, 32% yield, m/z: 503 [M+H]$^+$ observed).

8-Hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylic acid

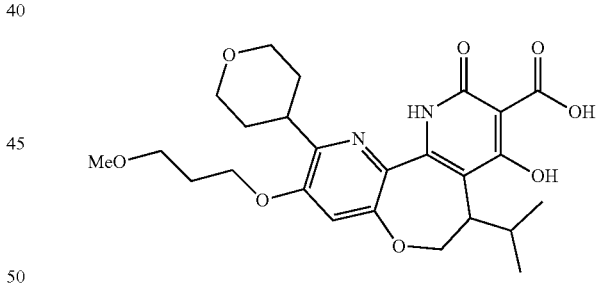

A mixture of methyl 8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylate (120 mg, 0.24 mmol) and lithium iodide (64 mg, 0.48 mmol) in EtOAc (2 mL) was degassed under vacuum and purged with nitrogen (cycle repeated 3 times). The reaction was stirred at 60° C. for 16 h. Water (10 mL) was added to the mixture and the aqueous phase was extracted with EtOAc (2×10 mL). The combined organic phase was washed with saturated aqueous brine solution (10 mL), dried with anhydrous sodium sulfate, filtered and concentrated under reduced pressure. The residue was purified by reverse phase HPLC to give 8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylic acid as a white solid (12 mg, 9% yield, m/z: 489 [M+H]±observed). ¹H NMR (400 MHz, DMSO-d₆): δ 11.28-11.10 (m, 1H), 7.19 (s, 1H), 4.83-4.80 (dd, J=12, 4.8 Hz, 1H), 4.18-4.15 (t, J=5.6 Hz, 2H), 4.00-3.97 (d, J=12 Hz, 2H), 3.51-3.46 (m, 3H), 3.28-3.27 (m, 6H), 3.24 (s, 3H), 2.02-1.99 (m, 2H), 1.97-1.71 (m, 4H), 1.61-1.59 (m, 1H), 1.04-0.99 (d, J=6.4 Hz, 3H), 0.83-0.81 (d, J=6.8 Hz, 3H).

Example 80: 7-(tert-Butyl)-2-ethyl-8-hydroxy-3-(3-methoxypropoxy)-10-oxo-6,7,10,11-tetrahydrooxepino[3,2-b:4,5-b']dipyridine-9-carboxylic acid (single enantiomer I)

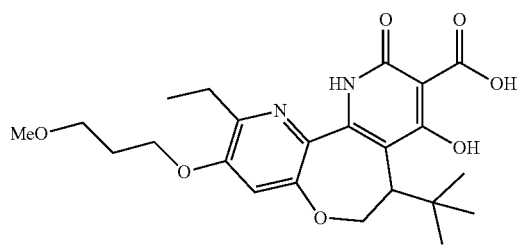 [SMILES: CCc1nc2c(cc1OCCCOC)OCC(C(C)(C)C)c1c-2[nH]c(=O)c(C(=O)O)c1O]

Methyl 7-(tert-butyl)-8-hydroxy-3-(3-methoxypropoxy)-10-oxo-2-vinyl-6,7,10,11-tetrahydrooxepino[3,2-b:4,5-b']dipyridine-9-carboxylate

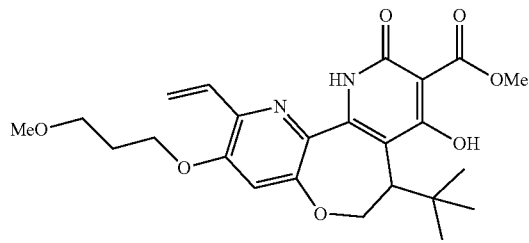 [SMILES: C=Cc1nc2c(cc1OCCCOC)OCC(C(C)(C)C)c1c-2[nH]c(=O)c(C(=O)OC)c1O]

To a mixture of methyl 7-(tert-butyl)-2-chloro-8-hydroxy-3-(3-methoxypropoxy)-10-oxo-6,7,10,11-tetrahydrooxepino[3,2-b:4,5-b']dipyridine-9-carboxylate (single enantiomer I, faster eluting enantiomer, 140 mg, 0.30 mmol) and potassium vinyltrifluoroborate (80 mg, 0.60 mmol) in THF:water (3:1, 4 mL) was added potassium carbonate (83 mg, 0.60 mmol) and [1,1'-bis(di-tert-butylphosphino)ferrocene]dichloropalladium(II) (97.7 mg, 0.15 mmol) under nitrogen. The reaction was stirred at 80° C. for 16 h. The mixture cooled to rt, filtered and washed with EtOAc (40 mL). Water (40 mL) was added to the filtrate and extracted with EtOAc (2×40 mL). The combined organic phase was washed with saturated aqueous brine solution (40 mL), dried with anhydrous sodium sulfate, filtered and the filtrate was concentrated under reduced pressure. The residue was purified by normal phase SiO₂ chromatography (EtOAc) to give methyl 7-(tert-butyl)-8-hydroxy-3-(3-methoxypropoxy)-10-oxo-2-vinyl-6,7,10,11-tetrahydrooxepino[3,2-b:4,5-b']dipyridine-9-carboxylate as a yellow oil (70 mg, 50% yield, m/z: 459 [M+H]⁺ observed).

Methyl 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylate

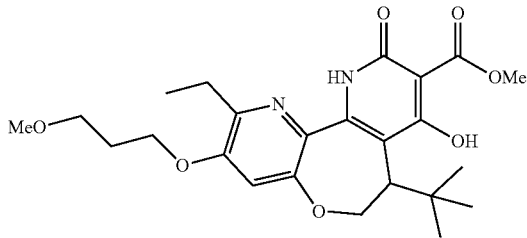 [SMILES: CCc1nc2c(cc1OCCCOC)OCC(C(C)(C)C)c1c-2[nH]c(=O)c(C(=O)OC)c1O]

To a solution of methyl 7-(tert-butyl)-8-hydroxy-3-(3-methoxypropoxy)-10-oxo-2-vinyl-6,7,10,11-tetrahydrooxepino[3,2-b:4,5-b']dipyridine-9-carboxylate (70 mg, 0.15 mmol) in MeOH (10 mL) was added palladium (10% on carbon, 0.05 g, 0.05 mmol). The suspension was degassed under vacuum and purged with hydrogen (cycle repeated 3 times). The mixture was stirred under hydrogen (15 psi) at rt for 12 h. The mixture was filtered, washed with MeOH (50 mL). and concentrated under reduced pressure. The residue was purified by normal phase SiO₂ chromatography (EtOAc) to give methyl 7-(tert-butyl)-2-ethyl-8-hydroxy-3-(3-methoxypropoxy)-10-oxo-6,7,10,11-tetrahydrooxepino [3,2-b:4,5-b']dipyridine-9-carboxylate as a yellow oil (50 mg, 71% yield, m/z: 461 [M+H]⁺ observed).

Example 80: 7-(tert-Butyl)-2-ethyl-8-hydroxy-3-(3-methoxypropoxy)-10-oxo-6,7,10,11-tetrahydrooxepino[3,2-b:4,5-b']dipyridine-9-carboxylic acid (single enantiomer I)

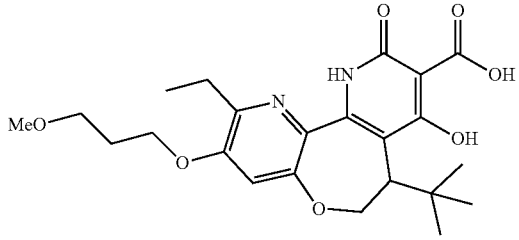 [SMILES: CCc1nc2c(cc1OCCCOC)OCC(C(C)(C)C)c1c-2[nH]c(=O)c(C(=O)O)c1O]

To a solution of methyl 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylate (50 mg, 0.11 mmol) in EtOAc (2 mL) was added lithium iodide (29 mg, 0.22 mmol) under nitrogen. The mixture was stirred at 60° C. for 4 h. Water (10 mL) was added to the mixture and extracted with EtOAc (2×10 mL). The combined organic phase was washed with saturated aqueous brine solution (10 mL), dried with anhydrous sodium sulfate, filtered and the filtrate was concentrated under reduced pressure. The residue was purified by reverse phase HPLC to give 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylic acid as a yellow solid (9.4 mg, 19% yield, m/z: 447 [M+H]⁺ observed). ¹H NMR (400 MHz, DMSO-d₆): δ 14.13 (s, 1H), 11.88 (s, 1H), 7.16 (s, 1H), 4.95-4.90 (dd, J=12.4, 4 Hz, 1H), 4.16-4.15 (t, J=5.6 Hz, 2H), 3.96-3.92 (d, J=12.8 Hz, 1H), 3.51-3.48 (d, J=6 Hz, 2H), 3.40-3.39 (d, J=3.6 Hz, 1H), 3.25 (s, 3H), 2.85-2.80 (q, J=7.2 Hz, 2H), 2.02-1.96 (m, 2H), 1.28-1.24 (t, J=7.6 Hz, 3H), 0.91 (s, 9H).

Example 81: 7-(tert-Butyl)-2-ethyl-8-hydroxy-3-(3-methoxypropoxy)-10-oxo-6,7,10,11-tetrahydrooxepino[3,2-b:4,5-b']dipyridine-9-carboxylic acid (single enantiomer II)

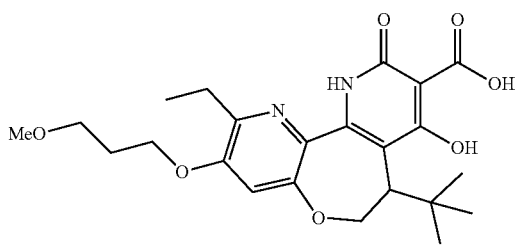 [SMILES: CCc1nc2c(cc1OCCCOC)OCC(C(C)(C)C)c1c-2[nH]c(=O)c(C(=O)O)c1O]

Methyl 7-(tert-butyl)-8-hydroxy-3-(3-methoxypropoxy)-10-oxo-2-vinyl-6,7,10,11-tetrahydrooxepino[3,2-b:4,5-b']dipyridine-9-carboxylate

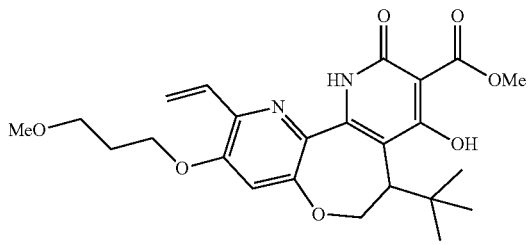 [SMILES: C=Cc1nc2c(cc1OCCCOC)OCC(C(C)(C)C)c1c-2[nH]c(=O)c(C(=O)OC)c1O]

To a mixture of methyl-(tert-butyl)-2-chloro-8-hydroxy-3-(3-methoxypropoxy)-10-oxo-6,7,10,11-tetrahydrooxepino[3,2-b:4,5-b']dipyridine-9-carboxylate (single enantiomer II, slower eluting enantiomer, 135 mg, 0.29 mmol) and potassium vinyltrifluoroborate (77 mg, 0.58 mmol) in THF:water (3:1, 4 mL) was added potassium carbonate (80 mg, 0.58 mmol) and [1,1'-bis(di-tert-butylphosphino)ferrocene]dichloropalladium(II) (94 mg, 0.14 mmol) under nitrogen. The reaction was stirred at 80° C. for 16 h. The mixture was cooled to rt, filtered and washed with EtOAc (40 mL). Water (40 mL) was added to the filtrate and extracted with EtOAc (2×40 mL). The combined organic phase was washed with saturated aqueous brine solution (40 mL), dried with anhydrous sodium sulfate, filtered and concentrated under vacuum. The residue was purified by normal phase SiO₂ chromatography (EtOAc) to give methyl 7-(tert-butyl)-8-hydroxy-3-(3-methoxypropoxy)-10-oxo-2-vinyl-6,7,10,11-tetrahydrooxepino[3,2-b:4,5-b']dipyridine-9-carboxylate as yellow oil (80 mg, 60% yield, m/z: 459 [M+H]⁺ observed).

Methyl 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylate

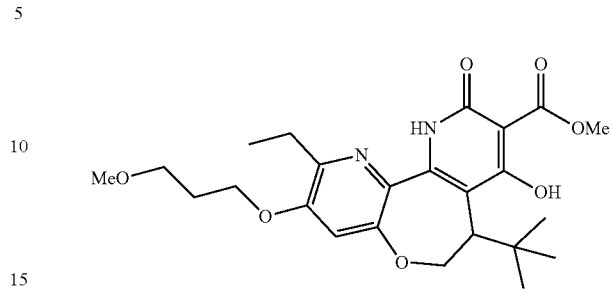

To a solution of methyl 7-(tert-butyl)-8-hydroxy-3-(3-methoxypropoxy)-10-oxo-2-vinyl-6,7,10,11-tetrahydrooxepino[3,2-b:4,5-b']dipyridine-9-carboxylate (80 mg, 0.17 mmol) in MeOH (10 mL) was added palladium (10% on carbon, 0.05 g, 0.05 mmol). The suspension was degassed under vacuum and purged with hydrogen (cycle repeated 3 times). The mixture was stirred under hydrogen (15 psi) at rt for 12 h. The mixture was filtered, washed with MeOH (50 mL) and concentrated under reduced pressure. The residue was purified by normal phase SiO₂ chromatography (EtOAc) to give methyl 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylate as a yellow oil (50 mg, 62% yield, m/z: 461 [M+H]⁺ observed).

Example 81: 7-(tert-Butyl)-2-ethyl-8-hydroxy-3-(3-methoxypropoxy)-10-oxo-6,7,10,11-tetrahydrooxepino[3,2-b:4,5-b']dipyridine-9-carboxylic acid (single enantiomer II)

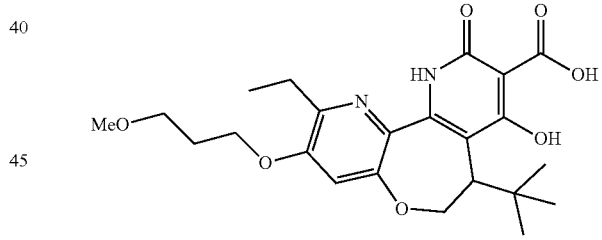

To a solution of methyl 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylate (50 mg, 0.11 mmol) in EtOAc (2 mL) was added lithium iodide (29 mg, 0.22 mmol) under nitrogen. The mixture was stirred at 60° C. for 4 h. Water (10 mL) was added to the mixture was extracted with EtOAc (2×10 mL). The combined organic phase was washed with saturated aqueous brine solution (10 mL), dried with anhydrous sodium sulfate, filtered and concentrated under reduced pressure. The residue was purified by purified by reverse phase HPLC to give 7-(tert-Butyl)-2-ethyl-8-hydroxy-3-(3-methoxypropoxy)-10-oxo-6,7,10,11-tetrahydrooxepino[3,2-b:4,5-b']dipyridine-9-carboxylic acid as a yellow solid (single enantiomer II) (12.9 mg, 26% yield, m/z: 447 [M+H]⁺ observed). ¹H NMR (400 MHz, DMSO-d₆): δ 14.13 (s, 1H), 11.88 (s, 1H), 7.16 (s, 1H), 4.95-4.90 (dd, J=12.4, 4 Hz, 1H), 4.16-4.15 (t, J=5.6 Hz, 2H), 3.96-3.92 (d, J=12.8 Hz, 1H), 3.51-3.48 (d, J=6 Hz, 2H), 3.40-3.39 (d, J=3.6 Hz, 1H), 3.25 (s, 3H), 2.85-2.80 (q, J=7.2 Hz, 2H), 2.02-1.96 (m, 2H), 1.28-1.24 (t, J=7.6 Hz, 3H), 0.91 (s, 9H).

The following examples were prepared in a similar manner as 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylic acid from methyl 7-(tert-butyl)-2-chloro-8-hydroxy-3-(3-methoxypropoxy)-10-oxo-6,7,10,11-tetrahydrooxepino[3,2-b:4,5-b']dipyridine-9-carboxylate and an appropriate organoboron species.

Example 82: 7-(tert-Butyl)-2-cyclopropyl-8-hydroxy-3-(3-methoxypropoxy)-10-oxo-6,7,10,11-tetrahydrooxepino[3,2-b:4,5-b']dipyridine-9-carboxylic acid (single enantiomer I)

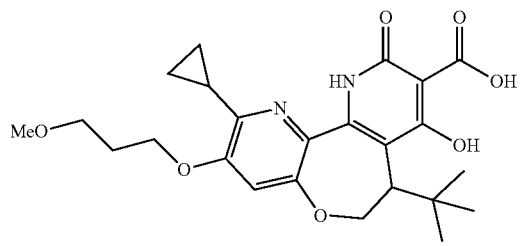 [SMILES: COCCCOc1cc2c(nc1C1CC1)-c1[nH]c(=O)c(C(=O)O)c(O)c1C(C(C)(C)C)CO2]

m/z: 459 [M+H]+ observed. 1H NMR (400 MHz, DMSO-d6): δ 7.12 (s, 1H), 4.91-4.87 (m, 1H), 4.21-4.17 (m, 2H), 3.89-3.85 (m, 1H), 3.53-3.50 (m, 2H), 3.43-3.42 (m, 1H), 3.26 (s, 3H), 2.04-1.96 (m, 2H), 1.36 (s, 1H) 1.05-0.99 (m, 4H), 0.89 (s, 9H).

Example 83: 7-(tert-Butyl)-2-cyclopropyl-8-hydroxy-3-(3-methoxypropoxy)-10-oxo-6,7,10,11-tetrahydrooxepino[3,2-b:4,5-b']dipyridine-9-carboxylic acid (single enantiomer II)

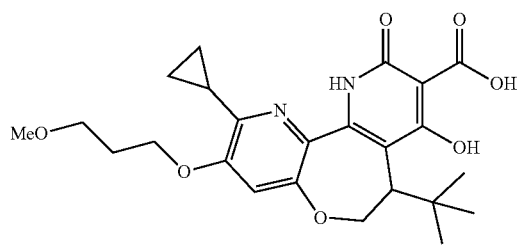 [SMILES: COCCCOc1cc2c(nc1C1CC1)-c1[nH]c(=O)c(C(=O)O)c(O)c1C(C(C)(C)C)CO2]

m/z: 459 [M+H]+ observed. 1H NMR (400 MHz, DMSO-d6): δ 7.12 (s, 1H), 4.91-4.87 (m, 1H), 4.21-4.17 (m, 2H), 3.89-3.85 (m, 1H), 3.53-3.50 (m, 2H), 3.43-3.42 (m, 1H), 3.26 (s, 3H), 2.04-1.96 (m, 2H), 1.36 (s, 1H) 1.05-0.99 (m, 4H), 0.89 (s, 9H).

Example 84: 8-Hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylic acid

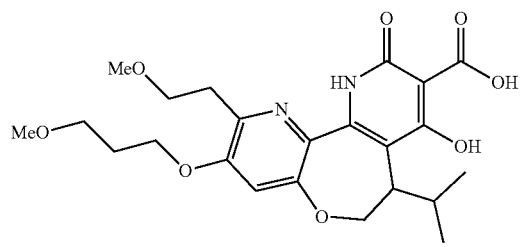 [SMILES: COCCCOc1cc2c(nc1CCOC)-c1[nH]c(=O)c(C(=O)O)c(O)c1C(C(C)C)CO2]

7-Isopropyl-3-(3-methoxypropoxy)-2-vinyl-7,8-dihydrooxepino[3,2-b]pyridin-9(6H)-one

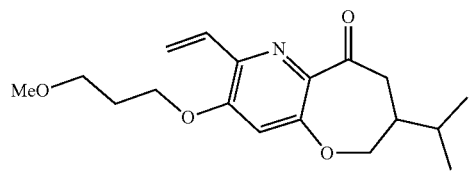 [SMILES: C=Cc1nc2c(cc1OCCCOC)OCC(C(C)C)CC2=O]

Tetrakis(triphenylphosphine)palladium(0) (176.26 mg, 0.15 mmol, 0.05 eq) was added to a stirred solution of 2-chloro-7-isopropyl-3-(3-methoxypropoxy)-7,8-dihydrooxepino[3,2-b]pyridin-9(6H)-one (1.0 g, 3.0 mmol) and 4,4,5,5-tetramethyl-2-vinyl-1,3,2-dioxaborolane (658 mg, 4.27 mmol) in a mixture of 1,4-dioxane (8 mL) and saturated aqueous sodium carbonate solution (4 mL). The mixture was stirred at 100° C. for 16 h under nitrogen. The mixture was cooled to rt, filtered and washed with EtOAc (50 mL). The filtrate was diluted with water (50 mL) and extracted with EtOAc (3×30 mL). The combined organic phase was dried over anhydrous sodium sulfate, filtered and concentrated in vacuum. The residue was purified by normal phase SiO2 chromatography (0-33% EtOAc/petroleum ether) to give 7-isopropyl-3-(3-methoxypropoxy)-2-vinyl-7,8-dihydrooxepino[3,2-b]pyridin-9(6H)-one) as a yellow oil (700 mg, 71% yield). 1H NMR (400 MHz, CDCl3): δ 7.11-7.04 (dd, J=17.6, 11.2 Hz, 1H), 6.86 (s, 1H), 6.44-6.39 (dd, J=17.6, 2.0 Hz, 1H), 5.51-5.47 (dd, J=17.6, 2.0 Hz, 1H), 4.35-4.30 (m, 1H), 4.19-4.11 (m, 3H), 3.59-3.56 (t, J=6.0 Hz, 2H), 3.36 (s, 3H), 2.91-2.87 (m, 2H), 2.15-2.09 (m, 3H), 1.84-1.82 (m, 1H), 1.03-0.98 (t, J=8 Hz, 6H).

7-Isopropyl-2-(2-methoxyethyl)-3-(3-methoxypropoxy)-7,8-dihydrooxepino[3,2-b]pyridin-9(6H)-one

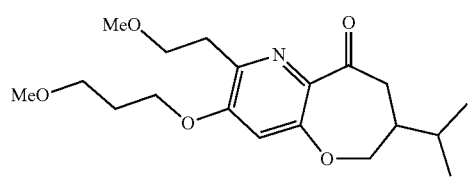 [SMILES: COCCCOc1cc2c(nc1CCOC)C(=O)CC(C(C)C)CO2]

Potassium bisulfate (1.49 g, 11.0 mmol) was added to a stirred solution of 7-isopropyl-3-(3-methoxypropoxy)-2-vinyl-7,8-dihydrooxepino[3,2-b]pyridin-9(6H)-one (700 mg, 2.19 mmol) and MeOH (17.7 mL, 438 mmol). The mixture was stirred under nitrogen at 80° C. for 20 h. The mixture was cooled to rt, filtered and washed with EtOAc (20 mL). The filtrate was concentrated under reduced pressure. The residue was purified by normal phase SiO₂ chromatography (50% EtOAc/petroleum ether then with 1:1:0.3 petroleum ether:EtOAc:EtOH) to give 7-isopropyl-2-(2-methoxyethyl)-3-(3-methoxypropoxy)-7,8-dihydrooxepino[3,2-b]pyridin-9(6H)-one as a yellow oil (500 mg, 51% yield, m/z: 352 [M+H]$^+$ observed).

N-Benzyl-7-isopropyl-2-(2-methoxyethyl)-3-(3-methoxypropoxy)-7,8-dihydrooxepino[3,2-b]pyridin-9(6H)-imine

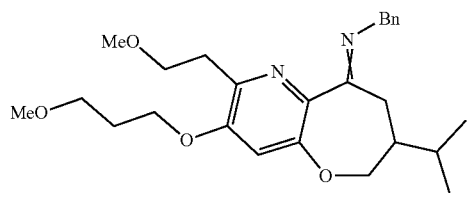 [SMILES: COCCCOc1cc2c(nc1CCOC)C(=NCc1ccccc1)CC(C(C)C)CO2]

To a mixture of 7-isopropyl-2-(2-methoxyethyl)-3-(3-methoxypropoxy)-7,8-dihydrooxepino[3,2-b]pyridin-9(6H)-one (450 mg, 1.28 mmol), benzylamine (0.2 mL, 1.54 mmol) and triethylamine (0.5 mL, 3.59 mmol) in CH₂Cl₂ (10 mL) was added a solution of titanium (IV) chloride (1 M in dichloromethane, 0.90 mL) in CH₂Cl₂ (5 mL) at 0° C. The mixture was stirred under nitrogen at rt for 16 h. The reaction mixture was quenched with saturated aqueous sodium bicarbonate solution (50 mL) and extracted with CH₂Cl₂ (3×30 mL). The combined organic layers were dried over sodium sulfate, filtered and concentrated under reduced pressure to give N-benzyl-7-isopropyl-2-(2-methoxyethyl)-3-(3-methoxypropoxy)-7,8-dihydrooxepino[3,2-b]pyridin-9(6H)-imine as a yellow oil, which was used in the next step without further purification (570 mg, >100% yield, m/z: 441 [M+H]$^+$ observed).

Methyl 11-benzyl-8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylate

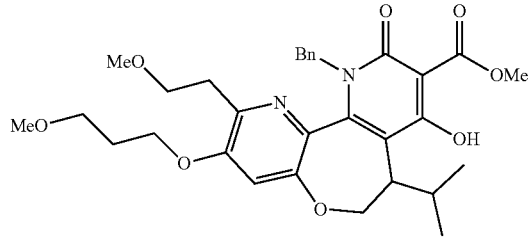 [SMILES: COCCCOc1cc2c(nc1CCOC)-c1c(c(O)c(C(=O)OC)c(=O)n1Cc1ccccc1)C(C(C)C)CO2]

A mixture of N-benzyl-7-isopropyl-2-(2-methoxyethyl)-3-(3-methoxypropoxy)-7,8-dihydrooxepino[3,2-b]pyridin-9(6H)-imine (570 mg, 1.29 mmol) and trimethyl methanetricarboxylate (492 mg, 2.59 mmol) in Ph₂O (6 mL) was heated to 220° C. and stirred for 20 minutes. The mixture was cooled to rt, diluted with petroleum ether (10 mL) and purified by normal phase SiO₂ chromatography (0-50% EtOAc/petroleum ether) to give methyl 11-benzyl-8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylate as a brown oil (330 mg, 45% yield, m/z: 567 [M+H]$^+$ observed).

Methyl 8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylate

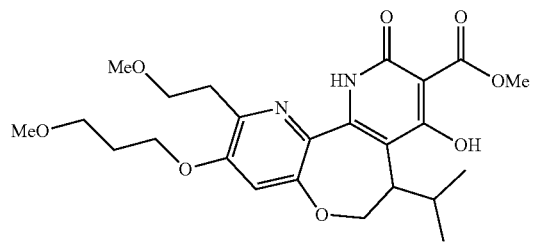 [SMILES: COCCCOc1cc2c(nc1CCOC)-c1[nH]c(=O)c(C(=O)OC)c(O)c1C(C(C)C)CO2]

A mixture of methyl 11-benzyl-8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylate (280 mg, 0.494 mmol) in trifluoroacetic acid (4 mL) was heated to 100° C. and stirred for 16 h. The mixture was cooled to rt and concentrated under reduced pressure. The residue was diluted with saturated sodium bicarbonate solution (50 mL) and extracted with EtOAc (3×20 mL). The combined organic phase was dried over anhydrous sodium sulfate, filtered and concentrated under reduced pressure. The crude residue was purified by normal phase SiO₂ chromatography (20:1 EtOAc:EtOH) to give methyl 8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylate as a yellow oil (72 mg, 30% yield, m/z: 477 [M+H]$^+$ observed).

8-Hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylic acid

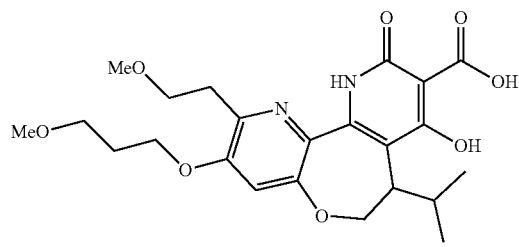 [SMILES: COCCCOc1cc2c(nc1CCOC)-c1[nH]c(=O)c(C(=O)O)c(O)c1C(C(C)C)CO2]

A mixture of methyl 8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylate (72 mg, 151 umol) and lithium iodide (81 mg, 604 umol) in EtOAc (4 mL) was heated to 60° C. and stirred for 2 h. The mixture was combined with another 10 mg batch, poured into H₂O (15 mL) and extracted with EtOAc (3×10 mL). The combined organic phase was dried with anhydrous sodium sulfate, filtered and concentrated under reduced pressure. The residue was purified by reverse phase HPLC to give 8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylic acid as a light yellow solid (12.91 mg, m/z: 463 [M+H]$^+$ observed). $^1$H NMR (400 MHz, DMSO-d$_6$): δ 13.98 (s, 1H), 11.83 (s, 1H), 7.20 (s, 1H), 4.85-4.81 (dd, J=12, 5.2 Hz, 1H), 4.18-4.15 (t, J=6.0 Hz, 2H), 4.04-4.01 (d, J=12 Hz, 1H), 3.75-3.71 (t, J=6.8 Hz, 2H), 3.51-3.48 (t, J=6.4 Hz, 2H), 3.29 (s, 3H), 3.25 (s, 4H), 3.07-3.04 (t, J=6.8 Hz, 2H), 2.02-1.97 (m, 2H), 1.62-1.60 (m, 1H), 1.06-1.05 (d, J=6.4 Hz, 3H), 0.84-0.82 (d, J=6.8 Hz, 3H).

Example 85: 7-(tert-Butyl)-8-hydroxy-2-methoxy-3-(3-methoxypropoxy)-10-oxo-6,7,10,11-tetrahydrooxepino[3,2-b:4,5-b']dipyridine-9-carboxylic acid (single enantiomer I)

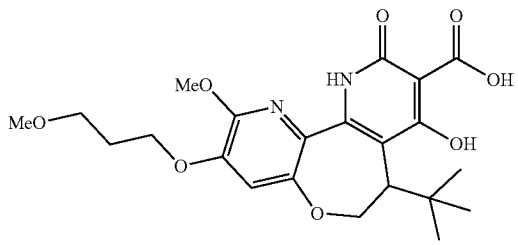 [SMILES: COCCCOc1cc2c(nc1OC)-c1[nH]c(=O)c(C(=O)O)c(O)c1C(C(C)(C)C)CO2]

Example 86: 7-(tert-Butyl)-8-hydroxy-2-methoxy-3-(3-methoxypropoxy)-10-oxo-6,7,10,11-tetrahydrooxepino[3,2-b:4,5-b']dipyridine-9-carboxylic acid (single enantiomer II)

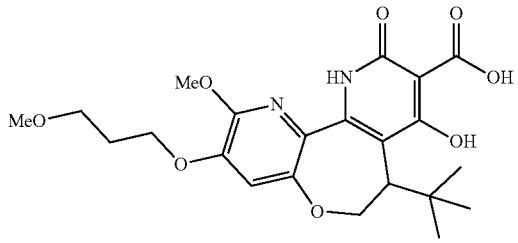 [SMILES: COCCCOc1cc2c(nc1OC)-c1[nH]c(=O)c(C(=O)O)c(O)c1C(C(C)(C)C)CO2]

7-(tert-Butyl)-2-methoxy-3-(3-methoxypropoxy)-7,8-dihydrooxepino[3,2-b]pyridin-9(6H)-one

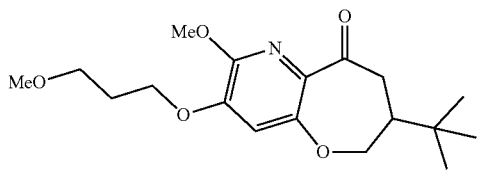 [SMILES: COCCCOc1cc2c(nc1OC)C(=O)CC(C(C)(C)C)CO2]

To a mixture of 7-(tert-butyl)-2-chloro-3-(3-methoxypropoxy)-7,8-dihydrooxepino[3,2-b]pyridin-9(6H)-one (0.50 g, 1.46 mmol), cesium carbonate (1.43 g, 4.39 mmol) and MeOH (0.09 mL, 2.2 mmol) in toluene (6 mL) was added tBuXPhos (0.12 g, 0.29 mmol) and palladium acetate (0.03 g, 0.15 mmol) in one portion under nitrogen. The mixture was stirred at 80° C. for 1 h in a microwave. The mixture was combined with a second 0.5 g batch. Water (30 mL) was added to the mixture and extracted with EtOAc (3×10 mL). The combined organic phase was washed with saturated aqueous brine solution (2×20 mL), dried with anhydrous sodium sulfate, filtered and the filtrate was concentrated under reduced pressure. The residue was purified by normal phase SiO$_2$ chromatography (0-15% EtOAc/petroleum ether) to give 7-(tert-butyl)-2-methoxy-3-(3-methoxypropoxy)-7,8-dihydrooxepino[3,2-b]pyridin-9(6H)-one as a yellow solid (0.60 g, 60% yield). $^1$H NMR (400 MHz, CDCl$_3$): δ 6.81 (s, 1H) 4.43-4.42 (m, 1H) 4.16-4.12 (m, 3H) 4.06 (s, 3H) 3.57-3.54 (t, J=6 Hz, 2H) 3.36 (s, 3H) 2.90-2.87 (m, 2H) 2.15-2.19 (m, 3H) 0.99 (s, 9H).

N-Benzyl-7-(tert-butyl)-2-methoxy-3-(3-methoxypropoxy)-7,8-dihydrooxepino[3,2-b]pyridin-9(6H)-imine

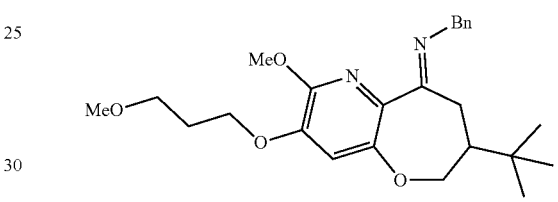

To a mixture of 7-(tert-butyl)-2-methoxy-3-(3-methoxypropoxy)-7,8-dihydrooxepino[3,2-b]pyridin-9(6H)-one (600 mg, 1.78 mmol), benzylamine (0.3 mL, 2.3 mmol) and triethylamine (0.6 mL, 4.6 mmol) in CH$_2$Cl$_2$ (10 mL) was added titanium (IV) chloride (1 M solution in dichloromethane, 1.2 mL, 1.2 mmol) in portions at 0° C. under nitrogen. The mixture was stirred at rt for 16 h. The mixture was quenched with saturated sodium bicarbonate solution (20 mL), filtered and the aqueous phase was extracted with CH$_2$Cl$_2$ (3×20 mL). The combined organic phase was washed with saturated aqueous brine solution (20 mL), dried with anhydrous sodium sulfate, filtered and concentrated under reduces pressure to give N-benzyl-7-(tert-butyl)-2-methoxy-3-(3-methoxypropoxy)-7,8-dihydrooxepino[3,2-b]pyridin-9(6H)-imine as a red oil, which was used in the next step without further purification (610 mg, 80% yield, m/z: 427 [M+H]$^+$ observed).

Methyl 11-benzyl-7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate

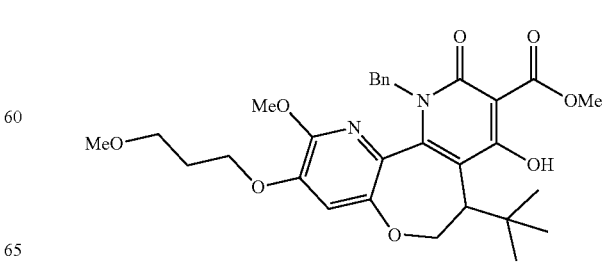

To a mixture of N-benzyl-7-(tert-butyl)-2-methoxy-3-(3-methoxypropoxy)-7,8-dihydrooxepino[3,2-b]pyridin-9(6H)-imine (610 mg, 1.43 mmol) in diglyme (6 mL) was added trimethyl methanetricarboxylate (544 mg, 2.86 mmol) in one portion under nitrogen. The mixture was stirred at 220° C. for 1 h. The mixture was purified by normal phase SiO₂ chromatography (0-25% EtOAc/petroleum ether) to give methyl 11-benzyl-7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate as a yellow oil (700 mg, 88% yield, m/z: 553 [M+H]⁺ observed).

Methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate

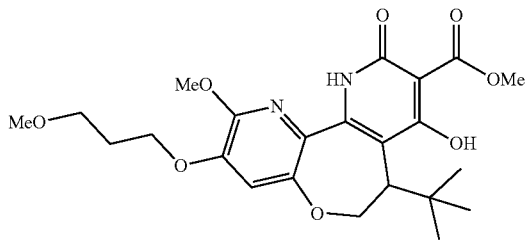

To methyl 11-benzyl-7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate (700 mg, 1.27 mmol) was added trifluoroacetic acid (25 mL) in one portion under nitrogen. The mixture was stirred at 100° C. for 16 h. The mixture was cooled to rt and concentrated under reduced pressure. To the residue was diluted with saturated sodium bicarbonate solution (100 mL) and extracted with EtOAc (2×50 mL). The combined organic phase was washed with saturated aqueous brine solution (50 mL), dried with anhydrous sodium sulfate, filtered and concentrated in vacuum. The residue was purified by normal phase SiO₂ chromatography (0-35% EtOAc/petroleum ether) to give methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate as a yellow solid (200 mg, 30% yield, m/z: 463 [M+H]⁺ observed).

Methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate (single enantiomer I)

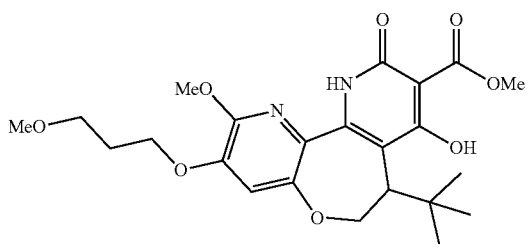 [SMILES: COCCCOc1cc2c(nc1OC)-c1[nH]c(=O)c(C(=O)OC)c(O)c1C(C(C)(C)C)CO2]

Methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate (single enantiomer II)

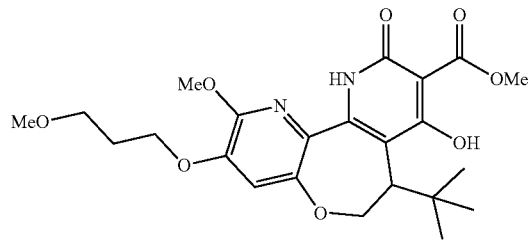 [SMILES: COCCCOc1cc2c(nc1OC)-c1[nH]c(=O)c(C(=O)OC)c(O)c1C(C(C)(C)C)CO2]

Racemic methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate (200 mg) was separated by SFC (supercritical fluid chromatography) on a CHIRALCEL OD column using 60% iPrOH (0.1% aq. NH₃) as a modifier to give methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate as a white solid (single enantiomer I, faster eluting enantiomer, 60 mg, 30% yield, m/z: 463 [M+H]⁺ observed) and methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate as a white solid (single enantiomer II, slower eluting enantiomer, 60 mg, 30% yield, m/z: 463 [M+H]⁺ observed).

Example 85: 7-(tert-Butyl)-8-hydroxy-2-methoxy-3-(3-methoxypropoxy)-10-oxo-6,7,10,11-tetrahydrooxepino[3,2-b:4,5-b']dipyridine-9-carboxylic acid (single enantiomer I)

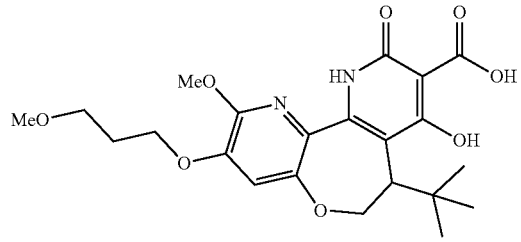 [SMILES: COCCCOc1cc2c(nc1OC)-c1[nH]c(=O)c(C(=O)O)c(O)c1C(C(C)(C)C)CO2]

To the mixture of methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate (single enantiomer I, slower eluting enantiomer on chiral SFC OD column, 60 mg, 0.13 mmol) in EtOAc (1 mL) was added lithium iodide (35 mg, 260 umol) in one portion under nitrogen. The mixture was stirred at 60° C. for 4 h. Water (20 mL) was added and the mixture extracted with EtOAc (3×10 mL). The combined organic phase was washed with saturated aqueous brine solution (2×20 mL), dried with anhydrous sodium sulfate, filtered and concentrated under reduced pressure. The residue was purified by reverse phase HPLC to give 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylic acid as a white solid (single enantiomer I, faster eluting enantiomer on chiral SFC IC-H column, 30 mg, 50% yield, m/z: 449 [M+H]+ observed). $^1$H NMR (400 MHz, DMSO-d$_6$): δ 7.15 (s, 1H) 4.93-4.89 (m, 1H) 4.16-4.13 (m, 2H) 4.03 (s, 3H) 3.92-3.90 (m, 1H) 3.47-3.44 (t, J=6.4 Hz, 2H) 3.39-3.38 (m, 1H) 3.24 (s, 3H) 2.00-1.94 (m, 2H) 0.90 (s, 9H).

Example 86: 7-(tert-Butyl)-8-hydroxy-2-methoxy-3-(3-methoxypropoxy)-10-oxo-6,7,10,11-tetrahydrooxepino[3,2-b:4,5-b']dipyridine-9-carboxylic acid (single enantiomer II)

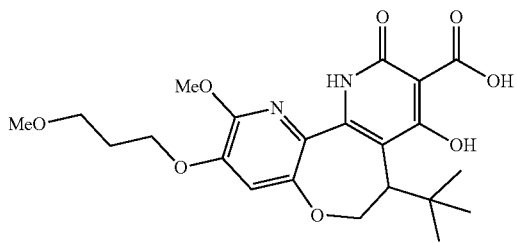 [SMILES: COCCCOc1cc2c(nc1OC)-c1[nH]c(=O)c(C(=O)O)c(O)c1C(C(C)(C)C)CO2]

To the mixture of methyl 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylate (single enantiomer II, faster eluting enantiomer on chiral SFC OD column, 60 mg, 0.13 mmol) in EtOAc (1 mL) was added lithium iodide (35 mg, 260 umol) in one portion under nitrogen. The mixture was stirred at 60° C. for 4 h. Water (20 mL) was added and the mixture extracted with EtOAc (3×10 mL). The combined organic phase was washed with saturated aqueous brine solution (2×20 mL), dried with anhydrous sodium sulfate, filtered and concentrated under reduced pressure. The residue was purified by reverse phase HPLC to give 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylic acid as a white solid (single enantiomer II, slower eluting enantiomer on chiral SFC IC-H column, 30 mg, 52% yield, m/z: 449 [M+H]+ observed). $^1$H NMR (400 MHz, DMSO-d$_6$): δ 7.15 (s, 1H) 4.93-4.89 (m, 1H) 4.16-4.13 (m, 2H) 4.03 (s, 3H) 3.92-3.90 (m, 1H) 3.47-3.44 (t, J=6.4 Hz, 2H) 3.39-3.38 (m, 1H) 3.24 (s, 3H) 2.00-1.94 (m, 2H) 0.90 (s, 9H).

Example 87: 5-Isopropyl-4,9-dimethoxy-8-(3-methoxypropoxy)-2-oxo-1,2,5,6-tetrahydrobenzo[h]quinoline-3-carboxylicacid

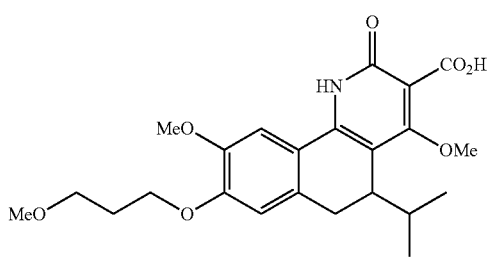 [SMILES: COCCCOc1cc2c(cc1OC)-c1[nH]c(=O)c(C(=O)O)c(OC)c1C(C(C)C)C2]

Methyl 1-benzyl-5-isopropyl-9-methoxy-8-(3-methoxypropoxy)-2-oxo-1,2,5,6-tetrahydro-1,10-phenanthroline-3-carboxylate

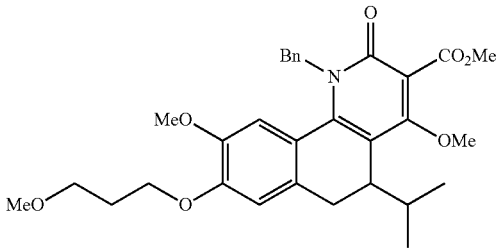 [SMILES: COCCCOc1cc2c(cc1OC)-c1c(c(OC)c(C(=O)OC)c(=O)n1Cc1ccccc1)C(C(C)C)C2]

A solution of methyl 1-benzyl-4-hydroxy-5-isopropyl-9-methoxy-8-(3-methoxypropoxy)-2-oxo-1,2,5,6-tetrahydrobenzo[h]quinoline-3-carboxylate (50 mg, 0.10 mmol) and potassium carbonate (30 mg, 0.2 mmol) in anhydrous acetonitrile (1.5 mL) in a sealed microwave vial was purged with nitrogen for 5 minutes. Iodomethane (20 uL, 0.29 mmol) was added to the reaction. The sealed vial was heated in a microwave at 80° C. for 20 min. The reaction mixture was cooled to rt, diluted with EtOAc (50 mL), washed with H$_2$O (2×20 mL) and saturated aqueous brine solution (10 mL). The combined organic phase was dried with anhydrous sodium sulfate, filtered and concentrated under reduced pressure. The crude product was purified by normal phase SiO$_2$ chromatography (0-80% EtOAc/hexanes) to afford methyl 1-benzyl-5-isopropyl-9-methoxy-8-(3-methoxypropoxy)-2-oxo-1,2,5,6-tetrahydro-1,10-phenanthroline-3-carboxylate as a yellow solid (23 mg, 45% yield, m/z: 536 [M+H]+ observed).

Methyl 5-isopropyl-4,9-dimethoxy-8-(3-methoxypropoxy)-2-oxo-1,2,5,6-tetrahydrobenzo[h]quinoline-3-carboxylate

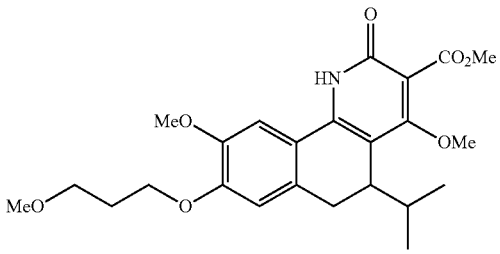 [SMILES: COCCCOc1cc2c(cc1OC)-c1[nH]c(=O)c(C(=O)OC)c(OC)c1C(C(C)C)C2]

A solution of methyl 1-benzyl-5-isopropyl-4,9-dimethoxy-8-(3-methoxypropoxy)-2-oxo-1,2,5,6-tetrahydrobenzo[h]quinoline-3-carboxylate (28 mg, 0.1 mmol) and palladium hydroxide (20% on carbon, 10 mg, 0.01 mmol) in methanol (5 mL) was purged with hydrogen gas for 2 min. The reaction mixture was stirred under an atmosphere of hydrogen at rt for 16 h. The mixture was filtered through Celite®, washed with MeOH (2×10 mL) and concentrated under reduced pressure to afford methyl 5-isopropyl-4,9-dimethoxy-8-(3-methoxypropoxy)-2-oxo-1,2,5,6-tetrahydrobenzo[h]quinoline-3-carboxylate as a yellow solid, which was used in the next step without further purification (23 mg, 100% yield, m/z: 446 [M+H]+ observed).

5-Isopropyl-4,9-dimethoxy-8-(3-methoxypropoxy)-2-oxo-1,2,5,6-tetrahydrobenzo[h]quinoline-3-carboxylicacid

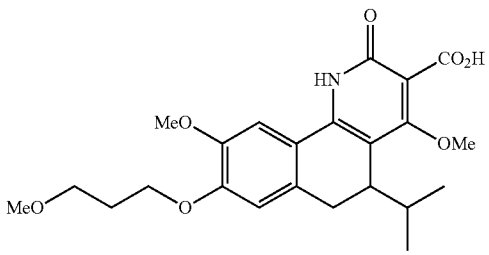

A solution of methyl 5-isopropyl-4,9-dimethoxy-8-(3-methoxypropoxy)-2-oxo-1,2,5,6-tetrahydrobenzo[h]quinoline-3-carboxylate (23 mg, 0.05 mmol) and lithium iodide (10 mg, 0.10 mmol) in EtOAc (10 mL) was stirred at 60° C. for 5 h. The solvent was removed under reduced pressure. The crude residue was purified by reverse phase HPLC to afford 5-isopropyl-4,9-dimethoxy-8-(3-methoxypropoxy)-2-oxo-1,2,5,6-tetrahydrobenzo[h]quinoline-3-carboxylic acid as a white solid (9 mg, 41% yield, m/z: 432 [M+H]$^+$ observed). $^1$H NMR (400 MHz, CDCl$_3$) δ 13.79 (s, 1H), 7.18 (s, 1H), 6.80 (s, 1H), 4.18 (q, J=6.4 Hz, 2H), 3.97 (d, J=6.7 Hz, 6H), 3.58 (t, J=5.9 Hz, 2H), 3.36 (s, 3H), 2.91 (s, 3H), 2.14 (q, J=6.2 Hz, 2H), 1.6 (m, 1H), 0.88-0.77 (m, 6H).

The following examples were prepared in a similar manner as 5-isopropyl-4,9-dimethoxy-8-(3-methoxypropoxy)-2-oxo-1,2,5,6-tetrahydrobenzo[h]quinoline-3-carboxylic acid from methyl 1-benzyl-4-hydroxy-5-isopropyl-9-methoxy-8-(3-methoxypropoxy)-2-oxo-1,2,5,6-tetrahydrobenzo[h]quinoline-3-carboxylate and an appropriate alkyl halide.

Example 88: 5-Isopropyl-9-methoxy-4-(2-methoxyethoxy)-8-(3-methoxypropoxy)-2-oxo-1,2,5,6-tetrahydrobenzo[h]quinoline-3-carboxylic acid

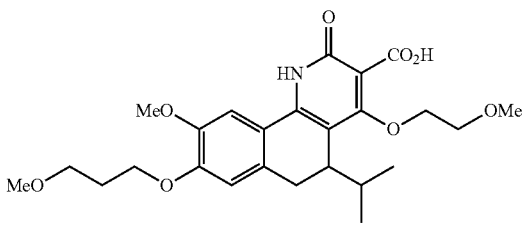 [SMILES: COCCCOc1cc2c(cc1OC)-c1[nH]c(=O)c(C(=O)O)c(OCCOC)c1C(C(C)C)C2]

m/z: 476 [M+H]$^+$ observed. $^1$H NMR (400 MHz, CDCl$_3$) δ 10.54 (s, 1H), 7.08 (s, 1H), 6.82 (s, 1H), 4.78 (d, J=11.7 Hz, 1H), 4.26-4.13 (m, 2H), 4.17-4.07 (m, 1H), 3.94 (s, 3H), 3.81 (t, J=10.8, 8.2, 2.3 Hz, 1H), 3.69-3.59 (m, 1H), 3.59 (t, J=6.1, 1.2 Hz, 2H), 3.37 (s, 6H), 3.13-3.06 (m, 1H), 2.93 (d, J=4.0 Hz, 2H), 2.20-2.09 (m, 2H), 1.25 (m, 1H), 0.85 (d, J=6.8 Hz, 3H), 0.74 (d, J=6.7 Hz, 3H).

Example 89: 4-(2-(Dimethylamino)ethoxy)-5-isopropyl-9-methoxy-8-(3-methoxypropoxy)-2-oxo-1,2,5,6-tetrahydrobenzo[h]quinoline-3-carboxylic acid

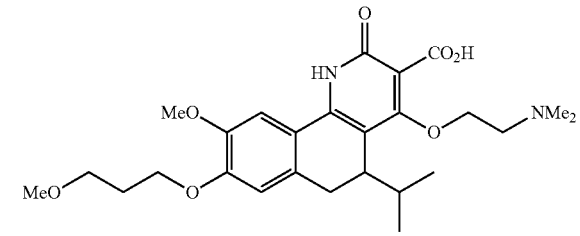 [SMILES: COCCCOc1cc2c(cc1OC)-c1[nH]c(=O)c(C(=O)O)c(OCCN(C)C)c1C(C(C)C)C2]

m/z: 489 [M+H]$^+$ observed. $^1$H NMR (400 MHz, CDCl$_3$) δ 7.38 (s, 1H), 6.67 (s, 1H), 4.46 (s, 1H), 4.33 (s, 1H), 4.12 (d, J=3.7 Hz, 2H), 3.89 (s, 3H), 3.82 (s, 3H), 3.57 (t, J=6.0 Hz, 2H), 3.45-3.27 (m, 6H), 2.83-2.71 (m, 5H), 2.17-2.03 (m, 2H), 1.44 (q, J=6.9 Hz, 1H), 0.73 (d, J=6.7 Hz, 6H).

Example 90: 4-(2-Hydroxyethoxy)-5-isopropyl-9-methoxy-8-(3-methoxypropoxy)-2-oxo-1,2,5,6-tetrahydrobenzo[h]quinoline-3-carboxylicacid

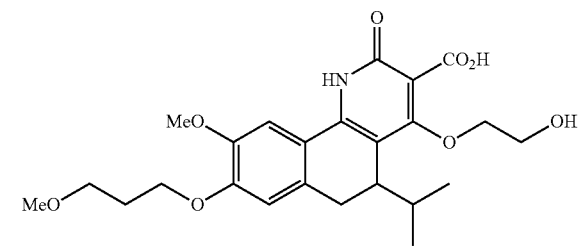 [SMILES: COCCCOc1cc2c(cc1OC)-c1[nH]c(=O)c(C(=O)O)c(OCCO)c1C(C(C)C)C2]

m/z: 462 [M+H]$^+$ observed. $^1$H NMR (400 MHz, CDCl$_3$) δ 7.06 (s, 1H), 6.83 (s, 1H), 4.41 (s, 1H), 4.27 (s, 1H), 4.20 (q, J=6.4 Hz, 2H), 4.03-3.92 (m, 5H), 3.59 (t, J=5.9 Hz, 2H), 3.37 (s, 3H), 2.96-2.90 (m, 3H), 2.20-2.09 (m, 2H), 1.61-1.59 (m, 1H), 0.81 (dd, J=26.7, 6.7 Hz, 6H).

Example 91: 4-Ethoxy-5-isopropyl-9-methoxy-8-(3-methoxypropoxy)-2-oxo-1,2,5,6-tetrahydrobenzo[h]quinoline-3-carboxylicacid

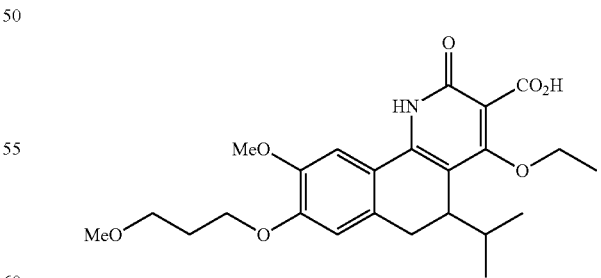

m/z: 446 [M+H]$^+$ observed. $^1$H NMR (400 MHz, CDCl$_3$) δ 7.15 (s, 1H), 6.82 (s, 1H), 4.62-4.50 (m, 1H), 4.26-4.09 (m, 3H), 3.94 (s, 3H), 3.66-3.52 (m, 2H), 3.37 (s, 3H), 2.96-2.91 (m, 3H), 2.20-2.09 (m, 2H), 1.61 (q, J=13.4, 6.7 Hz, 1H), 1.47 (t, J=14.0 Hz, 3H), 0.86 (d, J=6.8 Hz, 3H), 0.74 (d, J=6.7 Hz, 3H).

Example 92: 5-(tert-Butyl)-4,9-dimethoxy-8-(3-methoxypropoxy)-2-oxo-1,2,5,6-tetrahydro-1,10-phenanthroline-3-carboxylic acid

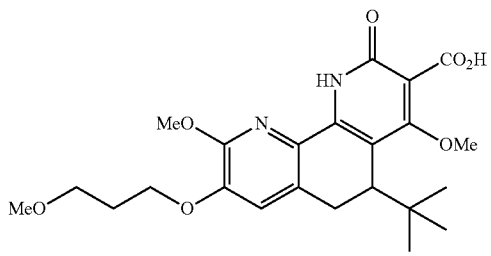

Methyl 1-benzyl-5-(tert-butyl)-4,9-dimethoxy-8-(3-methoxypropoxy)-2-oxo-1,2,5,6-tetrahydro-1,10-phenanthroline-3-carboxylate

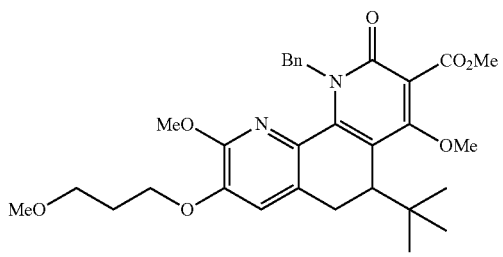 [SMILES: COCCCOc1cc2c(nc1OC)-c1c(c(OC)c(C(=O)OC)c(=O)n1Cc1ccccc1)C(C(C)(C)C)C2]

A solution of methyl 1-benzyl-5-(tert-butyl)-4-hydroxy-9-methoxy-8-(3-methoxypropoxy)-2-oxo-1,2,5,6-tetrahydro-1,10-phenanthroline-3-carboxylate (80 mg, 0.15 mmol) and potassium carbonate (40 mg, 0.3 mmol) in anhydrous acetonitrile (1.5 mL) in a sealed microwave vial was purged with nitrogen for 5 minutes. Iodomethane (50 uL, 0.75 mmol) was added to the reaction. The sealed vial was heated in a microwave at 90° C. for 40 min. The reaction mixture was cooled to rt, diluted with EtOAc (50 mL), washed with H$_2$O (2×20 mL), and saturated aqueous brine solution (10 mL). The combined organic phase was dried with anhydrous sodium sulfate, filtered and concentrated under reduced pressure. The crude product was purified by normal phase SiO$_2$ chromatography (0-80% EtOAc/hexanes) to afford methyl 1-benzyl-5-(tert-butyl)-4,9-dimethoxy-8-(3-methoxypropoxy)-2-oxo-1,2,5,6-tetrahydro-1,10-phenanthroline-3-carboxylate as a yellow solid (23 mg, 45% yield, m/z: 551 [M+H]$^+$ observed).

Methyl 5-(tert-butyl)-4,9-dimethoxy-8-(3-methoxypropoxy)-2-oxo-1,2,5,6-tetrahydro-1,10-phenanthroline-3-carboxylate

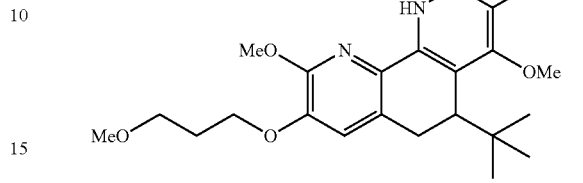

A solution of methyl 1-benzyl-5-(tert-butyl)-4,9-dimethoxy-8-(3-methoxypropoxy)-2-oxo-1,2,5,6-tetrahydro-1,10-phenanthroline-3-carboxylate (23 mg, 0.04 mmol) and palladium (10% on carbon, 7 mg, 0.007 mmol) in methanol (10 mL) was purged with hydrogen gas for 2 min. The reaction mixture was stirred under an atmosphere of hydrogen at rt for 16 h. The mixture was filtered through CELITE®, washed with MeOH (2×10 mL) and concentrated under reduced pressure to afford methyl 5-(tert-butyl)-4,9-dimethoxy-8-(3-methoxypropoxy)-2-oxo-1,2,5,6-tetrahydro-1,10-phenanthroline-3-carboxylate as a yellow solid, which was used in the next step without further purification (21 mg, 100% yield, m/z: 461 [M+H]$^+$ observed).

5-(tert-Butyl)-4,9-dimethoxy-8-(3-methoxypropoxy)-2-oxo-1,2,5,6-tetrahydro-1,10-phenanthroline-3-carboxylicacid

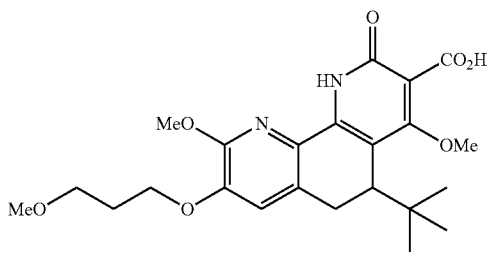

A solution of methyl 5-(tert-butyl)-4,9-dimethoxy-8-(3-methoxypropoxy)-2-oxo-1,2,5,6-tetrahydro-1,10-phenanthroline-3-carboxylate (21 mg, 0.05 mmol) and lithium hydroxide (10 mg, 0.18 mmol) in 1,4-dioxane/water (3/1 mixture, 2 mL) was stirred at rt for 1 h. The solvent was removed under reduced pressure. The crude residue was purified by reverse phase HPLC to afford 5-(tert-butyl)-4,9-dimethoxy-8-(3-methoxypropoxy)-2-oxo-1,2,5,6-tetrahydro-1,10-phenanthroline-3-carboxylic acid as a white solid (9 mg, 45% yield, m/z: 447 [M+H]$^+$ observed). $^1$H NMR (400 MHz, CDCl$_3$) δ 10.12 (s, 1H), 6.96 (s, 1H), 4.24-4.12 (m, 2H), 4.12 (s, 3H), 4.06 (s, 3H), 3.58 (t, J=5.9 Hz, 2H), 3.41-3.33 (m, 3H), 3.08 (s, 3H), 2.14 (q, J=6.2 Hz, 2H), 0.78 (s, 9H).

Example 93: 2-Cyclopropyl-8-hydroxy-7-isopropyl-3-(3-methoxypropoxy)-10-oxo-6,7,10,11-tetrahydrooxepino[3,2-b:4,5-b']dipyridine-9-carboxylic acid

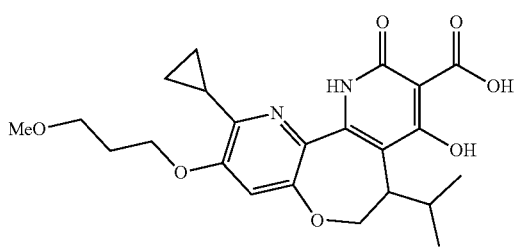 [SMILES: COCCCOc1cc2c(nc1C1CC1)-c1[nH]c(=O)c(C(=O)O)c(O)c1C(C(C)C)CO2]

This compound can be prepared using, in non-limiting embodiments, according to the procedure of Schemes XXI-XXIII. m/z: 445 [M+H]$^+$ observed. $^1$H NMR (400 MHz, DMSO-d$_6$): δ 14.02 (s, 1H), 11.28 (s, 1H), 7.16 (s, 1H), 4.83-4.79 (dd, J=12, 4.4 Hz, 1H), 4.21-4.13 (m, 2H), 3.98 (d, J=12.4 Hz, 1H), 3.53-3.50 (t, J=6 Hz, 2H), 3.26 (s, 3H), 2.05-1.99 (m, 2H), 1.63-1.59 (m, 1H), 1.37-1.24 (m, 2H), 1.05-1.02 (m, 6H), 0.90-0.81 (m, 4H).

Example 94: (S)-4-Hydroxy-5-isopropyl-9-(3-methoxypropoxy)-2-oxo-10-(tetrahydro-2H-pyran-4-yl)-1,2,5,6-tetrahydrobenzo[2,3]oxepino[4,5-b]pyridine-3-carboxylic acid

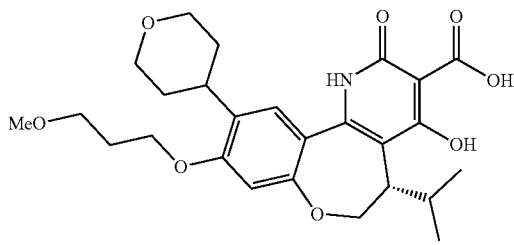 [SMILES: COCCCOc1cc2c(cc1C1CCOCC1)-c1[nH]c(=O)c(C(=O)O)c(O)c1[C@H](C(C)C)CO2]

This compound can be prepared using, in non-limiting embodiments, according to the procedure of Schemes XVIII. m/z: 486 [M−H]$^-$ observed. $^1$H NMR (400 MHz, DMSO-d6): δ 11.71 (s, 1H), 11.37 (s, 1H), 7.86-7.80 (m, 1H), 7.30-7.27 (m, 1H), 6.60-6.55 (m, 1H), 4.59 (s, 1H), 4.36-4.34 (m, 1H), 4.04-3.95 (m, 4H), 3.49 (s, 2H), 3.42 (s, 3H), 3.25 (s, 2H), 3.12-2.98 (m, 2H), 1.96-1.88 (m, 2H), 1.70-1.61 (m, 4H), 1.38 (s, 1H), 1.00-0.91 (m, 3H), 0.65-0.58 (m, 3H).

Example 95: Biological Examples

HBsAg Assay

Inhibition of HBsAg was determined in HepG2.2.15 cells. Cells were maintained in culture medium containing 10% fetal calf serum, G414, Glutamine, penicillin/streptomycin. Cells were seeded in 96-well collagen-coated plate at a density of 30,000 cells/well. Serially diluted compounds were added to cells next day at the final DMSO concentration of 0.5%. Cells were incubated with compounds for 2-3 days, after which medium was removed. Fresh medium containing compounds was added to cells for additional 3-4 days. At day 6 after exposure of compounds, supernatant was collected, the HBsAg immunoassay (microplate-based chemiluminescence immunoassay kits, CLIA, Autobio Diagnosics Co., Zhengzhou, China, Catalog #CL0310-2) was used to determine the level of HBsAg according to manufactory instruction. Dose-response curves were generated and the EC$_{50}$ value (effective concentrations that achieved 50% inhibitory effect) were determined using XLfit software. In addition, cells can be seeded at a density of 5,000 cells/well for determination of cell viability in the presence and absence of compounds by using CellTiter-Glo reagent (Promega). Tables 1-3 show EC$_{50}$ values obtained by the HBsAg assay for selected compounds.

TABLE 1

| Ex. No. | Structure | Nomenclature | sAg EC$_{50}$, μM |
|---|---|---|---|
| 1 | 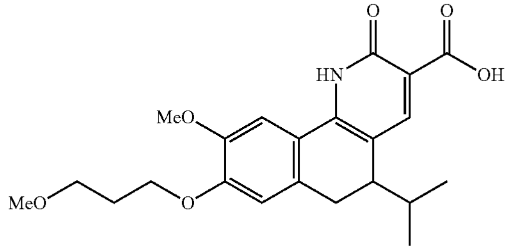 [SMILES: COCCCOc1cc2c(cc1OC)-c1[nH]c(=O)c(C(=O)O)cc1C(C(C)C)C2] | 5-isopropyl-9-methoxy-8-(3-methoxypropoxy)-2-oxo-1,2,5,6-tetrahydrobenzo[h]quinoline-3-carboxylic acid | 0.023 |

TABLE 1-continued

| Ex. No. | Structure | Nomenclature | sAg EC$_{50}$, µM |
|---|---|---|---|
| 2 | 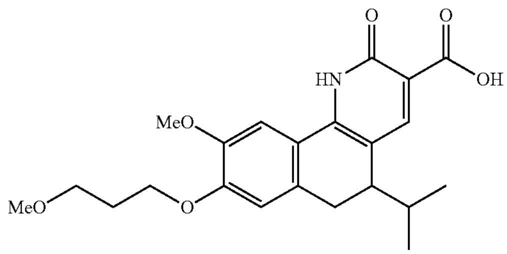 [SMILES: COCCCOc1cc2c(cc1OC)-c1[nH]c(=O)c(C(=O)O)cc1C(C(C)C)C2] | 5-isopropyl-9-methoxy-8-(3-methoxypropoxy)-2-oxo-1,2,5,6-tetrahydrobenzo[h]quinoline-3-carboxylic acid (single enantiomer I) | 0.011 |
| 3 | 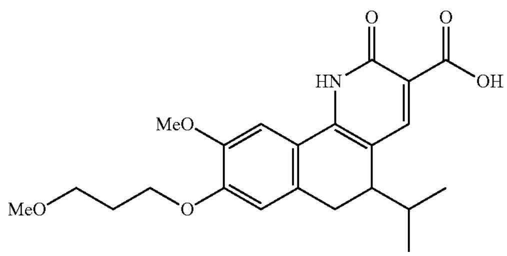 [SMILES: COCCCOc1cc2c(cc1OC)-c1[nH]c(=O)c(C(=O)O)cc1C(C(C)C)C2] | 5-isopropyl-9-methoxy-8-(3-methoxypropoxy)-2-oxo-1,2,5,6-tetrahydrobenzo[h]quinoline-3-carboxylic acid (single enantiomer II) | 2 |
| 4 | 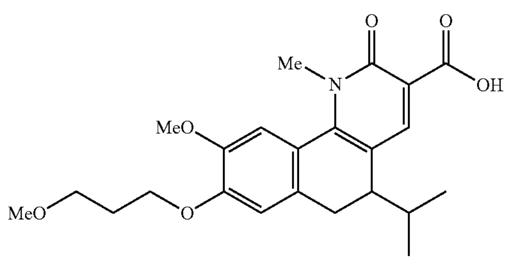 [SMILES: COCCCOc1cc2c(cc1OC)-c1c(cc(C(=O)O)c(=O)n1C)C(C(C)C)C2] | 5-isopropyl-9-methoxy-8-(3-methoxypropoxy)-1-methyl-2-oxo-1,2,5,6-tetrahydrobenzo[h]quinoline-3-carboxylic acid | 12 |
| 5 | 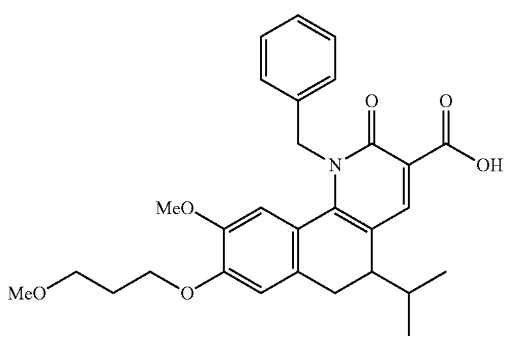 [SMILES: COCCCOc1cc2c(cc1OC)-c1c(cc(C(=O)O)c(=O)n1Cc1ccccc1)C(C(C)C)C2] | 1-benzyl-5-isopropyl-9-methoxy-8-(3-methoxypropoxy)-2-oxo-1,2,5,6-tetrahydrobenzo[h]quinoline-3-carboxylic acid | 15 |
| 6 | 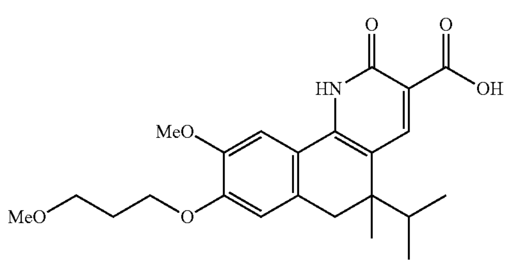 [SMILES: COCCCOc1cc2c(cc1OC)-c1[nH]c(=O)c(C(=O)O)cc1C(C)(C(C)C)C2] | 5-isopropyl-9-methoxy-8-(3-methoxypropoxy)-5-methyl-2-oxo-1,2,5,6-tetrahydrobenzo[h]quinoline-3-carboxylic acid | 0.044 |

TABLE 1-continued

| Ex. No. | Structure | Nomenclature | sAg EC$_{50}$, μM |
|---|---|---|---|
| 7 | 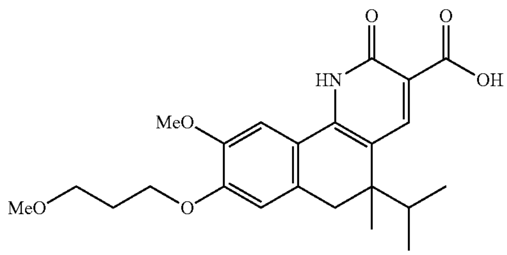 [SMILES: COCCCOc1cc2c(cc1OC)-c1[nH]c(=O)c(C(=O)O)cc1C(C)(C(C)C)C2] | 5-isopropyl-9-methoxy-8-(3-methoxypropoxy)-5-methyl-2-oxo-1,2,5,6-tetrahydrobenzo[h]quinoline-3-carboxylic acid (single enantiomer I) | 0.022 |
| 8 | 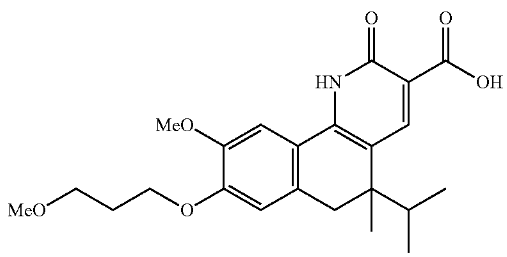 [SMILES: COCCCOc1cc2c(cc1OC)-c1[nH]c(=O)c(C(=O)O)cc1C(C)(C(C)C)C2] | 5-isopropyl-9-methoxy-8-(3-methoxypropoxy)-5-methyl-2-oxo-1,2,5,6-tetrahydrobenzo[h]quinoline-3-carboxylic acid (single enantiomer II) | 2.5 |
| 9 | 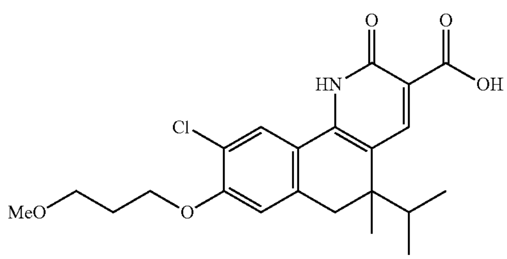 [SMILES: COCCCOc1cc2c(cc1Cl)-c1[nH]c(=O)c(C(=O)O)cc1C(C)(C(C)C)C2] | 9-chloro-5-isopropyl-8-(3-methoxypropoxy)-5-methyl-2-oxo-1,2,5,6-tetrahydrobenzo[h]quinoline-3-carboxylic acid | 0.031 |
| 10 | 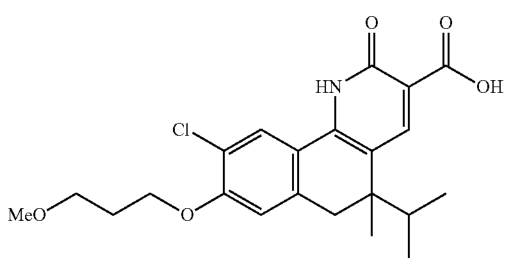 [SMILES: COCCCOc1cc2c(cc1Cl)-c1[nH]c(=O)c(C(=O)O)cc1C(C)(C(C)C)C2] | 9-chloro-5-isopropyl-8-(3-methoxypropoxy)-5-methyl-2-oxo-1,2,5,6-tetrahydrobenzo[h]quinoline-3-carboxylic acid (single enantiomer I) | 0.025 |
| 11 | 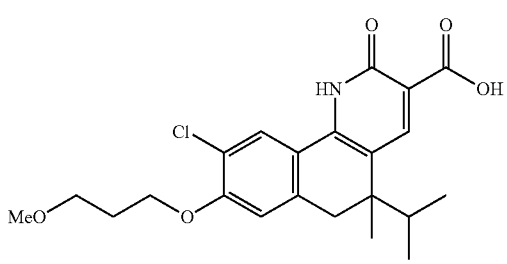 [SMILES: COCCCOc1cc2c(cc1Cl)-c1[nH]c(=O)c(C(=O)O)cc1C(C)(C(C)C)C2] | 9-chloro-5-isopropyl-8-(3-methoxypropoxy)-5-methyl-2-oxo-1,2,5,6-tetrahydrobenzo[h]quinoline-3-carboxylic acid (single enantiomer II) | 0.25 |
| 12 | 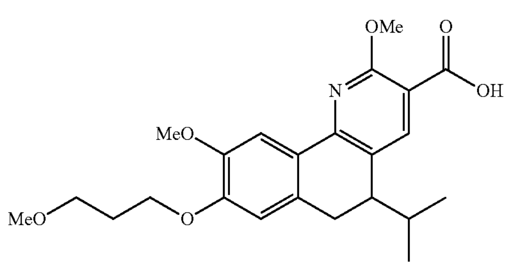 [SMILES: COCCCOc1cc2c(cc1OC)-c1nc(OC)c(C(=O)O)cc1C(C(C)C)C2] | 5-isopropyl-2,9-dimethoxy-8-(3-methoxypropoxy)benzo[h]quinoline-3-carboxylic acid | 1.2 |

TABLE 1-continued

| Ex. No. | Structure | Nomenclature | sAg EC$_{50}$, μM |
|---|---|---|---|
| 13 | 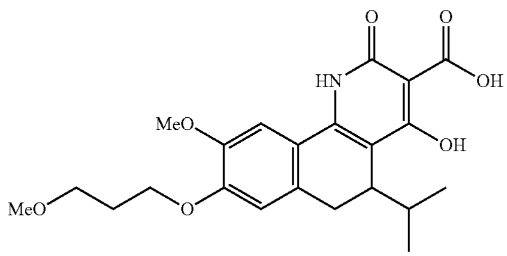 [SMILES: COCCCOc1cc2c(cc1OC)-c1[nH]c(=O)c(C(=O)O)c(O)c1C(C(C)C)C2] | 4-hydroxy-5-isopropyl-9-methoxy-8-(3-methoxypropoxy)-2-oxo-1,2,5,6-tetrahydrobenzo[h]quinoline-3-carboxylic acid | 0.006 |
| 14 | 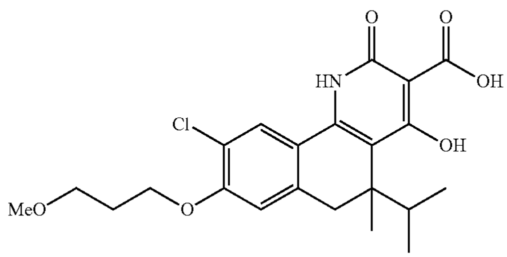 [SMILES: COCCCOc1cc2c(cc1Cl)-c1[nH]c(=O)c(C(=O)O)c(O)c1C(C)(C(C)C)C2] | 9-chloro-4-hydroxy-5-isopropyl-8-(3-methoxypropoxy)-5-methyl-2-oxo-1,2,5,6-tetrahydrobenzo[h]quinoline-3-carboxylic acid | 0.062 |
| 15 | 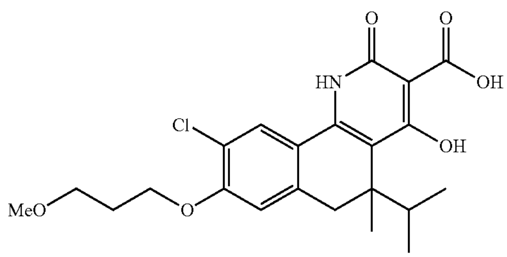 [SMILES: COCCCOc1cc2c(cc1Cl)-c1[nH]c(=O)c(C(=O)O)c(O)c1C(C)(C(C)C)C2] | 9-chloro-4-hydroxy-5-isopropyl-8-(3-methoxypropoxy)-5-methyl-2-oxo-1,2,5,6-tetrahydrobenzo[h]quinoline-3-carboxylic acid (single enantiomer I) | 0.018 |
| 16 | 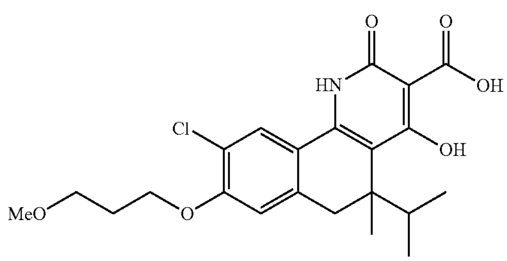 [SMILES: COCCCOc1cc2c(cc1Cl)-c1[nH]c(=O)c(C(=O)O)c(O)c1C(C)(C(C)C)C2] | 9-chloro-4-hydroxy-5-isopropyl-8-(3-methoxypropoxy)-5-methyl-2-oxo-1,2,5,6-tetrahydrobenzo[h]quinoline-3-carboxylic acid (single enantiomer II) | 2 |
| 17 | 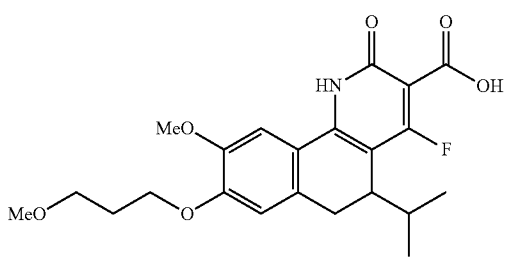 [SMILES: COCCCOc1cc2c(cc1OC)-c1[nH]c(=O)c(C(=O)O)c(F)c1C(C(C)C)C2] | 4-fluoro-5-isopropyl-9-methoxy-8-(3-methoxypropoxy)-2-oxo-1,2,5,6-tetrahydrobenzo[h]quinoline-3-carboxylic acid | 0.64 |
| 18 | 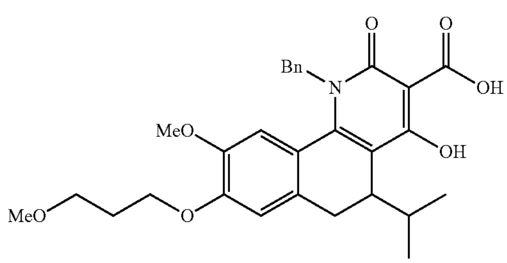 [SMILES: COCCCOc1cc2c(cc1OC)-c1c(c(O)c(C(=O)O)c(=O)n1Cc1ccccc1)C(C(C)C)C2] | 1-benzyl-4-hydroxy-5-isopropyl-9-methoxy-8-(3-methoxypropoxy)-2-oxo-1,2,5,6-tetrahydrobenzo[h]quinoline-3-carboxylic acid | 15 |

TABLE 1-continued

| Ex. No. | Structure | Nomenclature | sAg EC$_{50}$, μM |
|---|---|---|---|
| 19 | 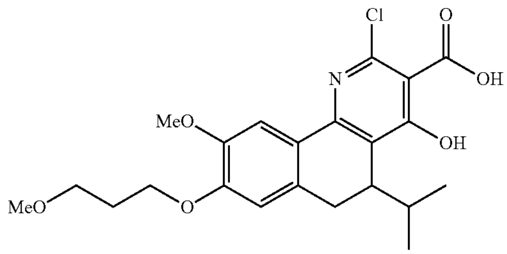 | 2-chloro-4-hydroxy-5-isopropyl-9-methoxy-8-(3-methoxypropoxy)-5,6-dihydrobenzo[h]quinoline-3-carboxylic acid | 8 |
| 20 | 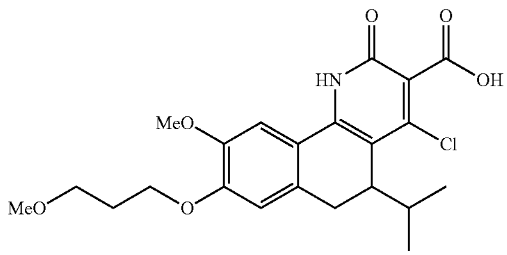 [SMILES: COCCCOc1cc2c(cc1OC)-c1[nH]c(=O)c(C(=O)O)c(Cl)c1C(C(C)C)C2] | 4-chloro-5-isopropyl-9-methoxy-8-(3-methoxypropoxy)-2-oxo-1,2,5,6-tetrahydrobenzo[h]quinoline-3-carboxylic acid | 3.8 |
| 21 | 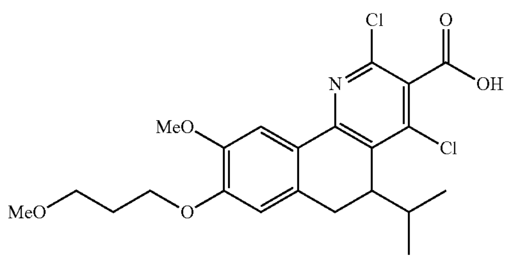 [SMILES: COCCCOc1cc2c(cc1OC)-c1nc(Cl)c(C(=O)O)c(Cl)c1C(C(C)C)C2] | 2,4-dichloro-5-isopropyl-9-methoxy-8-(3-methoxypropoxy)-5,6-dihydrobenzo[h]quinoline-3-carboxylic acid | 0.15 |
| 22 | 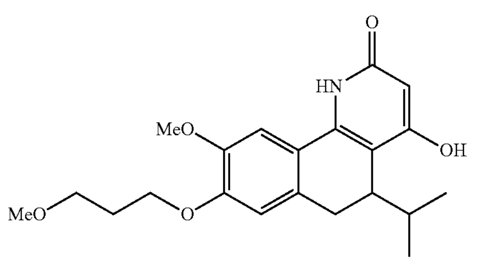 [SMILES: COCCCOc1cc2c(cc1OC)-c1[nH]c(=O)cc(O)c1C(C(C)C)C2] | 4-hydroxy-5-isopropyl-9-methoxy-8-(3-methoxypropoxy)-5,6-dihydrobenzo[h]quinolin-2(1H)-one | 0.34 |
| 23 | 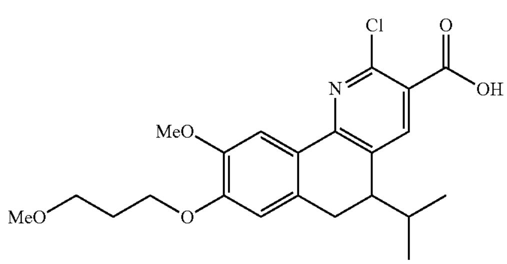 [SMILES: COCCCOc1cc2c(cc1OC)-c1nc(Cl)c(C(=O)O)cc1C(C(C)C)C2] | 2-chloro-5-isopropyl-9-methoxy-8-(3-methoxypropoxy)-5,6-dihydrobenzo[h]quinoline-3-carboxylic acid | 0.24 |
| 24 | 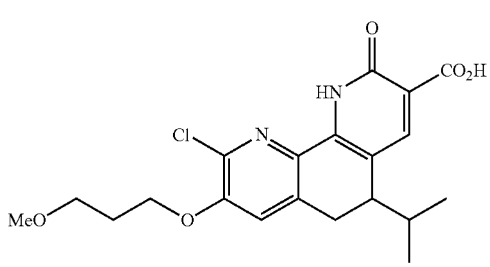 [SMILES: COCCCOc1cc2c(nc1Cl)-c1[nH]c(=O)c(C(=O)O)cc1C(C(C)C)C2] | 9-chloro-5-isopropyl-8-(3-methoxypropoxy)-2-oxo-1,2,5,6-tetrahydro-1,10-phenanthroline-3-carboxylic acid | 0.003 |

TABLE 1-continued

| Ex. No. | Structure | Nomenclature | sAg EC$_{50}$, μM |
|---|---|---|---|
| 25 | 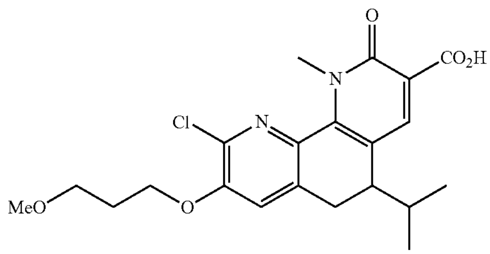 [SMILES: COCCCOc1cc2c(nc1Cl)-c1c(cc(C(=O)O)c(=O)n1C)C(C(C)C)C2] | 9-chloro-5-isopropyl-8-(3-methoxypropoxy)-1-methyl-2-oxo-1,2,5,6-tetrahydro-1,10-phenanthroline-3-carboxylic acid | 0.094 |
| 26 | 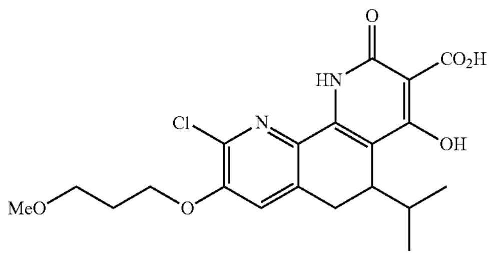 [SMILES: COCCCOc1cc2c(nc1Cl)-c1[nH]c(=O)c(C(=O)O)c(O)c1C(C(C)C)C2] | 9-chloro-4-hydroxy-5-isopropyl-8-(3-methoxypropoxy)-2-oxo-1,2,5,6-tetrahydro-1,10-phenanthroline-3-carboxylic acid | 0.003 |
| 27 | 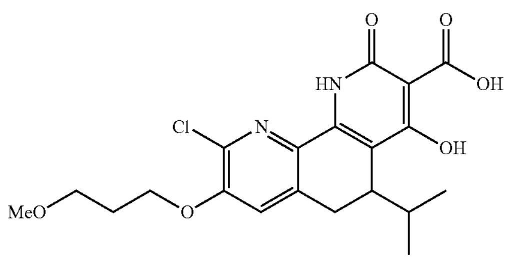 [SMILES: COCCCOc1cc2c(nc1Cl)-c1[nH]c(=O)c(C(=O)O)c(O)c1C(C(C)C)C2] | 9-chloro-4-hydroxy-5-isopropyl-8-(3-methoxypropoxy)-2-oxo-1,2,5,6-tetrahydro-1,10-phenanthroline-3-carboxylic acid (single enantiomer I) | 0.002 |
| 28 | 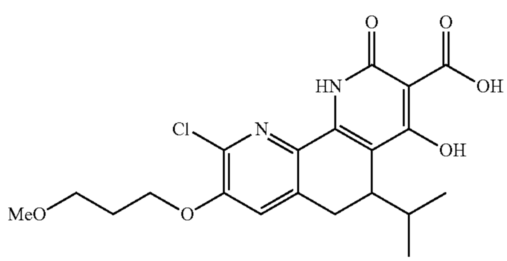 [SMILES: COCCCOc1cc2c(nc1Cl)-c1[nH]c(=O)c(C(=O)O)c(O)c1C(C(C)C)C2] | 9-chloro-4-hydroxy-5-isopropyl-8-(3-methoxypropoxy)-2-oxo-1,2,5,6-tetrahydro-1,10-phenanthroline-3-carboxylic acid (single enantiomer II) | 0.043 |
| 29 | 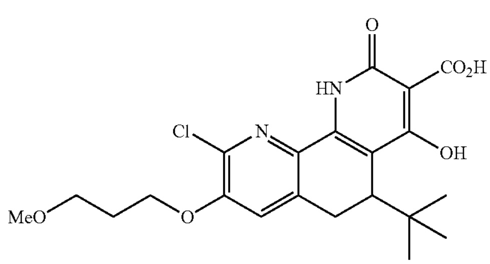 [SMILES: COCCCOc1cc2c(nc1Cl)-c1[nH]c(=O)c(C(=O)O)c(O)c1C(C(C)(C)C)C2] | 5-(tert-butyl)-9-chloro-4-hydroxy-8-(3-methoxypropoxy)-2-oxo-1,2,5,6-tetrahydro-1,10-phenanthroline-3-carboxylic acid | 0.001 |
| 30 | 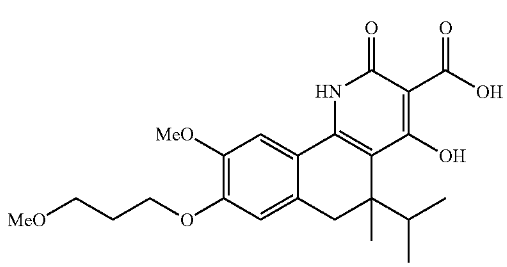 [SMILES: COCCCOc1cc2c(cc1OC)-c1[nH]c(=O)c(C(=O)O)c(O)c1C(C)(C(C)C)C2] | 4-hydroxy-5-isopropyl-9-methoxy-8-(3-methoxypropoxy)-5-methyl-2-oxo-1,2,5,6-tetrahydrobenzo[h]quinoline-3-carboxylic acid | 0.058 |

TABLE 1-continued

| Ex. No. | Structure | Nomenclature | sAg EC$_{50}$, μM |
|---|---|---|---|
| 31 | 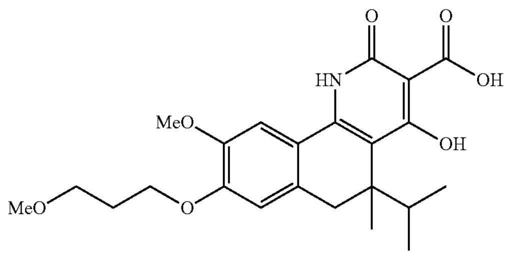 [SMILES: COCCCOc1cc2c(cc1OC)-c1[nH]c(=O)c(C(=O)O)c(O)c1C(C)(C(C)C)C2] | 4-hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer I) | 0.027 |
| 32 | 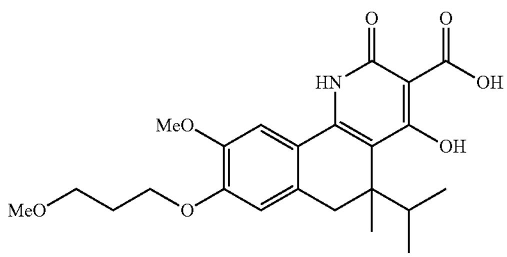 [SMILES: COCCCOc1cc2c(cc1OC)-c1[nH]c(=O)c(C(=O)O)c(O)c1C(C)(C(C)C)C2] | 4-hydroxy-5-isopropyl-9-methoxy-8-(3-methoxypropoxy)-5-methyl-2-oxo-1,2,5,6-tetrahydrobenzo[h]quinoline-3-carboxylic acid (single enantiomer II) | 10 |
| 33 | 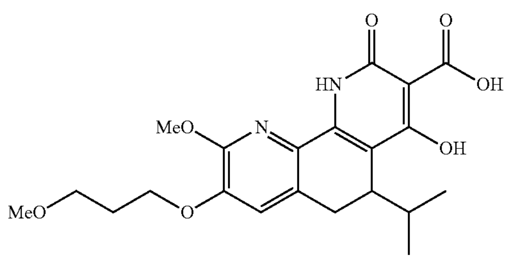 [SMILES: COCCCOc1cc2c(nc1OC)-c1[nH]c(=O)c(C(=O)O)c(O)c1C(C(C)C)C2] | 4-hydroxy-5-isopropyl-9-methoxy-8-(3-methoxypropoxy)-2-oxo-1,2,5,6-tetrahydro-1,10-phenanthroline-3-carboxylic acid | 0.004 |
| 34 | 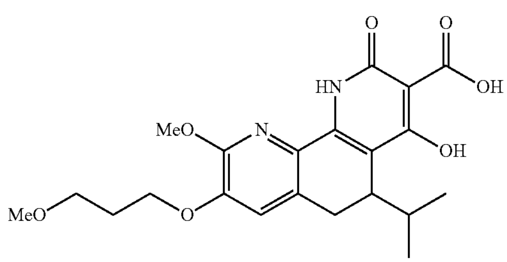 [SMILES: COCCCOc1cc2c(nc1OC)-c1[nH]c(=O)c(C(=O)O)c(O)c1C(C(C)C)C2] | 4-hydroxy-5-isopropyl-9-methoxy-8-(3-methoxypropoxy)-2-oxo-1,2,5,6-tetrahydro-1,10-phenanthroline-3-carboxylic acid (single enantiomer I) | 0.003 |
| 35 | 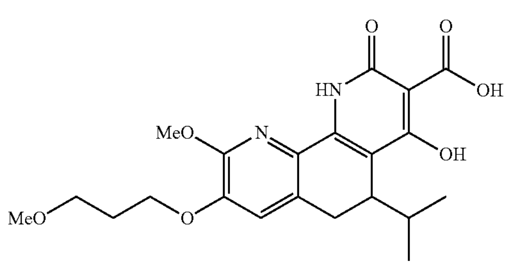 [SMILES: COCCCOc1cc2c(nc1OC)-c1[nH]c(=O)c(C(=O)O)c(O)c1C(C(C)C)C2] | 4-hydroxy-5-isopropyl-9-methoxy-8-(3-methoxypropoxy)-2-oxo-1,2,5,6-tetrahydro-1,10-phenanthroline-3-carboxylic acid (single enantiomer II) | 0.15 |
| 36 | 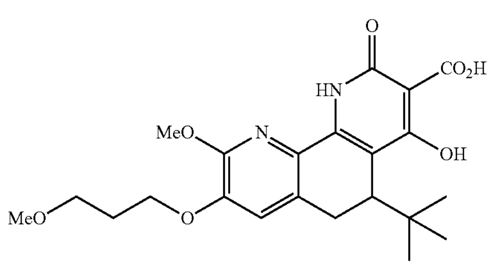 [SMILES: COCCCOc1cc2c(nc1OC)-c1[nH]c(=O)c(C(=O)O)c(O)c1C(C(C)(C)C)C2] | 5-(tert-butyl)-4-hydroxy-9-methoxy-8-(3-methoxypropoxy)-2-oxo-1,2,5,6-tetrahydro-1,10-phenanthroline-3-carboxylic acid | 0.001 |

TABLE 1-continued

| Ex. No. | Structure | Nomenclature | sAg EC$_{50}$, μM |
|---|---|---|---|
| 37 | 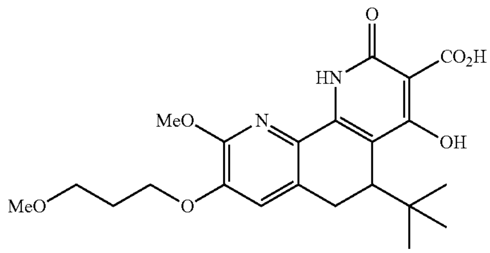 [SMILES: COCCCOc1cc2c(nc1OC)-c1[nH]c(=O)c(C(=O)O)c(O)c1C(C(C)(C)C)C2] | 5-(tert-butyl)-4-hydroxy-9-methoxy-8-(3-methoxypropoxy)-2-oxo-1,2,5,6-tetrahydro-1,10-phenanthroline-3-carboxylic acid (single enantiomer I) | 0.001 |
| 38 | 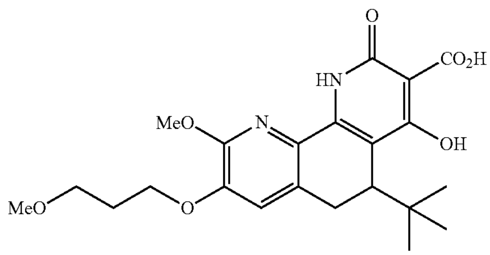 [SMILES: COCCCOc1cc2c(nc1OC)-c1[nH]c(=O)c(C(=O)O)c(O)c1C(C(C)(C)C)C2] | 5-(tert-butyl)-4-hydroxy-9-methoxy-8-(3-methoxypropoxy)-2-oxo-1,2,5,6-tetrahydro-1,10-phenanthroline-3-carboxylic acid (single enantiomer II) | 0.035 |
| 39 | 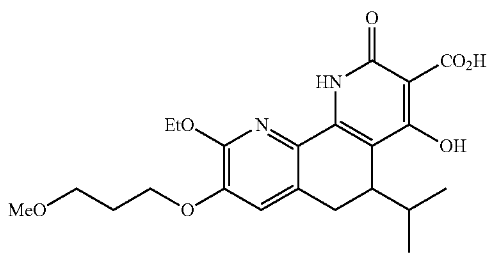 [SMILES: CCOc1nc2c(cc1OCCCOC)CC(C(C)C)c1c-2[nH]c(=O)c(C(=O)O)c1O] | 9-ethoxy-4-hydroxy-5-isopropyl-8-(3-methoxypropoxy)-2-oxo-1,2,5,6-tetrahydro-1,10-phenanthroline-3-carboxylic acid | 0.002 |
| 40 | 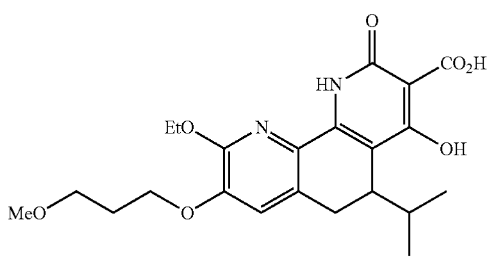 [SMILES: CCOc1nc2c(cc1OCCCOC)CC(C(C)C)c1c-2[nH]c(=O)c(C(=O)O)c1O] | 9-ethoxy-4-hydroxy-5-isopropyl-8-(3-methoxypropoxy)-2-oxo-1,2,5,6-tetrahydro-1,10-phenanthroline-3-carboxylic acid (single enantiomer I) | 0.087 |
| 41 | 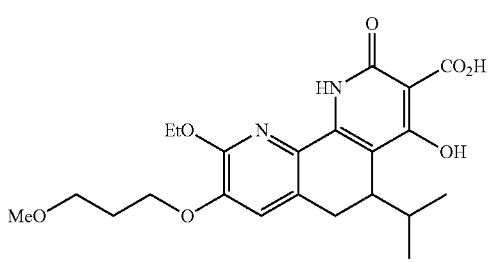 [SMILES: CCOc1nc2c(cc1OCCCOC)CC(C(C)C)c1c-2[nH]c(=O)c(C(=O)O)c1O] | 9-ethoxy-4-hydroxy-5-isopropyl-8-(3-methoxypropoxy)-2-oxo-1,2,5,6-tetrahydro-1,10-phenanthroline-3-carboxylic acid (single enantiomer II) | 0.001 |
| 42 | 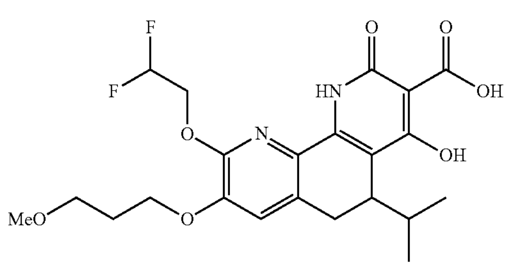 [SMILES: COCCCOc1cc2c(nc1OCC(F)F)-c1[nH]c(=O)c(C(=O)O)c(O)c1C(C(C)C)C2] | 9-(2,2-difluoroethoxy)-4-hydroxy-5-isopropyl-8-(3-methoxypropoxy)-2-oxo-1,2,5,6-tetrahydro-1,10-phenanthroline-3-carboxylic acid | 0.012 |

TABLE 1-continued

| Ex. No. | Structure | Nomenclature | sAg EC$_{50}$, μM |
|---|---|---|---|
| 43 | 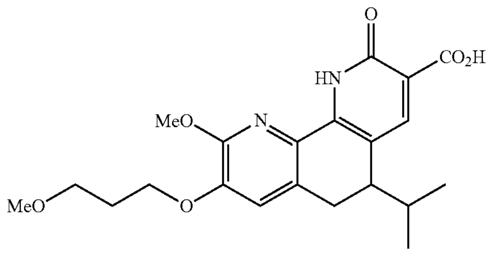 [SMILES: COCCCOc1cc2c(nc1OC)-c1[nH]c(=O)c(C(=O)O)cc1C(C(C)C)C2] | 5-isopropyl-9-methoxy-8-(3-methoxypropoxy)-2-oxo-1,2,5,6-tetrahydro-1,10-phenanthroline-3-carboxylic acid | 0.003 |
| 44 | 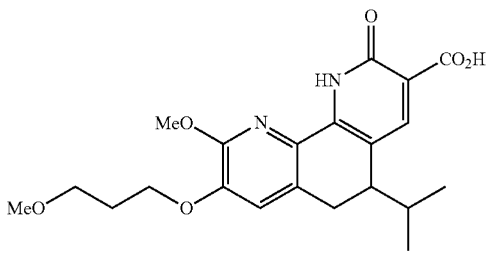 [SMILES: COCCCOc1cc2c(nc1OC)-c1[nH]c(=O)c(C(=O)O)cc1C(C(C)C)C2] | 5-isopropyl-9-methoxy-8-(3-methoxypropoxy)-2-oxo-1,2,5,6-tetrahydro-1,10-phenanthroline-3-carboxylic acid (single enantiomer I) | 0.002 |
| 45 | 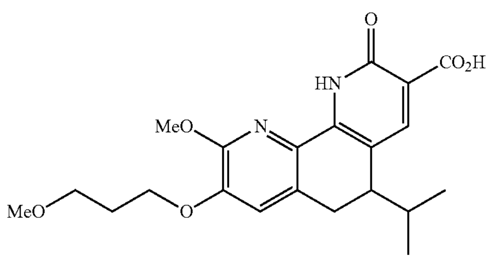 [SMILES: COCCCOc1cc2c(nc1OC)-c1[nH]c(=O)c(C(=O)O)cc1C(C(C)C)C2] | 5-isopropyl-9-methoxy-8-(3-methoxypropoxy)-2-oxo-1,2,5,6-tetrahydro-1,10-phenanthroline-3-carboxylic acid (single enantiomer II) | 0.016 |
| 46 | 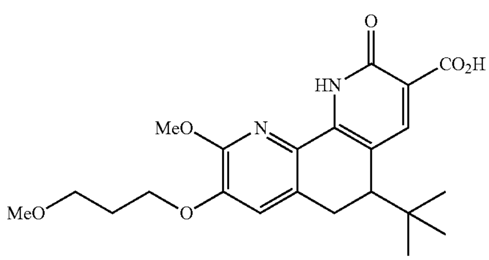 [SMILES: COCCCOc1cc2c(nc1OC)-c1[nH]c(=O)c(C(=O)O)cc1C(C(C)(C)C)C2] | 5-(tert-butyl)-9-methoxy-8-(3-methoxypropoxy)-2-oxo-1,2,5,6-tetrahydro-1,10-phenanthroline-3-carboxylic acid | 0.001 |
| 47 | 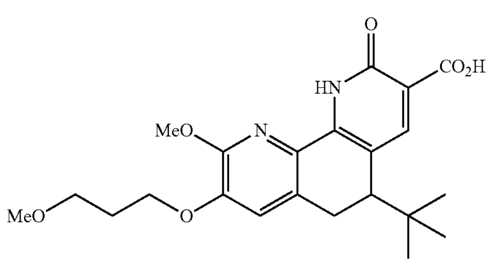 [SMILES: COCCCOc1cc2c(nc1OC)-c1[nH]c(=O)c(C(=O)O)cc1C(C(C)(C)C)C2] | 5-(tert-butyl)-9-methoxy-8-(3-methoxypropoxy)-2-oxo-1,2,5,6-tetrahydro-1,10-phenanthroline-3-carboxylic acid (single enantiomer I) | 0.001 |
| 48 | 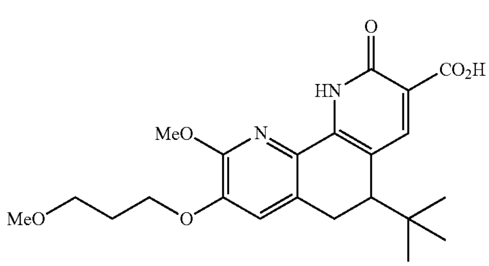 [SMILES: COCCCOc1cc2c(nc1OC)-c1[nH]c(=O)c(C(=O)O)cc1C(C(C)(C)C)C2] | 5-(tert-butyl)-9-methoxy-8-(3-methoxypropoxy)-2-oxo-1,2,5,6-tetrahydro-1,10-phenanthroline-3-carboxylic acid (single enantiomer II) | 0.042 |

TABLE 1-continued

| Ex. No. | Structure | Nomenclature | sAg EC$_{50}$, μM |
|---|---|---|---|
| 49 | 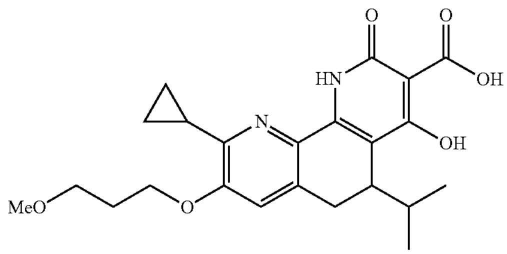 [SMILES: COCCCOc1cc2c(nc1C1CC1)-c1[nH]c(=O)c(C(=O)O)c(O)c1C(C(C)C)C2] | 9-cyclopropyl-4-hydroxy-5-isopropyl-8-(3-methoxypropoxy)-2-oxo-1,2,5,6-tetrahydro-1,10-phenanthroline-3-carboxylic acid | 0.001 |
| 50 | 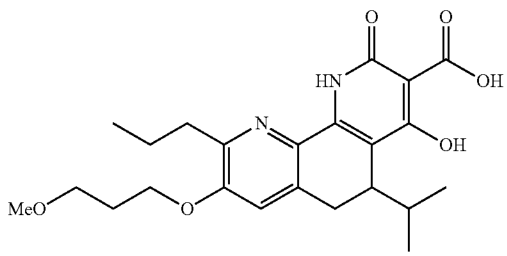 [SMILES: CCCc1nc2c(cc1OCCCOC)CC(C(C)C)c1c-2[nH]c(=O)c(C(=O)O)c1O] | 4-hydroxy-5-isopropyl-8-(3-methoxypropoxy)-2-oxo-9-propyl-1,2,5,6-tetrahydro-1,10-phenanthroline-3-carboxylic acid | 0.002 |
| 51 | 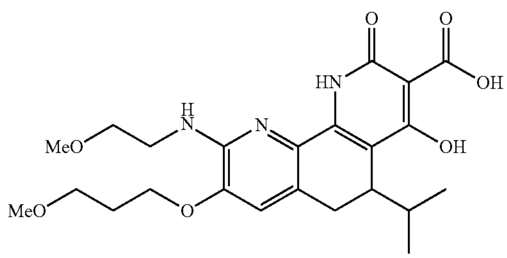 [SMILES: COCCCOc1cc2c(nc1NCCOC)-c1[nH]c(=O)c(C(=O)O)c(O)c1C(C(C)C)C2] | 4-hydroxy-5-isopropyl-9-((2-methoxyethyl)amino)-8-(3-methoxypropoxy)-2-oxo-1,2,5,6-tetrahydro-1,10-phenanthroline-3-carboxylic acid | 10 |
| 52 | 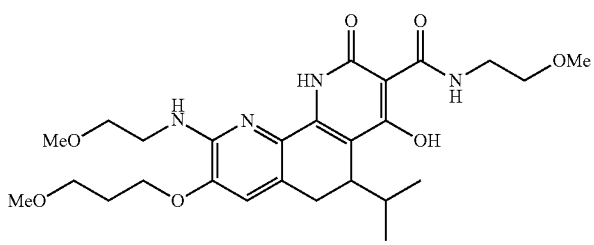 [SMILES: COCCCOc1cc2c(nc1NCCOC)-c1[nH]c(=O)c(C(=O)NCCOC)c(O)c1C(C(C)C)C2] | 4-hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide | 13 |
| 53 | 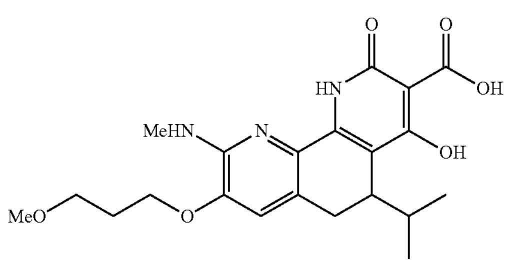 [SMILES: CNc1nc2c(cc1OCCCOC)CC(C(C)C)c1c-2[nH]c(=O)c(C(=O)O)c1O] | 4-hydroxy-5-isopropyl-8-(3-methoxypropoxy)-9-(methylamino)-2-oxo-1,2,5,6-tetrahydro-1,10-phenanthroline-3-carboxylic acid | 0.015 |
| 54 | 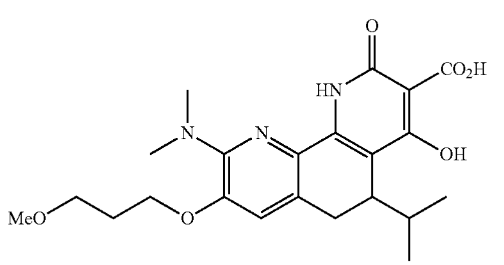 [SMILES: COCCCOc1cc2c(nc1N(C)C)-c1[nH]c(=O)c(C(=O)O)c(O)c1C(C(C)C)C2] | 9-(dimethylamino)-4-hydroxy-5-isopropyl-8-(3-methoxypropoxy)-2-oxo-1,2,5,6-tetrahydro-1,10-phenanthroline-3-carboxylic acid | 0.010 |

TABLE 1-continued

| Ex. No. | Structure | Nomenclature | sAg EC$_{50}$, μM |
|---|---|---|---|
| 55 | 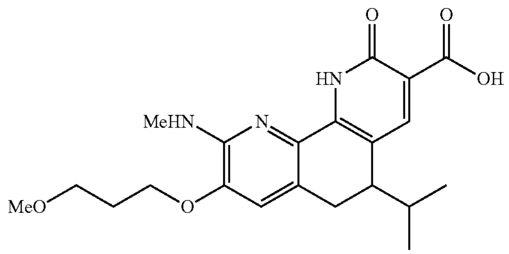 [SMILES: CNc1nc2c(cc1OCCCOC)CC(C(C)C)c1cc(C(=O)O)c(=O)[nH]c1-2] | 5-Isopropyl-8-(3-methoxypropoxy)-9-(methylamino)-2-oxo-1,2,5,6-tetrahydro-1,10-phenanthroline-3-carboxylic acid | 0.002 |
| 56 | 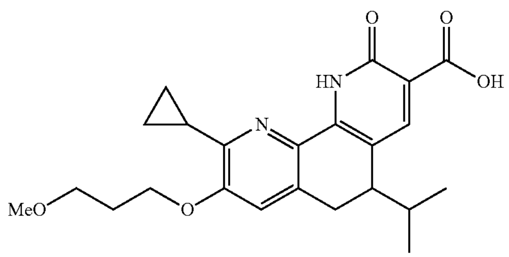 [SMILES: COCCCOc1cc2c(nc1C1CC1)-c1[nH]c(=O)c(C(=O)O)cc1C(C(C)C)C2] | 9-Cyclopropyl-5-isopropyl-8-(3-methoxypropoxy)-2-oxo-1,2,5,6-tetrahydro-1,10-phenanthroline-3-carboxylic acid | 0.001 |
| 57 | 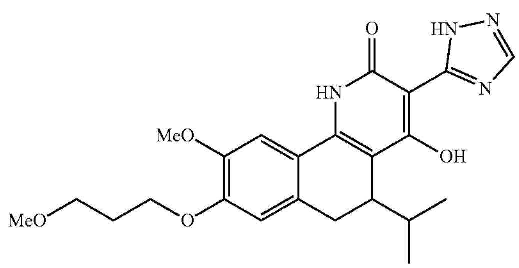 [SMILES: COCCCOc1cc2c(cc1OC)-c1[nH]c(=O)c(-c3ncn[nH]3)c(O)c1C(C(C)C)C2] | 4-hydroxy-5-isopropyl-9-methoxy-8-(3-methoxypropoxy)-3-(1H-1,2,4-triazol-5-yl)-5,6-dihydrobenzo[h]quinolin-2(1H)-one | 0.011 |
| 58 | 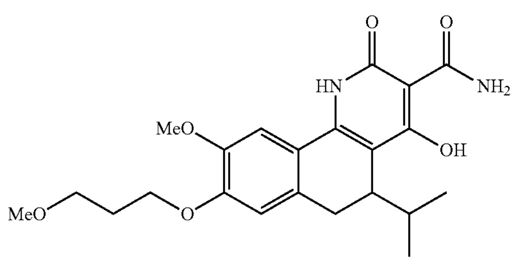 [SMILES: COCCCOc1cc2c(cc1OC)-c1[nH]c(=O)c(C(N)=O)c(O)c1C(C(C)C)C2] | 4-hydroxy-5-isopropyl-9-methoxy-8-(3-methoxypropoxy)-2-oxo-1,2,5,6-tetrahydrobenzo[h]quinoline-3-carboxamide | 0.02 |
| 59 | 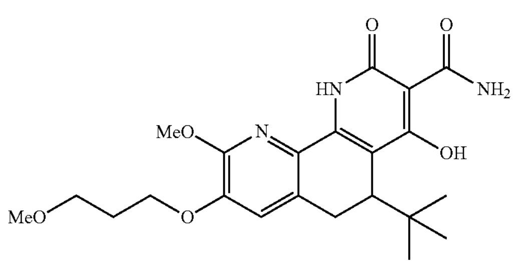 [SMILES: COCCCOc1cc2c(nc1OC)-c1[nH]c(=O)c(C(N)=O)c(O)c1C(C(C)(C)C)C2] | 5-(tert-butyl)-4-hydroxy-9-methoxy-8-(3-methoxypropoxy)-2-oxo-1,2,5,6-tetrahydro-1,10-phenanthroline-3-carboxamide | 0.003 |
| 60 | 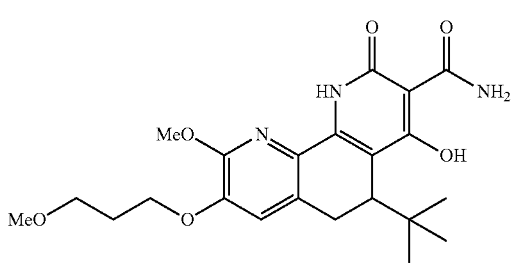 [SMILES: COCCCOc1cc2c(nc1OC)-c1[nH]c(=O)c(C(N)=O)c(O)c1C(C(C)(C)C)C2] | 5-(tert-butyl)-4-hydroxy-9-methoxy-8-(3-methoxypropoxy)-2-oxo-1,2,5,6-tetrahydro-1,10-phenanthroline-3-carboxamide (single enantiomer I) | 0.002 |

TABLE 1-continued

| Ex. No. | Structure | Nomenclature | sAg EC$_{50}$, µM |
|---|---|---|---|
| 61 | 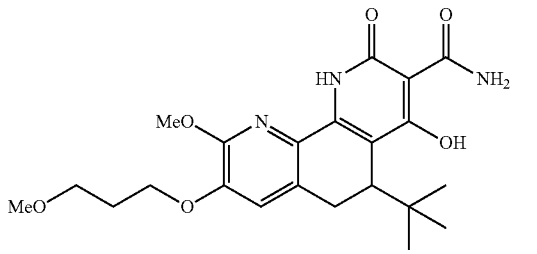 [SMILES: COCCCOc1cc2c(nc1OC)-c1[nH]c(=O)c(C(N)=O)c(O)c1C(C(C)(C)C)C2] | 5-(tert-butyl)-4-hydroxy-9-methoxy-8-(3-methoxypropoxy)-2-oxo-1,2,5,6-tetrahydro-1,10-phenanthroline-3-carboxamide (single enantiomer II) | 0.3 |
| 62 | 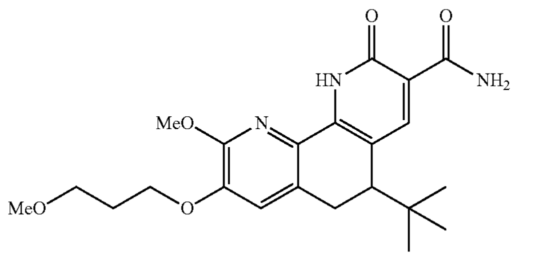 [SMILES: COCCCOc1cc2c(nc1OC)-c1[nH]c(=O)c(C(N)=O)cc1C(C(C)(C)C)C2] | 5-(tert-butyl)-9-methoxy-8-(3-methoxypropoxy)-2-oxo-1,2,5,6-tetrahydro-1,10-phenanthroline-3-carboxamide | 0.025 |
| 63 | 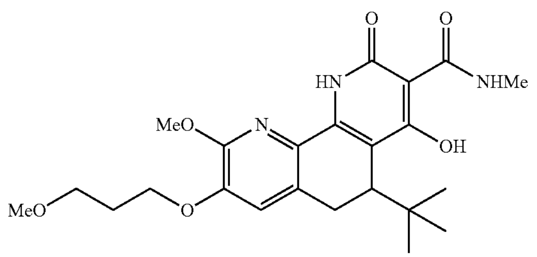 [SMILES: CNC(=O)c1c(O)c2c([nH]c1=O)-c1nc(OC)c(OCCCOC)cc1CC2C(C)(C)C] | 5-(tert-butyl)-4-hydroxy-9-methoxy-8-(3-methoxypropoxy)-N-methyl-2-oxo-1,2,5,6-tetrahydro-1,10-phenanthroline-3-carboxamide | 0.018 |
| 64 | 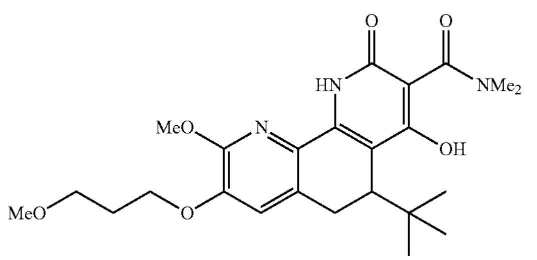 [SMILES: COCCCOc1cc2c(nc1OC)-c1[nH]c(=O)c(C(=O)N(C)C)c(O)c1C(C(C)(C)C)C2] | 5-(tert-butyl)-4-hydroxy-9-methoxy-8-(3-methoxypropoxy)-N,N-dimethyl-2-oxo-1,2,5,6-tetrahydro-1,10-phenanthroline-3-carboxamide | 2 |
| 65 | 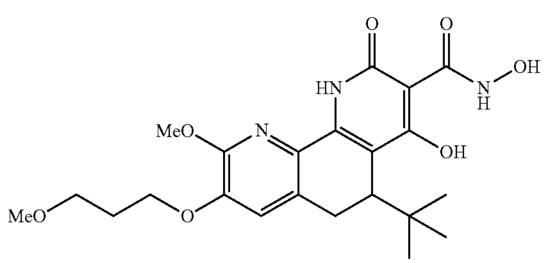 [SMILES: COCCCOc1cc2c(nc1OC)-c1[nH]c(=O)c(C(=O)NO)c(O)c1C(C(C)(C)C)C2] | 5-(tert-butyl)-N,4-dihydroxy-9-methoxy-8-(3-methoxypropoxy)-2-oxo-1,2,5,6-tetrahydro-1,10-phenanthroline-3-carboxamide | 0.002 |
| 66 | 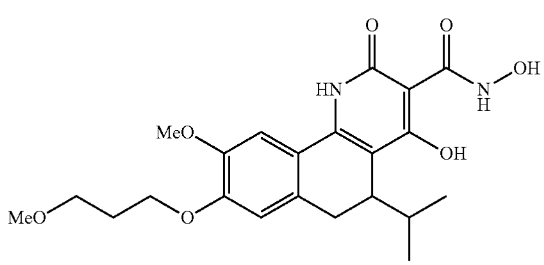 [SMILES: COCCCOc1cc2c(cc1OC)-c1[nH]c(=O)c(C(=O)NO)c(O)c1C(C(C)C)C2] | N,4-dihydroxy-5-isopropyl-9-methoxy-8-(3-methoxypropoxy)-2-oxo-1,2,5,6-tetrahydrobenzo[h]quinoline-3-carboxamide | 0.041 |

TABLE 1-continued

| Ex. No. | Structure | Nomenclature | sAg EC$_{50}$, μM |
|---|---|---|---|
| 67 | 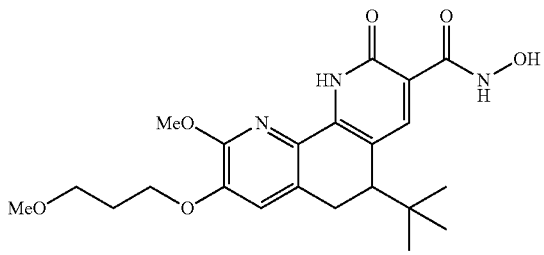 [SMILES: COCCCOc1cc2c(nc1OC)-c1[nH]c(=O)c(C(=O)NO)cc1C(C(C)(C)C)C2] | 5-(tert-butyl)-N-hydroxy-9-methoxy-8-(3-methoxypropoxy)-2-oxo-1,2,5,6-tetrahydro-1,10-phenanthroline-3-carboxamide | 0.005 |
| 68 | 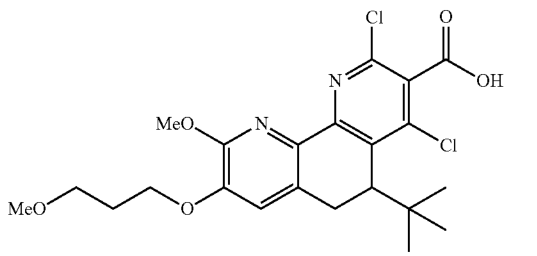 [SMILES: COCCCOc1cc2c(nc1OC)-c1nc(Cl)c(C(=O)O)c(Cl)c1C(C(C)(C)C)C2] | 5-(tert-butyl)-2,4-dichloro-9-methoxy-8-(3-methoxypropoxy)-5,6-dihydro-1,10-phenanthroline-3-carboxylic acid | 10 |
| 69 | 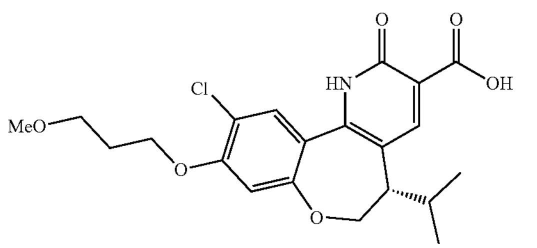 [SMILES: COCCCOc1cc2c(cc1Cl)-c1[nH]c(=O)c(C(=O)O)cc1[C@H](C(C)C)CO2] | (S)-10-chloro-5-isopropyl-9-(3-methoxypropoxy)-2-oxo-1,2,5,6-tetrahydrobenzo[2,3]oxepino[4,5-b]pyridine-3-carboxylic acid | 0.2 |
| 70 | 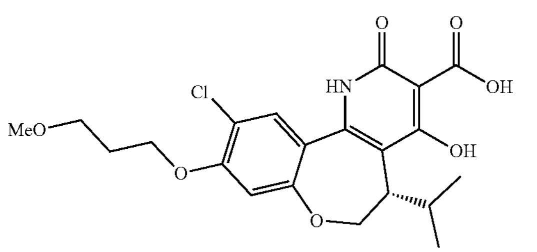 [SMILES: COCCCOc1cc2c(cc1Cl)-c1[nH]c(=O)c(C(=O)O)c(O)c1[C@H](C(C)C)CO2] | (S)-10-chloro-4-hydroxy-5-isopropyl-9-(3-methoxypropoxy)-2-oxo-1,2,5,6-tetrahydrobenzo[2,3]oxepino[4,5-b]pyridine-3-carboxylic acid | 0.12 |
| 71 | 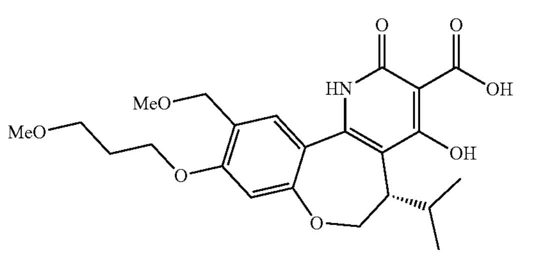 [SMILES: COCCCOc1cc2c(cc1COC)-c1[nH]c(=O)c(C(=O)O)c(O)c1[C@H](C(C)C)CO2] | (S)-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylic acid | 0.28 |
| 72 | 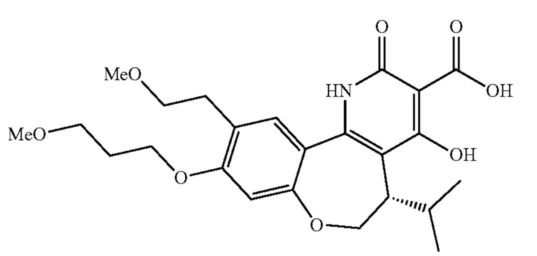 [SMILES: COCCCOc1cc2c(cc1CCOC)-c1[nH]c(=O)c(C(=O)O)c(O)c1[C@H](C(C)C)CO2] | (S)-4-hydroxy-5-isopropyl-10-(2-methoxyethyl)-9-(3-methoxypropoxy)-2-oxo-1,2,5,6-tetrahydrobenzo[2,3]oxepino[4,5-b]pyridine-3-carboxylic acid | 0.6 |

TABLE 1-continued

| Ex. No. | Structure | Nomenclature | sAg EC$_{50}$, μM |
|---|---|---|---|
| 73 | 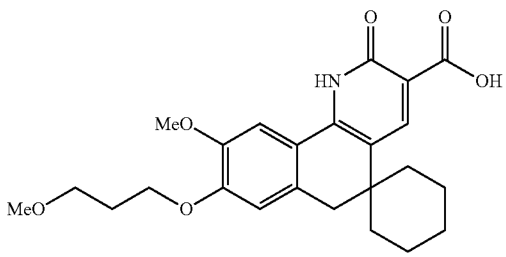 [SMILES: COCCCOc1cc2c(cc1OC)-c1[nH]c(=O)c(C(=O)O)cc1C1(CCCCC1)C2] | 9-methoxy-8-(3-methoxypropoxy)-2-oxo-2,6-dihydro-1H-spiro[benzo[h]quinoline-5,1'-cyclohexane]-3-carboxylic acid | 0.11 |
| 74 | 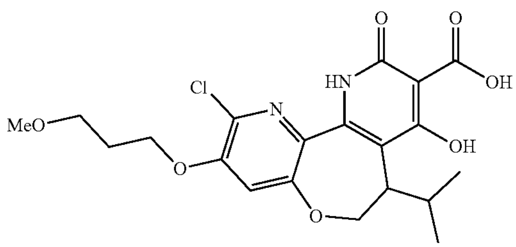 [SMILES: COCCCOc1cc2c(nc1Cl)-c1[nH]c(=O)c(C(=O)O)c(O)c1C(C(C)C)CO2] | 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid | 0.04 |
| 75 | 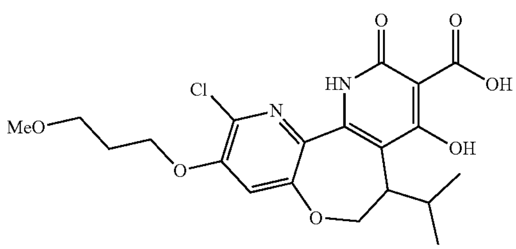 [SMILES: COCCCOc1cc2c(nc1Cl)-c1[nH]c(=O)c(C(=O)O)c(O)c1C(C(C)C)CO2] | 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid (single enantiomer I) | 0.022 |
| 76 | 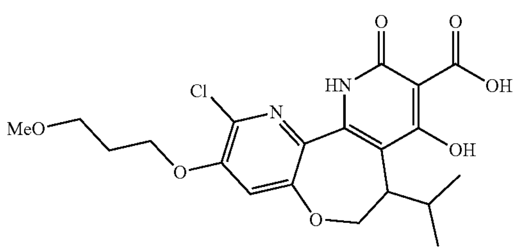 [SMILES: COCCCOc1cc2c(nc1Cl)-c1[nH]c(=O)c(C(=O)O)c(O)c1C(C(C)C)CO2] | 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid (single enantiomer II) | 0.56 |
| 77 | 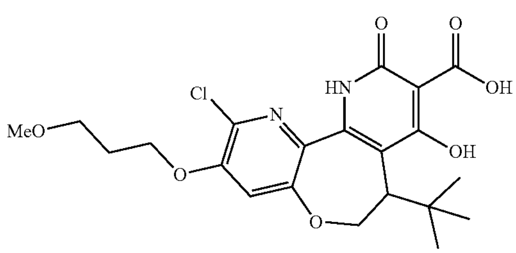 [SMILES: COCCCOc1cc2c(nc1Cl)-c1[nH]c(=O)c(C(=O)O)c(O)c1C(C(C)(C)C)CO2] | 7-(tert-butyl)-2-chloro-8-hydroxy-3-(3-methoxypropoxy)-10-oxo-6,7,10,11-tetrahydrooxepino[3,2-b:4,5-b']dipyridine-9-carboxylic acid (single enantiomer I) | 0.006 |
| 78 | 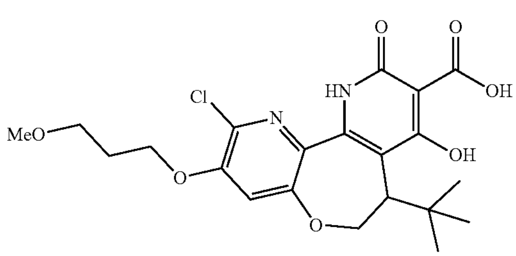 [SMILES: COCCCOc1cc2c(nc1Cl)-c1[nH]c(=O)c(C(=O)O)c(O)c1C(C(C)(C)C)CO2] | 7-(tert-butyl)-2-chloro-8-hydroxy-3-(3-methoxypropoxy)-10-oxo-6,7,10,11-tetrahydrooxepino[3,2-b:4,5-b']dipyridine-9-carboxylic acid (single enantiomer II) | 6 |

TABLE 1-continued

| Ex. No. | Structure | Nomenclature | sAg EC$_{50}$, μM |
|---|---|---|---|
| 79 | 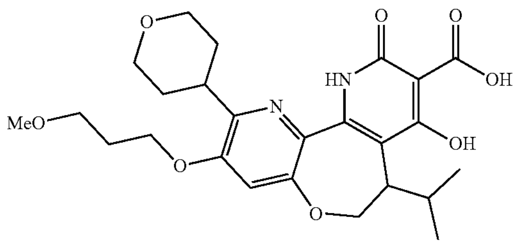 [SMILES: COCCCOc1cc2c(nc1C1CCOCC1)-c1[nH]c(=O)c(C(=O)O)c(O)c1C(C(C)C)CO2] | 8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylic acid | 5 |
| 80 | 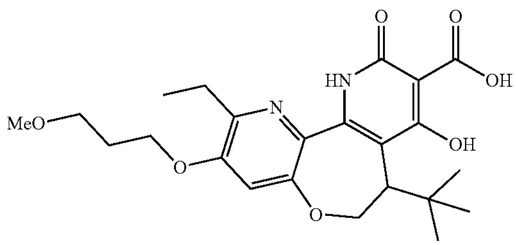 [SMILES: CCc1nc2c(cc1OCCCOC)OCC(C(C)(C)C)c1c-2[nH]c(=O)c(C(=O)O)c1O] | 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylic acid (single enantiomer I) | 7 |
| 81 | 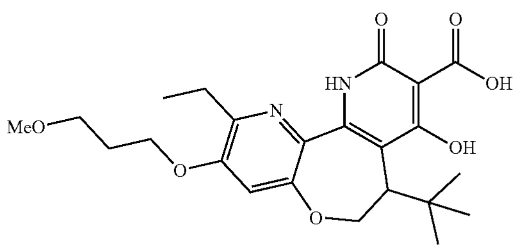 [SMILES: CCc1nc2c(cc1OCCCOC)OCC(C(C)(C)C)c1c-2[nH]c(=O)c(C(=O)O)c1O] | 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylic acid (single enantiomer II) | 0.004 |
| 82 | 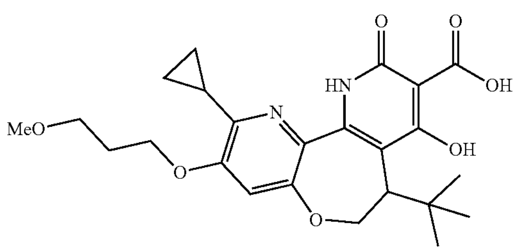 [SMILES: COCCCOc1cc2c(nc1C1CC1)-c1[nH]c(=O)c(C(=O)O)c(O)c1C(C(C)(C)C)CO2] | 7-(tert-butyl)-2-cyclopropyl-8-hydroxy-3-(3-methoxypropoxy)-10-oxo-6,7,10,11-tetrahydrooxepino[3,2-b:4,5-b']dipyridine-9-carboxylic acid (single enantiomer I) | 30 |
| 83 | 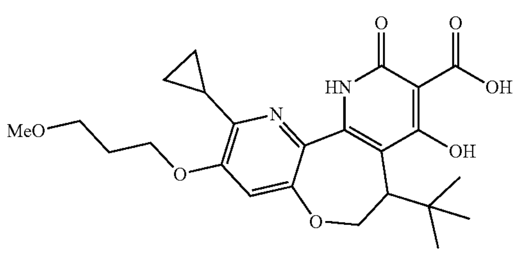 [SMILES: COCCCOc1cc2c(nc1C1CC1)-c1[nH]c(=O)c(C(=O)O)c(O)c1C(C(C)(C)C)CO2] | 7-(tert-butyl)-2-cyclopropyl-8-hydroxy-3-(3-methoxypropoxy)-10-oxo-6,7,10,11-tetrahydrooxepino[3,2-b:4,5-b']dipyridine-9-carboxylic acid (single enantiomer II) | 0.015 |
| 84 | 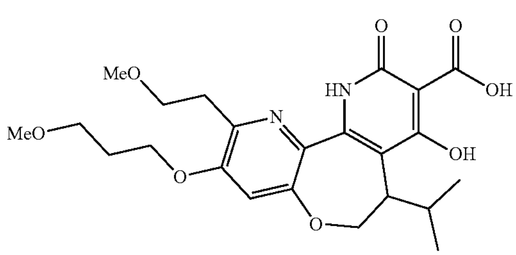 [SMILES: COCCCOc1cc2c(nc1CCOC)-c1[nH]c(=O)c(C(=O)O)c(O)c1C(C(C)C)CO2] | 8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylic acid | 1.2 |

TABLE 1-continued

| Ex. No. | Structure | Nomenclature | sAg EC$_{50}$, µM |
|---|---|---|---|
| 85 | 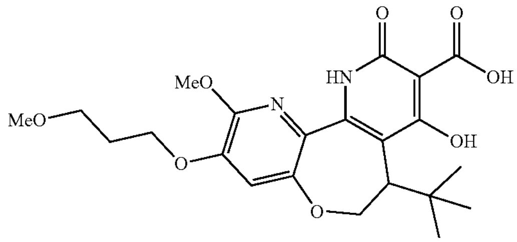 [SMILES: COCCCOc1cc2c(nc1OC)-c1[nH]c(=O)c(C(=O)O)c(O)c1C(C(C)(C)C)CO2] | 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylic acid (single enantiomer I) | 0.066 |
| 86 | 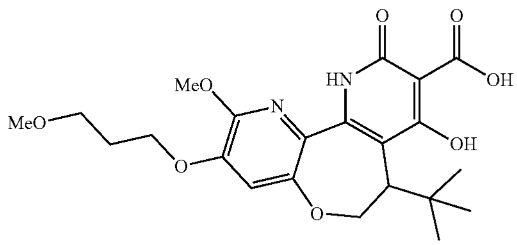 [SMILES: COCCCOc1cc2c(nc1OC)-c1[nH]c(=O)c(C(=O)O)c(O)c1C(C(C)(C)C)CO2] | 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylic acid (single enantiomer II) | 30 |
| 87 | 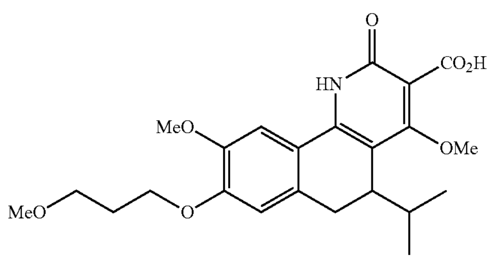 [SMILES: COCCCOc1cc2c(cc1OC)-c1[nH]c(=O)c(C(=O)O)c(OC)c1C(C(C)C)C2] | 5-isopropyl-4,9-dimethoxy-8-(3-methoxypropoxy)-2-oxo-1,2,5,6-tetrahydrobenzo[h]quinoline-3-carboxylic acid | 0.085 |
| 88 | 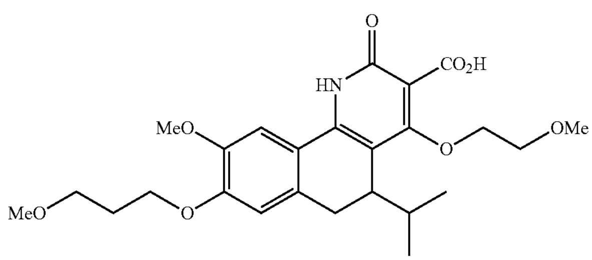 [SMILES: COCCCOc1cc2c(cc1OC)-c1[nH]c(=O)c(C(=O)O)c(OCCOC)c1C(C(C)C)C2] | 5-isopropyl-9-methoxy-4-(2-methoxyethoxy)-8-(3-methoxypropoxy)-2-oxo-1,2,5,6-tetrahydrobenzo[h]quinoline-3-carboxylic acid | 4.7 |
| 89 | 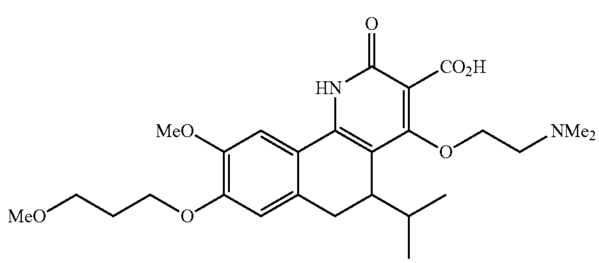 [SMILES: COCCCOc1cc2c(cc1OC)-c1[nH]c(=O)c(C(=O)O)c(OCCN(C)C)c1C(C(C)C)C2] | 4-(2-(dimethylamino)ethoxy)-5-isopropyl-9-methoxy-8-(3-methoxypropoxy)-2-oxo-1,2,5,6-tetrahydrobenzo[h]quinoline-3-carboxylic acid | 4.6 |
| 90 | 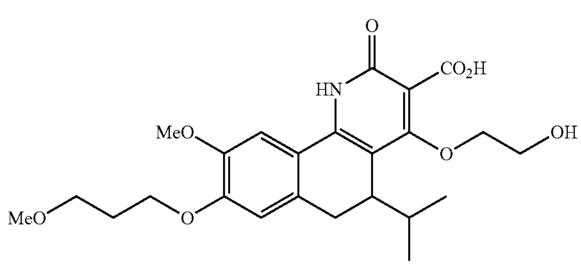 [SMILES: COCCCOc1cc2c(cc1OC)-c1[nH]c(=O)c(C(=O)O)c(OCCO)c1C(C(C)C)C2] | 4-(2-hydroxyethoxy)-5-isopropyl-9-methoxy-8-(3-methoxypropoxy)-2-oxo-1,2,5,6-tetrahydrobenzo[h]quinoline-3-carboxylic acid | 11 |

TABLE 1-continued

| Ex. No. | Structure | Nomenclature | sAg EC$_{50}$, μM |
|---|---|---|---|
| 91 | 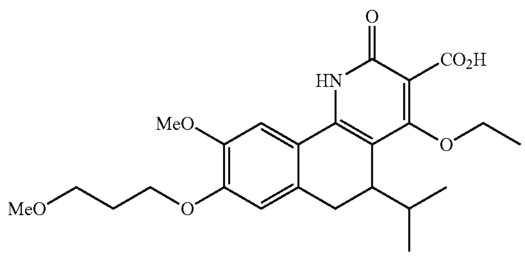 [SMILES: CCOc1c2c([nH]c(=O)c1C(=O)O)-c1cc(OC)c(OCCCOC)cc1CC2C(C)C] | 4-ethoxy-5-isopropyl-9-methoxy-8-(3-methoxypropoxy)-2-oxo-1,2,5,6-tetrahydrobenzo[h]quinoline-3-carboxylic acid | 1.7 |
| 92 | 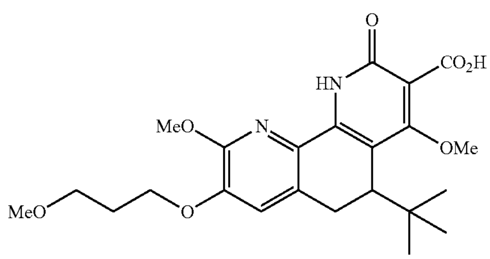 | 5-(tert-butyl)-4,9-dimethoxy-8-(3-methoxypropoxy)-2-oxo-1,2,5,6-tetrahydro-1,10-phenanthroline-3-carboxylic acid | 0.64 |
| 93 | 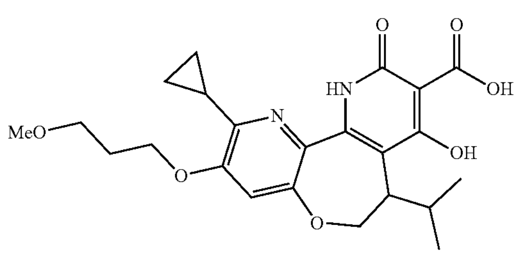 [SMILES: COCCCOc1cc2c(nc1C1CC1)-c1[nH]c(=O)c(C(=O)O)c(O)c1C(C(C)C)CO2] | 2-cyclopropyl-8-hydroxy-7-isopropyl-3-(3-methoxypropoxy)-10-oxo-6,7,10,11-tetrahydrooxepino[3,2-b:4,5-b']dipyridine-9-carboxylic acid | 0.12 |
| 94 | 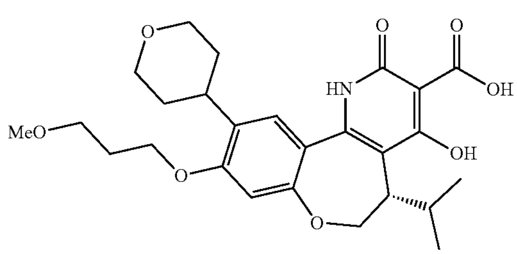 [SMILES: COCCCOc1cc2c(cc1C1CCOCC1)-c1[nH]c(=O)c(C(=O)O)c(O)c1[C@H](C(C)C)CO2] | (S)-4-hydroxy-5-isopropyl-9-(3-methoxypropoxy)-2-oxo-10-(tetrahydro-2H-pyran-tetrahydrobenzo[2,3]oxepino[4,5-b]pyridine-3-carboxylic acid | 0.73 |

Enumerated Embodiments

The following enumerated embodiments are provided, the numbering of which is not to be construed as designating levels of importance.

Embodiment 1 provides a compound of formula (Ib), or a salt, solvate, geometric isomer, stereoisomer, tautomer, and any mixtures thereof:

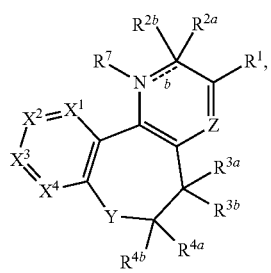

(Ib)

wherein:
Z is selected from the group consisting of N and $CR^{12}$;
$R^1$ is selected from the group consisting of H; halo; —C(=O)$R^8$; —C(=O)NH$R^8$; —C(=O)NH—O$R^8$; —C(=O)NHNH$R^8$; —C(=O)NHNHC(=O)$R^8$; —C(=O)NHS(=O)$_2R^8$; —CN; and 1H-1,2,4-triazol-5-yl;
$R^{2a}$, $R^{2b}$, and $R^7$ are selected such that:
  (i) $R^{2a}$ and $R^{2b}$ combine to form =O; bond b is a single bond; and $R^7$ is selected from the group consisting of H, optionally substituted $C_1$-$C_6$ alkyl, and optionally substituted $C_3$-$C_8$ cycloalkyl; or
  (ii) $R^{2a}$ is selected from the group consisting of H, halogen, and optionally substituted $C_1$-$C_6$ alkoxy; $R^{2b}$ is null; bond b is a double bond; and $R^7$ is null;
Y is selected from the group consisting of CH$R^5$ and O;
$R^{3a}$, $R^{3b}$, $R^{4a}$, and $R^{4b}$ are each independently selected from the group consisting of H, optionally substituted $C_1$-$C_6$ alkyl, and optionally substituted $C_3$-$C_8$ cycloalkyl;
  or one pair selected from the group consisting of $R^{3a}$/$R^{3b}$, $R^{4a}$/$R^{4b}$, and $R^{3a}$/$R^{4a}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and wherein each divalent group is optionally substituted with at least one $C_1$-$C_6$ alkyl or halo;
each occurrence of $R^5$ is independently selected from the group consisting of H, optionally substituted $C_1$-$C_6$ alkyl, and optionally substituted $C_3$-$C_8$ cycloalkyl;
$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;
or either $X^3$ and $X^4$, or $X^1$ and $X^2$, combine to form —S—;
wherein 0-2 substituents selected from the group consisting of $X^1$, $X^2$, $X^3$, and $X^4$ are N, each of which, if present, is optionally substituted with $C_1$-$C_6$ alkyl if the adjacent carbon atom in the ring is substituted with —OH;
$R^{6I}$, $R^{6II}$, $R^{6III}$, and $R^{6IV}$ are independently selected from the group consisting of H, halo, —CN, optionally substituted $C_1$-$C_6$ alkyl, optionally substituted $C_3$-$C_8$ cycloalkyl, —OR, —N(R)(R), optionally substituted heterocyclyl, and $C_1$-$C_6$ haloalkoxy,
  wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl,
  wherein each occurrence of R' is independently selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, or a 5- or 6-membered heterocyclic group, which is optionally N-linked;
  or $X^2$ is $CR^{6II}$, $X^3$ is $CR^{6III}$, and $R^{6II}$ and $R^{6III}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;
  or $X^3$ is $CR^{6III}$, $X^4$ is $CR^{6IV}$, and $R^{6III}$ and $R^{6IV}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;
each occurrence of $R^8$ is independently selected from the group consisting of H, optionally substituted $C_1$-$C_6$ alkyl, and optionally substituted $C_3$-$C_8$ cycloalkyl;
each occurrence of $R^9$ is independently selected from the group consisting of H and $C_1$-$C_6$ alkyl;
each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; wherein $R^{11}$ is not OH if it is bound to a carbon that is further bound to an oxygen atom;
  or two $R^{11}$ groups combine with the carbon atom to which they are bound to form a moiety selected from the group consisting of C=O, C=CH$_2$ and oxetane-3,3-diyl; and
$R^{12}$ is selected from the group consisting of H, OH, halo, optionally substituted $C_1$-$C_6$ alkoxy, optionally substituted $C_1$-$C_6$ alkyl, and optionally substituted $C_3$-$C_8$ cycloalkyl.

Embodiment 2 provides the compound of Embodiment 1, which is selected from the group consisting of:

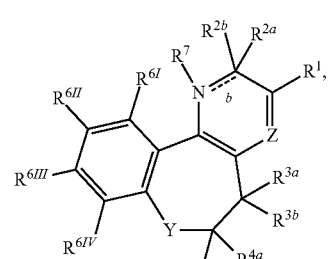

(Ic)

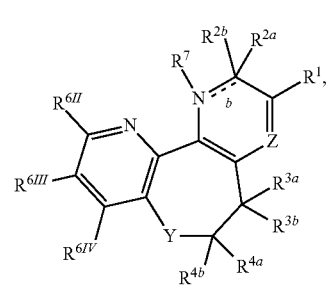

(Id)

-continued
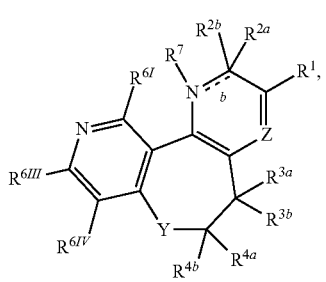
(Ie)
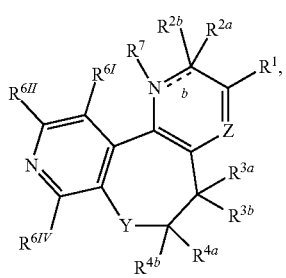
(If)
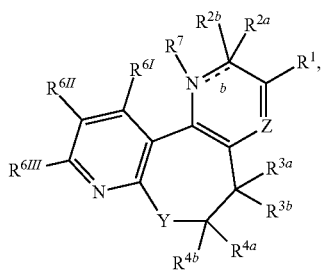
(Ig)
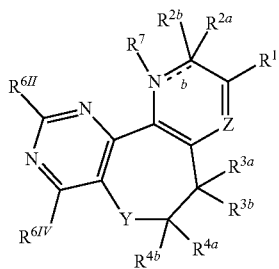
(Ih)
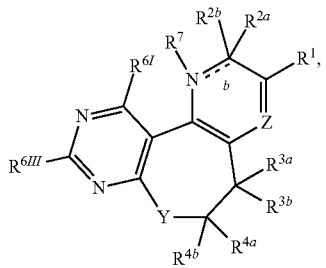
(Ii)
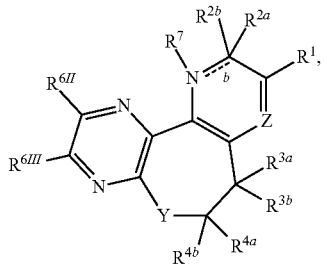
(Ij)
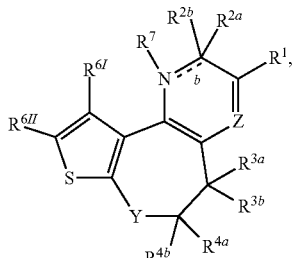
(Ik)
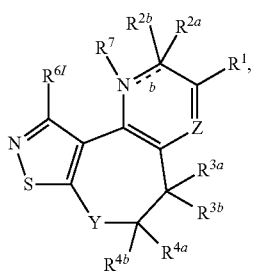
(Il)
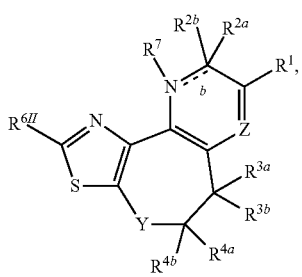
(Im)
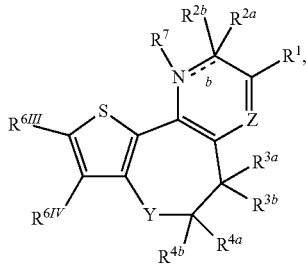
(In)
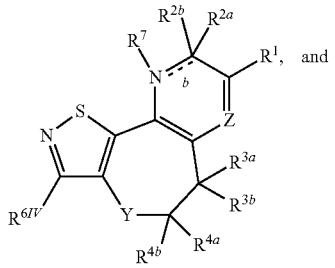
(Io)
and (Ip)

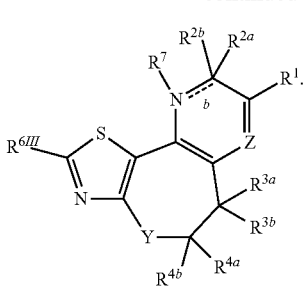

Embodiment 3 provides the compound of formula (II), or a salt, solvate, geometric isomer, stereoisomer, tautomer and any mixtures thereof:

(II)

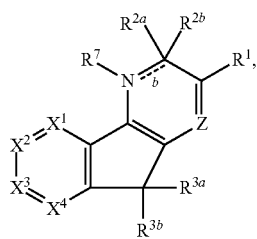

wherein:
Z is selected from the group consisting of N and $CR^{12}$;
$R^1$ is selected from the group consisting of H; halo; —C(=O)$OR^8$; —C(=O)$NHR^8$; —C(=O)NH—$OR^8$; —C(=O)$NHNHR^8$; —C(=O)NHNHC(=O)$R^8$; —C(=O)NHS(=O)$_2R^8$; —CN; and 1H-1,2,4-triazol-5-yl;
$R^{2a}$, $R^{2b}$, and $R^7$ are selected such that:
(i) $R^{2a}$ and $R^{2b}$ combine to form =O; bond b is a single bond; and $R^7$ is selected from the group consisting of H, optionally substituted $C_1$-$C_6$ alkyl, and optionally substituted $C_3$-$C_8$ cycloalkyl; or
(ii) $R^{2a}$ is selected from the group consisting of H, halogen, and optionally substituted $C_1$-$C_6$ alkoxy; $R^{2b}$ is null; bond b is a double bond; and $R^7$ is null;
$R^{3a}$ and $R^{3b}$ are each independently selected from the group consisting of H, optionally substituted $C_1$-$C_6$ alkyl, and optionally substituted $C_3$-$C_8$ cycloalkyl;
or $R^{3a}$ and $R^{3b}$ combine to form a divalent group selected from the group consisting of $C_1$-$C_6$ alkanediyl, —(CH$_2$)$_n$O(CH$_2$)$_n$—, —(CH$_2$)$_n$NR(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and wherein each divalent group is optionally substituted with at least one $C_1$-$C_6$ alkyl or halo;
$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;
wherein 0-2 substituents selected from the group consisting of $X^1$, $X^2$, $X^3$ and $X^4$ are N, each of which, if present, is optionally substituted with $C_1$-$C_6$ alkyl if the adjacent carbon atom in the ring is substituted with —OH;
$R^{6I}$, $R^{6II}$, $R^{6III}$ and $R^{6IV}$ are independently selected from the group consisting of H, halo, —CN, optionally substituted $C_1$-$C_6$ alkyl, optionally substituted $C_3$-$C_8$ cycloalkyl, —OR, —N(R)(R), optionally substituted heterocyclyl, and $C_1$-$C_6$ haloalkoxy,
wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl,
wherein each occurrence of R' is independently selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, and a 5- or 6-membered heterocyclic group, which is optionally N-linked;
or $X^2$ is $CR^{6II}$, $X^3$ is $CR^{6III}$, and $R^{6II}$ and $R^{6III}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;
or $X^3$ is $CR^{6III}$, $X^4$ is $CR^{6IV}$, and $R^{6III}$ and $R^{6IV}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;
each occurrence of $R^8$ is independently selected from the group consisting of H, optionally substituted $C_1$-$C_6$ alkyl, and optionally substituted $C_3$-$C_8$ cycloalkyl;
each occurrence of $R^9$ is independently selected from the group consisting of H and $C_1$-$C_6$ alkyl;
each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; and wherein $R^{11}$ is not OH if it is bound to a carbon that is further bound to an oxygen atom;
or two $R^{11}$ groups combine with the carbon atom to which they are bound to form a moiety selected from the group consisting of C=O, C=CH$_2$ and oxetane-3,3-diyl; and
$R^{12}$ is selected from the group consisting of H, OH, halo, optionally substituted $C_1$-$C_6$ alkoxy, optionally substituted $C_1$-$C_6$ alkyl, and optionally substituted $C_3$-$C_8$ cycloalkyl.

Embodiment 4 provides the compound of Embodiment 3, which is selected from the group consisting of:

(IIa)

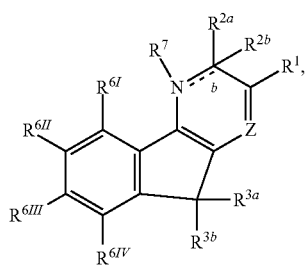

(IIb)

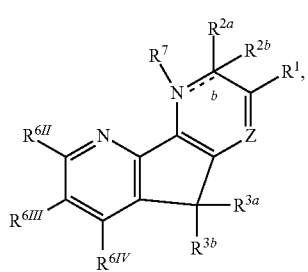

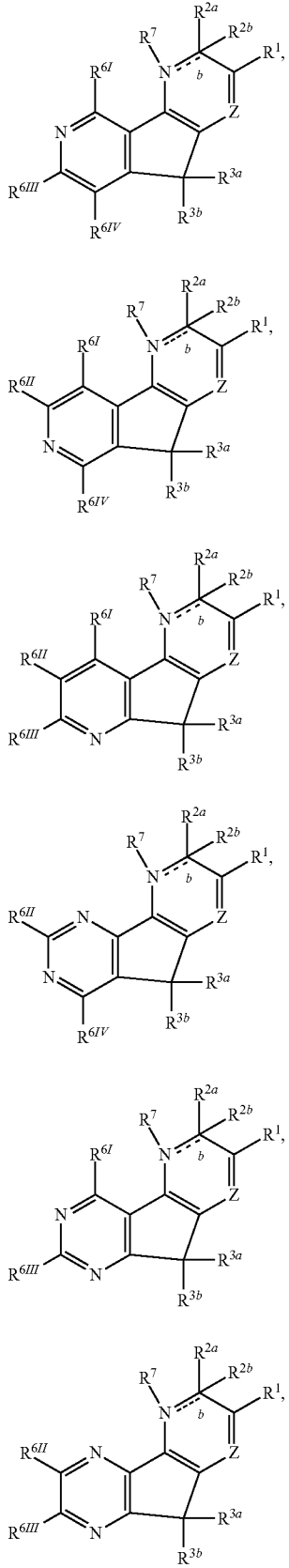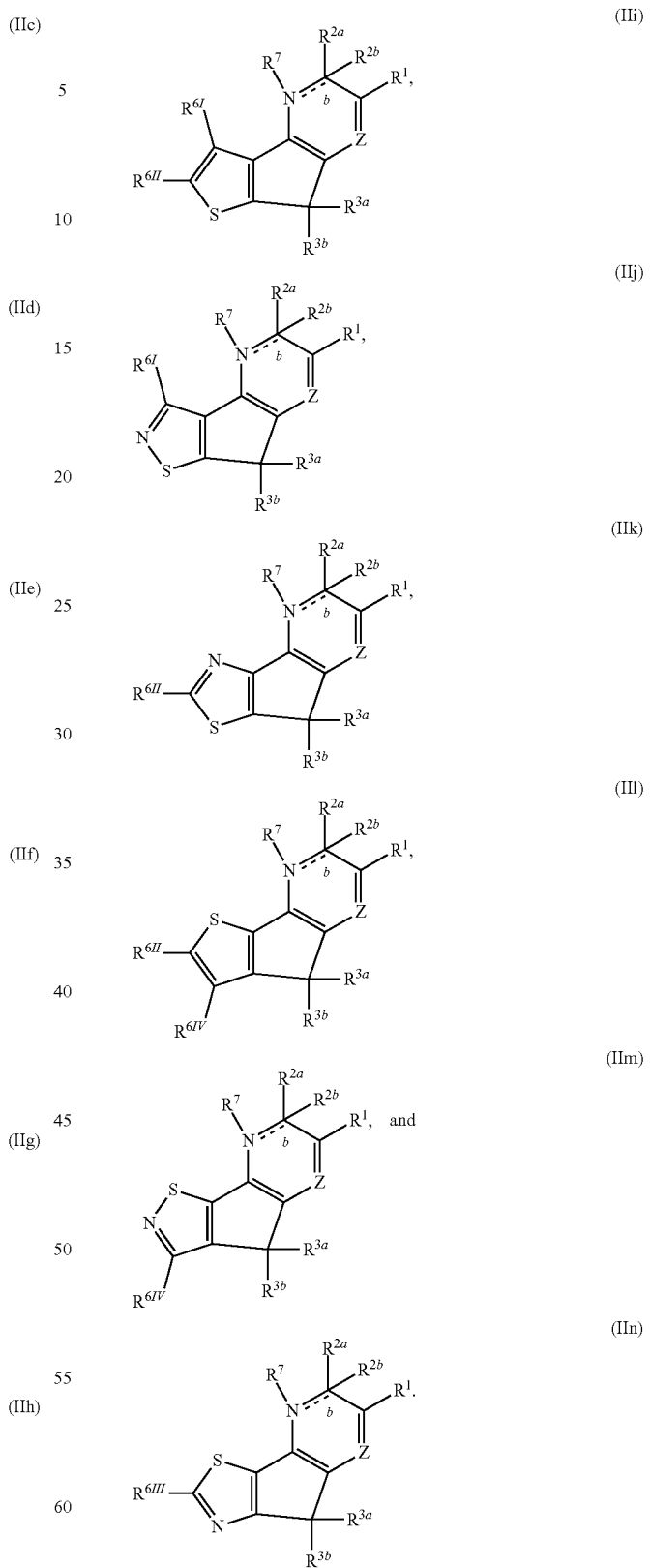
Embodiment 5 provides a compound of formula (III), or a salt, solvate, geometric isomer, stereoisomer, tautomer and any mixtures thereof:

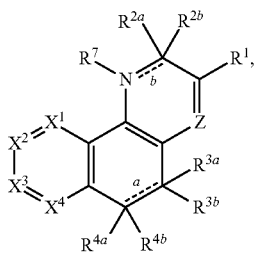

(III)

Z is selected from the group consisting of N and $CR^{12}$;

$R^1$ is selected from the group consisting of H; halo; —C(=O)$OR^8$; —C(=O)$NHR^8$; —C(=O)NH—$OR^8$; —C(=O)$NHNHR^8$; —C(=O)NHNHC(=O)$R^8$; —C(=O)NHS(=O)$_2R^8$; —CN; and 1H-1,2,4-triazol-5-yl;

$R^{2a}$, $R^{2b}$, and $R^7$ are selected such that:
(i) $R^{2a}$ and $R^{2b}$ combine to form =O; bond b is a single bond; and $R^7$ is selected from the group consisting of H, optionally substituted $C_1$-$C_6$ alkyl, and optionally substituted $C_3$-$C_8$ cycloalkyl; or
(ii) $R^{2a}$ is selected from the group consisting of H, halogen, and optionally substituted $C_1$-$C_6$ alkoxy; $R^{2b}$ is null; bond b is a double bond; and $R^7$ is null;

$R^{3a}$, $R^{3b}$, $R^{4a}$, and $R^{4b}$ are each independently selected from the group consisting of H, optionally substituted $C_1$-$C_6$ alkyl, and optionally substituted $C_3$—C cycloalkyl;
or one pair selected from the group consisting of $R^{3a}$/$R^{3b}$, $R^{4a}$/$R^{4b}$, and $R^{3a}$/$R^{4a}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and wherein each divalent group is optionally substituted with at least one $C_1$-$C_6$ alkyl or halo;

bond a is single; or bond a is double and $R^{3b}$ and $R^{4b}$ are both null;

$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;
or either $X^3$ and $X^4$, or $X^1$ and $X^2$, combine to form —S—;
wherein 0-2 substituents selected from the group consisting of $X^1$, $X^2$, $X^3$ and $X^4$ are N, each of which, if present, is optionally substituted with $C_1$-$C_6$ alkyl if the adjacent carbon atom in the ring is substituted with —OH;

$R^{6I}$, $R^{6II}$, $R^{6III}$, and $R^{6IV}$ are independently selected from the group consisting of H, halo, —CN, optionally substituted $C_1$-$C_6$ alkyl, optionally substituted $C_3$-$C_8$ cycloalkyl, —OR, —N(R)(R), optionally substituted heterocyclyl, and $C_1$-$C_6$ haloalkoxy,
wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl,
wherein each occurrence of R' is selected from the group consisting of —NH$_2$, —NH($C_1$-$C_6$ alkyl), —N($C_1$-$C_6$ alkyl)($C_1$-$C_6$ alkyl), —NHC(=O)O'Bu, —N($C_1$-$C_6$ alkyl)C(=O)O'Bu, and a 5- or 6-membered heterocyclic group, which is optionally N-linked;

or $X^2$ is $CR^{6II}$, $X^3$ is $CR^{6III}$, and $R^{6II}$ and $R^{6III}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;

or $X^3$ is $CR^{6III}$, $X^4$ is $CR^{6IV}$, and $R^{6III}$ and $R^{6IV}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;

each occurrence of $R^8$ is independently selected from the group consisting of H, optionally substituted $C_1$-$C_6$ alkyl, and optionally substituted $C_3$-$C_8$ cycloalkyl;

each occurrence of $R^9$ is independently selected from the group consisting of H and $C_1$-$C_6$ alkyl;

each occurrence of $R^{11}$ is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; and wherein $R^{11}$ is not OH if it is bound to a carbon that is further bound to an oxygen atom;
or two $R^{11}$ groups combine with the carbon atom to which they are bound to form a moiety selected from the group consisting of C=O, C=CH$_2$ and oxetane-3,3-diyl;

$R^{12}$ is selected from the group consisting of H, OH, halo, optionally substituted $C_1$-$C_6$ alkoxy, optionally substituted $C_1$-$C_6$ alkyl, and optionally substituted $C_3$-$C_8$ cycloalkyl.

Embodiment 6 provides the compound of Embodiment 5, which is selected from the group consisting of:

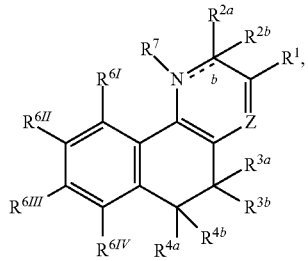

(IIIa)

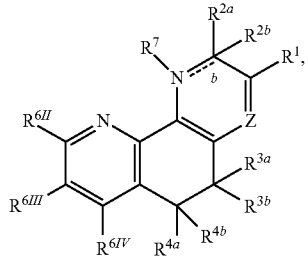

(IIIb)

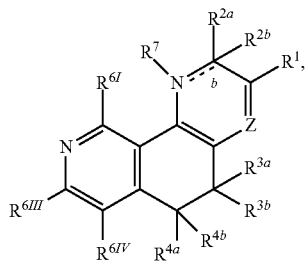

(IIIc)

(IIId) 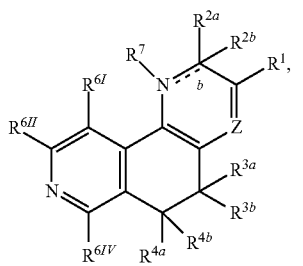

(IIIe) 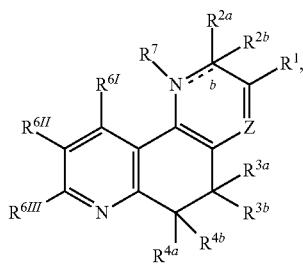

(IIIf) 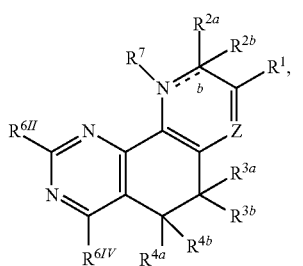

(IIIg) 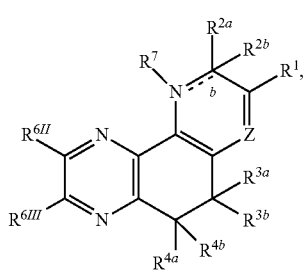

(IIIh) 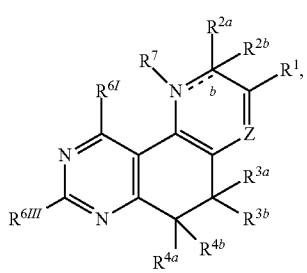

(IIIi) 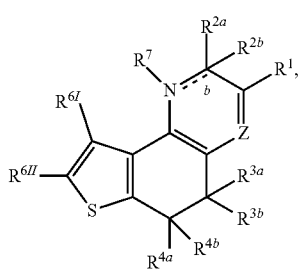

(IIIj) 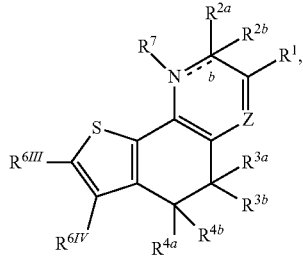

(IIIk) 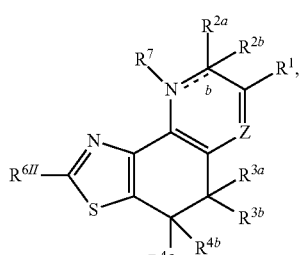

(IIIl) 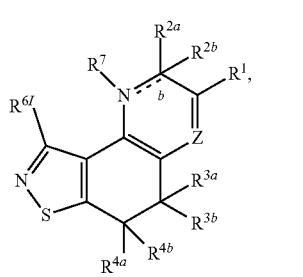

(IIIm) 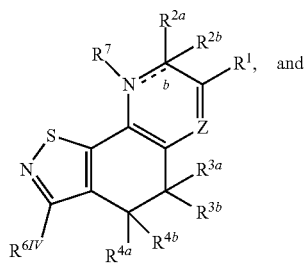

and (IIIn) 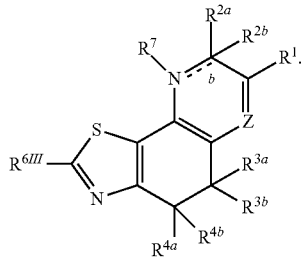

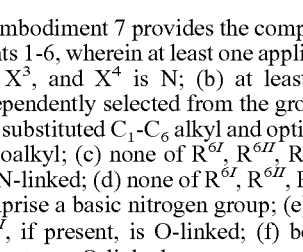

Embodiment 7 provides the compound of any of Embodiments 1-6, wherein at least one applies: (a) at least one of $X^1$, $X^2$, $X^3$, and $X^4$ is N; (b) at least one of $R^{3a}$ or $R^{3b}$ is independently selected from the group consisting of optionally substituted $C_1$-$C_6$ alkyl and optionally substituted $C_3$-$C_8$ cycloalkyl; (c) none of $R^{6I}$, $R^{6II}$, $R^{6III}$ and $R^{6IV}$, if present, are N-linked; (d) none of $R^{6I}$, $R^{6II}$, $R^{6III}$ and $R^{6IV}$, if present, comprise a basic nitrogen group; (e) at least one of $R^{6II}$ and $R^{6III}$, if present, is O-linked; (f) both of $R^{6II}$ and $R^{6III}$, if present, are O-linked.

Embodiment 8 provides the compound of any of Embodiments 1-7, wherein each occurrence of alkyl, alkenyl, or cycloalkyl is independently optionally substituted with at least one substituent selected from the group consisting of $C_1$-$C_6$ alkyl, halo, —OR", phenyl, and —N(R")(R"), wherein each occurrence of R" is independently H, $C_1$-$C_6$ alkyl, or $C_3$-$C_8$ cycloalkyl.

Embodiment 9 provides the compound of any of Embodiments 1-8, wherein each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), —NO$_2$, —S(=O)$_2$N(R")(R"), acyl, and $C_1$-$C_6$ alkoxycarbonyl, wherein each occurrence of R" is independently H, $C_1$-$C_6$ alkyl or $C_3$-$C_8$ cycloalkyl.

Embodiment 10 provides the compound of any of Embodiments 1-9, wherein each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), and $C_1$-$C_6$ alkoxycarbonyl, wherein each occurrence of R" is independently H, $C_1$-$C_6$ alkyl or $C_3$-$C_8$ cycloalkyl.

Embodiment 11 provides the compound of any of Embodiments 1-10, wherein one applies: $X^1=CR^{6I}$; $X^2=CR^{6II}$; $X^3=CR^{6III}$; and $X^4=CR^{6IV}$; $X^1=N$; $X^2=CR^{6II}$ $X^3=CR^{6III}$; and $X^4=CR^{6I}$; $X^1=CR^{6I}$; $X^2=N$; $X^3=CR^{6III}$; and $X^4=CR^{6IV}$; $X^1=CR^{6I}$; $X^2=CR^{6II}$; $X^3=N$; and $X^4=CR^{6I}$; $X^1=CR^{6I}$; $X^2=CR^{6II}$; $X^3=CR^{6III}$; and $X^4=N$; $X^1=N$; $X^2=CR^{6II}$; $X^3=N$; and $X^4=CR^{6I}$; $X^1=CR^{6I}$; $X^2=N$; $X^3=CR^{6III}$; and $X^4=N$; $X^1=N$; $X^2=CR^{6II}$; $X^3=CR^{6III}$; and $X^4=N$.

Embodiment 12 provides the compound of any of Embodiments 1-11, wherein at least one applies: $R^{3a}$ is H and $R^{3b}$ is isopropyl; $R^{3a}$ is H and $R^{3b}$ is tert-butyl; $R^{3a}$ is methyl and $R^{3b}$ is isopropyl; $R^{3a}$ is methyl and $R^{3b}$ is tert-butyl; $R^{3a}$ is methyl and $R^{3b}$ is methyl; $R^{3a}$ is methyl and $R^{3b}$ is ethyl; and $R^{3a}$ is ethyl and $R^{3b}$ is ethyl.

Embodiment 13 provides the compound of any of Embodiments 1-12, wherein $R^{3a}$ and $R^{3b}$ are not H.

Embodiment 14 provides the compound of any of Embodiments 1-13, which is selected from the group consisting of: 5-isopropyl-9-methoxy-8-(3-methoxypropoxy)-2-oxo-1,2,5,6-tetrahydrobenzo[h]quinoline-3-carboxylic acid; 5-isopropyl-9-methoxy-8-(3-methoxypropoxy)-1-methyl-2-oxo-1,2,5,6-tetrahydrobenzo[h]quinoline-3-carboxylic acid; 1-benzyl-5-isopropyl-9-methoxy-8-(3-methoxypropoxy)-2-oxo-1,2,5,6-tetrahydrobenzo[h]quinoline-3-carboxylic acid; 5-isopropyl-9-methoxy-8-(3-methoxypropoxy)-5-methyl-2-oxo-1,2,5,6-tetrahydrobenzo[h]quinoline-3-carboxylic acid; 9-chloro-5-isopropyl-8-(3-methoxypropoxy)-5-methyl-2-oxo-1,2,5,6-tetrahydrobenzo[h]quinoline-3-carboxylic acid; 5-isopropyl-2,9-dimethoxy-8-(3-methoxypropoxy)benzo[h]quinoline-3-carboxylic acid; 4-hydroxy-5-isopropyl-9-methoxy-8-(3-methoxypropoxy)-2-oxo-1,2,5,6-tetrahydrobenzo[h]quinoline-3-carboxylic acid; 9-chloro-4-hydroxy-5-isopropyl-8-(3-methoxypropoxy)-5-methyl-2-oxo-1,2,5,6-tetrahydrobenzo[h]quinoline-3-carboxylic acid; 4-fluoro-5-isopropyl-9-methoxy-8-(3-methoxypropoxy)-2-oxo-1,2,5,6-tetrahydrobenzo[h]quinoline-3-carboxylic acid; 1-benzyl-4-hydroxy-5-isopropyl-9-methoxy-8-(3-methoxypropoxy)-2-oxo-1,2,5,6-tetrahydrobenzo[h]quinoline-3-carboxylic acid; 2-chloro-4-hydroxy-5-isopropyl-9-methoxy-8-(3-methoxypropoxy)-5,6-dihydrobenzo[h]quinoline-3-carboxylic acid; 4-chloro-5-isopropyl-9-methoxy-8-(3-methoxypropoxy)-2-oxo-1,2,5,6-tetrahydrobenzo[h]quinoline-3-carboxylic acid; 2,4-dichloro-5-isopropyl-9-methoxy-8-(3-methoxypropoxy)-5,6-dihydrobenzo[h]quinoline-3-carboxylic acid; 4-hydroxy-5-isopropyl-9-methoxy-8-(3-methoxypropoxy)-5,6-dihydrobenzo[h]quinolin-2(1H)-one; 2-chloro-5-isopropyl-9-methoxy-8-(3-methoxypropoxy)-5,6-dihydrobenzo[h]quinoline-3-carboxylic acid; 9-chloro-5-isopropyl-8-(3-methoxypropoxy)-2-oxo-1,2,5,6-tetrahydro-1,10-phenanthroline-3-carboxylic acid; 9-chloro-5-isopropyl-8-(3-methoxypropoxy)-1-methyl-2-oxo-1,2,5,6-tetrahydro-1,10-phenanthroline-3-carboxylic acid; 9-chloro-4-hydroxy-5-isopropyl-8-(3-methoxypropoxy)-2-oxo-1,2,5,6-tetrahydro-1,10-phenanthroline-3-carboxylic acid; 5-(tert-butyl)-9-chloro-4-hydroxy-8-(3-methoxypropoxy)-2-oxo-1,2,5,6-tetrahydro-1,10-phenanthroline-3-carboxylic acid; 4-hydroxy-5-isopropyl-9-methoxy-8-(3-methoxypropoxy)-5-methyl-2-oxo-1,2,5,6-tetrahydrobenzo[h]quinoline-3-carboxylic acid; 4-hydroxy-5-isopropyl-9-methoxy-8-(3-methoxypropoxy)-2-oxo-1,2,5,6-tetrahydro-1,10-phenanthroline-3-carboxylic acid; 5-(tert-butyl)-4-hydroxy-9-methoxy-8-(3-methoxypropoxy)-2-oxo-1,2,5,6-tetrahydro-1,10-phenanthroline-3-carboxylic acid; 9-ethoxy-4-hydroxy-5-isopropyl-8-(3-methoxypropoxy)-2-oxo-1,2,5,6-tetrahydro-1,10-phenanthroline-3-carboxylic acid; 9-(2,2-difluoroethoxy)-4-hydroxy-5-isopropyl-8-(3-methoxypropoxy)-2-oxo-1,2,5,6-tetrahydro-1,10-phenanthroline-3-carboxylic acid; 5-isopropyl-9-methoxy-8-(3-methoxypropoxy)-2-oxo-1,2,5,6-tetrahydro-1,10-phenanthroline-3-carboxylic acid; 5-(tert-butyl)-9-methoxy-8-(3-methoxypropoxy)-2-oxo-1,2,5,6-tetrahydro-1,10-phenanthroline-3-carboxylic acid; 9-cyclopropyl-4-hydroxy-5-isopropyl-8-(3-methoxypropoxy)-2-oxo-1,2,5,6-tetrahydro-1,10-phenanthroline-3-carboxylic acid; 4-hydroxy-5-isopropyl-8-(3-methoxypropoxy)-2-oxo-9-propyl-1,2,5,6-tetrahydro-1,10-phenanthroline-3-carboxylic acid; 4-hydroxy-5-isopropyl-9-((2-methoxyethyl)amino)-8-(3-methoxypropoxy)-2-oxo-1,2,5,6-tetrahydro-1,10-phenanthroline-3-carboxylic acid; 4-hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide; 4-hydroxy-5-isopropyl-8-(3-methoxypropoxy)-9-(methylamino)-2-oxo-1,2,5,6-tetrahydro-1,10-phenanthroline-3-carboxylic acid; 9-(dimethylamino)-4-hydroxy-5-isopropyl-8-(3-methoxypropoxy)-2-oxo-1,2,5,6-tetrahydro-1,10-phenanthroline-3-carboxylic acid; 5-Isopropyl-8-(3-methoxypropoxy)-9-(methylamino)-2-oxo-1,2,5,6-tetrahydro-1,10-phenanthroline-3-carboxylic acid; 9-Cyclopropyl-5-isopropyl-8-(3-methoxypropoxy)-2-oxo-1,2,5,6-tetrahydro-1,10-phenanthroline-3-carboxylic acid; 4-hydroxy-5-isopropyl-9-methoxy-8-(3-methoxypropoxy)-3-(1H-1,2,4-triazol-5-yl)-5,6-dihydrobenzo[h]quinolin-2(1H)-one; 4-hydroxy-5-isopropyl-9-methoxy-8-(3-methoxypropoxy)-2-oxo-1,2,5,6-tetrahydrobenzo[h]quinoline-3-carboxamide; 5-(tert-butyl)-4-hydroxy-9-methoxy-8-(3-methoxypropoxy)-2-oxo-1,2,5,6-tetrahydro-1,10-phenanthroline-3-carboxamide; 5-(tert-butyl)-9-methoxy-8-(3-methoxypropoxy)-2-oxo-1,2,5,6-tetrahydro-1,10-phenanthroline-3-carboxamide; 5-(tert-butyl)-4-hydroxy-9-methoxy-8-(3-methoxypropoxy)-N-methyl-2-oxo-1,2,5,6-tetrahydro-1,10-phenanthroline-3-carboxamide; 5-(tert-butyl)-4-hydroxy-9-methoxy-8-(3-methoxypropoxy)-N,N-dimethyl-2-oxo-1,2,5,6-tetrahydro-1,10-phenanthroline-3-carboxamide; 5-(tert-butyl)-N,4-dihydroxy-9-methoxy-8-(3-methoxypropoxy)-2-oxo-1,2,5,6-tetrahydro-1,10-phenanthroline-3-carboxamide; N,4-dihydroxy-5-isopropyl-9-methoxy-8-(3-methoxypropoxy)-2-oxo-1,2,5,6-tetrahydrobenzo[h]quinoline-3-carboxamide; 5-(tert-butyl)-N-hydroxy-9-methoxy-8-(3-methoxypropoxy)-2-oxo-1,2,5,6-tetrahydro-1,10-phenanthroline-3-carboxamide; 5-(tert-butyl)-2,4- dichloro-9-methoxy-8-(3-methoxypropoxy)-5,6-dihydro-1,10-phenanthroline-3-carboxylic acid; (S)-10-chloro-5-isopropyl-9-(3-methoxypropoxy)-2-oxo-1,2,5,6-tetrahydrobenzo[2,3]oxepino[4,5-b]pyridine-3-carboxylic acid; (S)-10-chloro-4-hydroxy-5-isopropyl-9-(3-methoxypropoxy)-2-oxo-1,2,5,6-tetrahydrobenzo[2,3]oxepino[4,5-b]pyridine-3-carboxylic acid; (S)-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylic acid; (S)-4-hydroxy-5-isopropyl-10-(2-methoxyethyl)-9-(3-methoxypropoxy)-2-oxo-1,2,5,6-tetrahydrobenzo[2,3]oxepino[4,5-b]pyridine-3-carboxylic acid; 9-methoxy-8-(3-methoxypropoxy)-2-oxo-2,6-dihydro-1H-spiro[benzo[h]quinoline-5,1'-cyclohexane]-3-carboxylic acid; 2-chloro-8-hydroxy-7-isopropyl-3-(3-methoxypropoxy)-10-oxo-6,7,10,11-tetrahydrooxepino[3,2-b:4,5-b']dipyridine-9-carboxylic acid; 7-(tert-butyl)-2-chloro-8-hydroxy-3-(3-methoxypropoxy)-10-oxo-6,7,10,11-tetrahydrooxepino[3,2-b:4,5-b']dipyridine-9-carboxylic acid; 8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylic acid; 7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylic acid; 7-(tert-butyl)-2-cyclopropyl-8-hydroxy-3-(3-methoxypropoxy)-10-oxo-6,7,10,11-tetrahydrooxepino[3,2-b:4,5-b']dipyridine-9-carboxylic acid; 8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylic acid; 7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylic acid; 5-isopropyl-4,9-dimethoxy-8-(3-methoxypropoxy)-2-oxo-1,2,5,6-tetrahydrobenzo[h]quinoline-3-carboxylic acid; 5-isopropyl-9-methoxy-4-(2-methoxyethoxy)-8-(3-methoxypropoxy)-2-oxo-1,2,5,6-tetrahydrobenzo[h]quinoline-3-carboxylic acid; 4-(2-(dimethylamino)ethoxy)-5-isopropyl-9-methoxy-8-(3-methoxypropoxy)-2-oxo-1,2,5,6-tetrahydrobenzo[h]quinoline-3-carboxylic acid; 4-(2-hydroxyethoxy)-5-isopropyl-9-methoxy-8-(3-methoxypropoxy)-2-oxo-1,2,5,6-tetrahydrobenzo[h]quinoline-3-carboxylic acid; 4-ethoxy-5-isopropyl-9-methoxy-8-(3-methoxypropoxy)-2-oxo-1,2,5,6-tetrahydrobenzo[h]quinoline-3-carboxylic acid; 5-(tert-butyl)-4,9-dimethoxy-8-(3-methoxypropoxy)-2-oxo-1,2,5,6-tetrahydro-1,10-phenanthroline-3-carboxylic acid; 2-cyclopropyl-8-hydroxy-7-isopropyl-3-(3-methoxypropoxy)-10-oxo-6,7,10,11-tetrahydrooxepino[3,2-b:4,5-b']dipyridine-9-carboxylic acid; and (S)-4-hydroxy-5-isopropyl-9-(3-methoxypropoxy)-2-oxo-10-(tetrahydro-2H-pyran-4-yl)-1,2,5,6-tetrahydrobenzo[2,3]oxepino[4,5-b]pyridine-3-carboxylic acid.

Embodiment 15 provides a pharmaceutical composition comprising at least one compound of any of Embodiments 1-14 and a pharmaceutically acceptable carrier.

Embodiment 16 provides the pharmaceutical composition of Embodiment 15, further comprising at least one additional agent useful for treating hepatitis virus infection.

Embodiment 17 provides the pharmaceutical composition of Embodiment 16, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer.

Embodiment 18 provides the pharmaceutical composition of Embodiment 17, wherein the oligomeric nucleotide comprises one or more siRNAs.

Embodiment 19 provides the pharmaceutical composition of any of Embodiments 16-18, wherein the hepatitis virus is at least one selected from the group consisting of hepatitis B virus (HBV) and hepatitis D virus (HDV).

Embodiment 20 provides a method of treating or preventing hepatitis virus infection in a subject, the method comprising administering to the subject in need thereof a therapeutically effective amount of at least one compound of any of Embodiments 1-14 or at least one pharmaceutical composition of any of Embodiments 15-19.

Embodiment 21 provides the method of Embodiment 20, wherein the subject is infected with hepatitis B virus (HBV).

Embodiment 22 provides the method of Embodiment 20, wherein the subject is infected with hepatitis D virus (HDV).

Embodiment 23 provides the method of any of Embodiments 20-22, wherein the subject is infected with HBV and HDV.

Embodiment 24 provides a method of reducing or minimizing levels of at least one selected from the group consisting of hepatitis B virus surface antigen (HBsAg), hepatitis B e-antigen (HBeAg), hepatitis B core protein, and pregenomic (pg) RNA, in a HBV-infected subject, the method comprising administering to the subject in need thereof a therapeutically effective amount of at least one compound of any of Embodiments 1-14 or at least one pharmaceutical composition of any of Embodiments 15-19.

Embodiment 25 provides the method of any of Embodiments 20-24, wherein the at least one compound is administered to the subject in a pharmaceutically acceptable composition.

Embodiment 26 provides the method of any of Embodiments 20-25, wherein the subject is further administered at least one additional agent useful for treating the hepatitis virus infection.

Embodiment 27 provides the method of Embodiment 26, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer.

Embodiment 28 provides the method of Embodiment 27, wherein the oligomeric nucleotide comprises one or more siRNAs.

Embodiment 29 provides the method of any of Embodiments 26-28, wherein the subject is co-administered the at least one compound and the at least one additional agent.

Embodiment 30 provides the method of any of Embodiments 26-29, wherein the at least one compound and the at least one additional agent are coformulated.

Embodiment 31 provides the method of any of Embodiments 24-30, wherein the subject is further infected with HDV.

Embodiment 32 provides the method of any of Embodiments 20-31, wherein the subject is a mammal.

Embodiment 33 provides the method of Embodiment 32, wherein the mammal is a human.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (III), or a salt, solvate, geometric isomer, stereoisomer, tautomer, and any mixtures thereof:

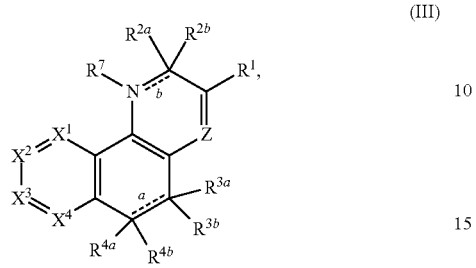

(III)

wherein:
Z is $CR^{12}$;
$R^1$ is selected from the group consisting of H, halogen, —C(=O)$OR^8$, —C(=O)$NHR^8$, —C(=O)NH—$OR^8$, —C(=O)$NHNHR^8$, —C(=O)NHNHC(=O)$R^8$, —C(=O)NHS(=O)$_2R^8$, —CN, and 1H-1,2,4-triazol-5-yl;
$R^{2a}$ and $R^{2b}$ combine to form =O;
bond b is a single bond;
$R^7$ is selected from the group consisting of H, optionally substituted $C_1$-$C_6$ alkyl, and optionally substituted $C_3$-$C_8$ cycloalkyl;
$R^{3a}$, $R^{3b}$, $R^{4a}$, and $R^{4b}$ are each independently selected from the group consisting of H, optionally substituted $C_1$-$C_6$ alkyl, and optionally substituted $C_3$-$C_8$ cycloalkyl;
or one pair selected from the group consisting of $R^{3a}/R^{3b}$, $R^{4a}/R^{4b}$, and $R^{3a}/R^{4a}$ combine to form a divalent group selected from the group consisting of $C_1$-$C_6$ alkanediyl, —(CH$_2$)$_n$O(CH$_2$)$_n$—, —(CH$_2$)$_n$NR$^9$(CH$_2$)$_n$—, —(CH$_2$)$_n$S(CH$_2$)$_n$—, —(CH$_2$)$_n$S(=O)(CH$_2$)$_n$—, and —(CH$_2$)$_n$S(=O)$_2$(CH$_2$)$_n$—, wherein each occurrence of n is independently selected from the group consisting of 1 and 2 and wherein each divalent group is optionally substituted with at least one $C_1$-$C_6$ alkyl or halo;
bond a is a single bond;
$X^1$ is selected from the group consisting of $CR^{6I}$ and N;
$X^2$ is selected from the group consisting of $CR^{6II}$ and N;
$X^3$ is selected from the group consisting of $CR^{6III}$ and N;
$X^4$ is selected from the group consisting of $CR^{6IV}$ and N;
or either $X^3$ and $X^4$, or $X^1$ and $X^2$, combine to form —S—;
wherein 0-2 substituents selected from the group consisting of $X^1$, $X^2$, $X^3$ and $X^4$ are N, each of which, if present, is optionally substituted with $C_1$-$C_6$ alkyl if the adjacent carbon atom in the ring is substituted with —OH;
$R^{6I}$, $R^{6II}$, $R^{6III}$, and $R^{6IV}$ are independently selected from the group consisting of H, halogen, —CN, optionally substituted $C_1$-$C_6$ alkyl, optionally substituted $C_3$-$C_8$ cycloalkyl, —OR, —N(R)(R), optionally substituted heterocyclyl, and $C_1$-$C_6$ haloalkoxy, wherein each occurrence of R is independently selected from the group consisting of H, $C_1$-$C_6$ alkyl, R'-substituted $C_1$-$C_6$ alkyl, $C_1$-$C_6$ hydroxyalkyl, optionally substituted ($C_1$-$C_6$ alkoxy)-$C_1$-$C_6$ alkyl, and optionally substituted $C_3$-$C_8$ cycloalkyl,
wherein each occurrence of R' is selected from the group consisting of —NH$_2$, —NH($C_1$-$C_6$ alkyl), —N($C_1$-$C_6$ alkyl)($C_1$-$C_6$ alkyl), —NHC(=O)O$^t$Bu, —N($C_1$-$C_6$ alkyl)C(=O)O$^t$Bu, and a 5- or 6-membered heterocyclic group, which is optionally N-linked;
or $X^2$ is $CR^{6II}$, $X^3$ is $CR^{6III}$, and $R^{6II}$ and $R^{6III}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;
or $X^3$ and $R^{6III}$, $X^4$ is $CR^{6IV}$, and $R^{6III}$ and $R^{6IV}$ combine to form a divalent group selected from the group consisting of —O(CR$^9$R$^{11}$)O—, —O(CR$^9$R$^{11}$)(CR$^9$R$^{11}$)O—, —O(CR$^9$R$^{11}$)(CR$^9$R$^{11}$)—, and —O(CR$^9$R$^{11}$)(CR$^9$R$^{11}$)(CR$^9$R$^{11}$)—;
each occurrence of $R^8$ is independently selected from the group consisting of H, optionally substituted $C_1$-$C_6$ alkyl, and optionally substituted $C_3$-$C_8$ cycloalkyl;
each occurrence of $R^9$ is independently selected from the group consisting of H and $C_1$-$C_6$ alkyl;
each occurrence of is independently selected from the group consisting of H, OH, $C_1$-$C_6$ alkyl, $C_1$-$C_6$ alkoxy, alkoxy-$C_1$-$C_6$ alkyl and alkoxy-$C_1$-$C_6$ alkoxy, wherein two $R^{11}$ groups bound to the same carbon atom are not simultaneously OH; and wherein $R^{11}$ is not OH if it is bound to a carbon that is further bound to an oxygen atom;
or two $R^{11}$ groups combine with the carbon atom to which they are bound to form a moiety selected from the group consisting of C=O, C=CH$_2$ and oxetane-3,3-diyl;
$R^{12}$ is selected from the group consisting of H, OH, halogen, optionally substituted $C_1$-$C_6$ alkoxy, optionally substituted $C_1$-$C_6$ alkyl, and optionally substituted $C_3$-$C_8$ cycloalkyl;
wherein each occurrence of optionally substituted alkyl and optionally substituted cycloalkyl is independently optionally substituted with at least one substituent selected from the group consisting of $C_1$-$C_6$ alkyl, halogen, —OR'', tetrahydro-2-H-pyranyl, —N(R'')(R''), 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C≡N, —C(=O)NH$_2$, —C(=O)NH($C_1$-$C_6$)alkyl, —C(=O)N(($C_1$-$C_6$)alkyl)$_2$, —SO$_2$NH$_2$, —SO$_2$NH($C_1$-$C_6$ alkyl), —SO$_2$N($C_1$-$C_6$ alkyl)$_2$, —C(=NH)NH$_2$, and —NO$_2$,
wherein each occurrence of R'' is independently H, $C_1$-$C_6$ alkyl, or $C_3$-$C_8$ cycloalkyl;
wherein each occurrence of optionally substituted heterocyclyl is independently optionally substituted with at least one substituent selected from the group consisting of $C_1$-$C_6$ alkyl, OH, $C_1$-$C_6$ alkoxy, halogen, amino, acetamido, and NO$_2$; and
wherein at least one of the following applies:
(a) at least one of $X^1$, $X^2$, $X^3$, and $X^4$ is N; and
(b) at least one of $R^{3a}$ or $R^{3b}$ is independently selected from the group consisting of n-propyl, isopropyl, n-butyl, isobutyl, sec-butyl, and tert-butyl.

2. The compound of claim 1, which is selected from the group consisting of:

(IIIa) 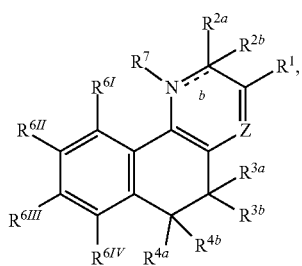
(IIIb) 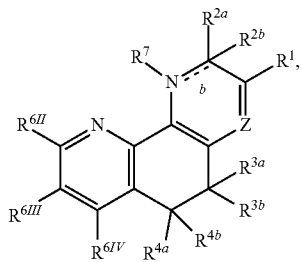
(IIIc) 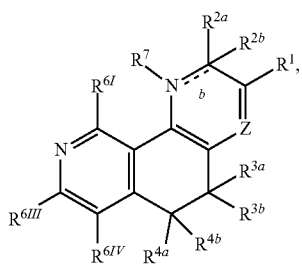
(IIId) 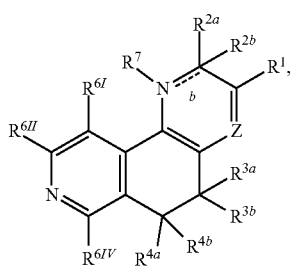
(IIIe) 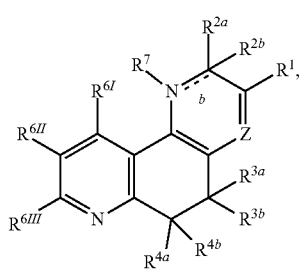
(IIIf) 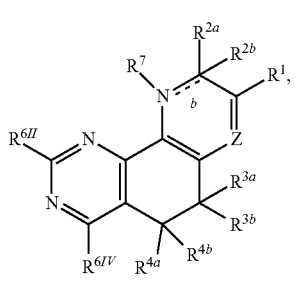
-continued
(IIIg) 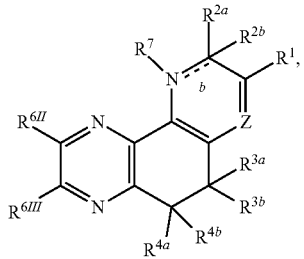
(IIIh) 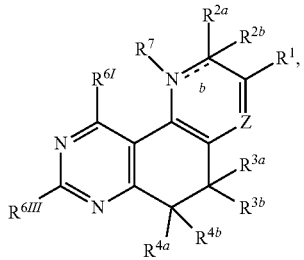
(IIIi) 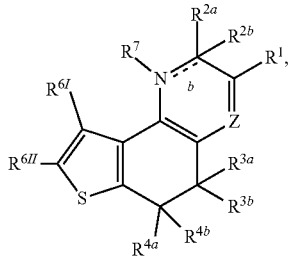
(IIIj) 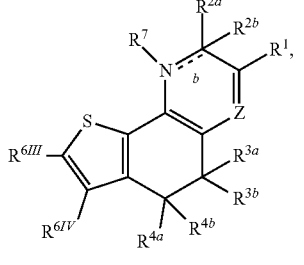
(IIIk) 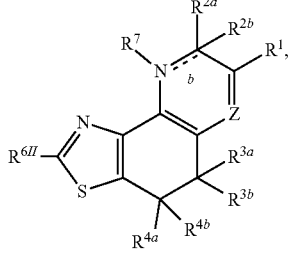
(IIIl) 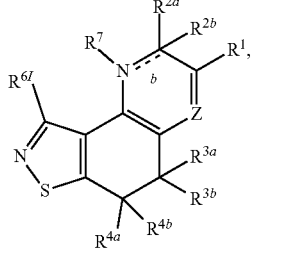

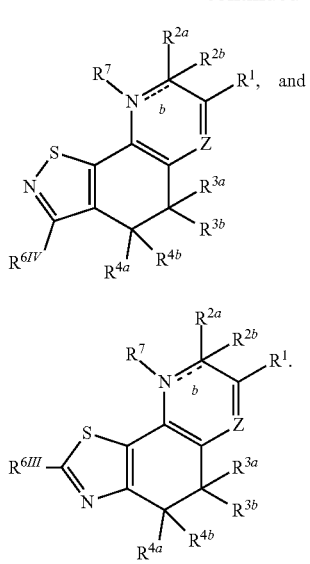

3. The compound of claim 1, wherein at least one applies:
(a) at least one of $X^1$, $X^2$, $X^3$, and $X^4$ is N;
(b) at least one of $R^{3a}$ or $R^{3b}$ is independently selected from the group consisting of optionally substituted $C_1$-$C_6$ alkyl and optionally substituted $C_3$-$C_8$ cycloalkyl;
(c) none of $R^{6I}$, $R^{6II}$, $R^{6III}$ and $R^{6IV}$, if present, are N-linked;
(d) none of $R^{6I}$, $R^{6II}$, $R^{6III}$ and $R^{6IV}$, if present, comprise a basic nitrogen group;
(e) at least one of $R^{6II}$ and $R^{6III}$, if present, is O-linked;
(f) both of $R^{6II}$ and $R^{6III}$, if present, are O-linked.

4. The compound of claim 1, wherein each occurrence of alkyl, alkenyl, or cycloalkyl is independently optionally substituted with at least one substituent selected from the group consisting of $C_1$-$C_6$ alkyl, halogen, —OR", phenyl, and —N(R")(R").

5. The compound of claim 1, wherein one applies:
$X^1$=$CR^{6I}$; $X^2$=$CR^{6II}$; $X^3$=$CR^{6III}$; and $X^4$=$CR^{6IV}$;
$X^1$=N; $X^2$=$CR^{6II}$; $X^3$=$CR^{6III}$; and $X^4$=$CR^{6IV}$;
$X^1$=$CR^{6I}$; $X^2$=N; $X^3$=$CR^{6III}$; and $X^4$=$CR^{6IV}$;
$X^1$=$CR^{6I}$; $X^2$=$CR^{6II}$; $X^3$=N; and $X^4$=$CR^{6IV}$;
$X^1$=$CR^{6I}$; $X^2$=$CR^{6II}$; $X^3$=$CR^{6III}$; and $X^4$=N;
$X^1$=N; $X^2$=$CR^{6II}$; $X^3$=N; and $X^4$=$CR^{6IV}$;
$X^1$=$CR^{6I}$; $X^2$=N; $X^3$=$CR^{6III}$; and $X^4$=N;
$X^1$=N; $X^2$=$CR^{6II}$; $X^3$=$CR^{6III}$; and $X^4$=N.

6. The compound of claim 1, wherein at least one applies: $R^{3a}$ is H and $R^{3b}$ is isopropyl; $R^{3a}$ is H and $R^{3b}$ is tert-butyl; $R^{3a}$ is methyl and $R^{3b}$ is isopropyl; $R^{3a}$ is methyl and $R^{3b}$ is tert-butyl; $R^{3a}$ is methyl and $R^{3b}$ is methyl; $R^{3a}$ is methyl and $R^{3b}$ is ethyl; $R^{3a}$ is ethyl and $R^{3b}$ is ethyl; and $R^{3a}$ and $R^{3b}$ are not H.

7. A compound selected from the group consisting of:
5-isopropyl-9-methoxy-8-(3-methoxypropoxy)-2-oxo-1,2,5,6-tetrahydrobenzo[h]quinoline-3-carboxylic acid;
5-isopropyl-9-methoxy-8-(3-methoxypropoxy)-1-methyl-2-oxo-1,2,5,6-tetrahydrobenzo[h]quinoline-3-carboxylic acid;
1-benzyl-5-isopropyl-9-methoxy-8-(3-methoxypropoxy)-2-oxo-1,2,5,6-tetrahydrobenzo[h]quinoline-3-carboxylic acid;
5-isopropyl-9-methoxy-8-(3-methoxypropoxy)-5-methyl-2-oxo-1,2,5,6-tetrahydrobenzo[h]quinoline-3-carboxylic acid;
9-chloro-5-isopropyl-8-(3-methoxypropoxy)-5-methyl-2-oxo-1,2,5,6-tetrahydrobenzo[h]quinoline-3-carboxylic acid;
4-hydroxy-5-isopropyl-9-methoxy-8-(3-methoxypropoxy)-2-oxo-1,2,5,6-tetrahydrobenzo[h]quinoline-3-carboxylic acid;
9-chloro-4-hydroxy-5-isopropyl-8-(3-methoxypropoxy)-5-methyl-2-oxo-1,2,5,6-tetrahydrobenzo[h]quinoline-3-carboxylic acid;
4-fluoro-5-isopropyl-9-methoxy-8-(3-methoxypropoxy)-2-oxo-1,2,5,6-tetrahydrobenzo[h]quinoline-3-carboxylic acid;
1-benzyl-4-hydroxy-5-isopropyl-9-methoxy-8-(3-methoxypropoxy)-2-oxo-1,2,5,6-tetrahydrobenzo[h]quinoline-3-carboxylic acid;
4-chloro-5-isopropyl-9-methoxy-8-(3-methoxypropoxy)-2-oxo-1,2,5,6-tetrahydrobenzo[h]quinoline-3-carboxylic acid;
4-hydroxy-5-isopropyl-9-methoxy-8-(3-methoxypropoxy)-5,6-dihydrobenzo[h]quinolin-2(1H)-one;
2-chloro-5-isopropyl-9-methoxy-8-(3-methoxypropoxy)-5,6-dihydrobenzo[h]quinoline-3-carboxylic acid;
9-chloro-5-isopropyl-8-(3-methoxypropoxy)-2-oxo-1,2,5,6-tetrahydro-1,10-phenanthroline-3-carboxylic acid;
9-chloro-5-isopropyl-8-(3-methoxypropoxy)-1-methyl-2-oxo-1,2,5,6-tetrahydro-1,10-phenanthroline-3-carboxylic acid;
9-chloro-4-hydroxy-5-isopropyl-8-(3-methoxypropoxy)-2-oxo-1,2,5,6-tetrahydro-1,10-phenanthroline-3-carboxylic acid;
5-(tert-butyl)-9-chloro-4-hydroxy-8-(3-methoxypropoxy)-2-oxo-1,2,5,6-tetrahydro-1,10-phenanthroline-3-carboxylic acid;
4-hydroxy-5-isopropyl-9-methoxy-8-(3-methoxypropoxy)-5-methyl-2-oxo-1,2,5,6-tetrahydrobenzo[h]quinoline-3-carboxylic acid;
4-hydroxy-5-isopropyl-9-methoxy-8-(3-methoxypropoxy)-2-oxo-1,2,5,6-tetrahydro-1,10-phenanthroline-3-carboxylic acid;
5-(tert-butyl)-4-hydroxy-9-methoxy-8-(3-methoxypropoxy)-2-oxo-1,2,5,6-tetrahydro-1,10-phenanthroline-3-carboxylic acid;
9-ethoxy-4-hydroxy-5-isopropyl-8-(3-methoxypropoxy)-2-oxo-1,2,5,6-tetrahydro-1,10-phenanthroline-3-carboxylic acid;
9-(2,2-difluoroethoxy)-4-hydroxy-5-isopropyl-8-(3-methoxypropoxy)-2-oxo-1,2,5,6-tetrahydro-1,10-phenanthroline-3-carboxylic acid;
5-isopropyl-9-methoxy-8-(3-methoxypropoxy)-2-oxo-1,2,5,6-tetrahydro-1,10-phenanthroline-3-carboxylic acid;
5-(tert-butyl)-9-methoxy-8-(3-methoxypropoxy)-2-oxo-1,2,5,6-tetrahydro-1,10-phenanthroline-3-carboxylic acid;
9-cyclopropyl-4-hydroxy-5-isopropyl-8-(3-methoxypropoxy)-2-oxo-1,2,5,6-tetrahydro-1,10-phenanthroline-3-carboxylic acid;
4-hydroxy-5-isopropyl-8-(3-methoxypropoxy)-2-oxo-9-propyl-1,2,5,6-tetrahydro-1,10-phenanthroline-3-carboxylic acid;
4-hydroxy-5-isopropyl-9-((2-methoxyethyl)amino)-8-(3-methoxypropoxy)-2-oxo-1,2,5,6-tetrahydro-1,10-phenanthroline-3-carboxylic acid;
4-hydroxy-5-isopropyl-N-(2-methoxyethyl)-9-((2-methoxyethyl)amino)-8-(3-methoxypropoxy)-2-oxo-1,2,5,6-tetrahydro-1,10-phenanthroline-3-carboxamide;

4-hydroxy-5-isopropyl-8-(3-methoxypropoxy)-9-(methylamino)-2-oxo-1,2,5,6-tetrahydro-1,10-phenanthroline-3-carboxylic acid;

9-(dimethylamino)-4-hydroxy-5-isopropyl-8-(3-methoxypropoxy)-2-oxo-1,2,5,6-tetrahydro-1,10-phenanthroline-3-carboxylic acid;

5-Isopropyl-8-(3-methoxypropoxy)-9-(methylamino)-2-oxo-1,2,5,6-tetrahydro-1,10-phenanthroline-3-carboxylic acid;

9-Cyclopropyl-5-isopropyl-8-(3-methoxypropoxy)-2-oxo-1,2,5,6-tetrahydro-1,10-phenanthroline-3-carboxylic acid;

4-hydroxy-5-isopropyl-9-methoxy-8-(3-methoxypropoxy)-3-(1H-1,2,4-triazol-5-yl)-5,6-dihydrobenzo[h]quinolin-2(1H)-one;

4-hydroxy-5-isopropyl-9-methoxy-8-(3-methoxypropoxy)-2-oxo-1,2,5,6-tetrahydrobenzo[h]quinoline-3-carboxamide;

5-(tert-butyl)-4-hydroxy-9-methoxy-8-(3-methoxypropoxy)-2-oxo-1,2,5,6-tetrahydro-1,10-phenanthroline-3-carboxamide;

5-(tert-butyl)-9-methoxy-8-(3-methoxypropoxy)-2-oxo-1,2,5,6-tetrahydro-1,10-phenanthroline-3-carboxamide;

5-(tert-butyl)-4-hydroxy-9-methoxy-8-(3-methoxypropoxy)-N-methyl-2-oxo-1,2,5,6-tetrahydro-1,10-phenanthroline-3-carboxamide;

5-(tert-butyl)-4-hydroxy-9-methoxy-8-(3-methoxypropoxy)-N,N-dimethyl-2-oxo-1,2,5,6-tetrahydro-1,10-phenanthroline-3-carboxamide;

5-(tert-butyl)-N,4-dihydroxy-9-methoxy-8-(3-methoxypropoxy)-2-oxo-1,2,5,6-tetrahydro-1,10-phenanthroline-3-carboxamide;

N,4-dihydroxy-5-isopropyl-9-methoxy-8-(3-methoxypropoxy)-2-oxo-1,2,5,6-tetrahydrobenzo[h]quinoline-3-carboxamide;

5-(tert-butyl)-N-hydroxy-9-methoxy-8-(3-methoxypropoxy)-2-oxo-1,2,5,6-tetrahydro-1,10-phenanthroline-3-carboxamide;

(S)-10-chloro-5-isopropyl-9-(3-methoxypropoxy)-2-oxo-1,2,5,6-tetrahydrobenzo[2,3]oxepino[4,5-b]pyridine-3-carboxylic acid;

(S)-10-chloro-4-hydroxy-5-isopropyl-9-(3-methoxypropoxy)-2-oxo-1,2,5,6-tetrahydrobenzo[2,3]oxepino[4,5-b]pyridine-3-carboxylic acid;

(S)-4-hydroxy-5-isopropyl-10-(methoxymethyl)-9-(3-methoxypropoxy)-2-oxo-1,2,5,6-tetrahydrobenzo[2,3]oxepino[4,5-b]pyridine-3-carboxylic acid;

(S)-4-hydroxy-5-isopropyl-10-(2-methoxyethyl)-9-(3-methoxypropoxy)-2-oxo-1,2,5,6-tetrahydrobenzo[2,3]oxepino[4,5-b]pyridine-3-carboxylic acid;

9-methoxy-8-(3-methoxypropoxy)-2-oxo-2,6-dihydro-1H-spiro[benzo[h]quinoline-5,1'-cyclohexane]-3-carboxylic acid;

2-chloro-8-hydroxy-7-isopropyl-3-(3-methoxypropoxy)-10-oxo-6,7,10,11-tetrahydrooxepino[3,2-b:4,5-b']dipyridine-9-carboxylic acid;

7-(tert-butyl)-2-chloro-8-hydroxy-3-(3-methoxypropoxy)-10-oxo-6,7,10,11-tetrahydrooxepino[3,2-b:4,5-b']dipyridine-9-carboxylic acid;

8-hydroxy-7-isopropyl-3-(3-methoxypropoxy)-10-oxo-2-(tetrahydro-2H-pyran-4-yl)-6,7,10,11-tetrahydrooxepino[3,2-b:4,5-b']dipyridine-9-carboxylic acid;

7-(tert-butyl)-2-ethyl-8-hydroxy-3-(3-methoxypropoxy)-10-oxo-6,7,10,11-tetrahydrooxepino[3,2-b:4,5-b']dipyridine-9-carboxylic acid;

7-(tert-butyl)-2-cyclopropyl-8-hydroxy-3-(3-methoxypropoxy)-10-oxo-6,7,10,11-tetrahydrooxepino[3,2-b:4,5-b']dipyridine-9-carboxylic acid;

8-hydroxy-7-isopropyl-2-(2-methoxyethyl)-3-(3-methoxypropoxy)-10-oxo-6,7,10,11-tetrahydrooxepino[3,2-b:4,5-b']dipyridine-9-carboxylic acid;

7-(tert-butyl)-8-hydroxy-2-methoxy-3-(3-methoxypropoxy)-10-oxo-6,7,10,11-tetrahydrooxepino[3,2-b:4,5-b']dipyridine-9-carboxylic acid;

5-isopropyl-4,9-dimethoxy-8-(3-methoxypropoxy)-2-oxo-1,2,5,6-tetrahydrobenzo[h]quinoline-3-carboxylic acid;

5-isopropyl-9-methoxy-4-(2-methoxyethoxy)-8-(3-methoxypropoxy)-2-oxo-1,2,5,6-tetrahydrobenzo[h]quinoline-3-carboxylic acid;

4-(2-(dimethylamino)ethoxy)-5-isopropyl-9-methoxy-8-(3-methoxypropoxy)-2-oxo-1,2,5,6-tetrahydrobenzo[h]quinoline-3-carboxylic acid;

4-(2-hydroxyethoxy)-5-isopropyl-9-methoxy-8-(3-methoxypropoxy)-2-oxo-1,2,5,6-tetrahydrobenzo[h]quinoline-3-carboxylic acid;

4-ethoxy-5-isopropyl-9-methoxy-8-(3-methoxypropoxy)-2-oxo-1,2,5,6-tetrahydrobenzo[h]quinoline-3-carboxylic acid;

5-(tert-butyl)-4,9-dimethoxy-8-(3-methoxypropoxy)-2-oxo-1,2,5,6-tetrahydro-1,10-phenanthroline-3-carboxylic acid;

2-cyclopropyl-8-hydroxy-7-isopropyl-3-(3-methoxypropoxy)-10-oxo-6,7,10,11-tetrahydrooxepino[3,2-b:4,5-b']dipyridine-9-carboxylic acid; and (S)-4-hydroxy-5-isopropyl-9-(3-methoxypropoxy)-2-oxo-10-(tetrahydro-2H-pyran-4-yl)-1,2,5,6-tetrahydrobenzo[2,3]oxepino[4,5-b]pyridine-3-carboxylic acid;

or a salt, solvate, geometric isomer, stereoisomer, tautomer, and any mixtures thereof.

8. A pharmaceutical composition comprising at least one compound of claim 1 and a pharmaceutically acceptable carrier.

9. The pharmaceutical composition of claim 8, further comprising at least one additional agent useful for treating hepatitis virus infection.

10. The pharmaceutical composition of claim 9, wherein the at least one additional agent comprises at least one selected from the group consisting of reverse transcriptase inhibitor, capsid inhibitor, cccDNA formation inhibitor, sAg secretion inhibitor, oligomeric nucleotide targeted to the Hepatitis B genome, immunostimulator, and RNA destabilizer.

11. The pharmaceutical composition of claim 10, wherein the oligomeric nucleotide comprises one or more siRNAs.

12. The pharmaceutical composition of claim 9, wherein the hepatitis virus is at least one selected from the group consisting of hepatitis B virus (HBV) and hepatitis D virus (HDV).

13. A pharmaceutical composition comprising at least one compound of claim 7 and a pharmaceutically acceptable carrier.

14. The pharmaceutical composition of claim 13, further comprising at least one additional agent useful for treating hepatitis virus infection.

15. The pharmaceutical composition of claim 14, wherein the at least one additional agent comprises at least one selected from the group consisting of reverse transcriptase inhibitor, capsid inhibitor, cccDNA formation inhibitor, sAg secretion inhibitor, oligomeric nucleotide targeted to the Hepatitis B genome, immunostimulator, and RNA destabilizer.

16. The pharmaceutical composition of claim 15, wherein the oligomeric nucleotide comprises one or more siRNAs.

17. The pharmaceutical composition of claim 14, wherein the hepatitis virus is at least one selected from the group consisting of hepatitis B virus (HBV) and hepatitis D virus (HDV).

18. A method of treating or ameliorating hepatitis B virus (HBV) infection in a subject, the method comprising administering to the subject in need thereof a therapeutically effective amount of at least one compound of claim 1.

19. The method of claim 18, wherein the subject is further infected with hepatitis D virus (HDV).

20. A method of reducing or minimizing levels of at least one selected from the group consisting of hepatitis B virus surface antigen (HBsAg), hepatitis B e-antigen (HBeAg), hepatitis B core protein, and pregenomic (pg) RNA, in a HBV-infected subject, the method comprising administering to the subject in need thereof a therapeutically effective amount of at least one compound of claim 1.

21. The method of claim 18, wherein the at least one compound is administered to the subject in a pharmaceutically acceptable composition.

22. The method of claim 18, wherein the subject is further administered at least one additional agent useful for treating the hepatitis virus infection.

23. The method of claim 22, wherein the at least one additional agent comprises at least one selected from the group consisting of reverse transcriptase inhibitor, capsid inhibitor, cccDNA formation inhibitor, sAg secretion inhibitor, oligomeric nucleotide targeted to the Hepatitis B genome, immunostimulator, and RNA destabilizer.

24. The method of claim 23, wherein the oligomeric nucleotide comprises one or more siRNAs.

25. The method of claim 22, wherein the subject is co-administered the at least one compound and the at least one additional agent.

26. The method of claim 22, wherein the at least one compound and the at least one additional agent are coformulated.

27. The method of claim 20, wherein the subject is further infected with HDV.

28. The method of claim 18, wherein the subject is a mammal.

29. The method of claim 28, wherein the mammal is a human.

30. A method of treating or ameliorating hepatitis B virus (HBV) infection in a subject, the method comprising administering to the subject in need thereof a therapeutically effective amount of at least one compound of claim 7.

31. The method of claim 30, wherein the subject is further infected with hepatitis D virus (HBD).

32. A method of reducing or minimizing levels of at least one selected from the group consisting of hepatitis B virus surface antigen (HBsAg), hepatitis B e-antigen (HBeAg), hepatitis B core protein, and pregenomic (pg) RNA, in a HBV-infected subject, the method comprising administering to the subject in need thereof a therapeutically effective amount of at least one compound of claim 7.

33. The method of claim 32, wherein the at least one compound is administered to the subject in a pharmaceutically acceptable composition.

34. The method of claim 32, wherein the subject is further administered at least one additional agent useful for treating the hepatitis virus infection.

35. The method of claim 34, wherein the at least one additional agent comprises at least one selected from the group consisting of reverse transcriptase inhibitor, capsid inhibitor, cccDNA formation inhibitor, sAg secretion inhibitor, oligomeric nucleotide targeted to the Hepatitis B genome, immunostimulator, and RNA destabilizer.

36. The method of claim 35, wherein the oligomeric nucleotide comprises one or more siRNAs.

37. The method of claim 34, wherein the subject is co-administered the at least one compound and the at least one additional agent.

38. The method of claim 34, wherein the at least one compound and the at least one additional agent are coformulated.

39. The method of claim 32, wherein the subject is further infected with HDV.

40. The method of claim 32, wherein the subject is a mammal.

41. The method of claim 40, wherein the mammal is a human.

* * * * *